(12) United States Patent
Allen et al.

(10) Patent No.: US 11,873,502 B2
(45) Date of Patent: Jan. 16, 2024

(54) TRANSGENIC PLANTS WITH ENHANCED TRAITS

(71) Applicant: Monsanto Technology LLC, St. Louis, MO (US)

(72) Inventors: Edwards M. Allen, O'Fallon, MO (US); Bettina Darveaux, Hillsborough, NC (US); Stephen M. Duff, St. Louis, MO (US); Mary Fernandes, St. Louis, MO (US); Barry S. Goldman, St. Louis, MO (US); Cara L. Griffith, Catawissa, MO (US); Balasulojini Karunanandaa, Creve Coeur, MO (US); Saritha V Kuriakose, Kottayam (IN); Paul J. Loida, Kirkwood, MO (US); Linda L Lutfiyya, St. Louis, MO (US); Robert J. Meister, St. Peters, MO (US); Monnanda S. Rajani, Chesterfield, MO (US); Dhanalakshmi Ramachandra, Bangalore (IN); Elena A. Rice, Olivette, MO (US); Daniel Ruzicka, St. Louis, MO (US); Anagha M. Sant, St. Louis, MO (US); Jon J. Schmuke, St. Louis, MO (US); Rebecca L. Thompson, St. Charles, MO (US); Srikanth Babu Venkatachalayya, Bangalore (IN); Tyamagondlu V. Venkatesh, St. Louis, MO (US); Huai Wang, Chesterfield, MO (US); Xiao Yang, St. Charles, MO (US); Qin Zeng, Chesterfield, MO (US); Jianmin Zhao, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/694,370

(22) Filed: Mar. 14, 2022

(65) Prior Publication Data
US 2022/0195452 A1 Jun. 23, 2022

Related U.S. Application Data

(62) Division of application No. 16/085,527, filed as application No. PCT/US2017/022617 on Mar. 16, 2017, now abandoned.

(60) Provisional application No. 62/310,136, filed on Mar. 18, 2016.

(51) Int. Cl.
*A01H 5/10* (2018.01)
*C12N 15/00* (2006.01)
*C12N 15/82* (2006.01)

(52) U.S. Cl.
CPC .......... *C12N 15/8273* (2013.01); *A01H 5/10* (2013.01); *C12N 15/00* (2013.01); *C12N 15/825* (2013.01); *C12N 15/8213* (2013.01); *C12N 15/8218* (2013.01)

(58) Field of Classification Search
None
See application file for complete search history.

(56) References Cited

U.S. PATENT DOCUMENTS

| | | | |
|---|---|---|---|
| 9,422,572 B2 | 8/2016 | Allen et al. | |
| 9,738,527 B2 | 8/2017 | Li et al. | |
| 2003/0233675 A1 | 12/2003 | Cao et al. | |
| 2004/0034888 A1* | 2/2004 | Liu | C07H 21/04 536/23.6 |
| 2008/0104730 A1 | 5/2008 | Wu et al. | |
| 2011/0167514 A1* | 7/2011 | Brover | C12Q 1/6895 800/290 |
| 2011/0252501 A1 | 10/2011 | Abad et al. | |
| 2011/0265221 A1 | 10/2011 | Abad et al. | |
| 2013/0232642 A1 | 9/2013 | Allen et al. | |
| 2014/0259212 A1 | 9/2014 | Plesch et al. | |
| 2014/0325710 A1 | 10/2014 | Abad et al. | |
| 2015/0047069 A1 | 2/2015 | Chomet et al. | |
| 2015/0143581 A1 | 5/2015 | Li et al. | |
| 2015/0259212 A1 | 9/2015 | Li et al. | |

FOREIGN PATENT DOCUMENTS

| | | |
|---|---|---|
| WO | 2014055477 A2 | 4/2014 |
| WO | 2015029031 A1 | 5/2015 |

OTHER PUBLICATIONS

International Search Report and Written Opinion for PCT/US2017/022617 dated Jul. 21, 2017.
Partial European Search Report regarding European Patent Application No. 17767490 dated Oct. 2, 2019.
Extended European Search Report regarding European Patent Application No. 17767490 dated Jan. 28, 2020.

* cited by examiner

*Primary Examiner* — Phuong T Bui
(74) *Attorney, Agent, or Firm* — Dentons US LLP; David Lanzotti

(57) ABSTRACT

This disclosure provides recombinant DNA constructs and transgenic plants having enhanced traits such as increased yield, increased nitrogen use efficiency, and enhanced drought tolerance or water use efficiency. Transgenic plants may include field crops as well as plant propagules and progeny of such transgenic plants. Methods of making and using such transgenic plants are also provided. This disclosure also provides methods of producing seed from such transgenic plants, growing such seed, and selecting progeny plants with enhanced traits. Also disclosed are transgenic plants with altered phenotypes which are useful for screening and selecting transgenic events for the desired enhanced trait.

14 Claims, No Drawings
Specification includes a Sequence Listing.

SEQUENCE LISTING

<160> NUMBER OF SEQ ID NOS: 101

<210> SEQ ID NO 1
<211> LENGTH: 918
<212> TYPE: DNA
<213> ORGANISM: Agrobacterium tumefaciens

<400> SEQUENCE: 1

```
atggcttcac ctaaacattt tctcgacctg tcggccgttg gcccgcagga cctgcggaca     60
attcttgacg atgcgcgcgc gcgcaaggtc gccacgaagg cgggaacggc ggaaaagccg    120
ctggccggca agatgctggc catgatcttc gaaaagccgt ccacccgcac ccgcgttttcc   180 ttcgatgtgg gcatgcgcca gctcggcggc gagacccttt tcctgtcggg cactgaaatg    240
cagctcggtc gtgcggaaac gatcggcgat accgccaagg tgctgtcgcg ttatgtggat    300
gccatcatga tccgtaccac ggatcattcg cgcctgctcg agcttgccga acacgcgacg    360
gtgcctgtta tcaacggcct gaccgatgat acccatccct gccagatcat ggccgacatc    420
atgacgttcg aggaacatcg tggtccggtc aaaggcaaga ccattgcctg gacgggcgac    480
ggcaacaacg tgctgcactc tttcgtcgag ggctccgcac gtttcggtta ccgcatgacg    540
```

```
atggcggtgc cgatgggttc cgaaccgcat gacaagttca tgaactgggc ccgcaacaat    600
ggcggcgaga tcgcgctgta tcatgatgcg acaaggcgg tcgcgggtgc ggattgtgtc     660
gtcaccgata cctgggtgtc catgaaccag gagcacaagg cgcgcggcca acatcttc      720 cagccctatc aggtcaatga ggccctgatg gccaaggcgc agaaggacgc gctgttcatg    780
cactgcctgc cggcgcatcg cggtgaagaa gtgacggacg ccgtgatcga cggcccgcaa    840
tcggtggtct tcgatgaggc ggagaaccgt ctccacgcgc agaaatccgt catcgcatgg    900
tgcatgggcg tgatctga                                                  918
```

<210> SEQ ID NO 2
<211> LENGTH: 645
<212> TYPE: DNA
<213> ORGANISM: Arabidopsis thaliana
<400> SEQUENCE: 2

```
atggtgaggg gcaaaactca gatgaagaga atagagaatg caacaagcag acaagtgact     60
ttctccaaaa gaaggaatgg tttgttgaag aaagcctttg agctctcagt gctttgtgat    120
gctgaagttt ctcttatcat cttctctcct aaaggcaaac tttatgaatt cgccagctcc    180
aatatgcaag ataccataga tcgttatctg aggcatacta aggatcgagt cagcaccaaa    240
ccggtttctg aagaaaatat gcagcatttg aaatatgaag cagcaaacat gatgaagaaa    300
attgaacaac tcgaagcttc taaacgtaaa ctcttgggag aaggcatagg aacatgctca    360
atcgaggagc tgcaacagat tgagcaacag cttgagaaaa gtgtcaaatg tattcgagca    420
agaaagactc aagtgtttaa ggaacaaatt gagcagctca agcaaaagga gaaagctcta    480
gctgcagaaa acgagaagct ctctgaaaag tggggatctc atgaaagcga gtttggtca    540 aataagaatc aagaaagtac tggaagaggt gatgaagaga gtagcccaag ttctgaagta    600
gagacgcaat tgttcattgg gttaccttgt tcttcaagaa agtag                    645
```

<210> SEQ ID NO 3
<211> LENGTH: 3021
<212> TYPE: DNA
<213> ORGANISM: Arabidopsis thaliana
<400> SEQUENCE: 3

```
atgggcgaac aacaaatctc agttacagtg cctcgtgata gaactgatga acaggcaatc     60
ttggctttga gaaaggtgc acagcttttg aaatgtcgaa gagagggaaa cccaaagttt    120 tgtccttta aactctcaat ggatgagaag tacttgattt ggtactcagg agaagggag     180 agacaattga gattgagttc tgttataacg attgttcgcg gacaaatcac accaaacttt    240
cagaaacaag cacaatctga tcgaaaggaa cagtctttt cactcattta tgcaaatgga    300
gaacacactc ttgatctcat atgtaaggat aaagcacaag cagactcatg gtttaaaggt    360
cttagagctg tgataacaaa gcatcataac attagaaact ctgtgaatca tcggagtagt    420
aggggagctc aaagttgcat caatagtcct gcgggtttta tgcgaaggaa acagaatctt    480
ggacttcttg aagagactcc tgacgtcact cagatacgta gcttatgtgg aagtccatcg    540
acgttacttg aagagcggtg tttgtcgaac gggttgtcat gttcttcaga tagttttgct    600
gaatctgatg ccttgggtcc agtttcttct tactatgaaa cagattatga tttcaggaac    660
tcggattgtg atcgtagtac aggttcagaa cttttgcaggt tttcatcaca agatttgct    720 gcttctcctc tctttctat cataacacag ccggttacaa gatccaatgt ccttaaggac    780
```

```
attatgatat ggggagctat aacgggtctt atcgatggat cgaagaatca gaacgatgcg      840
ttgtctccta agcttttgga atctgctacg atgtttgatg tacagagtat atctctaggt      900
gcaaaacatg ctgcgttggt tacaagacaa ggtgaagtgt tttgttgggg aatggaaat       960
agtgggaagc ttggacttaa agttaacatc gatatcgacc atccgaaacg cgttgagtct     1020
cttgaggatg ttgcagttcg atcagtggct tgtagtgatc atcaaacgtg tgctgttacg     1080
gaatctggtg agctgtattt atggggaatt gatggtggaa ccattgaaca gtcaggaagc     1140
cagttcttga ctcggaagat atccgatgtt cttggcggat cttgactgt tttaagtgtt      1200
gcttgtggcg cgtggcacac ggcaattgtg actagttctg gtcagctttt cacttatggt     1260
agtggaactt ttggagttct tggacatggg agtcttgaga gtgttacaaa gccgaaagaa     1320
gttgagtctt tgagacgcat gaaggtcata tctgtctctt gtggaccgtg gcacacggct     1380
gctatagtgg aaaccgcgaa cgaccggaaa ttctacaacg ccaagagttg tggaaagctg     1440
tttacttggg gagatggcga taaggacgg ttaggacatg ctgatagcaa agaaaagctt      1500
gtgccaactt gtgttactga actcattgat catgatttca taaaagtctc ttgtggatgg     1560
actttaactg ttgctttaag catttcagga acggtttata caatgggaag ctcgatccac     1620
ggacagttag gatgtccgcg ggcaaaggat aagtcggtaa atgttgtttt aggcaatcta     1680
acacgacaat tgtcaagga tattgcttca ggttcacatc atgtagctgt tctaacttca     1740
tttgaaaatg tttatacttg ggaaaaggc atgaatggac aacttggttt aggtgacgtt      1800
agagatagaa actctcctgt tcttgttgag cctttaggtg ataggttggt agaaagtata     1860
gcttgcgggt tgaatttgac ggctgcgatc tgtttacaca aagagatctc tttgaatgat     1920
caaaccgctt gtagttcttg caaatcagct tttggattca caaggagaaa gcataactgt     1980
tacaactgtg gtctattgtt ttgcaatgca tgtagtagca agaaagcggt aaatgcttcg     2040
ttagcaccga ataaaagcaa gctttctcgg gtttgcgatt cttgctttga tcatctatgg     2100
agtataacag agttttcaag aaatgttaag atggataatc acactccgag gatgcagatg     2160
gttacacgaa gagtatctga ggatttgaca gaaaaacaat cagagaatga gatgcagaat     2220
cttccacaag ctaatcgatc ttcggatgga cagcctcgat ggggacaagt ctctggtcct     2280
tctctgtttc gtttcgataa gatttcgaca agttcttctt tgaatctttc agtctcagca     2340
aggcgaacat cttcaacgaa gatttcaacc tcgtctgagt cgataagat cttaaccgaa      2400
gaaatcgaaa ggctaaaagc cgtgataaaa aatctccaga ggcagtgtga acttggcaat     2460
gagaagatgg aagaatgtca acaagagctc gacaagacat gggaagttgc taaagaagaa     2520
gcagagaaat cgaaagctgc taaagagata ataaaagcct tggcatcgaa gctccaagcg     2580
aataaagaga aaccgagtaa tcctctgaag accggcattg catgcaatcc ttctcaagtc     2640
tcaccaatct tgatgactc aatgtccatt ccatacctca caccaatcac cacagctcgt      2700
tcacaacacg aaaccaaaca acatgtgagag aaatgtgtca cgaaatcctc gaaccgtgac    2760
agcaacatta agctattagt agatgcatcg ccagccatca aagaacagg gtatctccaa      2820
aacgaaacac aagactcgtc agcagaacaa gttgagcaat acgagcccgg tgtatatata    2880
actttcacgg ccttgccttg cggtcagaag acgcttaaac gcgtacggtt tagtcggaag    2940
aggttttcag agaaggaagc acaaagatgg tgggaagaga agcaggtttt ggtctataac    3000
aagtatgatg ctgaaatata g                                              3021

<210> SEQ ID NO 4
<211> LENGTH: 2190
```

```
<212> TYPE: DNA
<213> ORGANISM: Arabidopsis thaliana

<400> SEQUENCE: 4
atgcgcatct tctctacatt cgtctttcat cgcagacaac aaatcttcaa tcttcgtcaa      60
ttccaaacca ccacaatcct tcgcaaccca atctccatcg ctccgatcca gattccgatg     120
gacgccaccg agcagtctct ccgtcaatct ctttccgaga atcctcatcc gtcgaagct      180 cagggtaacg ccgtccgagc tctcaaggct cccgtgcag ctaaaccaga atcgatgct      240 gccattgagc aactcaacaa attgaagctc gagaaatcta ccgtcgagaa ggagcttcag     300
tctattatca gtagctccgg taatggttcg cttaaccgtg aggcttttcg aaaagctgtt     360
gtcaatactc tcgagcggcg tttgttctat atcccttcgt ttaagatcta cagtggcgtc     420
gctggacttt ttgattatgg tcctcctggc tgtgctatta aatccaatgt tctcagcttt     480
tggcgtcaac atttcattct tgaggagaac atgctagaag ttgattgtcc atgtgtgaca     540
ccagaggttg ttctcaaggc atctgggcat gtagataagt tcactgatct tatggttaag     600
gatgagaaaa ctggaacatg ttaccgtgct gaccacttgc tcaaggatta ttgtaccgag     660
aagctggaga agatcttac catctctgct gagaaagctg ctgaattgaa ggatgttctt     720
gctgttatgg aagattttc tcctgaacag ctaggtgcca agatcaggga gtatgggatc     780
actgctccag acacgaagaa tccactctct gatccttacc cgtttaattt gatgtttcaa     840
acatccattg gcccatctgg tttgattcct ggttacatgc gtcctgaaac tgctcaaggt     900 attttttgtca actttaagga cttgtactat tacaatggga agaaacttcc ttttgccgcg     960
gctcaaattg gtcaagcctt tagaaatgag atatctcctc gacaagggct tcttagagtt    1020
cgtgaattca cgctggcaga gattgagcac ttcgttgatc ctgagaataa gtcacatcct    1080
aagttctctg acgtagcaaa attggaattc cttatgttcc aagggaaga acaaatgtct    1140 ggccaatctg ccaaaaaact ttgccttggt gaagctgttg ctaaaggtac tgtgaacaat    1200
gaaactctag gatacttcat tgggagagtg tatctttcc ttactcgtct tggcattgac    1260
aaggaacggc tgcgcttccg tcagcatcta gcaaatgaaa tggcccacta tgcagcagat    1320
tgttgggatg ctgaaattga aagttcatat gggtggattg aatgtgttgg gattgcagat    1380
aggtctgctt acgacttacg tgctcactct gacaaaagtg gtactcctct tgtggctgaa    1440
gagaaatttg cagaacctaa agaagtagag aaacttgtga taactcctgt gaagaaagaa    1500
ctgggtcttg cattcaaggg aaatcaaaag aatgtggttg aatctttgga ggcgatgaat    1560
gaggaagaag ctatggagat gaaagcaacc ctggaatcca aggggaagt ggagttttac    1620 gtgtgtaccc taaagaaaag cgtgaacatc aagaaaaaca tggtgtctat atcaaaggag    1680
aagaagaaag agcaccagcg ggttttcact ccatcagtgt tgaaccatc gtttgggatt    1740 ggtcggatca tatattgtct gtatgagcat tgtttcagca aaggccaag caaagcaggg    1800 gatgagcagt tgaacttgtt ccgtttccct cctcttgtag ctcccatcaa gtgcacggtt    1860
ttcccgcttg ttcagaacca acaattcgag gaagtagcca agttattc caaggaactc    1920 gcctctgtcg gtatctccca taagattgac atcactggta catcgatagg aagagatat    1980 gcgagaaccg atgagcttgg agtgccattt gcaataacag tggactcgga tacatcagtg    2040
acaatcagag aaagagacag caaagatcaa gtccgagtca ccttgaagga ggcagcttcc    2100
gttgtgagct cagtctcaga ggggaaaatg acgtggcaag acgtctgggc aaccttccct    2160
caccattctt ctgctgctgc agacgagtag                                     2190
```

<210> SEQ ID NO 5
<211> LENGTH: 1767
<212> TYPE: DNA
<213> ORGANISM: Arabidopsis thaliana

<400> SEQUENCE: 5

| | | | | | |
|---|---|---|---|---|---|
| atgtcttatg | atgagcacac | atcatcatca | ttcacataca | taagccaaat | gggtgtgtgg | 60 |
| tggatagtgc | tggtggtggc | tgtcttgact | cacacggcgt | ctgccgccgt | gagagaatat | 120 |
| cattgggagg | tggagtacaa | gtattggtcg | ccggactgca | agagggcgc | cgttatgacc | 180 |
| gtcaacggcg | agtttcctgg | tcccaccata | aaagccttcg | ccggagacac | catcgtcgtc | 240 |
| aatctcacca | acaaactcac | caccgaaggc | cttgtcatcc | attggcatgg | aatccgtcag | 300 |
| ttcggaagtc | catgggcaga | tggagcagca | ggagttactc | aatgcgcaat | taaccctgga | 360 |
| gagactttta | cctacaattt | cactgttgaa | agccgggaa | cacatttcta | ccatggacac | 420 |
| tatggcatgc | agagatcagc | tgggctatac | ggatcgttga | ttgtggacgt | ggctaaagga | 480 |
| aagagcgaga | gattgagata | cgatggtgag | tttaatctct | tactcagtga | ctggtggcat | 540 |
| gaggctattc | cctcccaaga | actcggtctt | tcttccaaac | ctatgcgctg | atcggtgaa | 600 |
| gctcagagca | tattgataaa | tgggagggga | caattcaatt | gttcattagc | ggcgcaattt | 660 |
| agcaacaaca | catcattacc | aatgtgcacg | tttaagaag | gtgatcagtg | cgccccacag | 720 |
| atactccacg | tggagccgaa | caagacttac | cgaatcagac | tctccagcac | caccgctctt | 780 |
| gcctccctca | acttggctgt | tcagggacac | aagctagtgg | tggtcgaagc | cgacggcaac | 840 |
| tacataacgc | cgttcacgac | cgacgatatc | gacatatact | ccggcgaaag | ctactccgtc | 900 |
| cttctcacca | ccgatcaaga | cccttcacaa | aactattaca | tctccgtcgg | cgtccgtggc | 960 |
| cggaaaccaa | acacaactca | ggcactcact | atattaaatt | acgtaactgc | ccctgcttca | 1020 |
| aaactcccctt | cttctcctcc | accggtgact | ccacggtggg | acgatttcga | acgaagcaaa | 1080 |
| aatttctcta | agaagatctt | ctcagcgatg | ggatcaccat | cgccgccgaa | gaaatacaga | 1140 |
| aaacggttga | ttcttctcaa | cacacagaat | ctaatcgacg | gatacacgaa | atgggcgatc | 1200 |
| aacaacgtct | ctctagtgac | tccggcaacg | ccgtatctcg | gttcggttaa | atacaacttg | 1260 |
| aaactcggat | ttaaccggaa | atcgccgccg | aggagttacc | gtatggatta | cgatattatg | 1320 |
| aatccaccgc | cgtttcctaa | caccactaca | ggaaacggaa | tatacgtttt | cccgtttaat | 1380 |
| gtaacggtcg | acgtgattat | ccaaaacgct | aacgttttaa | aaggtattgt | tagtgagatt | 1440 |
| catccatggc | atcttcacgg | tcacgatttc | tgggttttgg | gttacggtga | cgggaaattt | 1500 |
| aaaccgggaa | ttgatgagaa | gacgtataat | ttgaagaatc | cgccgttacg | gaatacggcg | 1560 |
| attttgtatc | cgtatggatg | gacggcgata | aggtttgtga | cggataatcc | aggggtttgg | 1620 |
| ttttttcatt | gtcacattga | accgcatttg | catatgggaa | tgggtgtggt | tttcgcggag | 1680 |
| ggattaaacc | gtattggtaa | ggtacctgat | gaggcgttgg | gttgtggttt | aaccaagcaa | 1740 |
| tttctcatga | accggaaccg | caattag | | | | 1767 |

<210> SEQ ID NO 6
<211> LENGTH: 1482
<212> TYPE: DNA
<213> ORGANISM: Arabidopsis thaliana

<400> SEQUENCE: 6

| | | | | | |
|---|---|---|---|---|---|
| atggttttgt | ctaagacagt | ttccgaatct | gatgtctcaa | tccattcaac | ttttgcttct | 60 |
| cgttacgtcc | gcaactctct | tccacgattc | gaaatgcctg | agaactcaat | cccaaaagaa | 120 |

```
gcagcttacc aaatcatcaa cgacgagcta atgctcgatg gtaacccaag gctgaaccta    180
gcttccttcg tgaccacatg gatggagcca gaatgtgaca agctcatgat ggagtccatc    240
aacaagaact acgtcgacat ggacgagtac cctgtcacca ctgagcttca gaaccgatgt    300
gttaacatga tagcacgtct cttcaacgcg ccgcttggtg acggtgaagc tgccgttggt    360
gttggcaccg tcggatcgtc ggaggcgatt atgttggccg gtttggcttt aagagacaa     420 tggcagaata agcgtaaggc ccaagggctt cctatgata  agcccaatat cgtaaccggt    480
gctaatgtcc aggtttgctg ggagaaattc gcaaggtatt tcgaagtgga gcttaaggaa    540
gtgaacctaa gaagacta  ttacgtgatg accctgtaa  aggcggtcga aatggtagac    600
gaaaacacaa tttgtgtcgc tgccatcctc ggttcaacgt taaccggtga attcgaagac    660
gttaagctcc tcaacgacct ccttgtcgag aaaaacaagc aaaccggatg ggacacgcca    720
atacacgtgg acgcagcgag tggtgggttt attgctccgt tcttgtatcc ggagctggag    780
tgggatttcc ggctaccgtt ggttaagagt attaatgtga gtggtcacaa atacggtttg    840
gtttacgccg gtattggttg ggttgtatgg agaaccaaaa ccgatttgcc tgatgaactt    900
atcttccata tcaattatct tggcgctgat caaccaacct ttacactcaa cttctccaaa    960
ggttcaagtc aagtgattgc tcagtactac cagctgattc gtcttggatt cgagggttat   1020
cgcaatgtga tggataattg tcgggaaaac atgatggtac taagacaagg attagagaaa   1080
acgggacgtt ttaaaatcgt ctccaaagaa aacggtgttc cgttagtggc gttttctctc   1140
aaagatagta gccgccacaa cgagttcgag gtggcccata cactccgtcg cttcggctgg   1200
atcgttccgg cctacacgat gcctgcggat gcgcagcatg tcactgtcct tcgagttgtt   1260
atccgagaag atttctctcg aaccttagcc gagagattgg tagctgattt cgagaaggtt   1320
ctacacgagc tcgatacgct tccggcgagg gttcacgcca agatggctaa tggaaaagtt   1380
aacggtgtta agaagacgcc agaggagacg cagagagaag tcacggccta ctggaagaag   1440
ttgttggaga ctaagaagac caacaagaac acaatttgct aa                      1482
```

<210> SEQ ID NO 7
<211> LENGTH: 849
<212> TYPE: DNA
<213> ORGANISM: Arabidopsis thaliana

<400> SEQUENCE: 7

```
atgggtacta gagctcagca gattccttta cttgaaggtg agactgataa ttacgatggt     60
gttactgtaa ccatggtgga acctatggat tctgaggttt ttactgaaag tcttagggct    120
tctctttcgc attggagaga agaggggaag aagggaattt ggataaagct gcctcttgga    180
ttggctaatc ttgtggaggc tgcagttagt gaaggattta gatatcacca cgcggagcct    240
gagtacttga tgcttgtatc ttggatctct gaaactcctg atacaatccc agccaatgct    300
tctcatgttg taggtgctgg tgctttggtc atcaacaaaa atactaaaga ggtcctcgtt    360
gtccaggaga ggagtgggtt tttcaaagat aaaaatgtgt ggaagctgcc tactggtgtt    420
atcaacgagg gcgaggatat atggactgga gtagctaggg aagtggaaga agaaactgga    480
attattgcag attttgtcga agtactggct ttcaggcaaa gccacaaagc catcttaaaa    540
aagaaaacag atatgttttt cctgtgtgtc ttaagtccgc gctcttacga tattactgaa    600
caaaaatctg agatcttgca agctaagtgg atgccgatcc aagagtatgt agaccaacca    660
tggaacaaga agaacgagat gttcaagttc atggctaaca tttgccaaaa gaagtgtgag    720
```

```
gaagaatact tgggattcgc cattgtgcca actaccacat catctggtaa agagagcttt      780
atctactgca atgcggatca tgccaagcgc cttaaagtat cgcgtgacca agcctctgct      840
tctctctga                                                              849

<210> SEQ ID NO 8
<211> LENGTH: 1383
<212> TYPE: DNA
<213> ORGANISM: Arabidopsis thaliana

<400> SEQUENCE: 8
atgacagttg ttggagatgt tgctccaatt ccaaggagga acagttctac ttgctctaat       60
gatatcgctg ctccgttatt accagagtgt catggagatg aagttgctca tgatgaattc      120
aatggagctt cttttagtgg cgcggttttt aacctcgcca cgactataat tggtgctggt      180
atcatggctt tgcctgctac aatgaagatt cttggacttg acttggaat cacgatgatt       240 gttgttatgg ctttcttgac tgatgcgtcg attgagttct tgcttaggtt tagtaaagct      300
gggaagaatc gatcttacgg tggtttaatg ggtggttctt ttggtaatcc tggaaggatt      360
ttgcttcaag tcgcggtttt agttaataac atcggtgttt tgattgtata catgatcatt      420
ataggtgatg tgttggctgg aaagacggaa gatggtatcc atcatttcgg tgttctcgaa      480
ggatggtttg gtcaccattg gtggaatgga agagctgcta ttcttctgat tactactctt      540
ggtgtgtttg ctccattggc ttgcttcaag cgaatcgatt ctttgaaatt tacatcggcc      600
ttatccgtgg ctctggcggt tgtgtttctc attattactg cgggaatttc aattatgaag      660
ttgatcagtg gcggtgtggc gatgccaaga ttgttaccag atgttactga cttaacatct      720
ttctggaatc tcttcacagt cgtacctgtt cttgtcacag cattcatttg ccattacaat      780
gttcacagta tacagaacga gctcgaagac ccctctcaga taagacctgt tgttcgatca      840
gcacttatgc tctgctcatc tgtttacata atgacaagta ttttcgggtt cctcttgttt      900
ggtgatgata ctcttgatga tgtccttgca aactttgaca ctgatcttgg aatccctttt      960
ggttctatcc ttaatgatgc ggttcgagtt agctacgcgc ttcatttgat gctcgtgttc     1020
ccgattgttt tctaccctct tcggattaac attgacgggc tcttgttccc ttccgctcga     1080
tcattatcta cctcaaatgt gaggttcggt tgcctcactg ccggtctcat ctctgtaatc     1140
ttcttgggtg caaacttcat cccaagcatt tgggatgctt tccaattcac tggagcaacc     1200
gccgctgttt gtctcggctt catcttccca gcttctatca tactaaagga tcgtcatgac     1260
aaagcaacaa acagggacac aaccttagct attttcatga ttgttcttgc ggtattgtcc     1320
aatgcaatcg ccatttacag cgatgcttat gcgctattca agaagaacgc tcctcgtgag     1380
taa                                                                   1383

<210> SEQ ID NO 9
<211> LENGTH: 402
<212> TYPE: DNA
<213> ORGANISM: Artificial Sequence
<220> FEATURE:
<223> OTHER INFORMATION: Arabidopsis thaliana putative AP2/EREBP
      transcription factor; with A33V mutation

<400> SEQUENCE: 9
atggatcaag gaggtcgtag cagtggtagt ggaggaggag gagccgagca agggaagtac       60
cgtggagtaa ggagacgacc ttggggtaaa tacgccgtgg aaataagaga ttcgaggaag      120
cacggagagc gtgtgtggct agggacattc gacactgcgg aagacgcggc tcgagcctat      180
```

| | |
|---|---|
| gaccgagccg cctattcaat gagaggcaaa gctgccattc tcaacttccc tcacgagtat | 240 |
| aacatgggaa ccggatcctc atccactgcg gctaattctt cttcctcgtc gcagcaagtt | 300 |
| tttgagtttg agtacttgga cgatagcgtt ttggatgaac ttcttgaata tggagagaac | 360 |
| tataacaaga ctcataatat caacatgggc aagaggcaat aa | 402 |

<210> SEQ ID NO 10
<211> LENGTH: 1074
<212> TYPE: DNA
<213> ORGANISM: Arabidopsis thaliana

<400> SEQUENCE: 10

| | |
|---|---|
| atggtaatat atcatcgcaa agtagtcttt acgtacgtaa gagcaaagcg tttctatcat | 60 |
| ttccttaata ttgaaatggt gacagacttc aaatccctac taccagttat cgacatcagt | 120 |
| cctttactgg ccaaatgtga tgatttcgac atggctgagg atgcgggggt tgtggaagta | 180 |
| gtcggaaaac tggacagggc atgtcggacg tcggattct tctacgtgat tggtcatgga | 240 |
| atatcggatg atcttataaa taaggtgaaa gagatgacgc atcagttctt cgagcttcct | 300 |
| tacgaggaga aacttaagat caagattact ccaactgctg atacagagg ataccaaaga | 360 |
| attggagtaa attttacgag tgggaaacaa gatatgcacg aagccattga ttgttacaga | 420 |
| gagttcaagc aagggaaaca tggggacatc ggaaaggtct ggaagggcc aaaccagtgg | 480 |
| ccaggaaatc ctcaagagta caagatttta tggagaagt atattaagct gtgcacagat | 540 |
| cttttctagaa atatcttaag gggaatctca ttagcccttg gtggatcacc ttatgagttt | 600 |
| gagggaaaga tgcttagaga ccctttttgg gtaatgcgta tcattggtta ccaggtgta | 660 |
| aaccaagaaa atgttattgg atgtggagct cacactgact atggcttgtt gacgcttata | 720 |
| aatcaagatg atgataaaac tgctcttcag gtgaaaaacg tggacggtga ttggatacca | 780 |
| gctattccga tccctggatc atttatctgc aacatcggtg acatgttaac gatactatca | 840 |
| aacgagtttt accaatccac actacataaa gtaatcaata actctcctaa ataccgtgta | 900 |
| tgtgttgcat ttttctacga gactaacttc gaggcggagg tagagccact tgatatcttt | 960 |
| aaagagaagc atccacgaaa agaaacatct caagttgcca aaagagtcgt ctatggacag | 1020 |
| catctgatta caaagtcct gacaaccttt gcaaatttag tggaaaacag ttaa | 1074 |

<210> SEQ ID NO 11
<211> LENGTH: 1116
<212> TYPE: DNA
<213> ORGANISM: Arabidopsis thaliana

<400> SEQUENCE: 11

| | |
|---|---|
| atgcctgtac ttttctcctc tcgttctctc tatactctcca ttattgtccc cttacttata | 60 |
| tctatcgctc tctacaaact cgacacattc gaccccgcta ttgttccttc cgatgcattc | 120 |
| acatcctctg ctacttcact cccgccgctt ataaacgacg aatttctcac cggagctgag | 180 |
| tttatcggtg tcggtcttct caatataccc gaagatatcg cctaccataa ggaatctaat | 240 |
| ctcatctaca ctggttgtgt tgatggatgg gtgaaacgag tcaaggtcgc cgactcggtt | 300 |
| aatgactcag tcgttgagga ttgggtcaat actggtggta gaccgctcgg aatcgcgttc | 360 |
| ggaatccacg gcgaagtcat tgtcgcagac gtacacaagg gactgttgaa tataagcggt | 420 |
| gacggaaaga agacggaatt gttgacggac gaagcggacg gtgtgaagtt taagctgacg | 480 |
| gatgcagtta ccgttgcaga taacggcgtt ttgtatttca cagatgcttc ttacaagtac | 540 |
| actctcaatc aattgagttt agacatgtta gaagggaaac cttttggacg actcttgagc | 600 |

```
tttgatccca ccacacgtgt tacaaaagta cttctcaaag acctctactt cgctaatggc       660
atcaccatct ctcctgatca aactcatctc atcttctgtg aaactccaat gaaaaggtgc       720
agcaagtatt acatcagtga ggagcgtgtg gaggtattca ctcaaagctt accaggttat       780
ccagataaca ttcgttacga tggagatgga cattactgga ttgcattgcc ttcgggagtc       840
acgacattgt ggaatatctc gttgaaatac ccttctgtga ggaaactcac agcaatggtg       900
gctaagtacg gcgtggatct tatgtttatg agaatgcag gcgttttaca ggtggatttg         960
gatggaaatc ccatcgcgta ctaccatgat ccaaaactct ctcacatagc cacatgtgac      1020
aagattggga atatctcta ttgtggaagt ctctcgcaat cacatatcct ccgacttgat      1080
ctcctgaaat atcctgcaca gaacaagaaa ctttga                               1116

<210> SEQ ID NO 12
<211> LENGTH: 1407
<212> TYPE: DNA
<213> ORGANISM: Arabidopsis thaliana

<400> SEQUENCE: 12
atgggtcgtg tccgaaaatc agatttcggt tccattgttc ttgttctgtg ttgtgtccta        60
aatagcttac tctgtaatgg aggcatcacc agtagatatg tcagaaaatt agaagcaacc      120
gttgatatgc tcttgatag cgatgttttt cgtgttcctt gtggctacaa tgctcctcaa        180
caggtgcata taacacaagg agatgtagaa ggaaaggcag tgatagtatc atgggtgaca       240
caagaagcaa aaggatctaa caaagtcatt tactggaaag agaatagcac caaaaagcac       300
aaagctcatg gcaaaaccaa tacttacaag ttctacaatt atacttctgg ttttatccat      360
cattgcccta tcagaaactt agagtatgac accaagtact attatgtgtt aggtgtggga      420
caaacggagc gtaagttttg gttcttcact cctcctgaga tcggtcctga tgttccctac      480
acttttggtc tcattgggga tcttgggcag agttatgact caaacataac cttaacacat      540
tatgagaata acccaacaaa agggcaagcg gttttgttcg tcggcgatat ctcatacgct      600
gatacttatc cggatcatga caataggaga tgggacagtt ggggaagatt tgctgaaaga      660
agcacagctt atcagccttg gatttggact accggaaacc atgaactcga ttttgccccg      720
gagattggtg aaaacagacc gtttaagccg ttcacgcata ggtaccgaac tccttaccga      780
tcatcaggca gcaccgaacc attctggtac tcgataaaga gaggaccggc ttacataatc      840
gtgctagctt catattcagc atatggaaaa tacacaccac agtaccaatg gctcgaagag      900
gagttcccaa aggttaacag aacgaaaact ccgtggttga ttgttctgat gcattccacca     960 tggtacaaca gctatgatta ccattacatg gaaggtgaaa caatgagggt aatgtatgag     1020
gcttggtttg tcaagtacaa agtagatgta gttttttgcag gtcatgtcca cgcctacgaa     1080
agatcggaac gtgtatcaaa catagcttac aatgttgtta acggcatttg cactccagtc     1140
aaagatcaat cagctccagt ctatatcacc attggtgatg gaggcaatat tgagggcttg     1200
gctaccaaaa tgactgagcc tcagcctaag tactctgcct ttagagaagc aagcttcggg     1260
catgctatat tctcgataaa gaacaggacg catgctcact atggatggca taggaaccat     1320
gatggttatg ctgtggaggg tgacagaatg tggttttata acagattttg gcatcctgtt     1380
gatgattctc cttcttgtaa ttcttga                                        1407

<210> SEQ ID NO 13
<211> LENGTH: 1500
<212> TYPE: DNA
```

<213> ORGANISM: Arabidopsis thaliana

<400> SEQUENCE: 13

| | | | | | |
|---|---|---|---|---|---|
| atgttattga | aacccggaaa | taagcttgtc | tcgccggaga | cgagtcatca | tcgtgactct | 60 |
| gcctcaaact | catcaaacca | taaatgtcaa | caacaaaaac | cgcgtaaaga | taagcagaag | 120 |
| caagttgagc | aaaacacaaa | gaagattgaa | gaacatcaaa | taaaatcaga | gtcgactctg | 180 |
| ttaatcagca | atcacaacgt | taacatgagc | tcccaaagca | acaacagcga | agcacatcc | 240 |
| actaataatt | cctctaagcc | tcacacggga | ggagatatta | ggtgggacgc | agtgaattcc | 300 |
| ttgaaatcta | gaggaatcaa | gcttggaatc | agcgattttc | gtgttttgaa | acggctaggc | 360 |
| tacggagata | tcggtagtgt | ttatcttgtt | gaactcaaag | gggcaaatcc | cacgacgtat | 420 |
| ttcgcgatga | agtgatgga | caaggcttct | cttgtgagca | ggaacaagct | gttgagagct | 480 |
| cagactgaaa | gagagatctt | gtctcagctt | gatcatcctt | tcttgcctac | tctttactct | 540 |
| cacttcgaaa | ctgataaatt | ctattgcttg | gtgatggagt | tttgtagtgg | tggaaatctc | 600 |
| tattccttga | acagaagca | acccaacaag | tgtttcacag | aagacgctgc | aaggttcttt | 660 |
| gcatcagaag | tgttattagc | attagagtac | ttacatatgc | tcggaatcgt | ataccgagat | 720 |
| ttaaagccag | agaacgttct | ggttcgagac | gacggtcaca | ttatgctctc | cgatttcgat | 780 |
| ttatccctcc | gatgttcagt | caacccaaca | cttgtcaaat | ctttcaacgg | cggtggaacc | 840 |
| accggaatca | ttgacgacaa | tgcgcggta | caaggatgtt | accaaccatc | cgcattcttc | 900 |
| ccacgaatgc | tccaatcctc | gaagaaaaac | cgtaaatcca | atccgatttt | cgatggatcg | 960 |
| ttaccagaac | tcatggcaga | gccgacaaac | gtgaaatcaa | tgtcttttgt | cggaacacac | 1020 |
| gagtatttag | cgccggagat | tatcaaaaac | gaaggtcacg | gaagcgccgt | cgattggtgg | 1080 |
| acgttcggga | tattcatcta | cgagcttctt | catggagcaa | caccatttaa | aggacaagga | 1140 |
| aacaaagcca | cgctttataa | tgtaatcgga | caacctctta | gattcccgga | atattctcag | 1200 |
| gttagctcga | cggcgaagga | tttgatcaaa | ggtttattgg | taaagagcc | gcaaaacaga | 1260 |
| attgcgtata | agcgaggcgc | gacggagatc | aagcaacatc | cattttttga | aggtgtgaat | 1320 |
| tgggcgttga | ttcgtggaga | aacaccgcca | catttgccgg | agccggtgga | tttctcgtgt | 1380 |
| tatgtgaaga | aggagaagga | gtcttttgccg | ccggcggcaa | cggaaaagaa | gagcaagatg | 1440 |
| tttgatgaag | ctaataagag | cggtagtgat | cctgattaca | ttgtttttga | atattttag | 1500 |

<210> SEQ ID NO 14
<211> LENGTH: 4659
<212> TYPE: DNA
<213> ORGANISM: Chlamydomonas reinhardtii

<400> SEQUENCE: 14

| | | | | | |
|---|---|---|---|---|---|
| atggaggcgg | tcgcgaccgt | tgtggccaac | gagcccaagg | ttgctgatat | ggaggagatt | 60 |
| ctcgccgagc | gcgatgcctg | cggcgtgggc | ttcatcgcga | acctgaagaa | cgttcagagc | 120 |
| cacaccgtcg | tgaagcaggc | tctgaccgct | ctgggctgca | tggagcaccg | cggtgcttgc | 180 |
| tctgcggacg | atgactcggg | agatggtgcg | ggtcttatga | ctcaaatccc | ctggaagctg | 240 |
| ctgaagaagg | agatgcccgc | gctgaacgag | acgaccacgg | tgtcggcat | ggtgttcatg | 300 |
| cccaatgatg | acgctctaga | ggcgcagtgc | aagcagatcc | tggagcaggt | ctgcgccaag | 360 |
| gagggcgtga | aggtggtggg | ctggcgcaag | gtgcccgtca | accacgacat | cgtgggccgc | 420 |
| ttcgccaaag | tgacggagcc | gcgcatctgg | caggtcctga | ttgagggcaa | gtccggtcag | 480 |
| gtcggcgacg | agctggagcg | tgagctgttc | ctggtgcgca | agctggtgga | gaaggctaag | 540 |

```
aacgccgcgc tgcccgctga gttcgctccc gacttctaca tttgcacgct gtccagccgc    600
accattgtgt acaagggcat gctgcgctcg gcggtcgtgg gcaccttctt ccgcgacctg    660
gaaaaccccg acttcgagtc ggcgttcgcc atctaccacc gccgcttctc caccaacacc    720
accccccaagt ggccactggc gcagcccatg cgcgtgctgg gccacaacgg cgagatcaac   780
accctgcagg gcaacctgaa ctgggttgcc tcgcgcgagc acgagctgag caaccccatc    840
tggaagggcc gcgaggcgga gctgacgccg ctgtgcaacg ccgcgcagtc ggacagcgcc    900
aacctggaca acgtggcgga gctgctggtg cgcaccggca ccgacccgca ggacgcgctc    960
atgctgctgg tgccggaggc ctaccgcaac caccccgacc tcatgaagga gtaccccgag   1020
gtggtggact tctacgagtt ctacgagggc ctgcaggagg gctgggacgg ccccgcgctg   1080
ctggtgttct ccgacggcaa gcgcgtgggc gcccgcctgg accgcaacgg cctgcgcccc   1140
gcgcgcttct ggcagaccaa ggacgacatg atttacgtgg cctccgaggt gggcgtgctg   1200
ggtgacgcca tcaccaacgc cgagaacatc gtggccaagg ccgcctgggc ccccggccag   1260
atggtgtgcg ccgatctgga agggcatt ttctcggaga cgtcggccat cagcaagctg    1320
gtggctggcc gcaagcccta caaggagtgg ctggccgcct cgctgcgccg cctgacggac   1380
ctgggcgaga gcaccttcct gaacgagccc atgtacgacg ccgctaccat gctgcgcctg   1440
cagtccgcca tcggcatgga cgccgagaac gcgcagatgg tggtggagag ccaggcgcag   1500
accggcgtgg agcccaccta ctgcatgggt gacgacatcc cgctggccgt gctgtcggac   1560
aagccgcaca tgctgtacga ctacttcaag cagcgcttcg cgcaggtgac caacccgccc   1620
atcgacccgc tgcgtgaggg cctggtcatg agcctggaga tgcgcctggg cgcgcgcggc   1680
aacctgctga cccccggcgc cgacagctac aagcaggtgc tactggactc gcccatcctg   1740
ctggagagcg agatgcaggc catctccacc gacaaggtgc tgggctccaa gaccttcaag   1800
ctgttcttcg aggccggcaa gcccggcgcc atggaggcgg cgctgaagaa gctgtgctcg   1860
gacgtggagg ccgccgtcaa ggccggctgc cagtgcgtgg tgctgtcgga ccgccccgac   1920
ggcggtatgg acgccggtaa ggcgcccatc cccgcgctgc tggccaccgg cgccgtgcac   1980
caccacctga tccgcacctc gctgcgcagc gacacctcga tcgtggtgga caccgccacc   2040
tgctacagca cccaccacgc cgccatgctg atcggcttcg gcgcgcacgc catctgcccc   2100
tacctgggct acgagaccag ccgccagtgg cgcctgtcgg cgcgcacgca gagcctgatc   2160
aaggccggca aggtgccgga catcagcgtc aaggtggcgc agaagaactt caagaagtcg   2220
ctggagaagg gcgtgctcaa gatcctgtcc aagatgggca tctcgctgct gtcgtgctac   2280
cacggcgcgc agatcttcga ggcgtacggc ctgggcaagg acgtgatgga catgtgcttc   2340
aagggcaccg tgtcgcgcat tggcggcatg agcctggcgg acctgcagcg cgagtccgag   2400
agcctgtggg ccaagggctt ccccgagaag gccatgacca agctggagga ctacggcttc   2460
atccagtcca agcccaaggg tgagttccac tccaacaacc agaccatggc caagctgctg   2520
cacaaggcca tcggcctggg caacggctcc gctgccgaca aggacgccta caaggcctac   2580
cagcagcact cgcgggactc gcccgtggcc gtcctgcgcg actgcctgga gttcaagtcg   2640
gaccgcggcc ccatctccat tgaccaggtg agcccgccg ccgccatcat ggagcgcttc    2700
tgcaccggtg gcatgtcgct gggcgccatc tcgcgcgaga cgcacgagac catcgccatc   2760
gccatgaacc gcatcggcgg caagtccaac tcgggcgagg cggcgagga cccgatccgc   2820
tggctgcacc tgtcggacgt ggacggcgag ggcaagtccg ccaccgcctc ctacctgcgc   2880
```

```
ggcctgcgca acggcgacac cgccacctcc aagatcaagc aggtggcgtc gggccgcttc    2940
ggcgtcacgc ccgagtacat catgaacgcg gagcagatgg agattaagat tgcgcagggc    3000
gccaagcccg gtgagggcgg ccagctgccc ggccagaagg tgtcgcccta catcgcgcag    3060
ctgcgccgct ccaagcccgg cgtgccgctc atctcgcccc ctccccacca cgacatctac    3120
tccattgagg acctggcgca gctcatctac gacctgcacc aggtcaaccc ccgcgccaag    3180
gtgtcggtca agctggtggc cgaggccggc atcggcgtcg tcgccagcgg cgtgccaag    3240 gccaacgccg acatcatcca ggtgtctggc cacgacggcg gcaccggcgc ctcgcccatc    3300
tcgtccatca agcacgcggg cggccccatg gagatgggcc tggcggagac gcaccagacg    3360
ctggtgcgca acgagctgcg cgagcgcgtg gtgctgcgcg tggacggcgg cgtgcgcaac    3420
ggccgcgacg tgctgatggg cgcgctgatg ggcgccgacg agttcggctt cggcaccgtg    3480
gccatgattg ccaccggctg catcatggcg cgcgtgtgcc acaccaacaa ctgccccgtg    3540
ggcgtggcgt cgcagcgcga ggagctgcgc gcgcgcttcc ctggcgcccc cgaggacctg    3600
gtcaactact tccacttcgt tgccgaggag gtccgtgccg agctggccaa catgggctac    3660
cgcagcctgg atgaggtcat tggccgcgcc gacctgctga agcagcgctc cgtcaagctg    3720
gccaagaccg agggcctgga cctgtccttc ctcaccacct tcgccggcgc cagcggcaag    3780
tcctcgaccc ccgcgcgca ggaggtgcac gacaacggcc cgcagctgga cgaccgcatc    3840
ctggcggaac ccgaggtgat ggccgccatc aaggaccaca agaccgtgtc caaggccttc    3900
gagatcgtca acgtggaccg ctcctcgcta ggccgcgttg ccggtgtcat cgccaagcac    3960
cacggcgaca gcggcttcca gggcaaggtc aagctgacgc tgaccggctc gggcggccag    4020
tcgttcggct gcttctgcgt caagggcctg gaggtgaagc tggtgggtga ggccaacgac    4080
tacgtgggca agggcatgaa cggcggcgag atcgccatcg tgccgcccgc caactcgccc    4140
ttcaagcccg aggaggcctc gctggtcggc aacacttgcc tgtacggcgc caccggcggc    4200
cggctgttcg tgaacggccg cgccggcgag cgcttcgcgg tgcgcaactc gctagcggag    4260
gcggtggtgg agggcgcggg cgaccactgc tgcgagtaca tgactggcgg ctgcgtgatc    4320
gtgctgggct cggtgggccg caacgtggcg gcgggcatga cgggcggcct gggctacttc    4380
ctggatgagg acggctcgtt cacggacaag gtcaacacgg agatcgttag cgtgcagcgc    4440
gtgatcacca aggccggaga ggcgcagctg cggggggctgc tggaggcgca cgtgcgcac    4500 actggcagcg ccaaggccaa gagcctgctg gccaactggg aggcgtcgct gggcaagttc    4560
tggcagctgg tgccgcccgc ggagaagaac accgccgagg tcaacccctc ggtggcgcag    4620
ccggcggcgg ctggcgccaa ggtggctgtc agcgcatga                           4659
```

<210> SEQ ID NO 15
<211> LENGTH: 1350
<212> TYPE: DNA
<213> ORGANISM: Artificial Sequence
<220> FEATURE:
<223> OTHER INFORMATION: Chlorella sorokiniana NADP-specific glutamate
      dehydrogenase (NADP-GDH), N terminus residues 1 to 74 truncated

<400> SEQUENCE: 15

```
atgcacggca tcaagaaccc cgagctgcgc cagctgctga ccgagatctt catgaaggac     60
ccggagcagc aggagttcat gcaggcggtg cgcgaggtgg ccgtctccct gcagcccgtg    120
ttcgagaagc gccccgagct gctgcccatc ttcaagcaga tcgttgagcc tgagcgcgtg    180
atcaccttcc gcgtgtcctg gctggacgac gccggcaacc tgcaggtcaa ccgcggcttc    240
```

```
cgcgtgcagt actcgtccgc catcggcccc tacaagggcg gcctgcgctt ccacccctcc      300
gtgaacctgt ccatcatgaa gttccttgcc tttgagcaga tcttcaagaa cagcctgacc      360
accctgccca tgggcggcgg caagggcggc tccgacttcg accccaaggg caagagcgac      420
gcggaggtga tgcgcttctg ccagtccttc atgaccgagc tgcagcgcca catcagctac      480
gtgcaggacg tgcccgccgg cgacatcggc gtgggcgcgc gcgagattgg ctacttttc       540 ggccagtaca agcgcatcac caagaactac accggcgtgc tgaccggcaa gggccaggag      600
tatggcggct ccgagatccg ccccgaggcc accggctacg cgccgtgct gtttgtggag       660 aacgtgctga aggacaaggg cgagagcctc aagggcaagc gctgcctggt gtctggcgcg      720
ggcaacgtgg cccagtactg cgcggagctg ctgctggaga agggcgccat cgtgctgtcg      780
ctgtccgact cccagggcta cgtgtacgag cccaacggct tcacgcgcga gcagctgcag      840
gcggtgcagg acatgaagaa gaagaacaac agcgcccgca tctccgagta caagagcgac      900
accgccgtgt atgtgggcga ccgccgcaag ccttgggagc tggactgcca ggtggacatc      960
gccttcccct gcgccaccca gaacgagatc gatgagcacg acgccgagct gctgatcaag     1020
cacggctgcc agtacgtggt ggagggcgcc aacatgccct ccaccaacga ggccatccac     1080
aagtacaaca aggccggcat catctactgc cccggcaagg cggccaacgc cggcggcgtg     1140
gcggtcagcg gcctggagat gacccagaac cgcatgagcc tgaactggac tcgcgaggag     1200
gttcgcgaca agctggagcg catcatgaag gacatctacg actccgccat gggcgcgtcc     1260
cgcgagtaca atgttgacct ggctgcgggc gccaacatcg cgggcttcac caaggtggct     1320
gatgccgtca aggcccaggg cgctgtttag                                       1350

<210> SEQ ID NO 16
<211> LENGTH: 1344
<212> TYPE: DNA
<213> ORGANISM: Escherichia coli

<400> SEQUENCE: 16
atggatcaga catattctct ggagtcattc ctcaaccatg tccaaaagcg cgacccgaat       60
caaaccgagt tcgcgcaagc cgttcgtgaa gtaatgacca cactctggcc ttttcttgaa      120
caaaatccaa aatatcgcca gatgtcatta ctggagcgtc tggttgaacc ggagcgcgtg      180
atccagtttc gcgtggtatg ggttgatgat cgcaaccaga tacaggtcaa ccgtgcatgg      240
cgtgtgcagt tcagctctgc catcggcccg tacaaggcg gtatgcgctt ccatccgtca       300
gttaaccttt ccattctcaa attcctcggc tttgaacaaa ccttcaaaaa tgccctgact      360
actctgccga tgggcggtgg taaaggcggc agcgatttcg atccgaaagg aaaaagcgaa      420
ggtgaagtga tgcgttttg ccaggcgctg atgactgaac tgtatcgcca cctgggcgcg       480
gataccgacg ttccggcagg tgatatcggg gttggtggtc gtgaagtcgg ctttatggcg      540
gggatgatga aaagctctc caacaatacc gcctgcgtct tcaccggtaa gggccttca        600 tttggcggca gtcttattcg cccggaagct accggctacg gtctggttta tttcacagaa      660
gcaatgctaa aacgccacgg tatgggtttt gaagggatgc gcgtttccgt ttctggctcc      720
ggcaacgtcg cccagtacgc tatcgaaaaa gcgatggaat ttggtgctcg tgtgatcact      780
gcgtcagact ccagcggcac tgtagttgat gaaagcggat tcacgaaaga gaaactggca      840
cgtcttatcg aaatcaaagc cagccgcgat ggtcgagtgg cagattcgc caaagaattt       900 ggtctggtct atcgaagg ccaacagccg tggtctctac cggttgatat cgccctgcct        960
tgcgccaccc agaatgaact ggatgttgac gccgcgcatc agcttatcgc taatggcgtt     1020
```

```
aaagccgtcg ccgaaggggc aaatatgccg accaccatcg aagcgactga actgttccag    1080
caggcaggcg tactatttgc accgggtaaa gcggctaatg ctggtggcgt cgctacatcg    1140
ggcctggaaa tggcacaaaa cgctgcgcgc ctgggctgga aagccgagaa agttgacgca    1200
cgtttgcatc acatcatgct ggatatccac catgcctgtg ttgagcatgg tggtgaaggt    1260
gagcaaacca actacgtgca gggcgcgaac attgccggtt ttgtgaaggt tgccgatgcg    1320
atgctggcgc agggtgtgat ttaa                                           1344
```

<210> SEQ ID NO 17
<211> LENGTH: 861
<212> TYPE: DNA
<213> ORGANISM: Artificial Sequence
<220> FEATURE:
<223> OTHER INFORMATION: Homeobox fusion protein, Arabidopsis HB-17 N
      terminus residues 1 to 91 fused to soybean HB-17 C terminus
      residues 20-213

<400> SEQUENCE: 17

```
atgataaaac tactatttac gtacatatgc acatacacat ataaactata tgctctatat     60
catatggatt acgcatgcgt gtgtatgtat aaatataaag gcatcgtcac gcttcaagtt    120
tgtctctttt atattaaact gagagttttc ctctcaaact ttaccttttc ttcttcgatc    180
ctagctctta agaaccctaa taattcattg atcaaaataa tggcgatttt gccgaaaaac    240
tcttcaaact tggatcttac tatctccgtt ccaggttttg cttcttcacc aacccttctt    300
ccctcatcat ctgtgaaaga attggacata aatcaagtac ctcttgaaga agattggatg    360
gcatcaaaca tggaagatga agaagaaagc agcaatggag aacctcctcg aaagaaactc    420
cgtctcacaa aggaacaatc tcttctcctt gaagaaagct ttagacaaaa ccacacgttg    480
aacccaaagc agaaagagtc tttggcaatg caactgaagc tgcgaccaag gcaagtggag    540
gtgtggtttc agaaccgtag ggccaggagc aagctgaagc agacagagat ggagtgcgag    600
tacctcaaga ggtggttcgg ttccctcaca gagcagaacc ggaggctcca gagggaagtg    660
gaggagctgc gagccattaa ggtgggccca cccaccgtga tctcccctca ctcctgcgaa    720
ccgctcccgg cctccacact ttccatgtgt ccccgctgcg agcgtgtcac ctccaccgcc    780
gacaaaccgc cctccgccgc ggccactttg tccgctaaag tgccgccaac tcaatcccgc    840
caaccctccg cggcctgtta g                                              861
```

<210> SEQ ID NO 18
<211> LENGTH: 1038
<212> TYPE: DNA
<213> ORGANISM: Glycine max

<400> SEQUENCE: 18

```
atgtgtggag gagctatcat ctctgatttc attccggcgg cggcgatcgc cgggtctcgc     60
cgcctgaccg ccgattacct gtggccggat ttgaagaagc ggaagtctga cttggacgtt    120
gacttcgagg ctgatttcag ggattttaaa gacgattctg atatcgacga cgacgacgac    180
gatcaccaag tcaagccctt tgctttcgcc gcctcttctc gtctgtctac ggcagcgaaa    240
tctgtggcat tccaaggtcg ggctgagata tctgcaaata gaaagaggaa gaatcagtat    300
aggggaatcc gtcaacgccc ttggggaaaa tgggcagctg agattcggga tccaagaaag    360 gggggttcgtg tctggcttgg aaccttcaac actgctgaag aagctgcaag agcttatgat    420
gctgaagcac ggaggattcg tggcaagaaa gccaaggtga attttcctga ggcaccaggt    480
```

```
acttcttctg taaaacgttc caaggtaaat ccacaggaaa atcttaagac tgttcagccc      540
aatctgggtc acaagttcag tgctggcaac aatcacatgg atctggtgga acagaaaccc      600
ctagttagcc agtatgctaa catggcttcc ttccctggca gtggaaatgg gctaagatcc      660
cttccttcgt ctgatgatgc aacccttac ttcagttcag atcaagggag taattcattt       720
gattatgctc ctgagatctc atccatgctt tctgctcctt tggattgtga atctcatttt      780
gtgcaaaatg ccaaccagca gcagcctaac tctcagaatg tggtatctat tgaagatgat      840
tctgcaaaga cactctctga ggagcttgtg gatattgaat ctgagttgaa gttctttcag      900
atgccttatc ttgaagggag ctggggcgat acttcattgg aatccttgct atctggtgac      960
acaactcagg atggtggaaa cctcatgaac ctttggtgct tgatgacat tccttccatg      1020 gctggtggag ttttctga                                                    1038

<210> SEQ ID NO 19
<211> LENGTH: 774
<212> TYPE: DNA
<213> ORGANISM: Oryza sativa

<400> SEQUENCE: 19
atgtcgatgg gaccagcagc cggagaagga tgtggcctgt gcggcgccga cggtggcggc       60
tgttgctccc gccatcgcca cgatgatgat ggattcccct cgtcttccc gccgagtgcg       120 tgccagggga tcggcgcccc ggcgccaccg gtgcacgagt ccagttcttt cggcaacgac      180
ggcggcggcg acgacggcga gagcgtggcc tggctgttcg atgactaccc gccgccgtcg      240
cccgttgctg ccgccgccgg gatgcatcat cggcagccgc cgtacgacgg cgtcgtggcg      300
ccgccgtcgc tgttcaggag gaacaccggc gccggcgggc tcacgttcga cgtctccctc      360
ggcggacggc ccgacctgga cgccgggctc ggcctcggcg gcggcagcgg ccggcacgcc      420
gaggccgcgg ccagcgccac catcatgtca tattgtggga gcacgttcac tgacgcagcg      480
agctcgatgc ccaaggagat ggtggccgcc atggccgatg ttggggagag cttgaaccca      540
aacacggtgg ttggcgcaat ggtggagagg gaggccaagc tgatgaggta caaggagaag      600
aggaagaaga ggtgctacga gaagcaaatc cggtacgcgt ccagaaaagc ctatgccgag      660
atgaggcccc gagtgagagg tcgcttcgcc aaagaagctg atcaggaagc tgtcgcaccg      720
ccatccacct atgtcgatcc tagtaggctt gagcttggac aatggttcag atag            774

<210> SEQ ID NO 20
<211> LENGTH: 2916
<212> TYPE: DNA
<213> ORGANISM: Zea mays

<400> SEQUENCE: 20
atgatcgtgc aacccatcga gctacgcgcg tggactgcct tccctgggtc ggcgcaggag       60
gggatcggaa ggatggcggc gtcggtttcc agggccatct gcgttcagaa gccgggctca      120
aaatgcacca gggacaggga agcgacctcc ttcgcccgcc gatcggtcgc agcgccgagg      180
cccccgcacg ccaaagccgc cggcgtcatc cgctccgact ccggcgcggg acggggccag      240
cattgctcgc cgctgagggc cgtcgttgac gccgcgccga tacagacgac caaaaagagg      300
gtgttccact tcggcaaggg caagagcgag ggcaacaaga ccatgaagga actgctgggc      360
ggcaagggcg cgaacctggc ggagatggcg agcatcgggc tgtcggtgcc gccggggttc      420
acggtgtcga cggaggcgtg ccagcagtac caggacgccg gtgcgccct ccccgcgggg      480 ctctgggccg agatcgtcga cggcctgcag tgggtggagg agtacatggg cgccacctg       540
```

```
ggcgatccgc agcgcccgct cctgctctcc gtccgctccg gcgccgccgt gtccatgccc    600
ggcatgatgg acacggtgct caacctgggg ctcaacgacg aagtggccgc cgggctggcg    660
gccaagagcg gggagcgctt cgcctacgac tccttccgcc gcttcctcga catgttcggc    720
aacgtcgtca tggacatccc ccgctcactg ttcgaagaga agcttgagca catgaaggaa    780 tccaagggc tgaagaacga caccgacctc acggcctctg acctcaaaga gctcgtgggt    840
cagtacaagg aggtctacct ctcagccaag ggagagccat tccctcaga ccccaagaag    900 cagctggagc tagcagtgct ggctgtgttc aactcgtggg agagcccag ggccaagaag    960 tacaggagca tcaaccagat cactggcctc aggggcaccg ccgtgaacgt gcagtgcatg    1020
gtgttcggca acatggggaa cacttctggc accggcgtgc tcttcactag gaaccccaac    1080
accggagaga agaagctgta tggcgagttc ctggtgaacg ctcagggtga ggatgtggtt    1140
gccggaataa gaaccccaga ggaccttgac gccatgaaga acctcatgcc acaggcctac    1200
gacgagcttg ttgagaactg caacatcctg gagagccact ataaggaaat gcaggatatc    1260
gagttcactg tccaggaaaa caggctgtgg atgttgcagt gcaggacagg gaaacgtacg    1320
ggcaaaagtg ccgtgaagat cgccgtggac atggttaacg agggccttgt tgagcccccgc    1380 tcagcgatca agatggtaga gccaggccac ctggaccagc ttctccatcc tcagtttgag    1440
aacccgtcgg cgtacaagga tcaagtcatt gccactggtc tgccagcctc acctggggct    1500
gctgtgggcc aggttgtgtt cactgctgag gatgctgaag catggcattc caagggaaa    1560 gctgctattc tggtaagggc ggagaccagc cctgaggacg ttggtggcat gcacgctgct    1620
gtggggattc ttacagagag gggtggcatg acttcccacg ctgctgtggt cgcacgtggg    1680
tgggggaaat gctgcgtctc gggatgctca ggcattcgcg taaacgatgc ggagaagctc    1740
gtgacgatcg gaggccatgt gctgcgcgaa ggtgagtggc tgtcgctgaa tgggtcgact    1800
ggtgaggtga tccttggaaa gcagccgctt tccccaccag cccttagtgg cgatctggga    1860
actttcatgg cctgggtgga tgatgttaga aagctcaagg tcctggctaa cgccgatacc    1920
cctgatgatg cattgactgc gcgaaacaat ggggcacaag gaattggatt atgccggaca    1980
gagcacatgt tctttgcttc agacgagagg attaaggctg tcaggcagat gattatggct    2040
cccacgcttg agctgaggca gcaggcgctc gaccgtctct tgccgtatca gaggtctgac    2100
ttcgaaggca ttttccgtgc tatggatgga ctcccggtga ccatccgact cctgacccct    2160
cccctccacg agttccttcc agaagggaac atcgaggaca ttgtaagtga attatgtgct    2220
gagacgggag ccaaccagga ggatgccctc gcgcgaattg aaaagctttc agaagtaaac    2280
ccgatgcttg gcttccgtgg gtgcaggctt ggtatatcgt accctgaatt gacagagatg    2340
caagcccggg ccattttga gctgctata gcaatgacca accagggtgt tcaagtgttc    2400
ccagagataa tggttcctct tgttggaaca ccacaggaac tggggcatca agtgactctt    2460
atccgccaag ttgctgagaa agtgttcgcc aatgtgggca agactatcgg gtacaaagtt    2520
ggaacaatga ttgagatccc cagggcagct ctggtggctg atgagatagc ggagcaggct    2580
gaattcttct ccttcggaac gaacgacctg acgcagatga cctttgggta cagcagggat    2640
gatgtgggga agttcattcc cgtctatcct gctcagggca tcctccaaca tgacccttc    2700 gaggtcctgg accagagggg agtgggcgag ctggtgaagt ttgctacaga gaggggccgc    2760
aaagctaggc ctaacttgaa ggtgggcatt tgtggagaac acggtggaga gccttcctct    2820
gtggccttct tcgcgaaggc tgggctggat tacgtttctt gctccccttt caggttccg    2880
```

```
attgctaggc tagctgcagc tcaggtgctt gtctag                              2916
```

<210> SEQ ID NO 21
<211> LENGTH: 792
<212> TYPE: DNA
<213> ORGANISM: Zea mays

<400> SEQUENCE: 21

```
atgttggagt tgcgtctggt gcagggagc ctcctcaaga aggtcttgga ggcgatccgc       60
gagctggtca cggacgccaa cttcgactgc tccgggaccg ggttctcgct gcaggccatg     120
gactcgagcc acgtcgcgct cgtcgcgctg ctccttcgcg ccgagggctt cgagcactac     180
cgctgcgacc gcaacctctc catgggcatg aacctcaaca catggccaa gatgctccgc      240
tgcgctggca acgaggacat catcaccatc aaggccgacg acggctccga caccgtcact     300
ttcatgttcg agtcgcccaa gcaagataag atcgcggatt tcgagatgaa actgatggac    360
attgatagcg agcacctcgg aatcccggat tccgagtacc aggccatcgt ccgcatgcct    420
tctgctgagt ttatgaggat ctgcaaagat cttagcagca tcggagacac agtcgtcatc    480
tcggtgacta aggagggcgt gaagttctcc acatctggag aaattgggag tgcaaacatt   540
gtctgcaggc agaaccaaac tattgacaag ccagaagagg ctaccattat agagatgcag   600
gagccggttt ccctgacctt tgccctgcgg tacatgaact ccttcaccaa ggcgtcttca   660
ctgtctgagc aagtcactat cagcctgtcg tccgagcttc cagtggtggt cgagtacaag   720
atcgctgaga tgggttacat tagattttac ctggccccca agatcgacga tgacgaggag   780
atgaagccct ag                                                         792
```

<210> SEQ ID NO 22
<211> LENGTH: 2670
<212> TYPE: DNA
<213> ORGANISM: Zea mays

<400> SEQUENCE: 22

```
atggcgaagt cgagcgcgga cgacgccgag ctgcggcgcg cgtgcgccgc ggccgtggcg     60
gcgtcaggcg cgcgcgggga ggaggtggcc ttctccatcc gcgtcgccaa gggccgcggc    120
atcttcgaga agctcggcag gctcgccaag ccccgtgtcc tcgcgctcac cgttaaacaa    180
tcatcaagag gcgaggcgaa caaagctttt ctccgagtat aaaatattc atctggggca     240
gtgctcgagc cagccaaact ttacaagctg aaacatctaa caaaggttga ggttatttcc    300
aatgatccca gtggttgtac atttgttctg ggatttgata accttaggag tcagagtgtt    360
gccccgcctc aatggacaat gcgtaacatt gatgacagaa atcgtctact tttttgtatt    420
ctgaatatgt gcaaggagat actcagttat cttccaaaag ttgttggaat tgatattgtg    480
gagctagctc tttgggcgaa ggaaaacaca ctgaccatag ataatcaagt gagtacccaa    540
gatggtcaag aaacatcagt tgctactcaa accgagagga agtaacagt aactgttgaa     600
aatgatctcg tgtcccaagc aaaagaggag gaagaagaca tggaggcact tcttgacacg    660
tatgttatgg gaataggtga agcagatgca ttctctgaga gattgaagca ggagcttgtg    720
gctttggagg ctgcaaatgt atatcaatta ctggaaagcg agcctttaat agaagaggtc    780
ttgcagggtc tggatgctgc tagtgcaact gtagatgata tggatgagtg gttacggatt    840
ttcaatctga agctgaggca catgagagaa gatattgcat cgattgaatc acgtaacaat    900
ggcttggaga tgcagtctgt aaacaacaaa gggcttatgg aagagctaga taaattgctt    960
gagcgtctgc ggattccaca agagtttgca gcatcattaa ctggaggctc atttgaagaa   1020
```

```
tcacggatgc tgaaaaatgt tgaggcatgt gaatggttga caggggccat tcgcagtctt    1080
gaagttccta atttggaccc atgctatgtc aacatgcgcg ctgttagaga gaaaaaggca    1140
gagctggaga aactgaaaac aacttttgtt cgacgagcat cagagttttt gcggaactac    1200
ttctccagtt tggtagactt catgatcagt gacaaaagct acttttcaca gcgtggacaa    1260
ttgaagcggc ctgatcatgc agaccttagg tataaatgca ggacatatgc ccgacttctg    1320
cagcacttaa agagtctgga caagagctgc ttaggtccct taaggaaggc atactgtcat    1380
tcccttaatt tactactacg acgagaggca cgtgaatttg ccaatgaact tcgtgcaagt    1440
acaaaagcac cgaagaatcc tgctgtttgg cttgaaggtt ctggcggctc tggtcataat    1500
ggaagcagtt ctgatacttc acaggtctca gatgcatact caaagatgct tacaatattt    1560
atcccgcttc ttgtggatga gagttccttt tttgcacatt ttatgtgctt tgaagtacct    1620
gcacttgttc cagctggttc tcctaatgct aataagagca aatccggagg aaatgacccg    1680
gatgatgatc tgggtcttat ggatccagat ggcaacgatc tgaaacctga tagtacctct    1740
gctgaactgg gtacattgaa tgaagctctt caagaattac tcgatggaat ccaggaagac    1800
ttctatgcgg tcgtagattg gcttataaaa attgacccct gcgttgcat ctcaatgcat     1860 gggattacag agcgttacct ttctggacag aaagctgatg ctgcaggatt tgttcgcaaa    1920
ctacttgatg acttggaatc aagaatatca gtacagttca gccggtttat tgatgaagca    1980
tgccatcaaa ttgagcgtaa cgaaagaaat gtgcggcaaa ctggaattct agcctacatt    2040
ccaagatttg ctgtccttgc atcacgtatg aacaatata tccaagggca gtccagggat    2100
ttaattgata aagcatacac aaagctagtt agcacaatgt tcgcaacttt ggagaaaatt    2160
gcacagagtg atcctaaaac tgctgatatt gtgctgattg agaattatgc tgctttccag    2220
aacagtcttt atgacttggc taatgttgtg ccaacgcttg caaagttcta ccatcaagcc    2280
agtgaatcat atgaactagc ttgcactcgc catatcagct cactcattta tctgcaattt    2340
gagaggttat tcaattcaa ccggaaagtt gacgaattga cttacactat tgctgctgag    2400
gagataccgt ttcagctggg attatcaaaa actgacctaa ggagggtact gaaatccagc    2460
ttatctggga ttgataagtc gattagcgcc atgtacagga ggttacagaa gacacttacc    2520
tccgatgagt tgtttccttc gctgtgggac aagtgcaaga aggagttttt ggacaaatac    2580
gagagttttg ttcagatggt gacacggata tatgggaatg agccgatcat gtcagtcaac    2640
gaaatgaaag acgtccttgc tggttttttag                                    2670
```

<210> SEQ ID NO 23
<211> LENGTH: 1179
<212> TYPE: DNA
<213> ORGANISM: Zea mays

<400> SEQUENCE: 23

```
atgggcactc aaatagtaag ggaacaaacg agtggtagcc tcactgccat tgttgtggac      60
gaaaatctat gccatgccag ggctgcaagc tgcatgcttg ccaacctcca gtgtaaagtg     120
attgtgtatg cgagtcctgt tgatgcgctc aagtttctta aggatcacca aagagatact     180
gattttgcgt tagtggaagt caacatgaaa gagatgcatg gttttcagtt ccttgacatg     240
tccaggaagt tgcacaaaag ccttcaagtg atcatgatgt cagctgatac gacatggccc     300
acgatgaaga gaagtgtcga gcttggtgca cgtttcttga ttaaaaagcc tcttgatgca     360
aatacgatga ataacctgtg gcagcatctt gacctaaaat ttcaacggac cgacaagatc     420
```

| | |
|---|---|
| aaggccttat tcccaggtat tgaagggaaa acggggaatg catttgagga agggaccaac | 480 |
| aagcagaagg gaactcacct gatgtggact ccattcctgc agaggaagtt tttgcaagct | 540 |
| gttgaactac ttggggaaga cgcatctccg aagaagatac agttgctcat gaatgtgaac | 600 |
| tccgttagtc gcaaacagat ctctgctcat cttcagaaac accgaaagaa ggtcgagaaa | 660 |
| gaactacgta attcaaatgc aaacaactcc agccatggca ttggcggcgc ctcgaattca | 720 |
| cggccttcga ggattttga ataagccat ggcagattcc agtacaatcg tcccgacgtc | 780 |
| caaccagaac atagatctga tgaatccgta tccgtggagc agacagaaac catcgaggaa | 840 |
| acacaaagca acaggttgta tgaagcgatg cgaagagcct tgcagcttgg gagtgttttc | 900 |
| gaggaaccac agttgcccaa tgatcctcct gctggtaaag atgcaagaga gttgaagaa | 960 |
| gtcgaaatga cgatgaggga tggtaattat cgagatgctg gcacagatgc atttggtgat | 1020 |
| aagaatgagg catctggaac tcacagttca gatggtaata cgcgaaggt caagagcaag | 1080 |
| gatgattctg ctgacaagct ggtttcttgt cacgatgagc tgcgaccagt tgtgacgctt | 1140 |
| gtgacctatt cagactcgga agatggtgaa acgctctag | 1179 |

```
<210> SEQ ID NO 24
<211> LENGTH: 768
<212> TYPE: DNA
<213> ORGANISM: Zea mays

<400> SEQUENCE: 24
```

| | |
|---|---|
| atggggaggg gacgagttga gctcaagcgg atcgagaaca agatcaaccg ccaggtcacc | 60 |
| ttctccaagc gccgcaacgg cctgctcaag aaggcctacg agctctccgt gctctgcgac | 120 |
| gccgaggtcg cgctcatcat cttctccagc cgcggcaagc tctacgagtt cggcagcgcc | 180 |
| ggcataacaa aaactttaga aaggtaccaa cattgctgct acaatgctca agattccaat | 240 |
| ggcgcactct ctgaaactca gagctggtac caggaaatgt caaaactgag gcaaaattc | 300 |
| gaggccttgc agcgcactca gaggcacttg cttggggagg aacttggccc actgagtgtg | 360 |
| aaggagttgc agcagctaga gaaacagctc gaatgtgctt tgtcacaggc aagacagaga | 420 |
| aagacacaac ttatgatgga gcaagtggaa gagctccgca gaaaggagcg cacctgggga | 480 |
| gaaatgaaca ggcaactcaa acacaagctt gaagctgaag gttgtagcaa ctacagaacc | 540 |
| ctgcagcatg cagcctggcc agctcccggc agcaccatgg tggagcatga cggcgccacc | 600 |
| tatcatgtgc atccaacaac tgctcaatcg gttgcaatgg actgtgaacc cactctgcaa | 660 |
| atcgggtacc ctcctcatca ccagtttctg ccttccgagg cagccaataa tatcccaagg | 720 |
| agcccccctg gaggcgagaa caacttcatg ctgggatggg ttctttag | 768 |

```
<210> SEQ ID NO 25
<211> LENGTH: 600
<212> TYPE: DNA
<213> ORGANISM: Zea mays

<400> SEQUENCE: 25
```

| | |
|---|---|
| atggctgagg aggaggccaa gaaggtggag gtggaggtca ccaaggagcc cgaggcggca | 60 |
| gcgaaggagg acgtagccga tgacaaggcc gtcatccccg cgaccgaccc gccgccgccg | 120 |
| ccgccgccgg ccgacgactc caaggccctg gccatcgtcg agaaagttgc agatgaacct | 180 |
| gctcccgaga agcctgcccc tgcgaagcaa ggggctccca tgacaggga tctcgctctt | 240 |
| gcaagggtgg aaacagagaa gaggaactct ttgatcaaag cttgggaaga gaatgagaag | 300 |
| acaaaagctg agaacaaggc tgctaagaaa gtatccgcta ttctttcatg ggaaaacaca | 360 |

```
aagaaagcaa acatagaagc tgaactgaag aagattgagg aacaactgga aaagaagaag    420
gctgaatatg cagagaagat gaagaacaag gttgcaatga tacacaagga agccgaagag    480
aagcgagcga tggtggaggc aaaacgcggt gaggaggtcc tgaaggccga ggagatggct    540
gccaagtacc gggccaccgg ccacgctcct aagaagctca tcggttgctt cggagcctag    600
```

<210> SEQ ID NO 26
<211> LENGTH: 537
<212> TYPE: DNA
<213> ORGANISM: Zea mays

<400> SEQUENCE: 26

```
atggcggaag ctccggcgag ccctggcggc ggcggcggga ccacgagag cgggagcccc      60 aggggaggcg gaggcggtgg cagcgtcagg gagcaggaca ggttcctgcc catcgccaac    120
atcagtcgca tcatgaagaa ggccatcccg gctaacggga agatcgccaa ggacgctaag    180
gagaccgtgc aggagtgcgt ctccgagttc atctccttca tcactagcga agcgagtgac    240
aagtgccaga gggagaagcg gaagaccatc aatggcgacg atctgctgtg gccatggcc     300 acgctggggt ttgaagacta cattgaaccc ctcaaggtgt acctgcagaa gtacagagag    360
atggagggtg atagcaagtt aactgcaaaa tctagcgatg gctcaattaa aaaggatgcc    420
cttggtcatg tgggagcaag tagctcagct gcacaaggga tgggccaaca gggagcatac    480
aaccaaggaa tgggttatat gcaaccccag taccataacg gggatatctc aaactga       537
```

<210> SEQ ID NO 27
<211> LENGTH: 642
<212> TYPE: DNA
<213> ORGANISM: Zea mays

<400> SEQUENCE: 27

```
atgtcgagcg gcagcggcag cgggaataag cgcgccgcgg cggagaggtc ggccggcgcc     60
ggcgccggta gcgcgacga ggacgacgac ggtgccgcac gcaagaagct gcggctgtcc     120
aaagaccagg ccgccgtgct cgaggagtgc ttcaagacgc accacacgct cactccgaag    180
cagaaggtgg cgctggccag cagcctgggc ctccggccgc ggcaggtgga ggtgtggttc    240
cagaaccggc gcgcccggac caagctgaag cagacggagg tggactgcga gtacctcaag    300
cgctggtgcg agcagctcgc cgaggagaac cgccgcctgg caaggaggt cgccgagctc     360 agggcgctca gcgccgcgcc ggcggccccg ctcaccaccc tcacgatgtg cctctcctgc    420
cggcgcgtcg cctcctcgtc cccgtcgtcg tcgtcgtcgc ccaggcctag catccccggc    480
gccgcagctg ccagtggcgg gagcatggcc tctccggcgg cggcggcgac gttgcccgcc    540
cacaggcagt tcttctgcgg gttcagagac gccggggcg cggccgcggc gtacgggaca     600
gcctcggcgg ggctcgcgaa gcctgtcagg gctgccagat ag                      642
```

<210> SEQ ID NO 28
<211> LENGTH: 1272
<212> TYPE: DNA
<213> ORGANISM: Artificial Sequence
<220> FEATURE:
<223> OTHER INFORMATION: corn putative glutamine synthetase (with C299A
      mutation)

<400> SEQUENCE: 28

```
atggcgcagg cggtggtgcc ggcgatgcag tgccgggtcg gagtgaaggc ggcggcgggg     60
agggtgtgga gcgccggcag gactaggacc ggccgcggcg gcgcctcgcc ggggttcaag    120
```

```
gtcatggccg tcagcacggg cagcaccggg gtggtgccgc gcctcgagca gctgctcaac      180
atggacacca cgccctacac cgacaaggtc atcgccgagt acatctgggt cggaggatct      240
ggaatcgaca tccgaagcaa atcaaggacg atttcgaaac ccgtggagga ccctcggaa       300 ctaccaaaat ggaactacga tggatctagc acaggacaag ccccgggaga agacagtgaa      360
gtcattctat accccaggc tatcttcaag gacccattcc gaggtggcaa caacgttttg       420
gttatctgtg acacctacac gccacagggg gaacccttc caactaacaa acgccacagg       480
gctgcgcaaa ttttcagtga cccaaaggtc gctgaacaag tgccatggtt tggcatagag      540
caagagtaca ctttgctcca gaaagatgta aattggcctc ttggttggcc tgttggaggc      600
ttccctggtc cccagggtcc atactactgt gccgtaggag ccgacaaatc atttggccgt      660
gacatatcag atgctcacta caaggcatgc ctctacgctg gaatcaacat tagtggaaca      720
aacggggagg tcatgcctgg tcagtgggag taccaagttg gacctagtgt tggtattgaa      780
gcaggagatc acatatggat ttcgagatac attctcgaga gaatcacaga gcaagctggg      840
gttgtcctta cccttgatcc aaaaccaatt cagggtgact ggaacggagc tggcgcacac      900
acaaattaca gcacaaagac catgcgcgaa gacggcgggt ttgaagagat caagagagca      960
atcctgaacc tttctctgcg ccatgatctg catattagtg catacggaga aggaaatgaa     1020
agaagactga ctgggaaaca tgagactgcg agcatcggaa cgttctcatg gggtgtggca     1080
aaccgcggct gctctatccg tgtggggcgg gataccgagg caaaagggaa aggttacctg     1140
gaagaccgtc ggccggcatc aaacatggac ccgtacattg tgacgggct actggccgag      1200 accacgatcc tctggcagcc atccctcgag gcggaggctc ttgccgccaa gaagctggcg     1260
ctgaaggtgt ga                                                        1272

<210> SEQ ID NO 29
<211> LENGTH: 1785
<212> TYPE: DNA
<213> ORGANISM: Zea mays

<400> SEQUENCE: 29
atggtgaaga ggagcaagaa gagcaagagc aagcgagtca cgctgcggca gaagcacaag       60
gtgcagcgca aggtgaagga gcaccaccgc aagaagcgca aggaggccaa gaaggcgggc      120
aaggccggcc agcggaggaa ggtcgagaag gaccccggga tccccaacga gtggcccttc      180
aaggagcagg agctcaaggc gctcgaggcc cgacgcgcgc aggcgctcca ggagctcgag      240
ctcaagaagc aggcgcgcaa ggagagggct cagaagagga aggcaggatt gcttgaggac      300
gaggacattg ctagtttggc atctgcagct tccgcacagg gcagtgagtt tgcagcaaag      360
gagaatgctc ccttattagt ggcaaagatc aacgatcatt cagagaggtc tttttacaag      420
gagcttgtta agtaattga agcttccgat gtgattatgg aggttcttga tgcaagggat      480
ccgctgggca cccgttgcat tgacatgaaa agatggttaa ggaaggctga tccaagtaaa      540
cggattgtac tacttctcaa caagatagat cttgttccca aggaggcggc agagaaatgg      600
cttacatatc taagagaaga attgccaaca gttgcttta agtgcaatac ccaggagcag      660
aggaccaagc tgggatggaa atcttcaaaa ttagataaaa caagcaacat cccacaaagc      720
agtgattgtc ttggtgccga aatctaatc aaattgctta agaattattc cagaagccat      780
gagctcaaac tgacaattac ggtgggtatt gttggacttc ctaatgttgg caagagcagt      840
ctgatcaaca gcctgaagag gtcccgagtg gtcaatgtcg gttctactcc agggattact      900
```

-continued

```
agatcaatgc aagaagttca attagacaag aaggtaaagt tgttggattg tcctggtgtt    960
gttatgctca aatcttccaa cagtggtgtg tctgtagccc ttcgaaactg caaaaaggtt   1020
gagaaaatag aagatccagt cgctcctgtt aagcagatcc taagtatttg cccacatgag   1080
aagttgctgt ctctatacaa ggttccaaac tttggttcag ttgatgattt tcttcagaaa   1140
gtagcaactg tacgtgggaa attgaaaaag ggtggtgtag tggatgttga agctgcagcg   1200
agaattgtgc ttcatgactg gaatgaaggt aaaataccat attttacact gccgcctaaa   1260
agagatgctg gggaggactc agatgcagtg attatatccg aggatgggaa agaatttaat   1320
atcgatgaga tttacaaagc tgaatcttca tatattggtg gtttgaagtc cattgaggag   1380
ttccatcata ttgagattcc tcctaatgct ccactggcga tcgatgaaga gatgctagag   1440
gatggtggca agaaaccaag cgaagccatc caggaaagcc gggacaggga ggagcaaatg   1500
cccgacgtga aggactcagg aggaagcaag gcagccagcg ccagcacgca gaacgacaag   1560
ttgtacaccg ccgagggcgt actcgaccct cgcaagagca agcagagaa gaaacggcgc   1620
aaggcgagca ggcccagcgc gctgaacgac atggacgcgg actacgattt caaggtggat   1680
tatcggatgg aggacggtgg gagcgagggt gcacacgcgg atgatgaaga tggcggagat   1740
ggatccgagg ataatgaacc aatgaccggt gtcgatgatg catga              1785
```

<210> SEQ ID NO 30
<211> LENGTH: 305
<212> TYPE: PRT
<213> ORGANISM: Agrobacterium tumefaciens

<400> SEQUENCE: 30

```
Met Ala Ser Pro Lys His Phe Leu Asp Leu Ser Ala Val Gly Pro Gln
1               5                   10                  15

Asp Leu Arg Thr Ile Leu Asp Asp Ala Arg Ala Arg Lys Val Ala Thr
            20                  25                  30

Lys Ala Gly Thr Ala Glu Lys Pro Leu Ala Gly Lys Met Leu Ala Met
        35                  40                  45

Ile Phe Glu Lys Pro Ser Thr Arg Thr Arg Val Ser Phe Asp Val Gly
    50                  55                  60

Met Arg Gln Leu Gly Gly Glu Thr Leu Phe Leu Ser Gly Thr Glu Met
65                  70                  75                  80

Gln Leu Gly Arg Ala Glu Thr Ile Gly Asp Thr Ala Lys Val Leu Ser
                85                  90                  95

Arg Tyr Val Asp Ala Ile Met Ile Arg Thr Thr Asp His Ser Arg Leu
            100                 105                 110

Leu Glu Leu Ala Glu His Ala Thr Val Pro Val Ile Asn Gly Leu Thr
        115                 120                 125

Asp Asp Thr His Pro Cys Gln Ile Met Ala Asp Ile Met Thr Phe Glu
    130                 135                 140

Glu His Arg Gly Pro Val Lys Gly Lys Thr Ile Ala Trp Thr Gly Asp
145                 150                 155                 160

Gly Asn Asn Val Leu His Ser Phe Val Glu Gly Ser Ala Arg Phe Gly
                165                 170                 175

Tyr Arg Met Thr Met Ala Val Pro Met Gly Ser Glu Pro His Asp Lys
            180                 185                 190

Phe Met Asn Trp Ala Arg Asn Asn Gly Gly Glu Ile Ala Leu Tyr His
        195                 200                 205

Asp Ala Asp Lys Ala Val Ala Gly Ala Asp Cys Val Val Thr Asp Thr
    210                 215                 220
```

Trp Val Ser Met Asn Gln Glu His Lys Ala Arg Gly His Asn Ile Phe
225                 230                 235                 240

Gln Pro Tyr Gln Val Asn Glu Ala Leu Met Ala Lys Ala Gln Lys Asp
            245                 250                 255

Ala Leu Phe Met His Cys Leu Pro Ala His Arg Gly Glu Glu Val Thr
        260                 265                 270

Asp Ala Val Ile Asp Gly Pro Gln Ser Val Val Phe Asp Glu Ala Glu
    275                 280                 285

Asn Arg Leu His Ala Gln Lys Ser Val Ile Ala Trp Cys Met Gly Val
    290                 295                 300

Ile
305

<210> SEQ ID NO 31
<211> LENGTH: 214
<212> TYPE: PRT
<213> ORGANISM: Arabidopsis thaliana

<400> SEQUENCE: 31

Met Val Arg Gly Lys Thr Gln Met Lys Arg Ile Glu Asn Ala Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ser Leu Ile Ile Phe
        35                  40                  45

Ser Pro Lys Gly Lys Leu Tyr Glu Phe Ala Ser Ser Asn Met Gln Asp
    50                  55                  60

Thr Ile Asp Arg Tyr Leu Arg His Thr Lys Asp Arg Val Ser Thr Lys
65                  70                  75                  80

Pro Val Ser Glu Glu Asn Met Gln His Leu Lys Tyr Glu Ala Ala Asn
                85                  90                  95

Met Met Lys Lys Ile Glu Gln Leu Glu Ala Ser Lys Arg Lys Leu Leu
            100                 105                 110

Gly Glu Gly Ile Gly Thr Cys Ser Ile Glu Glu Leu Gln Gln Ile Glu
        115                 120                 125

Gln Gln Leu Glu Lys Ser Val Lys Cys Ile Arg Ala Arg Lys Thr Gln
    130                 135                 140

Val Phe Lys Glu Gln Ile Glu Gln Leu Lys Gln Lys Glu Lys Ala Leu
145                 150                 155                 160

Ala Ala Glu Asn Glu Lys Leu Ser Glu Lys Trp Gly Ser His Glu Ser
                165                 170                 175

Glu Val Trp Ser Asn Lys Asn Gln Glu Ser Thr Gly Arg Gly Asp Glu
            180                 185                 190

Glu Ser Ser Pro Ser Ser Glu Val Glu Thr Gln Leu Phe Ile Gly Leu
        195                 200                 205

Pro Cys Ser Ser Arg Lys
    210

<210> SEQ ID NO 32
<211> LENGTH: 1006
<212> TYPE: PRT
<213> ORGANISM: Arabidopsis thaliana

<400> SEQUENCE: 32

Met Gly Glu Gln Gln Ile Ser Val Thr Val Pro Arg Asp Arg Thr Asp
1               5                   10                  15

```
Glu Gln Ala Ile Leu Ala Leu Lys Lys Gly Ala Gln Leu Leu Lys Cys
                20                  25                  30

Arg Arg Arg Gly Asn Pro Lys Phe Cys Pro Phe Lys Leu Ser Met Asp
            35                  40                  45

Glu Lys Tyr Leu Ile Trp Tyr Ser Gly Glu Glu Arg Gln Leu Arg
 50                  55                  60

Leu Ser Ser Val Ile Thr Ile Val Arg Gly Gln Ile Thr Pro Asn Phe
 65                  70                  75                  80

Gln Lys Gln Ala Gln Ser Asp Arg Lys Glu Gln Ser Phe Ser Leu Ile
                85                  90                  95

Tyr Ala Asn Gly Glu His Thr Leu Asp Leu Ile Cys Lys Asp Lys Ala
                100                 105                 110

Gln Ala Asp Ser Trp Phe Lys Gly Leu Arg Ala Val Ile Thr Lys His
            115                 120                 125

His Asn Ile Arg Asn Ser Val Asn His Arg Ser Ser Arg Gly Ala Gln
130                 135                 140

Ser Cys Ile Asn Ser Pro Ala Gly Phe Met Arg Arg Lys Gln Asn Leu
145                 150                 155                 160

Gly Leu Leu Glu Glu Thr Pro Asp Val Thr Gln Ile Arg Ser Leu Cys
                165                 170                 175

Gly Ser Pro Ser Thr Leu Leu Glu Glu Arg Cys Leu Ser Asn Gly Leu
            180                 185                 190

Ser Cys Ser Ser Asp Ser Phe Ala Glu Ser Asp Ala Leu Gly Pro Val
        195                 200                 205

Ser Ser Tyr Tyr Glu Thr Asp Tyr Asp Phe Arg Asn Ser Asp Cys Asp
        210                 215                 220

Arg Ser Thr Gly Ser Glu Leu Cys Arg Phe Ser Ser Gln Arg Phe Ala
225                 230                 235                 240

Ala Ser Pro Pro Leu Ser Ile Ile Thr Gln Pro Val Thr Arg Ser Asn
                245                 250                 255

Val Leu Lys Asp Ile Met Ile Trp Gly Ala Ile Thr Gly Leu Ile Asp
                260                 265                 270

Gly Ser Lys Asn Gln Asn Asp Ala Leu Ser Pro Lys Leu Leu Glu Ser
            275                 280                 285

Ala Thr Met Phe Asp Val Gln Ser Ile Ser Leu Gly Ala Lys His Ala
        290                 295                 300

Ala Leu Val Thr Arg Gln Gly Glu Val Phe Cys Trp Gly Asn Gly Asn
305                 310                 315                 320

Ser Gly Lys Leu Gly Leu Lys Val Asn Ile Asp Ile Asp His Pro Lys
                325                 330                 335

Arg Val Glu Ser Leu Glu Asp Val Ala Val Arg Ser Val Ala Cys Ser
            340                 345                 350

Asp His Gln Thr Cys Ala Val Thr Glu Ser Gly Glu Leu Tyr Leu Trp
        355                 360                 365

Gly Ile Asp Gly Gly Thr Ile Glu Gln Ser Gly Ser Gln Phe Leu Thr
        370                 375                 380

Arg Lys Ile Ser Asp Val Leu Gly Gly Ser Leu Thr Val Leu Ser Val
385                 390                 395                 400

Ala Cys Gly Ala Trp His Thr Ala Ile Val Thr Ser Ser Gly Gln Leu
                405                 410                 415

Phe Thr Tyr Gly Ser Gly Thr Phe Gly Val Leu Gly His Gly Ser Leu
            420                 425                 430
```

```
Glu Ser Val Thr Lys Pro Lys Glu Val Glu Ser Leu Arg Arg Met Lys
            435                 440                 445

Val Ile Ser Val Ser Cys Gly Pro Trp His Thr Ala Ala Ile Val Glu
450                 455                 460

Thr Ala Asn Asp Arg Lys Phe Tyr Asn Ala Lys Ser Cys Gly Lys Leu
465                 470                 475                 480

Phe Thr Trp Gly Asp Asp Lys Gly Arg Leu Gly His Ala Asp Ser
                485                 490                 495

Lys Arg Lys Leu Val Pro Thr Cys Val Thr Glu Leu Ile Asp His Asp
                500                 505                 510

Phe Ile Lys Val Ser Cys Gly Trp Thr Leu Thr Val Ala Leu Ser Ile
                515                 520                 525

Ser Gly Thr Val Tyr Thr Met Gly Ser Ser Ile His Gly Gln Leu Gly
        530                 535                 540

Cys Pro Arg Ala Lys Asp Lys Ser Val Asn Val Val Leu Gly Asn Leu
545                 550                 555                 560

Thr Arg Gln Phe Val Lys Asp Ile Ala Ser Gly Ser His His Val Ala
                565                 570                 575

Val Leu Thr Ser Phe Gly Asn Val Tyr Thr Trp Gly Lys Gly Met Asn
                580                 585                 590

Gly Gln Leu Gly Leu Gly Asp Val Arg Asp Arg Asn Ser Pro Val Leu
            595                 600                 605

Val Glu Pro Leu Gly Asp Arg Leu Val Glu Ser Ile Ala Cys Gly Leu
        610                 615                 620

Asn Leu Thr Ala Ala Ile Cys Leu His Lys Glu Ile Ser Leu Asn Asp
625                 630                 635                 640

Gln Thr Ala Cys Ser Ser Cys Lys Ser Ala Phe Gly Phe Thr Arg Arg
                645                 650                 655

Lys His Asn Cys Tyr Asn Cys Gly Leu Leu Phe Cys Asn Ala Cys Ser
            660                 665                 670

Ser Lys Lys Ala Val Asn Ala Ser Leu Ala Pro Asn Lys Ser Lys Leu
            675                 680                 685

Ser Arg Val Cys Asp Ser Cys Phe Asp His Leu Trp Ser Ile Thr Glu
        690                 695                 700

Phe Ser Arg Asn Val Lys Met Asp Asn His Thr Pro Arg Met Gln Met
705                 710                 715                 720

Val Thr Arg Arg Val Ser Glu Asp Leu Thr Glu Lys Gln Ser Glu Asn
                725                 730                 735

Glu Met Gln Asn Leu Pro Gln Ala Asn Arg Ser Ser Asp Gly Gln Pro
            740                 745                 750

Arg Trp Gly Gln Val Ser Gly Pro Ser Leu Phe Arg Phe Asp Lys Ile
            755                 760                 765

Ser Thr Ser Ser Ser Leu Asn Leu Ser Val Ser Ala Arg Arg Thr Ser
        770                 775                 780

Ser Thr Lys Ile Ser Thr Ser Ser Glu Ser Asn Lys Ile Leu Thr Glu
785                 790                 795                 800

Glu Ile Glu Arg Leu Lys Ala Val Ile Lys Asn Leu Gln Arg Gln Cys
                805                 810                 815

Glu Leu Gly Asn Glu Lys Met Glu Glu Cys Gln Gln Glu Leu Asp Lys
            820                 825                 830

Thr Trp Glu Val Ala Lys Glu Glu Ala Glu Lys Ser Lys Ala Ala Lys
    835                 840                 845

Glu Ile Ile Lys Ala Leu Ala Ser Lys Leu Gln Ala Asn Lys Glu Lys
```

```
                850             855             860
Pro Ser Asn Pro Leu Lys Thr Gly Ile Ala Cys Asn Pro Ser Gln Val
865             870             875             880

Ser Pro Ile Phe Asp Asp Ser Met Ser Ile Pro Tyr Leu Thr Pro Ile
            885             890             895

Thr Thr Ala Arg Ser Gln His Glu Thr Lys Gln His Val Glu Lys Cys
        900             905             910

Val Thr Lys Ser Ser Asn Arg Asp Ser Asn Ile Lys Leu Leu Val Asp
        915             920             925

Ala Ser Pro Ala Ile Thr Arg Thr Gly Tyr Leu Gln Asn Glu Thr Gln
    930             935             940

Asp Ser Ser Ala Glu Gln Val Glu Gln Tyr Glu Pro Gly Val Tyr Ile
945             950             955             960

Thr Phe Thr Ala Leu Pro Cys Gly Gln Lys Thr Leu Lys Arg Val Arg
            965             970             975

Phe Ser Arg Lys Arg Phe Ser Glu Lys Glu Ala Gln Arg Trp Trp Glu
            980             985             990

Glu Lys Gln Val Leu Val Tyr Asn  Lys Tyr Asp Ala Glu  Ile
        995             1000            1005

<210> SEQ ID NO 33
<211> LENGTH: 729
<212> TYPE: PRT
<213> ORGANISM: Arabidopsis thaliana

<400> SEQUENCE: 33

Met Arg Ile Phe Ser Thr Phe Val Phe His Arg Arg Gln Gln Ile Phe
1               5                   10                  15

Asn Leu Arg Gln Phe Gln Thr Thr Thr Ile Leu Arg Asn Pro Ile Ser
            20                  25                  30

Ile Ala Pro Ile Gln Ile Pro Met Asp Ala Thr Glu Gln Ser Leu Arg
        35                  40                  45

Gln Ser Leu Ser Glu Lys Ser Ser Val Glu Ala Gln Gly Asn Ala
    50                  55                  60

Val Arg Ala Leu Lys Ala Ser Arg Ala Ala Lys Pro Glu Ile Asp Ala
65                  70                  75                  80

Ala Ile Glu Gln Leu Asn Lys Leu Lys Leu Glu Lys Ser Thr Val Glu
                85                  90                  95

Lys Glu Leu Gln Ser Ile Ile Ser Ser Ser Gly Asn Gly Ser Leu Asn
            100                 105                 110

Arg Glu Ala Phe Arg Lys Ala Val Val Asn Thr Leu Glu Arg Arg Leu
        115                 120                 125

Phe Tyr Ile Pro Ser Phe Lys Ile Tyr Ser Gly Val Ala Gly Leu Phe
    130                 135                 140

Asp Tyr Gly Pro Pro Gly Cys Ala Ile Lys Ser Asn Val Leu Ser Phe
145                 150                 155                 160

Trp Arg Gln His Phe Ile Leu Glu Glu Asn Met Leu Glu Val Asp Cys
                165                 170                 175

Pro Cys Val Thr Pro Glu Val Val Leu Lys Ala Ser Gly His Val Asp
            180                 185                 190

Lys Phe Thr Asp Leu Met Val Lys Asp Glu Lys Thr Gly Thr Cys Tyr
        195                 200                 205

Arg Ala Asp His Leu Leu Lys Asp Tyr Cys Thr Glu Lys Leu Glu Lys
    210                 215                 220
```

-continued

Asp Leu Thr Ile Ser Ala Glu Lys Ala Ala Glu Leu Lys Asp Val Leu
225                 230                 235                 240

Ala Val Met Glu Asp Phe Ser Pro Glu Gln Leu Gly Ala Lys Ile Arg
            245                 250                 255

Glu Tyr Gly Ile Thr Ala Pro Asp Thr Lys Asn Pro Leu Ser Asp Pro
        260                 265                 270

Tyr Pro Phe Asn Leu Met Phe Gln Thr Ser Ile Gly Pro Ser Gly Leu
    275                 280                 285

Ile Pro Gly Tyr Met Arg Pro Glu Thr Ala Gln Gly Ile Phe Val Asn
290                 295                 300

Phe Lys Asp Leu Tyr Tyr Tyr Asn Gly Lys Lys Leu Pro Phe Ala Ala
305                 310                 315                 320

Ala Gln Ile Gly Gln Ala Phe Arg Asn Glu Ile Ser Pro Arg Gln Gly
            325                 330                 335

Leu Leu Arg Val Arg Glu Phe Thr Leu Ala Glu Ile Glu His Phe Val
        340                 345                 350

Asp Pro Glu Asn Lys Ser His Pro Lys Phe Ser Asp Val Ala Lys Leu
    355                 360                 365

Glu Phe Leu Met Phe Pro Arg Glu Gln Met Ser Gly Gln Ser Ala
370                 375                 380

Lys Lys Leu Cys Leu Gly Glu Ala Val Ala Lys Gly Thr Val Asn Asn
385                 390                 395                 400

Glu Thr Leu Gly Tyr Phe Ile Gly Arg Val Tyr Leu Phe Leu Thr Arg
            405                 410                 415

Leu Gly Ile Asp Lys Glu Arg Leu Arg Phe Arg Gln His Leu Ala Asn
        420                 425                 430

Glu Met Ala His Tyr Ala Ala Asp Cys Trp Asp Ala Glu Ile Glu Ser
    435                 440                 445

Ser Tyr Gly Trp Ile Glu Cys Val Gly Ile Ala Asp Arg Ser Ala Tyr
450                 455                 460

Asp Leu Arg Ala His Ser Asp Lys Ser Gly Thr Pro Leu Val Ala Glu
465                 470                 475                 480

Glu Lys Phe Ala Glu Pro Lys Glu Val Glu Lys Leu Val Ile Thr Pro
            485                 490                 495

Val Lys Lys Glu Leu Gly Leu Ala Phe Lys Gly Asn Gln Lys Asn Val
        500                 505                 510

Val Glu Ser Leu Glu Ala Met Asn Glu Glu Ala Met Glu Met Lys
    515                 520                 525

Ala Thr Leu Glu Ser Lys Gly Glu Val Glu Phe Tyr Val Cys Thr Leu
530                 535                 540

Lys Lys Ser Val Asn Ile Lys Lys Asn Met Val Ser Ile Ser Lys Glu
545                 550                 555                 560

Lys Lys Lys Glu His Gln Arg Val Phe Thr Pro Ser Val Ile Glu Pro
            565                 570                 575

Ser Phe Gly Ile Gly Arg Ile Ile Tyr Cys Leu Tyr Glu His Cys Phe
        580                 585                 590

Ser Thr Arg Pro Ser Lys Ala Gly Asp Glu Gln Leu Asn Leu Phe Arg
    595                 600                 605

Phe Pro Pro Leu Val Ala Pro Ile Lys Cys Thr Val Phe Pro Leu Val
610                 615                 620

Gln Asn Gln Gln Phe Glu Glu Val Ala Lys Val Ile Ser Lys Glu Leu
625                 630                 635                 640

Ala Ser Val Gly Ile Ser His Lys Ile Asp Ile Thr Gly Thr Ser Ile

```
                    645                 650                 655
Gly Lys Arg Tyr Ala Arg Thr Asp Glu Leu Gly Val Pro Phe Ala Ile
                660                 665                 670

Thr Val Asp Ser Asp Thr Ser Val Thr Ile Arg Glu Arg Asp Ser Lys
            675                 680                 685

Asp Gln Val Arg Val Thr Leu Lys Glu Ala Ala Ser Val Val Ser Ser
        690                 695                 700

Val Ser Glu Gly Lys Met Thr Trp Gln Asp Val Trp Ala Thr Phe Pro
705                 710                 715                 720

His His Ser Ser Ala Ala Ala Asp Glu
                725

<210> SEQ ID NO 34
<211> LENGTH: 588
<212> TYPE: PRT
<213> ORGANISM: Arabidopsis thaliana

<400> SEQUENCE: 34

Met Ser Tyr Asp Glu His Thr Ser Ser Phe Thr Tyr Ile Ser Gln
1               5                   10                  15

Met Gly Val Trp Trp Ile Val Leu Val Val Ala Val Leu Thr His Thr
                20                  25                  30

Ala Ser Ala Ala Val Arg Glu Tyr His Trp Glu Val Glu Tyr Lys Tyr
            35                  40                  45

Trp Ser Pro Asp Cys Lys Glu Gly Ala Val Met Thr Val Asn Gly Glu
        50                  55                  60

Phe Pro Gly Pro Thr Ile Lys Ala Phe Ala Gly Asp Thr Ile Val Val
65                  70                  75                  80

Asn Leu Thr Asn Lys Leu Thr Thr Glu Gly Leu Val Ile His Trp His
                85                  90                  95

Gly Ile Arg Gln Phe Gly Ser Pro Trp Ala Asp Gly Ala Ala Gly Val
                100                 105                 110

Thr Gln Cys Ala Ile Asn Pro Gly Glu Thr Phe Thr Tyr Asn Phe Thr
            115                 120                 125

Val Glu Lys Pro Gly Thr His Phe Tyr His Gly His Tyr Gly Met Gln
        130                 135                 140

Arg Ser Ala Gly Leu Tyr Gly Ser Leu Ile Val Asp Val Ala Lys Gly
145                 150                 155                 160

Lys Ser Glu Arg Leu Arg Tyr Asp Gly Glu Phe Asn Leu Leu Leu Ser
                165                 170                 175

Asp Trp Trp His Glu Ala Ile Pro Ser Gln Glu Leu Gly Leu Ser Ser
                180                 185                 190

Lys Pro Met Arg Trp Ile Gly Glu Ala Gln Ser Ile Leu Ile Asn Gly
            195                 200                 205

Arg Gly Gln Phe Asn Cys Ser Leu Ala Ala Gln Phe Ser Asn Asn Thr
        210                 215                 220

Ser Leu Pro Met Cys Thr Phe Lys Glu Gly Asp Gln Cys Ala Pro Gln
225                 230                 235                 240

Ile Leu His Val Glu Pro Asn Lys Thr Tyr Arg Ile Arg Leu Ser Ser
                245                 250                 255

Thr Thr Ala Leu Ala Ser Leu Asn Leu Ala Val Gln Gly His Lys Leu
            260                 265                 270

Val Val Val Glu Ala Asp Gly Asn Tyr Ile Thr Pro Phe Thr Thr Asp
        275                 280                 285
```

```
Asp Ile Asp Ile Tyr Ser Gly Glu Ser Tyr Ser Val Leu Leu Thr Thr
    290                 295                 300

Asp Gln Asp Pro Ser Gln Asn Tyr Tyr Ile Ser Val Gly Val Arg Gly
305                 310                 315                 320

Arg Lys Pro Asn Thr Thr Gln Ala Leu Thr Ile Leu Asn Tyr Val Thr
                325                 330                 335

Ala Pro Ala Ser Lys Leu Pro Ser Ser Pro Pro Val Thr Pro Arg
            340                 345                 350

Trp Asp Asp Phe Glu Arg Ser Lys Asn Phe Ser Lys Lys Ile Phe Ser
                355                 360                 365

Ala Met Gly Ser Pro Ser Pro Pro Lys Lys Tyr Arg Lys Arg Leu Ile
    370                 375                 380

Leu Leu Asn Thr Gln Asn Leu Ile Asp Gly Tyr Thr Lys Trp Ala Ile
385                 390                 395                 400

Asn Asn Val Ser Leu Val Thr Pro Ala Thr Pro Tyr Leu Gly Ser Val
                405                 410                 415

Lys Tyr Asn Leu Lys Leu Gly Phe Asn Arg Lys Ser Pro Pro Arg Ser
            420                 425                 430

Tyr Arg Met Asp Tyr Asp Ile Met Asn Pro Pro Phe Pro Asn Thr
    435                 440                 445

Thr Thr Gly Asn Gly Ile Tyr Val Phe Pro Phe Asn Val Thr Val Asp
    450                 455                 460

Val Ile Ile Gln Asn Ala Asn Val Leu Lys Gly Ile Val Ser Glu Ile
465                 470                 475                 480

His Pro Trp His Leu His Gly His Asp Phe Trp Val Leu Gly Tyr Gly
                485                 490                 495

Asp Gly Lys Phe Lys Pro Gly Ile Asp Glu Lys Thr Tyr Asn Leu Lys
            500                 505                 510

Asn Pro Pro Leu Arg Asn Thr Ala Ile Leu Tyr Pro Tyr Gly Trp Thr
            515                 520                 525

Ala Ile Arg Phe Val Thr Asp Asn Pro Gly Val Trp Phe Phe His Cys
    530                 535                 540

His Ile Glu Pro His Leu His Met Gly Met Gly Val Val Phe Ala Glu
545                 550                 555                 560

Gly Leu Asn Arg Ile Gly Lys Val Pro Asp Glu Ala Leu Gly Cys Gly
                565                 570                 575

Leu Thr Lys Gln Phe Leu Met Asn Arg Asn Arg Asn
                580                 585
```

<210> SEQ ID NO 35
<211> LENGTH: 493
<212> TYPE: PRT
<213> ORGANISM: Arabidopsis thaliana

<400> SEQUENCE: 35

```
Met Val Leu Ser Lys Thr Val Ser Glu Ser Asp Val Ser Ile His Ser
1               5                   10                  15

Thr Phe Ala Ser Arg Tyr Val Arg Asn Ser Leu Pro Arg Phe Glu Met
                20                  25                  30

Pro Glu Asn Ser Ile Pro Lys Glu Ala Ala Tyr Gln Ile Ile Asn Asp
            35                  40                  45

Glu Leu Met Leu Asp Gly Asn Pro Arg Leu Asn Leu Ala Ser Phe Val
    50                  55                  60

Thr Thr Trp Met Glu Pro Glu Cys Asp Lys Leu Met Met Glu Ser Ile
65                  70                  75                  80
```

```
Asn Lys Asn Tyr Val Asp Met Asp Glu Tyr Pro Val Thr Thr Glu Leu
                85                  90                  95

Gln Asn Arg Cys Val Asn Met Ile Ala Arg Leu Phe Asn Ala Pro Leu
            100                 105                 110

Gly Asp Gly Glu Ala Ala Val Gly Val Gly Thr Val Gly Ser Ser Glu
        115                 120                 125

Ala Ile Met Leu Ala Gly Leu Ala Phe Lys Arg Gln Trp Gln Asn Lys
    130                 135                 140

Arg Lys Ala Gln Gly Leu Pro Tyr Asp Lys Pro Asn Ile Val Thr Gly
145                 150                 155                 160

Ala Asn Val Gln Val Cys Trp Glu Lys Phe Ala Arg Tyr Phe Glu Val
                165                 170                 175

Glu Leu Lys Glu Val Asn Leu Arg Glu Asp Tyr Tyr Val Met Asp Pro
            180                 185                 190

Val Lys Ala Val Glu Met Val Asp Glu Asn Thr Ile Cys Val Ala Ala
        195                 200                 205

Ile Leu Gly Ser Thr Leu Thr Gly Glu Phe Glu Asp Val Lys Leu Leu
    210                 215                 220

Asn Asp Leu Leu Val Glu Lys Asn Lys Gln Thr Gly Trp Asp Thr Pro
225                 230                 235                 240

Ile His Val Asp Ala Ala Ser Gly Gly Phe Ile Ala Pro Phe Leu Tyr
                245                 250                 255

Pro Glu Leu Glu Trp Asp Phe Arg Leu Pro Leu Val Lys Ser Ile Asn
            260                 265                 270

Val Ser Gly His Lys Tyr Gly Leu Val Tyr Ala Gly Ile Gly Trp Val
        275                 280                 285

Val Trp Arg Thr Lys Thr Asp Leu Pro Asp Glu Leu Ile Phe His Ile
    290                 295                 300

Asn Tyr Leu Gly Ala Asp Gln Pro Thr Phe Thr Leu Asn Phe Ser Lys
305                 310                 315                 320

Gly Ser Ser Gln Val Ile Ala Gln Tyr Tyr Gln Leu Ile Arg Leu Gly
                325                 330                 335

Phe Glu Gly Tyr Arg Asn Val Met Asp Asn Cys Arg Glu Asn Met Met
            340                 345                 350

Val Leu Arg Gln Gly Leu Glu Lys Thr Gly Arg Phe Lys Ile Val Ser
        355                 360                 365

Lys Glu Asn Gly Val Pro Leu Val Ala Phe Ser Leu Lys Asp Ser Ser
    370                 375                 380

Arg His Asn Glu Phe Glu Val Ala His Thr Leu Arg Arg Phe Gly Trp
385                 390                 395                 400

Ile Val Pro Ala Tyr Thr Met Pro Ala Asp Ala Gln His Val Thr Val
                405                 410                 415

Leu Arg Val Val Ile Arg Glu Asp Phe Ser Arg Thr Leu Ala Glu Arg
            420                 425                 430

Leu Val Ala Asp Phe Glu Lys Val Leu His Glu Leu Asp Thr Leu Pro
        435                 440                 445

Ala Arg Val His Ala Lys Met Ala Asn Gly Lys Val Asn Gly Val Lys
    450                 455                 460

Lys Thr Pro Glu Glu Thr Gln Arg Glu Val Thr Ala Tyr Trp Lys Lys
465                 470                 475                 480

Leu Leu Glu Thr Lys Lys Thr Asn Lys Asn Thr Ile Cys
                485                 490
```

<210> SEQ ID NO 36
<211> LENGTH: 282
<212> TYPE: PRT
<213> ORGANISM: Arabidopsis thaliana

<400> SEQUENCE: 36

Met Gly Thr Arg Ala Gln Gln Ile Pro Leu Leu Glu Gly Glu Thr Asp
1               5                   10                  15

Asn Tyr Asp Gly Val Thr Val Thr Met Val Glu Pro Met Asp Ser Glu
            20                  25                  30

Val Phe Thr Glu Ser Leu Arg Ala Ser Leu Ser His Trp Arg Glu Glu
        35                  40                  45

Gly Lys Lys Gly Ile Trp Ile Lys Leu Pro Leu Gly Leu Ala Asn Leu
    50                  55                  60

Val Glu Ala Ala Val Ser Glu Gly Phe Arg Tyr His His Ala Glu Pro
65                  70                  75                  80

Glu Tyr Leu Met Leu Val Ser Trp Ile Ser Glu Thr Pro Asp Thr Ile
                85                  90                  95

Pro Ala Asn Ala Ser His Val Val Gly Ala Gly Ala Leu Val Ile Asn
            100                 105                 110

Lys Asn Thr Lys Glu Val Leu Val Val Gln Glu Arg Ser Gly Phe Phe
        115                 120                 125

Lys Asp Lys Asn Val Trp Lys Leu Pro Thr Gly Val Ile Asn Glu Gly
    130                 135                 140

Glu Asp Ile Trp Thr Gly Val Ala Arg Glu Val Glu Glu Glu Thr Gly
145                 150                 155                 160

Ile Ile Ala Asp Phe Val Glu Val Leu Ala Phe Arg Gln Ser His Lys
                165                 170                 175

Ala Ile Leu Lys Lys Thr Asp Met Phe Phe Leu Cys Val Leu Ser
            180                 185                 190

Pro Arg Ser Tyr Asp Ile Thr Glu Gln Lys Ser Glu Ile Leu Gln Ala
        195                 200                 205

Lys Trp Met Pro Ile Gln Glu Tyr Val Asp Gln Pro Trp Asn Lys Lys
    210                 215                 220

Asn Glu Met Phe Lys Phe Met Ala Asn Ile Cys Gln Lys Lys Cys Glu
225                 230                 235                 240

Glu Glu Tyr Leu Gly Phe Ala Ile Val Pro Thr Thr Thr Ser Ser Gly
                245                 250                 255

Lys Glu Ser Phe Ile Tyr Cys Asn Ala Asp His Ala Lys Arg Leu Lys
            260                 265                 270

Val Ser Arg Asp Gln Ala Ser Ala Ser Leu
        275                 280

<210> SEQ ID NO 37
<211> LENGTH: 460
<212> TYPE: PRT
<213> ORGANISM: Arabidopsis thaliana

<400> SEQUENCE: 37

Met Thr Val Val Gly Asp Val Ala Pro Ile Pro Arg Arg Asn Ser Ser
1               5                   10                  15

Thr Cys Ser Asn Asp Ile Ala Ala Pro Leu Leu Pro Glu Cys His Gly
            20                  25                  30

Asp Glu Val Ala His Asp Glu Phe Asn Gly Ala Ser Phe Ser Gly Ala
        35                  40                  45

```
Val Phe Asn Leu Ala Thr Thr Ile Ile Gly Ala Gly Ile Met Ala Leu
 50                  55                  60
Pro Ala Thr Met Lys Ile Leu Gly Leu Gly Leu Gly Ile Thr Met Ile
 65                  70                  75                  80
Val Val Met Ala Phe Leu Thr Asp Ala Ser Ile Glu Phe Leu Leu Arg
                 85                  90                  95
Phe Ser Lys Ala Gly Lys Asn Arg Ser Tyr Gly Gly Leu Met Gly Gly
                100                 105                 110
Ser Phe Gly Asn Pro Gly Arg Ile Leu Leu Gln Val Ala Val Leu Val
                115                 120                 125
Asn Asn Ile Gly Val Leu Ile Val Tyr Met Ile Ile Gly Asp Val
130                 135                 140
Leu Ala Gly Lys Thr Glu Asp Gly Ile His His Phe Gly Val Leu Glu
145                 150                 155                 160
Gly Trp Phe Gly His His Trp Trp Asn Gly Arg Ala Ala Ile Leu Leu
                165                 170                 175
Ile Thr Thr Leu Gly Val Phe Ala Pro Leu Ala Cys Phe Lys Arg Ile
                180                 185                 190
Asp Ser Leu Lys Phe Thr Ser Ala Leu Ser Val Ala Leu Ala Val Val
                195                 200                 205
Phe Leu Ile Ile Thr Ala Gly Ile Ser Ile Met Lys Leu Ile Ser Gly
210                 215                 220
Gly Val Ala Met Pro Arg Leu Leu Pro Asp Val Thr Asp Leu Thr Ser
225                 230                 235                 240
Phe Trp Asn Leu Phe Thr Val Val Pro Val Leu Val Thr Ala Phe Ile
                245                 250                 255
Cys His Tyr Asn Val His Ser Ile Gln Asn Glu Leu Glu Asp Pro Ser
                260                 265                 270
Gln Ile Arg Pro Val Val Arg Ser Ala Leu Met Leu Cys Ser Ser Val
                275                 280                 285
Tyr Ile Met Thr Ser Ile Phe Gly Phe Leu Leu Phe Gly Asp Asp Thr
                290                 295                 300
Leu Asp Asp Val Leu Ala Asn Phe Asp Thr Asp Leu Gly Ile Pro Phe
305                 310                 315                 320
Gly Ser Ile Leu Asn Asp Ala Val Arg Val Ser Tyr Ala Leu His Leu
                325                 330                 335
Met Leu Val Phe Pro Ile Val Phe Tyr Pro Leu Arg Ile Asn Ile Asp
                340                 345                 350
Gly Leu Leu Phe Pro Ser Ala Arg Ser Leu Ser Thr Ser Asn Val Arg
                355                 360                 365
Phe Gly Cys Leu Thr Ala Gly Leu Ile Ser Val Ile Phe Leu Gly Ala
                370                 375                 380
Asn Phe Ile Pro Ser Ile Trp Asp Ala Phe Gln Phe Thr Gly Ala Thr
385                 390                 395                 400
Ala Ala Val Cys Leu Gly Phe Ile Phe Pro Ala Ser Ile Ile Leu Lys
                405                 410                 415
Asp Arg His Asp Lys Ala Thr Asn Arg Asp Thr Thr Leu Ala Ile Phe
                420                 425                 430
Met Ile Val Leu Ala Val Leu Ser Asn Ala Ile Ala Ile Tyr Ser Asp
                435                 440                 445
Ala Tyr Ala Leu Phe Lys Lys Asn Ala Pro Arg Glu
450                 455                 460
```

```
<210> SEQ ID NO 38
<211> LENGTH: 133
<212> TYPE: PRT
<213> ORGANISM: Artificial Sequence
<220> FEATURE:
<223> OTHER INFORMATION: Arabidopsis thaliana putative AP2/EREBP
      transcription factor, with A33V mutation
<220> FEATURE:
<221> NAME/KEY: MUTAGEN
<222> LOCATION: (33)..(33)
<223> OTHER INFORMATION: A33V mutation

<400> SEQUENCE: 38

Met Asp Gln Gly Gly Arg Ser Ser Gly Ser Gly Gly Gly Ala Glu
1               5                   10                  15

Gln Gly Lys Tyr Arg Gly Val Arg Arg Pro Trp Gly Lys Tyr Ala
                20                  25                  30

Val Glu Ile Arg Asp Ser Arg Lys His Gly Glu Arg Val Trp Leu Gly
                35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Tyr
65                  70                  75                  80

Asn Met Gly Thr Gly Ser Ser Ser Thr Ala Ala Asn Ser Ser Ser Ser
                85                  90                  95

Ser Gln Gln Val Phe Glu Phe Glu Tyr Leu Asp Asp Ser Val Leu Asp
                100                 105                 110

Glu Leu Leu Glu Tyr Gly Glu Asn Tyr Asn Lys Thr His Asn Ile Asn
                115                 120                 125

Met Gly Lys Arg Gln
    130

<210> SEQ ID NO 39
<211> LENGTH: 357
<212> TYPE: PRT
<213> ORGANISM: Arabidopsis thaliana

<400> SEQUENCE: 39

Met Val Ile Tyr His Arg Lys Val Val Phe Thr Tyr Val Arg Ala Lys
1               5                   10                  15

Arg Phe Tyr His Phe Leu Asn Ile Glu Met Val Thr Asp Phe Lys Ser
                20                  25                  30

Leu Leu Pro Val Ile Asp Ile Ser Pro Leu Leu Ala Lys Cys Asp Asp
                35                  40                  45

Phe Asp Met Ala Glu Asp Ala Gly Val Val Glu Val Val Gly Lys Leu
    50                  55                  60

Asp Arg Ala Cys Arg Asp Val Gly Phe Phe Tyr Val Ile Gly His Gly
65                  70                  75                  80

Ile Ser Asp Asp Leu Ile Asn Lys Val Lys Glu Met Thr His Gln Phe
                85                  90                  95

Phe Glu Leu Pro Tyr Glu Glu Lys Leu Lys Ile Lys Ile Thr Pro Thr
                100                 105                 110

Ala Gly Tyr Arg Gly Tyr Gln Arg Ile Gly Val Asn Phe Thr Ser Gly
                115                 120                 125

Lys Gln Asp Met His Glu Ala Ile Asp Cys Tyr Arg Glu Phe Lys Gln
    130                 135                 140

Gly Lys His Gly Asp Ile Gly Lys Val Leu Glu Gly Pro Asn Gln Trp
145                 150                 155                 160
```

Pro Gly Asn Pro Gln Glu Tyr Lys Asp Leu Met Glu Lys Tyr Ile Lys
            165                 170                 175

Leu Cys Thr Asp Leu Ser Arg Asn Ile Leu Arg Gly Ile Ser Leu Ala
        180                 185                 190

Leu Gly Gly Ser Pro Tyr Glu Phe Glu Gly Lys Met Leu Arg Asp Pro
    195                 200                 205

Phe Trp Val Met Arg Ile Ile Gly Tyr Pro Gly Val Asn Gln Glu Asn
210                 215                 220

Val Ile Gly Cys Gly Ala His Thr Asp Tyr Gly Leu Leu Thr Leu Ile
225                 230                 235                 240

Asn Gln Asp Asp Lys Thr Ala Leu Gln Val Lys Asn Val Asp Gly
                245                 250                 255

Asp Trp Ile Pro Ala Ile Pro Ile Pro Gly Ser Phe Ile Cys Asn Ile
            260                 265                 270

Gly Asp Met Leu Thr Ile Leu Ser Asn Gly Val Tyr Gln Ser Thr Leu
        275                 280                 285

His Lys Val Ile Asn Asn Ser Pro Lys Tyr Arg Val Cys Val Ala Phe
    290                 295                 300

Phe Tyr Glu Thr Asn Phe Glu Ala Glu Val Glu Pro Leu Asp Ile Phe
305                 310                 315                 320

Lys Glu Lys His Pro Arg Lys Glu Thr Ser Gln Val Ala Lys Arg Val
                325                 330                 335

Val Tyr Gly Gln His Leu Ile Asn Lys Val Leu Thr Thr Phe Ala Asn
            340                 345                 350

Leu Val Glu Asn Ser
        355

<210> SEQ ID NO 40
<211> LENGTH: 371
<212> TYPE: PRT
<213> ORGANISM: Arabidopsis thaliana

<400> SEQUENCE: 40

Met Pro Val Leu Phe Ser Ser Arg Ser Leu Ile Leu Ser Ile Ile Val
1               5                   10                  15

Pro Leu Leu Ile Ser Ile Ala Leu Tyr Lys Leu Asp Thr Phe Asp Pro
            20                  25                  30

Ala Ile Val Pro Ser Asp Ala Phe Thr Ser Ser Ala Thr Ser Leu Pro
        35                  40                  45

Pro Leu Ile Asn Asp Glu Phe Leu Thr Gly Ala Glu Phe Ile Gly Val
    50                  55                  60

Gly Leu Leu Asn Ile Pro Glu Asp Ile Ala Tyr His Lys Glu Ser Asn
65                  70                  75                  80

Leu Ile Tyr Thr Gly Cys Val Asp Gly Trp Val Lys Arg Val Lys Val
            85                  90                  95

Ala Asp Ser Val Asn Asp Ser Val Val Glu Asp Trp Val Asn Thr Gly
                100                 105                 110

Gly Arg Pro Leu Gly Ile Ala Phe Gly Ile His Gly Glu Val Ile Val
            115                 120                 125

Ala Asp Val His Lys Gly Leu Leu Asn Ile Ser Gly Asp Gly Lys Lys
        130                 135                 140

Thr Glu Leu Leu Thr Asp Glu Ala Asp Gly Val Lys Phe Lys Leu Thr
145                 150                 155                 160

Asp Ala Val Thr Val Ala Asp Asn Gly Val Leu Tyr Phe Thr Asp Ala
                165                 170                 175

```
Ser Tyr Lys Tyr Thr Leu Asn Gln Leu Ser Leu Asp Met Leu Glu Gly
            180                 185                 190

Lys Pro Phe Gly Arg Leu Leu Ser Phe Asp Pro Thr Thr Arg Val Thr
        195                 200                 205

Lys Val Leu Leu Lys Asp Leu Tyr Phe Ala Asn Gly Ile Thr Ile Ser
    210                 215                 220

Pro Asp Gln Thr His Leu Ile Phe Cys Glu Thr Pro Met Lys Arg Cys
225                 230                 235                 240

Ser Lys Tyr Tyr Ile Ser Glu Glu Arg Val Glu Val Phe Thr Gln Ser
                245                 250                 255

Leu Pro Gly Tyr Pro Asp Asn Ile Arg Tyr Asp Gly Asp Gly His Tyr
            260                 265                 270

Trp Ile Ala Leu Pro Ser Gly Val Thr Thr Leu Trp Asn Ile Ser Leu
        275                 280                 285

Lys Tyr Pro Phe Leu Arg Lys Leu Thr Ala Met Val Ala Lys Tyr Gly
    290                 295                 300

Val Asp Leu Met Phe Met Glu Asn Ala Gly Val Leu Gln Val Asp Leu
305                 310                 315                 320

Asp Gly Asn Pro Ile Ala Tyr Tyr His Asp Pro Lys Leu Ser His Ile
                325                 330                 335

Ala Thr Cys Asp Lys Ile Gly Lys Tyr Leu Tyr Cys Gly Ser Leu Ser
            340                 345                 350

Gln Ser His Ile Leu Arg Leu Asp Leu Leu Lys Tyr Pro Ala Gln Asn
        355                 360                 365

Lys Lys Leu
    370

<210> SEQ ID NO 41
<211> LENGTH: 468
<212> TYPE: PRT
<213> ORGANISM: Arabidopsis thaliana

<400> SEQUENCE: 41

Met Gly Arg Val Arg Lys Ser Asp Phe Gly Ser Ile Val Leu Val Leu
1               5                   10                  15

Cys Cys Val Leu Asn Ser Leu Leu Cys Asn Gly Gly Ile Thr Ser Arg
            20                  25                  30

Tyr Val Arg Lys Leu Glu Ala Thr Val Asp Met Pro Leu Asp Ser Asp
        35                  40                  45

Val Phe Arg Val Pro Cys Gly Tyr Asn Ala Pro Gln Gln Val His Ile
    50                  55                  60

Thr Gln Gly Asp Val Glu Gly Lys Ala Val Ile Val Ser Trp Val Thr
65                  70                  75                  80

Gln Glu Ala Lys Gly Ser Asn Lys Val Ile Tyr Trp Lys Glu Asn Ser
                85                  90                  95

Thr Lys Lys His Lys Ala His Gly Lys Thr Asn Thr Tyr Lys Phe Tyr
            100                 105                 110

Asn Tyr Thr Ser Gly Phe Ile His His Cys Pro Ile Arg Asn Leu Glu
        115                 120                 125

Tyr Asp Thr Lys Tyr Tyr Val Leu Gly Val Gly Gln Thr Glu Arg
    130                 135                 140

Lys Phe Trp Phe Phe Thr Pro Pro Glu Ile Gly Pro Asp Val Pro Tyr
145                 150                 155                 160

Thr Phe Gly Leu Ile Gly Asp Leu Gly Gln Ser Tyr Asp Ser Asn Ile
```

```
            165                 170                 175
Thr Leu Thr His Tyr Glu Asn Asn Pro Thr Lys Gly Gln Ala Val Leu
        180                 185                 190

Phe Val Gly Asp Ile Ser Tyr Ala Asp Thr Tyr Pro Asp His Asp Asn
        195                 200                 205

Arg Arg Trp Asp Ser Trp Gly Arg Phe Ala Glu Arg Ser Thr Ala Tyr
210                 215                 220

Gln Pro Trp Ile Trp Thr Thr Gly Asn His Glu Leu Asp Phe Ala Pro
225                 230                 235                 240

Glu Ile Gly Glu Asn Arg Pro Phe Lys Pro Phe Thr His Arg Tyr Arg
                245                 250                 255

Thr Pro Tyr Arg Ser Ser Gly Ser Thr Glu Pro Phe Trp Tyr Ser Ile
                260                 265                 270

Lys Arg Gly Pro Ala Tyr Ile Ile Val Leu Ala Ser Tyr Ser Ala Tyr
                275                 280                 285

Gly Lys Tyr Thr Pro Gln Tyr Gln Trp Leu Glu Glu Phe Pro Lys
        290                 295                 300

Val Asn Arg Thr Glu Thr Pro Trp Leu Ile Val Leu Met His Ser Pro
305                 310                 315                 320

Trp Tyr Asn Ser Tyr Asp Tyr His Tyr Met Glu Gly Glu Thr Met Arg
                325                 330                 335

Val Met Tyr Glu Ala Trp Phe Val Lys Tyr Lys Val Asp Val Val Phe
                340                 345                 350

Ala Gly His Val His Ala Tyr Glu Arg Ser Glu Arg Val Ser Asn Ile
                355                 360                 365

Ala Tyr Asn Val Val Asn Gly Ile Cys Thr Pro Val Lys Asp Gln Ser
        370                 375                 380

Ala Pro Val Tyr Ile Thr Ile Gly Asp Gly Gly Asn Ile Glu Gly Leu
385                 390                 395                 400

Ala Thr Lys Met Thr Glu Pro Gln Pro Lys Tyr Ser Ala Phe Arg Glu
                405                 410                 415

Ala Ser Phe Gly His Ala Ile Phe Ser Ile Lys Asn Arg Thr His Ala
                420                 425                 430

His Tyr Gly Trp His Arg Asn His Asp Gly Tyr Ala Val Glu Gly Asp
        435                 440                 445

Arg Met Trp Phe Tyr Asn Arg Phe Trp His Pro Val Asp Asp Ser Pro
    450                 455                 460

Ser Cys Asn Ser
465

<210> SEQ ID NO 42
<211> LENGTH: 499
<212> TYPE: PRT
<213> ORGANISM: Arabidopsis thaliana

<400> SEQUENCE: 42

Met Leu Leu Lys Pro Gly Asn Lys Leu Val Ser Pro Glu Thr Ser His
1               5                   10                  15

His Arg Asp Ser Ala Ser Asn Ser Ser Asn His Lys Cys Gln Gln Gln
            20                  25                  30

Lys Pro Arg Lys Asp Lys Gln Lys Val Glu Gln Asn Thr Lys Lys
        35                  40                  45

Ile Glu Glu His Gln Ile Lys Ser Glu Ser Thr Leu Leu Ile Ser Asn
50                  55                  60
```

-continued

His Asn Val Asn Met Ser Ser Gln Ser Asn Ser Glu Ser Thr Ser
 65                  70                  75                  80

Thr Asn Asn Ser Ser Lys Pro His Thr Gly Gly Asp Ile Arg Trp Asp
                 85                  90                  95

Ala Val Asn Ser Leu Lys Ser Arg Gly Ile Lys Leu Gly Ile Ser Asp
            100                 105                 110

Phe Arg Val Leu Lys Arg Leu Gly Tyr Gly Asp Ile Gly Ser Val Tyr
        115                 120                 125

Leu Val Glu Leu Lys Gly Ala Asn Pro Thr Thr Tyr Phe Ala Met Lys
    130                 135                 140

Val Met Asp Lys Ala Ser Leu Val Ser Arg Asn Lys Leu Leu Arg Ala
145                 150                 155                 160

Gln Thr Glu Arg Glu Ile Leu Ser Gln Leu Asp His Pro Phe Leu Pro
                165                 170                 175

Thr Leu Tyr Ser His Phe Glu Thr Asp Lys Phe Tyr Cys Leu Val Met
            180                 185                 190

Glu Phe Cys Ser Gly Gly Asn Leu Tyr Ser Leu Arg Gln Lys Gln Pro
        195                 200                 205

Asn Lys Cys Phe Thr Glu Asp Ala Ala Arg Phe Phe Ala Ser Glu Val
    210                 215                 220

Leu Leu Ala Leu Glu Tyr Leu His Met Leu Gly Ile Val Tyr Arg Asp
225                 230                 235                 240

Leu Lys Pro Glu Asn Val Leu Val Arg Asp Asp Gly His Ile Met Leu
                245                 250                 255

Ser Asp Phe Asp Leu Ser Leu Arg Cys Ser Val Asn Pro Thr Leu Val
            260                 265                 270

Lys Ser Phe Asn Gly Gly Gly Thr Thr Gly Ile Ile Asp Asp Asn Ala
        275                 280                 285

Ala Val Gln Gly Cys Tyr Gln Pro Ser Ala Phe Phe Pro Arg Met Leu
    290                 295                 300

Gln Ser Ser Lys Lys Asn Arg Lys Ser Lys Ser Asp Phe Asp Gly Ser
305                 310                 315                 320

Leu Pro Glu Leu Met Ala Glu Pro Thr Asn Val Lys Ser Met Ser Phe
                325                 330                 335

Val Gly Thr His Glu Tyr Leu Ala Pro Glu Ile Ile Lys Asn Glu Gly
            340                 345                 350

His Gly Ser Ala Val Asp Trp Trp Thr Phe Gly Ile Phe Ile Tyr Glu
        355                 360                 365

Leu Leu His Gly Ala Thr Pro Phe Lys Gly Gln Gly Asn Lys Ala Thr
    370                 375                 380

Leu Tyr Asn Val Ile Gly Gln Pro Leu Arg Phe Pro Glu Tyr Ser Gln
385                 390                 395                 400

Val Ser Ser Thr Ala Lys Asp Leu Ile Lys Gly Leu Leu Val Lys Glu
                405                 410                 415

Pro Gln Asn Arg Ile Ala Tyr Lys Arg Gly Ala Thr Glu Ile Lys Gln
            420                 425                 430

His Pro Phe Phe Glu Gly Val Asn Trp Ala Leu Ile Arg Gly Glu Thr
        435                 440                 445

Pro Pro His Leu Pro Glu Pro Val Asp Phe Ser Cys Tyr Val Lys Lys
    450                 455                 460

Glu Lys Glu Ser Leu Pro Pro Ala Ala Thr Glu Lys Lys Ser Lys Met
465                 470                 475                 480

Phe Asp Glu Ala Asn Lys Ser Gly Ser Asp Pro Asp Tyr Ile Val Phe

```
                      485                 490                 495

Glu Tyr Phe

<210> SEQ ID NO 43
<211> LENGTH: 1552
<212> TYPE: PRT
<213> ORGANISM: Chlamydomonas reinhardtii

<400> SEQUENCE: 43

Met Glu Ala Val Ala Thr Val Val Ala Asn Glu Pro Lys Val Ala Asp
1               5                   10                  15

Met Glu Glu Ile Leu Ala Glu Arg Asp Ala Cys Gly Val Gly Phe Ile
                20                  25                  30

Ala Asn Leu Lys Asn Val Gln Ser His Thr Val Val Lys Gln Ala Leu
            35                  40                  45

Thr Ala Leu Gly Cys Met Glu His Arg Gly Ala Cys Ser Ala Asp Asp
        50                  55                  60

Asp Ser Gly Asp Gly Ala Gly Leu Met Thr Gln Ile Pro Trp Lys Leu
65                  70                  75                  80

Leu Lys Lys Glu Met Pro Ala Leu Asn Glu Thr Thr Gly Val Gly
                85                  90                  95

Met Val Phe Met Pro Asn Asp Asp Ala Leu Glu Ala Gln Cys Lys Gln
                100                 105                 110

Ile Leu Glu Gln Val Cys Ala Lys Glu Gly Val Lys Val Val Gly Trp
            115                 120                 125

Arg Lys Val Pro Val Asn His Asp Ile Val Gly Arg Phe Ala Lys Val
        130                 135                 140

Thr Glu Pro Arg Ile Trp Gln Val Leu Ile Glu Gly Lys Ser Gly Gln
145                 150                 155                 160

Val Gly Asp Glu Leu Glu Arg Glu Leu Phe Leu Val Arg Lys Leu Val
                165                 170                 175

Glu Lys Ala Lys Asn Ala Ala Leu Pro Ala Glu Phe Ala Pro Asp Phe
                180                 185                 190

Tyr Ile Cys Thr Leu Ser Ser Arg Thr Ile Val Tyr Lys Gly Met Leu
            195                 200                 205

Arg Ser Ala Val Val Gly Thr Phe Phe Arg Asp Leu Glu Asn Pro Asp
        210                 215                 220

Phe Glu Ser Ala Phe Ala Ile Tyr His Arg Arg Phe Ser Thr Asn Thr
225                 230                 235                 240

Thr Pro Lys Trp Pro Leu Ala Gln Pro Met Arg Val Leu Gly His Asn
                245                 250                 255

Gly Glu Ile Asn Thr Leu Gln Gly Asn Leu Asn Trp Val Ala Ser Arg
                260                 265                 270

Glu His Glu Leu Ser Asn Pro Ile Trp Lys Gly Arg Glu Ala Glu Leu
            275                 280                 285

Thr Pro Leu Cys Asn Ala Ala Gln Ser Asp Ser Ala Asn Leu Asp Asn
        290                 295                 300

Val Ala Glu Leu Leu Val Arg Thr Gly Thr Asp Pro Gln Asp Ala Leu
305                 310                 315                 320

Met Leu Leu Val Pro Glu Ala Tyr Arg Asn His Pro Asp Leu Met Lys
                325                 330                 335

Glu Tyr Pro Glu Val Val Asp Phe Tyr Glu Phe Tyr Glu Gly Leu Gln
                340                 345                 350

Glu Gly Trp Asp Gly Pro Ala Leu Leu Val Phe Ser Asp Gly Lys Arg
```

```
                355                 360                 365
Val Gly Ala Arg Leu Asp Arg Asn Gly Leu Arg Pro Ala Arg Phe Trp
370                 375                 380

Gln Thr Lys Asp Asp Met Ile Tyr Val Ala Ser Glu Val Gly Val Leu
385                 390                 395                 400

Gly Asp Ala Ile Thr Asn Ala Glu Asn Ile Val Ala Lys Gly Arg Leu
                405                 410                 415

Gly Pro Gly Gln Met Val Cys Ala Asp Leu Glu Lys Gly Ile Phe Ser
                420                 425                 430

Glu Thr Ser Ala Ile Ser Lys Leu Val Ala Gly Arg Lys Pro Tyr Lys
                435                 440                 445

Glu Trp Leu Ala Ala Ser Leu Arg Arg Leu Thr Asp Leu Gly Glu Ser
                450                 455                 460

Thr Phe Leu Asn Glu Pro Met Tyr Asp Ala Ala Thr Met Leu Arg Leu
465                 470                 475                 480

Gln Ser Ala Ile Gly Met Asp Ala Glu Asn Ala Gln Met Val Val Glu
                485                 490                 495

Ser Gln Ala Gln Thr Gly Val Glu Pro Thr Tyr Cys Met Gly Asp Asp
                500                 505                 510

Ile Pro Leu Ala Val Leu Ser Asp Lys Pro His Met Leu Tyr Asp Tyr
                515                 520                 525

Phe Lys Gln Arg Phe Ala Gln Val Thr Asn Pro Pro Ile Asp Pro Leu
530                 535                 540

Arg Glu Gly Leu Val Met Ser Leu Glu Met Arg Leu Gly Ala Arg Gly
545                 550                 555                 560

Asn Leu Leu Asn Pro Gly Ala Asp Ser Tyr Lys Gln Val Leu Leu Asp
                565                 570                 575

Ser Pro Ile Leu Leu Glu Ser Glu Met Gln Ala Ile Ser Thr Asp Lys
                580                 585                 590

Val Leu Gly Ser Lys Thr Phe Lys Leu Phe Phe Glu Ala Gly Lys Pro
                595                 600                 605

Gly Ala Met Glu Ala Ala Leu Lys Lys Leu Cys Ser Asp Val Glu Ala
                610                 615                 620

Ala Val Lys Ala Gly Cys Gln Cys Val Val Leu Ser Asp Arg Pro Asp
625                 630                 635                 640

Gly Gly Met Asp Ala Gly Lys Ala Pro Ile Pro Ala Leu Leu Ala Thr
                645                 650                 655

Gly Ala Val His His His Leu Ile Arg Thr Ser Leu Arg Ser Asp Thr
                660                 665                 670

Ser Ile Val Val Asp Thr Ala Thr Cys Tyr Ser Thr His His Ala Ala
                675                 680                 685

Met Leu Ile Gly Phe Gly Ala His Ala Ile Cys Pro Tyr Leu Gly Tyr
                690                 695                 700

Glu Thr Ser Arg Gln Trp Arg Leu Ser Ala Arg Thr Gln Ser Leu Ile
705                 710                 715                 720

Lys Ala Gly Lys Val Pro Asp Ile Ser Val Lys Val Ala Gln Lys Asn
                725                 730                 735

Phe Lys Lys Ser Leu Glu Lys Gly Val Leu Lys Ile Leu Ser Lys Met
                740                 745                 750

Gly Ile Ser Leu Leu Ser Cys Tyr His Gly Ala Gln Ile Phe Glu Ala
                755                 760                 765

Tyr Gly Leu Gly Lys Asp Val Met Asp Met Cys Phe Lys Gly Thr Val
                770                 775                 780
```

-continued

```
Ser Arg Ile Gly Gly Met Ser Leu Ala Asp Leu Gln Arg Glu Ser Glu
785                 790                 795                 800

Ser Leu Trp Ala Lys Gly Phe Pro Glu Lys Ala Met Thr Lys Leu Glu
            805                 810                 815

Asp Tyr Gly Phe Ile Gln Ser Lys Pro Lys Gly Glu Phe His Ser Asn
        820                 825                 830

Asn Gln Thr Met Ala Lys Leu Leu His Lys Ala Ile Gly Leu Gly Asn
    835                 840                 845

Gly Ser Ala Ala Asp Lys Asp Ala Tyr Lys Ala Tyr Gln Gln His Phe
850                 855                 860

Ala Asp Ser Pro Val Ala Val Leu Arg Asp Cys Leu Glu Phe Lys Ser
865                 870                 875                 880

Asp Arg Gly Pro Ile Ser Ile Asp Gln Val Glu Pro Ala Ala Ile
            885                 890                 895

Met Glu Arg Phe Cys Thr Gly Gly Met Ser Leu Gly Ala Ile Ser Arg
            900                 905                 910

Glu Thr His Glu Thr Ile Ala Ile Ala Met Asn Arg Ile Gly Gly Lys
            915                 920                 925

Ser Asn Ser Gly Glu Gly Gly Glu Asp Pro Ile Arg Trp Leu His Leu
930                 935                 940

Ser Asp Val Asp Gly Glu Gly Lys Ser Ala Thr Ala Ser Tyr Leu Arg
945                 950                 955                 960

Gly Leu Arg Asn Gly Asp Thr Ala Thr Ser Lys Ile Lys Gln Val Ala
                965                 970                 975

Ser Gly Arg Phe Gly Val Thr Pro Glu Tyr Ile Met Asn Ala Glu Gln
            980                 985                 990

Met Glu Ile Lys Ile Ala Gln Gly Ala Lys Pro Gly Glu Gly Gly Gln
            995                 1000                1005

Leu Pro Gly Gln Lys Val Ser Pro Tyr Ile Ala Gln Leu Arg Arg
    1010                1015                1020

Ser Lys Pro Gly Val Pro Leu Ile Ser Pro Pro His His Asp
    1025                1030                1035

Ile Tyr Ser Ile Glu Asp Leu Ala Gln Leu Ile Tyr Asp Leu His
    1040                1045                1050

Gln Val Asn Pro Arg Ala Lys Val Ser Val Lys Leu Val Ala Glu
    1055                1060                1065

Ala Gly Ile Gly Val Val Ala Ser Gly Val Ala Lys Ala Asn Ala
    1070                1075                1080

Asp Ile Ile Gln Val Ser Gly His Asp Gly Gly Thr Gly Ala Ser
    1085                1090                1095

Pro Ile Ser Ser Ile Lys His Ala Gly Gly Pro Met Glu Met Gly
    1100                1105                1110

Leu Ala Glu Thr His Gln Thr Leu Val Arg Asn Glu Leu Arg Glu
    1115                1120                1125

Arg Val Val Leu Arg Val Asp Gly Gly Val Arg Asn Gly Arg Asp
    1130                1135                1140

Val Leu Met Gly Ala Leu Met Gly Ala Asp Glu Phe Gly Phe Gly
    1145                1150                1155

Thr Val Ala Met Ile Ala Thr Gly Cys Ile Met Ala Arg Val Cys
    1160                1165                1170

His Thr Asn Asn Cys Pro Val Gly Val Ala Ser Gln Arg Glu Glu
    1175                1180                1185
```

```
Leu Arg Ala Arg Phe Pro Gly Ala Pro Glu Asp Leu Val Asn Tyr
1190            1195            1200

Phe His Phe Val Ala Glu Glu Val Arg Ala Glu Leu Ala Asn Met
1205            1210            1215

Gly Tyr Arg Ser Leu Asp Glu Val Ile Gly Arg Ala Asp Leu Leu
1220            1225            1230

Lys Gln Arg Ser Val Lys Leu Ala Lys Thr Glu Gly Leu Asp Leu
1235            1240            1245

Ser Phe Leu Thr Thr Phe Ala Gly Ala Ser Gly Lys Ser Ser Thr
1250            1255            1260

Arg Arg Ala Gln Glu Val His Asp Asn Gly Pro Gln Leu Asp Asp
1265            1270            1275

Arg Ile Leu Ala Glu Pro Glu Val Met Ala Ala Ile Lys Asp His
1280            1285            1290

Lys Thr Val Ser Lys Ala Phe Glu Ile Val Asn Val Asp Arg Ser
1295            1300            1305

Ser Leu Gly Arg Val Ala Gly Val Ile Ala Lys His His Gly Asp
1310            1315            1320

Ser Gly Phe Gln Gly Lys Val Lys Leu Thr Leu Thr Gly Ser Gly
1325            1330            1335

Gly Gln Ser Phe Gly Cys Phe Cys Val Lys Gly Leu Glu Val Lys
1340            1345            1350

Leu Val Gly Glu Ala Asn Asp Tyr Val Gly Lys Gly Met Asn Gly
1355            1360            1365

Gly Glu Ile Ala Ile Val Pro Pro Ala Asn Ser Pro Phe Lys Pro
1370            1375            1380

Glu Glu Ala Ser Leu Val Gly Asn Thr Cys Leu Tyr Gly Ala Thr
1385            1390            1395

Gly Gly Arg Leu Phe Val Asn Gly Arg Ala Gly Glu Arg Phe Ala
1400            1405            1410

Val Arg Asn Ser Leu Ala Glu Ala Val Val Glu Gly Ala Gly Asp
1415            1420            1425

His Cys Cys Glu Tyr Met Thr Gly Gly Cys Val Ile Val Leu Gly
1430            1435            1440

Ser Val Gly Arg Asn Val Ala Ala Gly Met Thr Gly Gly Leu Gly
1445            1450            1455

Tyr Phe Leu Asp Glu Asp Gly Ser Phe Thr Asp Lys Val Asn Thr
1460            1465            1470

Glu Ile Val Ser Val Gln Arg Val Ile Thr Lys Ala Gly Glu Ala
1475            1480            1485

Gln Leu Arg Gly Leu Leu Glu Ala His Val Ala His Thr Gly Ser
1490            1495            1500

Ala Lys Ala Lys Ser Leu Leu Ala Asn Trp Glu Ala Ser Leu Gly
1505            1510            1515

Lys Phe Trp Gln Leu Val Pro Pro Ala Glu Lys Asn Thr Ala Glu
1520            1525            1530

Val Asn Pro Ser Val Ala Gln Pro Ala Ala Gly Ala Lys Val
1535            1540            1545

Ala Val Ser Ala
1550

<210> SEQ ID NO 44
<211> LENGTH: 449
<212> TYPE: PRT
```

<213> ORGANISM: Artificial Sequence
<220> FEATURE:
<223> OTHER INFORMATION: Chlorella sorokiniana NADP-specific glutamate
    dehydrogenase (NADP-GDH), N terminus residues 1 to 74 truncated

<400> SEQUENCE: 44

```
Met His Gly Ile Lys Asn Pro Glu Leu Arg Gln Leu Leu Thr Glu Ile
1               5                   10                  15

Phe Met Lys Asp Pro Glu Gln Gln Phe Met Gln Ala Val Arg Glu
            20                  25                  30

Val Ala Val Ser Leu Gln Pro Val Phe Glu Lys Arg Pro Glu Leu Leu
            35                  40                  45

Pro Ile Phe Lys Gln Ile Val Glu Pro Glu Arg Val Ile Thr Phe Arg
50                  55                  60

Val Ser Trp Leu Asp Asp Ala Gly Asn Leu Gln Val Asn Arg Gly Phe
65                  70                  75                  80

Arg Val Gln Tyr Ser Ser Ala Ile Gly Pro Tyr Lys Gly Gly Leu Arg
                85                  90                  95

Phe His Pro Ser Val Asn Leu Ser Ile Met Lys Phe Leu Ala Phe Glu
                100                 105                 110

Gln Ile Phe Lys Asn Ser Leu Thr Thr Leu Pro Met Gly Gly Gly Lys
            115                 120                 125

Gly Gly Ser Asp Phe Asp Pro Lys Gly Lys Ser Asp Ala Glu Val Met
130                 135                 140

Arg Phe Cys Gln Ser Phe Met Thr Glu Leu Gln Arg His Ile Ser Tyr
145                 150                 155                 160

Val Gln Asp Val Pro Ala Gly Asp Ile Gly Val Gly Ala Arg Glu Ile
                165                 170                 175

Gly Tyr Leu Phe Gly Gln Tyr Lys Arg Ile Thr Lys Asn Tyr Thr Gly
            180                 185                 190

Val Leu Thr Gly Lys Gly Gln Glu Tyr Gly Gly Ser Glu Ile Arg Pro
            195                 200                 205

Glu Ala Thr Gly Tyr Gly Ala Val Leu Phe Val Glu Asn Val Leu Lys
210                 215                 220

Asp Lys Gly Glu Ser Leu Lys Gly Lys Arg Cys Leu Val Ser Gly Ala
225                 230                 235                 240

Gly Asn Val Ala Gln Tyr Cys Ala Glu Leu Leu Leu Glu Lys Gly Ala
                245                 250                 255

Ile Val Leu Ser Leu Ser Asp Ser Gln Gly Tyr Val Tyr Glu Pro Asn
            260                 265                 270

Gly Phe Thr Arg Glu Gln Leu Gln Ala Val Gln Asp Met Lys Lys Lys
            275                 280                 285

Asn Asn Ser Ala Arg Ile Ser Glu Tyr Lys Ser Asp Thr Ala Val Tyr
290                 295                 300

Val Gly Asp Arg Arg Lys Pro Trp Glu Leu Asp Cys Gln Val Asp Ile
305                 310                 315                 320

Ala Phe Pro Cys Ala Thr Gln Asn Glu Ile Asp Glu His Asp Ala Glu
                325                 330                 335

Leu Leu Ile Lys His Gly Cys Gln Tyr Val Val Glu Gly Ala Asn Met
            340                 345                 350

Pro Ser Thr Asn Glu Ala Ile His Lys Tyr Asn Lys Ala Gly Ile Ile
            355                 360                 365

Tyr Cys Pro Gly Lys Ala Ala Asn Ala Gly Gly Val Ala Val Ser Gly
370                 375                 380
```

```
Leu Glu Met Thr Gln Asn Arg Met Ser Leu Asn Trp Thr Arg Glu Glu
385                 390                 395                 400

Val Arg Asp Lys Leu Glu Arg Ile Met Lys Asp Ile Tyr Asp Ser Ala
                405                 410                 415

Met Gly Ala Ser Arg Glu Tyr Asn Val Asp Leu Ala Ala Gly Ala Asn
            420                 425                 430

Ile Ala Gly Phe Thr Lys Val Ala Asp Ala Val Lys Ala Gln Gly Ala
        435                 440                 445

Val

<210> SEQ ID NO 45
<211> LENGTH: 447
<212> TYPE: PRT
<213> ORGANISM: Escherichia coli

<400> SEQUENCE: 45

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
                100                 105                 110

Gln Thr Phe Lys Asn Ala Leu Thr Thr Leu Pro Met Gly Gly Gly Lys
            115                 120                 125

Gly Gly Ser Asp Phe Asp Pro Lys Gly Lys Ser Glu Gly Glu Val Met
130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
290                 295                 300
```

```
Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
            325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
            355                 360                 365

Gly Lys Ala Ala Asn Ala Gly Val Ala Thr Ser Gly Leu Glu Met
370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
            435                 440                 445

<210> SEQ ID NO 46
<211> LENGTH: 286
<212> TYPE: PRT
<213> ORGANISM: Artificial Sequence
<220> FEATURE:
<223> OTHER INFORMATION: Homeobox fusion protein, Arabidopsis HB-17 N
      terminus residues 1 to 91 fused to soybean HB-17 C terminus
      residues 20-213
<220> FEATURE:
<221> NAME/KEY: MUTAGEN
<222> LOCATION: (1)..(91)
<223> OTHER INFORMATION: source: Arabidopsis HB-17 N terminus residues 1
      to 91
<220> FEATURE:
<221> NAME/KEY: MUTAGEN
<222> LOCATION: (92)..(286)
<223> OTHER INFORMATION: source: soybean HB-17 C terminus residues
      20-213

<400> SEQUENCE: 46

Met Ile Lys Leu Leu Phe Thr Tyr Ile Cys Thr Tyr Thr Tyr Lys Leu
1               5                   10                  15

Tyr Ala Leu Tyr His Met Asp Tyr Ala Cys Val Cys Met Tyr Lys Tyr
            20                  25                  30

Lys Gly Ile Val Thr Leu Gln Val Cys Leu Phe Tyr Ile Lys Leu Arg
            35                  40                  45

Val Phe Leu Ser Asn Phe Thr Phe Ser Ser Ser Ile Leu Ala Leu Lys
50                  55                  60

Asn Pro Asn Asn Ser Leu Ile Lys Ile Met Ala Ile Leu Pro Glu Asn
65                  70                  75                  80

Ser Ser Asn Leu Asp Leu Thr Ile Ser Val Pro Gly Phe Ala Ser Ser
            85                  90                  95

Pro Thr Leu Leu Pro Ser Ser Val Lys Glu Leu Asp Ile Asn Gln
            100                 105                 110

Val Pro Leu Glu Glu Asp Trp Met Ala Ser Asn Met Glu Asp Glu Glu
            115                 120                 125

Glu Ser Ser Asn Gly Glu Pro Pro Arg Lys Lys Leu Arg Leu Thr Lys
            130                 135                 140

Glu Gln Ser Leu Leu Leu Glu Glu Ser Phe Arg Gln Asn His Thr Leu
145                 150                 155                 160
```

```
Asn Pro Lys Gln Lys Glu Ser Leu Ala Met Gln Leu Lys Leu Arg Pro
                165                 170                 175

Arg Gln Val Glu Val Trp Phe Gln Asn Arg Arg Ala Arg Ser Lys Leu
            180                 185                 190

Lys Gln Thr Glu Met Glu Cys Glu Tyr Leu Lys Arg Trp Phe Gly Ser
        195                 200                 205

Leu Thr Glu Gln Asn Arg Arg Leu Gln Arg Glu Val Glu Glu Leu Arg
    210                 215                 220

Ala Ile Lys Val Gly Pro Thr Val Ile Ser Pro His Ser Cys Glu
225                 230                 235                 240

Pro Leu Pro Ala Ser Thr Leu Ser Met Cys Pro Arg Cys Glu Arg Val
                245                 250                 255

Thr Ser Thr Ala Asp Lys Pro Pro Ser Ala Ala Thr Leu Ser Ala
            260                 265                 270

Lys Val Pro Pro Thr Gln Ser Arg Gln Pro Ser Ala Ala Cys
        275                 280                 285

<210> SEQ ID NO 47
<211> LENGTH: 345
<212> TYPE: PRT
<213> ORGANISM: Glycine max

<400> SEQUENCE: 47

Met Cys Gly Gly Ala Ile Ile Ser Asp Phe Ile Pro Ala Ala Ala Ile
1               5                   10                  15

Ala Gly Ser Arg Arg Leu Thr Ala Asp Tyr Leu Trp Pro Asp Leu Lys
            20                  25                  30

Lys Arg Lys Ser Asp Leu Asp Val Asp Phe Glu Ala Asp Phe Arg Asp
        35                  40                  45

Phe Lys Asp Asp Ser Asp Ile Asp Asp Asp Asp Asp His Gln Val
    50                  55                  60

Lys Pro Phe Ala Phe Ala Ala Ser Ser Arg Leu Ser Thr Ala Ala Lys
65                  70                  75                  80

Ser Val Ala Phe Gln Gly Arg Ala Glu Ile Ser Ala Asn Arg Lys Arg
                85                  90                  95

Lys Asn Gln Tyr Arg Gly Ile Arg Gln Arg Pro Trp Gly Lys Trp Ala
            100                 105                 110

Ala Glu Ile Arg Asp Pro Arg Lys Gly Val Arg Val Trp Leu Gly Thr
        115                 120                 125

Phe Asn Thr Ala Glu Glu Ala Ala Arg Ala Tyr Asp Ala Glu Ala Arg
    130                 135                 140

Arg Ile Arg Gly Lys Lys Ala Lys Val Asn Phe Pro Glu Ala Pro Gly
145                 150                 155                 160

Thr Ser Ser Val Lys Arg Ser Lys Val Asn Pro Gln Glu Asn Leu Lys
                165                 170                 175

Thr Val Gln Pro Asn Leu Gly His Lys Phe Ser Ala Gly Asn His
            180                 185                 190

Met Asp Leu Val Glu Gln Lys Pro Leu Val Ser Gln Tyr Ala Asn Met
        195                 200                 205

Ala Ser Phe Pro Gly Ser Gly Asn Gly Leu Arg Ser Leu Pro Ser Ser
    210                 215                 220

Asp Asp Ala Thr Leu Tyr Phe Ser Ser Asp Gln Gly Ser Asn Ser Phe
225                 230                 235                 240

Asp Tyr Ala Pro Glu Ile Ser Ser Met Leu Ser Ala Pro Leu Asp Cys
                245                 250                 255
```

```
Glu Ser His Phe Val Gln Asn Ala Asn Gln Gln Gln Pro Asn Ser Gln
            260                 265                 270

Asn Val Val Ser Ile Glu Asp Ser Ala Lys Thr Leu Ser Glu Glu
            275                 280                 285

Leu Val Asp Ile Glu Ser Glu Leu Lys Phe Phe Gln Met Pro Tyr Leu
            290                 295                 300

Glu Gly Ser Trp Gly Asp Thr Ser Leu Glu Ser Leu Leu Ser Gly Asp
305                 310                 315                 320

Thr Thr Gln Asp Gly Gly Asn Leu Met Asn Leu Trp Cys Phe Asp Asp
            325                 330                 335

Ile Pro Ser Met Ala Gly Gly Val Phe
            340                 345

<210> SEQ ID NO 48
<211> LENGTH: 257
<212> TYPE: PRT
<213> ORGANISM: Oryza sativa

<400> SEQUENCE: 48

Met Ser Met Gly Pro Ala Ala Gly Glu Gly Cys Gly Leu Cys Gly Ala
1               5                   10                  15

Asp Gly Gly Gly Cys Cys Ser Arg His Arg His Asp Asp Asp Gly Phe
            20                  25                  30

Pro Phe Val Phe Pro Pro Ser Ala Cys Gln Gly Ile Gly Ala Pro Ala
            35                  40                  45

Pro Pro Val His Glu Phe Gln Phe Phe Gly Asn Asp Gly Gly Gly Asp
50                  55                  60

Asp Gly Glu Ser Val Ala Trp Leu Phe Asp Asp Tyr Pro Pro Pro Ser
65                  70                  75                  80

Pro Val Ala Ala Ala Ala Gly Met His His Arg Gln Pro Pro Tyr Asp
                85                  90                  95

Gly Val Val Ala Pro Pro Ser Leu Phe Arg Arg Asn Thr Gly Ala Gly
            100                 105                 110

Gly Leu Thr Phe Asp Val Ser Leu Gly Gly Arg Pro Asp Leu Asp Ala
            115                 120                 125

Gly Leu Gly Leu Gly Gly Ser Gly Arg His Ala Glu Ala Ala Ala
            130                 135                 140

Ser Ala Thr Ile Met Ser Tyr Cys Gly Ser Thr Phe Thr Asp Ala Ala
145                 150                 155                 160

Ser Ser Met Pro Lys Glu Met Val Ala Met Ala Asp Val Gly Glu
                165                 170                 175

Ser Leu Asn Pro Asn Thr Val Val Gly Ala Met Val Glu Arg Glu Ala
            180                 185                 190

Lys Leu Met Arg Tyr Lys Glu Lys Arg Lys Arg Cys Tyr Glu Lys
            195                 200                 205

Gln Ile Arg Tyr Ala Ser Arg Lys Ala Tyr Ala Glu Met Arg Pro Arg
            210                 215                 220

Val Arg Gly Arg Phe Ala Lys Glu Ala Asp Gln Glu Ala Val Ala Pro
225                 230                 235                 240

Pro Ser Thr Tyr Val Asp Pro Ser Arg Leu Glu Leu Gly Gln Trp Phe
            245                 250                 255

Arg

<210> SEQ ID NO 49
```

<211> LENGTH: 971
<212> TYPE: PRT
<213> ORGANISM: Zea mays

<400> SEQUENCE: 49

```
Met Ile Val Gln Pro Ile Glu Leu Arg Ala Trp Thr Ala Phe Pro Gly
1               5                   10                  15

Ser Ala Gln Glu Gly Ile Gly Arg Met Ala Ala Ser Val Ser Arg Ala
            20                  25                  30

Ile Cys Val Gln Lys Pro Gly Ser Lys Cys Thr Arg Asp Arg Glu Ala
        35                  40                  45

Thr Ser Phe Ala Arg Arg Ser Val Ala Ala Pro Arg Pro His Ala
    50                  55                  60

Lys Ala Ala Gly Val Ile Arg Ser Asp Ser Gly Ala Gly Arg Gly Gln
65                  70                  75                  80

His Cys Ser Pro Leu Arg Ala Val Val Asp Ala Ala Pro Ile Gln Thr
                85                  90                  95

Thr Lys Lys Arg Val Phe His Phe Gly Lys Gly Lys Ser Glu Gly Asn
            100                 105                 110

Lys Thr Met Lys Glu Leu Leu Gly Gly Lys Gly Ala Asn Leu Ala Glu
        115                 120                 125

Met Ala Ser Ile Gly Leu Ser Val Pro Pro Gly Phe Thr Val Ser Thr
    130                 135                 140

Glu Ala Cys Gln Gln Tyr Gln Asp Ala Gly Cys Ala Leu Pro Ala Gly
145                 150                 155                 160

Leu Trp Ala Glu Ile Val Asp Gly Leu Gln Trp Val Glu Glu Tyr Met
                165                 170                 175

Gly Ala Thr Leu Gly Asp Pro Gln Arg Pro Leu Leu Leu Ser Val Arg
            180                 185                 190

Ser Gly Ala Ala Val Ser Met Pro Gly Met Met Asp Thr Val Leu Asn
        195                 200                 205

Leu Gly Leu Asn Asp Glu Val Ala Ala Gly Leu Ala Ala Lys Ser Gly
    210                 215                 220

Glu Arg Phe Ala Tyr Asp Ser Phe Arg Arg Phe Leu Asp Met Phe Gly
225                 230                 235                 240

Asn Val Val Met Asp Ile Pro Arg Ser Leu Phe Glu Glu Lys Leu Glu
                245                 250                 255

His Met Lys Glu Ser Lys Gly Leu Lys Asn Asp Thr Asp Leu Thr Ala
            260                 265                 270

Ser Asp Leu Lys Glu Leu Val Gly Gln Tyr Lys Glu Val Tyr Leu Ser
        275                 280                 285

Ala Lys Gly Glu Pro Phe Pro Ser Asp Pro Lys Lys Gln Leu Glu Leu
    290                 295                 300

Ala Val Leu Ala Val Phe Asn Ser Trp Glu Ser Pro Arg Ala Lys Lys
305                 310                 315                 320

Tyr Arg Ser Ile Asn Gln Ile Thr Gly Leu Arg Gly Thr Ala Val Asn
                325                 330                 335

Val Gln Cys Met Val Phe Gly Asn Met Gly Asn Thr Ser Gly Thr Gly
            340                 345                 350

Val Leu Phe Thr Arg Asn Pro Asn Thr Gly Glu Lys Lys Leu Tyr Gly
        355                 360                 365

Glu Phe Leu Val Asn Ala Gln Gly Glu Asp Val Ala Gly Ile Arg
    370                 375                 380

Thr Pro Glu Asp Leu Asp Ala Met Lys Asn Leu Met Pro Gln Ala Tyr
```

```
           385                 390                 395                 400
Asp Glu Leu Val Glu Asn Cys Asn Ile Leu Glu Ser His Tyr Lys Glu
                    405                 410                 415

Met Gln Asp Ile Glu Phe Thr Val Gln Glu Asn Arg Leu Trp Met Leu
                    420                 425                 430

Gln Cys Arg Thr Gly Lys Arg Thr Gly Lys Ser Ala Val Lys Ile Ala
                    435                 440                 445

Val Asp Met Val Asn Glu Gly Leu Val Glu Pro Arg Ser Ala Ile Lys
                    450                 455                 460

Met Val Glu Pro Gly His Leu Asp Gln Leu Leu His Pro Gln Phe Glu
465                 470                 475                 480

Asn Pro Ser Ala Tyr Lys Asp Gln Val Ile Ala Thr Gly Leu Pro Ala
                    485                 490                 495

Ser Pro Gly Ala Ala Val Gly Gln Val Val Phe Thr Ala Glu Asp Ala
                    500                 505                 510

Glu Ala Trp His Ser Gln Gly Lys Ala Ala Ile Leu Val Arg Ala Glu
                    515                 520                 525

Thr Ser Pro Glu Asp Val Gly Gly Met His Ala Ala Val Gly Ile Leu
                    530                 535                 540

Thr Glu Arg Gly Gly Met Thr Ser His Ala Ala Val Val Ala Arg Gly
545                 550                 555                 560

Trp Gly Lys Cys Cys Val Ser Gly Cys Ser Gly Ile Arg Val Asn Asp
                    565                 570                 575

Ala Glu Lys Leu Val Thr Ile Gly Gly His Val Leu Arg Glu Gly Glu
                    580                 585                 590

Trp Leu Ser Leu Asn Gly Ser Thr Gly Glu Val Ile Leu Gly Lys Gln
                    595                 600                 605

Pro Leu Ser Pro Pro Ala Leu Ser Gly Asp Leu Gly Thr Phe Met Ala
                    610                 615                 620

Trp Val Asp Asp Val Arg Lys Leu Lys Val Leu Ala Asn Ala Asp Thr
625                 630                 635                 640

Pro Asp Asp Ala Leu Thr Ala Arg Asn Asn Gly Ala Gln Gly Ile Gly
                    645                 650                 655

Leu Cys Arg Thr Glu His Met Phe Phe Ala Ser Asp Glu Arg Ile Lys
                    660                 665                 670

Ala Val Arg Gln Met Ile Met Ala Pro Thr Leu Glu Leu Arg Gln Gln
                    675                 680                 685

Ala Leu Asp Arg Leu Leu Pro Tyr Gln Arg Ser Asp Phe Glu Gly Ile
                    690                 695                 700

Phe Arg Ala Met Asp Gly Leu Pro Val Thr Ile Arg Leu Leu Asp Pro
705                 710                 715                 720

Pro Leu His Glu Phe Leu Pro Glu Gly Asn Ile Glu Asp Ile Val Ser
                    725                 730                 735

Glu Leu Cys Ala Glu Thr Gly Ala Asn Gln Glu Asp Ala Leu Ala Arg
                    740                 745                 750

Ile Glu Lys Leu Ser Glu Val Asn Pro Met Leu Gly Phe Arg Gly Cys
                    755                 760                 765

Arg Leu Gly Ile Ser Tyr Pro Glu Leu Thr Glu Met Gln Ala Arg Ala
                    770                 775                 780

Ile Phe Glu Ala Ala Ile Ala Met Thr Asn Gln Gly Val Gln Val Phe
785                 790                 795                 800

Pro Glu Ile Met Val Pro Leu Val Gly Thr Pro Gln Glu Leu Gly His
                    805                 810                 815
```

Gln Val Thr Leu Ile Arg Gln Val Ala Glu Lys Val Phe Ala Asn Val
                820                 825                 830

Gly Lys Thr Ile Gly Tyr Lys Val Gly Thr Met Ile Glu Ile Pro Arg
                835                 840                 845

Ala Ala Leu Val Ala Asp Glu Ile Ala Glu Gln Ala Glu Phe Phe Ser
850                 855                 860

Phe Gly Thr Asn Asp Leu Thr Gln Met Thr Phe Gly Tyr Ser Arg Asp
865                 870                 875                 880

Asp Val Gly Lys Phe Ile Pro Val Tyr Pro Ala Gln Gly Ile Leu Gln
                885                 890                 895

His Asp Pro Phe Glu Val Leu Asp Gln Arg Gly Val Gly Glu Leu Val
                900                 905                 910

Lys Phe Ala Thr Glu Arg Gly Arg Lys Ala Arg Pro Asn Leu Lys Val
                915                 920                 925

Gly Ile Cys Gly Glu His Gly Gly Glu Pro Ser Ser Val Ala Phe Phe
                930                 935                 940

Ala Lys Ala Gly Leu Asp Tyr Val Ser Cys Ser Pro Phe Arg Val Pro
945                 950                 955                 960

Ile Ala Arg Leu Ala Ala Gln Val Leu Val
                965                 970

<210> SEQ ID NO 50
<211> LENGTH: 263
<212> TYPE: PRT
<213> ORGANISM: Zea mays

<400> SEQUENCE: 50

Met Leu Glu Leu Arg Leu Val Gln Gly Ser Leu Leu Lys Lys Val Leu
1               5                   10                  15

Glu Ala Ile Arg Glu Leu Val Thr Asp Ala Asn Phe Asp Cys Ser Gly
                20                  25                  30

Thr Gly Phe Ser Leu Gln Ala Met Asp Ser Ser His Val Ala Leu Val
                35                  40                  45

Ala Leu Leu Leu Arg Ala Glu Gly Phe Glu His Tyr Arg Cys Asp Arg
            50                  55                  60

Asn Leu Ser Met Gly Met Asn Leu Asn Asn Met Ala Lys Met Leu Arg
65                  70                  75                  80

Cys Ala Gly Asn Glu Asp Ile Ile Thr Ile Lys Ala Asp Asp Gly Ser
                85                  90                  95

Asp Thr Val Thr Phe Met Phe Glu Ser Pro Lys Gln Asp Lys Ile Ala
                100                 105                 110

Asp Phe Glu Met Lys Leu Met Asp Ile Asp Ser Glu His Leu Gly Ile
            115                 120                 125

Pro Asp Ser Glu Tyr Gln Ala Ile Val Arg Met Pro Ser Ala Glu Phe
            130                 135                 140

Met Arg Ile Cys Lys Asp Leu Ser Ser Ile Gly Asp Thr Val Val Ile
145                 150                 155                 160

Ser Val Thr Lys Glu Gly Val Lys Phe Ser Thr Ser Gly Glu Ile Gly
                165                 170                 175

Ser Ala Asn Ile Val Cys Arg Gln Asn Gln Thr Ile Asp Lys Pro Glu
                180                 185                 190

Glu Ala Thr Ile Ile Glu Met Gln Glu Pro Val Ser Leu Thr Phe Ala
            195                 200                 205

Leu Arg Tyr Met Asn Ser Phe Thr Lys Ala Ser Ser Leu Ser Glu Gln

```
            210                 215                 220
Val Thr Ile Ser Leu Ser Ser Glu Leu Pro Val Val Glu Tyr Lys
225                 230                 235                 240

Ile Ala Glu Met Gly Tyr Ile Arg Phe Tyr Leu Ala Pro Lys Ile Asp
                245                 250                 255

Asp Asp Glu Glu Met Lys Pro
            260
```

<210> SEQ ID NO 51
<211> LENGTH: 889
<212> TYPE: PRT
<213> ORGANISM: Zea mays

<400> SEQUENCE: 51

```
Met Ala Lys Ser Ser Ala Asp Asp Ala Glu Leu Arg Arg Ala Cys Ala
1               5                   10                  15

Ala Ala Val Ala Ala Ser Gly Ala Arg Gly Glu Glu Val Ala Phe Ser
                20                  25                  30

Ile Arg Val Ala Lys Gly Arg Gly Ile Phe Glu Lys Leu Gly Arg Leu
            35                  40                  45

Ala Lys Pro Arg Val Leu Ala Leu Thr Val Lys Gln Ser Ser Arg Gly
50                  55                  60

Glu Ala Asn Lys Ala Phe Leu Arg Val Leu Lys Tyr Ser Ser Gly Ala
65              70                  75                  80

Val Leu Glu Pro Ala Lys Leu Tyr Lys Leu Lys His Leu Thr Lys Val
                85                  90                  95

Glu Val Ile Ser Asn Asp Pro Ser Gly Cys Thr Phe Val Leu Gly Phe
            100                 105                 110

Asp Asn Leu Arg Ser Gln Ser Val Ala Pro Pro Gln Trp Thr Met Arg
        115                 120                 125

Asn Ile Asp Asp Arg Asn Arg Leu Leu Phe Cys Ile Leu Asn Met Cys
130                 135                 140

Lys Glu Ile Leu Ser Tyr Leu Pro Lys Val Val Gly Ile Asp Ile Val
145                 150                 155                 160

Glu Leu Ala Leu Trp Ala Lys Glu Asn Thr Leu Thr Ile Asp Asn Gln
                165                 170                 175

Val Ser Thr Gln Asp Gly Gln Glu Thr Ser Val Ala Thr Gln Thr Glu
            180                 185                 190

Arg Lys Val Thr Val Thr Val Glu Asn Asp Leu Val Ser Gln Ala Lys
        195                 200                 205

Glu Glu Glu Glu Asp Met Glu Ala Leu Leu Asp Thr Tyr Val Met Gly
210                 215                 220

Ile Gly Glu Ala Asp Ala Phe Ser Glu Arg Leu Lys Gln Glu Leu Val
225                 230                 235                 240

Ala Leu Glu Ala Ala Asn Val Tyr Gln Leu Leu Glu Ser Glu Pro Leu
                245                 250                 255

Ile Glu Glu Val Leu Gln Gly Leu Asp Ala Ala Ser Ala Thr Val Asp
            260                 265                 270

Asp Met Asp Glu Trp Leu Arg Ile Phe Asn Leu Lys Leu Arg His Met
        275                 280                 285

Arg Glu Asp Ile Ala Ser Ile Glu Ser Arg Asn Asn Gly Leu Glu Met
        290                 295                 300

Gln Ser Val Asn Asn Lys Gly Leu Met Glu Glu Leu Asp Lys Leu Leu
305                 310                 315                 320
```

```
Glu Arg Leu Arg Ile Pro Gln Glu Phe Ala Ser Leu Thr Gly Gly
            325                 330                 335

Ser Phe Glu Glu Ser Arg Met Leu Lys Asn Val Glu Ala Cys Glu Trp
        340                 345                 350

Leu Thr Gly Ala Ile Arg Ser Leu Glu Val Pro Asn Leu Asp Pro Cys
            355                 360                 365

Tyr Val Asn Met Arg Ala Val Arg Glu Lys Lys Ala Glu Leu Glu Lys
    370                 375                 380

Leu Lys Thr Thr Phe Val Arg Arg Ala Ser Glu Phe Leu Arg Asn Tyr
385                 390                 395                 400

Phe Ser Ser Leu Val Asp Phe Met Ile Ser Asp Lys Ser Tyr Phe Ser
                405                 410                 415

Gln Arg Gly Gln Leu Lys Arg Pro Asp His Ala Asp Leu Arg Tyr Lys
            420                 425                 430

Cys Arg Thr Tyr Ala Arg Leu Leu Gln His Leu Lys Ser Leu Asp Lys
            435                 440                 445

Ser Cys Leu Gly Pro Leu Arg Lys Ala Tyr Cys His Ser Leu Asn Leu
    450                 455                 460

Leu Leu Arg Arg Glu Ala Arg Glu Phe Ala Asn Glu Leu Arg Ala Ser
465                 470                 475                 480

Thr Lys Ala Pro Lys Asn Pro Ala Val Trp Leu Glu Gly Ser Gly Gly
                485                 490                 495

Ser Gly His Asn Gly Ser Ser Ser Asp Thr Ser Gln Val Ser Asp Ala
            500                 505                 510

Tyr Ser Lys Met Leu Thr Ile Phe Ile Pro Leu Leu Val Asp Glu Ser
    515                 520                 525

Ser Phe Phe Ala His Phe Met Cys Phe Glu Val Pro Ala Leu Val Pro
530                 535                 540

Ala Gly Ser Pro Asn Ala Asn Lys Ser Lys Ser Gly Gly Asn Asp Pro
545                 550                 555                 560

Asp Asp Asp Leu Gly Leu Met Asp Pro Asp Gly Asn Asp Leu Lys Pro
                565                 570                 575

Asp Ser Thr Ser Ala Glu Leu Gly Thr Leu Asn Glu Ala Leu Gln Glu
            580                 585                 590

Leu Leu Asp Gly Ile Gln Glu Asp Phe Tyr Ala Val Val Asp Trp Ala
595                 600                 605

Tyr Lys Ile Asp Pro Leu Arg Cys Ile Ser Met His Gly Ile Thr Glu
    610                 615                 620

Arg Tyr Leu Ser Gly Gln Lys Ala Asp Ala Ala Gly Phe Val Arg Lys
625                 630                 635                 640

Leu Leu Asp Asp Leu Glu Ser Arg Ile Ser Val Gln Phe Ser Arg Phe
                645                 650                 655

Ile Asp Glu Ala Cys His Gln Ile Glu Arg Asn Glu Arg Asn Val Arg
            660                 665                 670

Gln Thr Gly Ile Leu Ala Tyr Ile Pro Arg Phe Ala Val Leu Ala Ser
    675                 680                 685

Arg Met Glu Gln Tyr Ile Gln Gly Gln Ser Arg Asp Leu Ile Asp Lys
690                 695                 700

Ala Tyr Thr Lys Leu Val Ser Thr Met Phe Ala Thr Leu Glu Lys Ile
705                 710                 715                 720

Ala Gln Ser Asp Pro Lys Thr Ala Asp Ile Val Leu Ile Glu Asn Tyr
                725                 730                 735

Ala Ala Phe Gln Asn Ser Leu Tyr Asp Leu Ala Asn Val Val Pro Thr
```

```
                      740                 745                 750
Leu Ala Lys Phe Tyr His Gln Ala Ser Glu Ser Tyr Glu Leu Ala Cys
            755                 760                 765

Thr Arg His Ile Ser Ser Leu Ile Tyr Leu Gln Phe Glu Arg Leu Phe
770                 775                 780

Gln Phe Asn Arg Lys Val Asp Glu Leu Thr Tyr Thr Ile Ala Ala Glu
785                 790                 795                 800

Glu Ile Pro Phe Gln Leu Gly Leu Ser Lys Thr Asp Leu Arg Arg Val
                805                 810                 815

Leu Lys Ser Ser Leu Ser Gly Ile Asp Lys Ser Ile Ser Ala Met Tyr
            820                 825                 830

Arg Arg Leu Gln Lys Thr Leu Thr Ser Asp Glu Leu Phe Pro Ser Leu
        835                 840                 845

Trp Asp Lys Cys Lys Lys Glu Phe Leu Asp Lys Tyr Glu Ser Phe Val
    850                 855                 860

Gln Met Val Thr Arg Ile Tyr Gly Asn Glu Pro Ile Met Ser Val Asn
865                 870                 875                 880

Glu Met Lys Asp Val Leu Ala Gly Phe
                885

<210> SEQ ID NO 52
<211> LENGTH: 392
<212> TYPE: PRT
<213> ORGANISM: Zea mays

<400> SEQUENCE: 52

Met Gly Thr Gln Ile Val Arg Glu Gln Thr Ser Gly Ser Leu Thr Ala
1               5                   10                  15

Ile Val Val Asp Glu Asn Leu Cys His Ala Arg Ala Ala Ser Cys Met
                20                  25                  30

Leu Ala Asn Leu Gln Cys Lys Val Ile Val Tyr Ala Ser Pro Val Asp
            35                  40                  45

Ala Leu Lys Phe Leu Lys Asp His Gln Arg Asp Thr Asp Phe Ala Leu
        50                  55                  60

Val Glu Val Asn Met Lys Glu Met His Gly Phe Gln Phe Leu Asp Met
65                  70                  75                  80

Ser Arg Lys Leu His Lys Ser Leu Gln Val Ile Met Met Ser Ala Asp
                85                  90                  95

Thr Thr Trp Pro Thr Met Lys Arg Ser Val Glu Leu Gly Ala Arg Phe
            100                 105                 110

Leu Ile Lys Lys Pro Leu Asp Ala Asn Thr Met Asn Asn Leu Trp Gln
        115                 120                 125

His Leu Asp Leu Lys Phe Gln Arg Thr Asp Lys Ile Lys Ala Leu Phe
    130                 135                 140

Pro Gly Ile Glu Gly Lys Thr Gly Asn Ala Phe Glu Glu Gly Thr Asn
145                 150                 155                 160

Lys Gln Lys Gly Thr His Leu Met Trp Thr Pro Phe Leu Gln Arg Lys
                165                 170                 175

Phe Leu Gln Ala Val Glu Leu Leu Gly Glu Asp Ala Ser Pro Lys Lys
            180                 185                 190

Ile Gln Leu Leu Met Asn Val Asn Ser Val Ser Arg Lys Gln Ile Ser
        195                 200                 205

Ala His Leu Gln Lys His Arg Lys Lys Val Glu Lys Glu Leu Arg Asn
    210                 215                 220
```

```
Ser Asn Ala Asn Asn Ser Ser His Gly Ile Gly Gly Ala Ser Asn Ser
225                 230                 235                 240

Arg Pro Ser Arg Ile Phe Glu Ile Ser His Gly Arg Phe Gln Tyr Asn
                245                 250                 255

Arg Pro Asp Val Gln Pro Glu His Arg Ser Asp Glu Ser Val Ser Val
            260                 265                 270

Glu Gln Thr Glu Thr Ile Glu Glu Thr Gln Ser Asn Arg Leu Tyr Glu
        275                 280                 285

Ala Met Arg Arg Ala Leu Gln Leu Gly Ser Val Phe Glu Glu Pro Gln
    290                 295                 300

Leu Pro Asn Asp Pro Pro Ala Gly Lys Asp Ala Arg Glu Val Glu Glu
305                 310                 315                 320

Val Glu Met Thr Met Arg Asp Gly Asn Tyr Arg Asp Ala Gly Thr Asp
                325                 330                 335

Ala Phe Gly Asp Lys Asn Glu Ala Ser Gly Thr His Ser Ser Asp Gly
                340                 345                 350

Asn Asn Ala Lys Val Lys Ser Lys Asp Asp Ser Ala Asp Lys Leu Val
                355                 360                 365

Ser Cys His Asp Glu Leu Arg Pro Val Val Thr Leu Val Thr Tyr Ser
370                 375                 380

Asp Ser Glu Asp Gly Glu Thr Leu
385                 390

<210> SEQ ID NO 53
<211> LENGTH: 255
<212> TYPE: PRT
<213> ORGANISM: Zea mays

<400> SEQUENCE: 53

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Ile Thr Lys
    50                  55                  60

Thr Leu Glu Arg Tyr Gln His Cys Cys Tyr Asn Ala Gln Asp Ser Asn
65                  70                  75                  80

Gly Ala Leu Ser Glu Thr Gln Ser Trp Tyr Gln Glu Met Ser Lys Leu
                85                  90                  95

Arg Ala Lys Phe Glu Ala Leu Gln Arg Thr Gln Arg His Leu Leu Gly
            100                 105                 110

Glu Glu Leu Gly Pro Leu Ser Val Lys Glu Leu Gln Gln Leu Glu Lys
        115                 120                 125

Gln Leu Glu Cys Ala Leu Ser Gln Ala Arg Gln Arg Lys Thr Gln Leu
    130                 135                 140

Met Met Glu Gln Val Glu Glu Leu Arg Arg Lys Glu Arg His Leu Gly
145                 150                 155                 160

Glu Met Asn Arg Gln Leu Lys His Lys Leu Glu Ala Glu Gly Cys Ser
                165                 170                 175

Asn Tyr Arg Thr Leu Gln His Ala Ala Trp Pro Ala Pro Gly Ser Thr
            180                 185                 190

Met Val Glu His Asp Gly Ala Thr Tyr His Val His Pro Thr Thr Ala
        195                 200                 205
```

```
Gln Ser Val Ala Met Asp Cys Glu Pro Thr Leu Gln Ile Gly Tyr Pro
    210                 215                 220

Pro His His Gln Phe Leu Pro Ser Glu Ala Ala Asn Asn Ile Pro Arg
225                 230                 235                 240

Ser Pro Pro Gly Gly Glu Asn Asn Phe Met Leu Gly Trp Val Leu
                245                 250                 255

<210> SEQ ID NO 54
<211> LENGTH: 199
<212> TYPE: PRT
<213> ORGANISM: Zea mays

<400> SEQUENCE: 54

Met Ala Glu Glu Glu Ala Lys Lys Val Glu Val Thr Lys Glu
1               5                   10                  15

Pro Glu Ala Ala Ala Lys Glu Asp Val Ala Asp Lys Ala Val Ile
                20                  25                  30

Pro Ala Thr Asp Pro Pro Pro Pro Pro Ala Asp Asp Ser Lys
            35                  40                  45

Ala Leu Ala Ile Val Glu Lys Val Ala Asp Glu Pro Ala Pro Glu Lys
50                  55                  60

Pro Ala Pro Ala Lys Gln Gly Gly Ser Asn Asp Arg Asp Leu Ala Leu
65                  70                  75                  80

Ala Arg Val Glu Thr Glu Lys Arg Asn Ser Leu Ile Lys Ala Trp Glu
                85                  90                  95

Glu Asn Glu Lys Thr Lys Ala Gly Asn Lys Ala Ala Lys Lys Val Ser
                100                 105                 110

Ala Ile Leu Ser Trp Glu Asn Thr Lys Lys Ala Asn Ile Glu Ala Glu
            115                 120                 125

Leu Lys Lys Ile Glu Glu Gln Leu Glu Lys Lys Ala Glu Tyr Ala
130                 135                 140

Glu Lys Met Lys Asn Lys Val Ala Met Ile His Lys Glu Ala Glu Glu
145                 150                 155                 160

Lys Arg Ala Met Val Glu Ala Lys Arg Gly Glu Glu Val Leu Lys Ala
                165                 170                 175

Glu Glu Met Ala Ala Lys Tyr Arg Ala Thr Gly His Ala Pro Lys Lys
            180                 185                 190

Leu Ile Gly Cys Phe Gly Ala
            195

<210> SEQ ID NO 55
<211> LENGTH: 178
<212> TYPE: PRT
<213> ORGANISM: Zea mays

<400> SEQUENCE: 55

Met Ala Glu Ala Pro Ala Ser Pro Gly Gly Gly Gly Ser His Glu
1               5                   10                  15

Ser Gly Ser Pro Arg Gly Gly Gly Gly Gly Ser Val Arg Glu Gln
                20                  25                  30

Asp Arg Phe Leu Pro Ile Ala Asn Ile Ser Arg Ile Met Lys Lys Ala
            35                  40                  45

Ile Pro Ala Asn Gly Lys Ile Ala Lys Asp Ala Lys Glu Thr Val Gln
50                  55                  60

Glu Cys Val Ser Glu Phe Ile Ser Phe Ile Thr Ser Glu Ala Ser Asp
65                  70                  75                  80
```

-continued

```
Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
            100                 105                 110

Val Tyr Leu Gln Lys Tyr Arg Glu Met Glu Gly Asp Ser Lys Leu Thr
        115                 120                 125

Ala Lys Ser Ser Asp Gly Ser Ile Lys Lys Asp Ala Leu Gly His Val
    130                 135                 140

Gly Ala Ser Ser Ala Ala Gln Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175

Ser Asn

<210> SEQ ID NO 56
<211> LENGTH: 213
<212> TYPE: PRT
<213> ORGANISM: Zea mays

<400> SEQUENCE: 56

Met Ser Ser Gly Ser Gly Ser Gly Asn Lys Arg Ala Ala Glu Arg
1               5                   10                  15

Ser Ala Gly Ala Gly Ala Gly Ser Gly Asp Glu Asp Asp Gly Ala
            20                  25                  30

Ala Arg Lys Lys Leu Arg Leu Ser Lys Asp Gln Ala Ala Val Leu Glu
        35                  40                  45

Glu Cys Phe Lys Thr His His Thr Leu Thr Pro Lys Gln Lys Val Ala
    50                  55                  60

Leu Ala Ser Ser Leu Gly Leu Arg Pro Arg Gln Val Glu Val Trp Phe
65                  70                  75                  80

Gln Asn Arg Arg Ala Arg Thr Lys Leu Lys Gln Thr Glu Val Asp Cys
                85                  90                  95

Glu Tyr Leu Lys Arg Trp Cys Glu Gln Leu Ala Glu Glu Asn Arg Arg
            100                 105                 110

Leu Gly Lys Glu Val Ala Glu Leu Arg Ala Leu Ser Ala Ala Pro Ala
        115                 120                 125

Ala Pro Leu Thr Thr Leu Thr Met Cys Leu Ser Cys Arg Arg Val Ala
    130                 135                 140

Ser Ser Ser Pro Ser Ser Ser Ser Pro Arg Pro Ser Ile Pro Gly
145                 150                 155                 160

Ala Ala Ala Ala Ser Gly Gly Ser Met Ala Ser Pro Ala Ala Ala Ala
                165                 170                 175

Thr Leu Pro Ala His Arg Gln Phe Phe Cys Gly Phe Arg Asp Ala Gly
            180                 185                 190

Ala Ala Ala Ala Ala Tyr Gly Thr Ala Ser Ala Gly Leu Ala Lys Pro
        195                 200                 205

Val Arg Ala Ala Arg
    210

<210> SEQ ID NO 57
<211> LENGTH: 423
<212> TYPE: PRT
<213> ORGANISM: Artificial Sequence
<220> FEATURE:
<223> OTHER INFORMATION: corn putative glutamine synthetase (with C299A
      mutation)
```

```
<220> FEATURE:
<221> NAME/KEY: MUTAGEN
<222> LOCATION: (299)..(299)
<223> OTHER INFORMATION: C299A mutation

<400> SEQUENCE: 57
```

| | | | | | | | | | | | | | | |
|---|---|---|---|---|---|---|---|---|---|---|---|---|---|---|
| Met | Ala | Gln | Ala | Val | Val | Pro | Ala | Met | Gln | Cys | Arg | Val | Gly | Val | Lys |
| 1 | | | | 5 | | | | | 10 | | | | | 15 |
| Ala | Ala | Ala | Gly | Arg | Val | Trp | Ser | Ala | Gly | Arg | Thr | Arg | Thr | Gly | Arg |
| | | | 20 | | | | | 25 | | | | | 30 | |
| Gly | Gly | Ala | Ser | Pro | Gly | Phe | Lys | Val | Met | Ala | Val | Ser | Thr | Gly | Ser |
| | | | 35 | | | | 40 | | | | | 45 | | |
| Thr | Gly | Val | Val | Pro | Arg | Leu | Glu | Gln | Leu | Leu | Asn | Met | Asp | Thr | Thr |
| | 50 | | | | | 55 | | | | | 60 | | | |
| Pro | Tyr | Thr | Asp | Lys | Val | Ile | Ala | Glu | Tyr | Ile | Trp | Val | Gly | Gly | Ser |
| 65 | | | | 70 | | | | | 75 | | | | | 80 |
| Gly | Ile | Asp | Ile | Arg | Ser | Lys | Ser | Arg | Thr | Ile | Ser | Lys | Pro | Val | Glu |
| | | | | 85 | | | | | 90 | | | | | 95 |
| Asp | Pro | Ser | Glu | Leu | Pro | Lys | Trp | Asn | Tyr | Asp | Gly | Ser | Ser | Thr | Gly |
| | | | 100 | | | | | 105 | | | | | 110 | |
| Gln | Ala | Pro | Gly | Glu | Asp | Ser | Glu | Val | Ile | Leu | Tyr | Pro | Gln | Ala | Ile |
| | | | | 115 | | | | | 120 | | | | | 125 |
| Phe | Lys | Asp | Pro | Phe | Arg | Gly | Gly | Asn | Asn | Val | Leu | Val | Ile | Cys | Asp |
| | 130 | | | | | 135 | | | | | 140 | | | |
| Thr | Tyr | Thr | Pro | Gln | Gly | Glu | Pro | Leu | Pro | Thr | Asn | Lys | Arg | His | Arg |
| 145 | | | | 150 | | | | | 155 | | | | | 160 |
| Ala | Ala | Gln | Ile | Phe | Ser | Asp | Pro | Lys | Val | Ala | Glu | Gln | Val | Pro | Trp |
| | | | | 165 | | | | | 170 | | | | | 175 |
| Phe | Gly | Ile | Glu | Gln | Glu | Tyr | Thr | Leu | Leu | Gln | Lys | Asp | Val | Asn | Trp |
| | | | 180 | | | | | 185 | | | | | 190 | |
| Pro | Leu | Gly | Trp | Pro | Val | Gly | Gly | Phe | Pro | Gly | Pro | Gln | Gly | Pro | Tyr |
| | | | 195 | | | | | 200 | | | | | 205 | |
| Tyr | Cys | Ala | Val | Gly | Ala | Asp | Lys | Ser | Phe | Gly | Arg | Asp | Ile | Ser | Asp |
| | 210 | | | | | 215 | | | | | 220 | | | |
| Ala | His | Tyr | Lys | Ala | Cys | Leu | Tyr | Ala | Gly | Ile | Asn | Ile | Ser | Gly | Thr |
| 225 | | | | | 230 | | | | | 235 | | | | | 240 |
| Asn | Gly | Glu | Val | Met | Pro | Gly | Gln | Trp | Glu | Tyr | Gln | Val | Gly | Pro | Ser |
| | | | | 245 | | | | | 250 | | | | | 255 |
| Val | Gly | Ile | Glu | Ala | Gly | Asp | His | Ile | Trp | Ile | Ser | Arg | Tyr | Ile | Leu |
| | | | 260 | | | | | 265 | | | | | 270 | |
| Glu | Arg | Ile | Thr | Glu | Gln | Ala | Gly | Val | Val | Leu | Thr | Leu | Asp | Pro | Lys |
| | | | 275 | | | | | 280 | | | | | 285 | |
| Pro | Ile | Gln | Gly | Asp | Trp | Asn | Gly | Ala | Gly | Ala | His | Thr | Asn | Tyr | Ser |
| | 290 | | | | | 295 | | | | | 300 | | | |
| Thr | Lys | Thr | Met | Arg | Glu | Asp | Gly | Gly | Phe | Glu | Glu | Ile | Lys | Arg | Ala |
| 305 | | | | | 310 | | | | | 315 | | | | | 320 |
| Ile | Leu | Asn | Leu | Ser | Leu | Arg | His | Asp | Leu | His | Ile | Ser | Ala | Tyr | Gly |
| | | | | 325 | | | | | 330 | | | | | 335 |
| Glu | Gly | Asn | Glu | Arg | Arg | Leu | Thr | Gly | Lys | His | Glu | Thr | Ala | Ser | Ile |
| | | | 340 | | | | | 345 | | | | | 350 | |
| Gly | Thr | Phe | Ser | Trp | Gly | Val | Ala | Asn | Arg | Gly | Cys | Ser | Ile | Arg | Val |
| | | | 355 | | | | | 360 | | | | | 365 | |
| Gly | Arg | Asp | Thr | Glu | Ala | Lys | Gly | Lys | Gly | Tyr | Leu | Glu | Asp | Arg | Arg |
| | 370 | | | | | 375 | | | | | 380 | | | |

```
Pro Ala Ser Asn Met Asp Pro Tyr Ile Val Thr Gly Leu Leu Ala Glu
385                 390                 395                 400

Thr Thr Ile Leu Trp Gln Pro Ser Leu Glu Ala Glu Ala Leu Ala Ala
                405                 410                 415

Lys Lys Leu Ala Leu Lys Val
            420

<210> SEQ ID NO 58
<211> LENGTH: 594
<212> TYPE: PRT
<213> ORGANISM: Zea mays

<400> SEQUENCE: 58

Met Val Lys Arg Ser Lys Lys Ser Lys Ser Lys Arg Val Thr Leu Arg
1               5                   10                  15

Gln Lys His Lys Val Gln Arg Lys Val Lys Glu His His Arg Lys Lys
                20                  25                  30

Arg Lys Glu Ala Lys Lys Ala Gly Lys Ala Gly Gln Arg Arg Lys Val
            35                  40                  45

Glu Lys Asp Pro Gly Ile Pro Asn Glu Trp Pro Phe Lys Glu Gln Glu
    50                  55                  60

Leu Lys Ala Leu Glu Ala Arg Arg Ala Gln Ala Leu Gln Glu Leu Glu
65                  70                  75                  80

Leu Lys Lys Gln Ala Arg Lys Glu Arg Ala Gln Lys Arg Lys Ala Gly
                85                  90                  95

Leu Leu Glu Asp Glu Asp Ile Ala Ser Leu Ala Ser Ala Ala Ser Ala
            100                 105                 110

Gln Gly Ser Glu Phe Ala Ala Lys Glu Asn Ala Pro Leu Leu Val Ala
        115                 120                 125

Lys Ile Asn Asp His Ser Glu Arg Ser Phe Tyr Lys Glu Leu Val Lys
    130                 135                 140

Val Ile Glu Ala Ser Asp Val Ile Met Glu Val Leu Asp Ala Arg Asp
145                 150                 155                 160

Pro Leu Gly Thr Arg Cys Ile Asp Met Glu Lys Met Val Arg Lys Ala
                165                 170                 175

Asp Pro Ser Lys Arg Ile Val Leu Leu Asn Lys Ile Asp Leu Val
            180                 185                 190

Pro Lys Glu Ala Ala Glu Lys Trp Leu Thr Tyr Leu Arg Glu Glu Leu
        195                 200                 205

Pro Thr Val Ala Phe Lys Cys Asn Thr Gln Glu Gln Arg Thr Lys Leu
    210                 215                 220

Gly Trp Lys Ser Ser Lys Leu Asp Lys Thr Ser Asn Ile Pro Gln Ser
225                 230                 235                 240

Ser Asp Cys Leu Gly Ala Glu Asn Leu Ile Lys Leu Leu Lys Asn Tyr
                245                 250                 255

Ser Arg Ser His Glu Leu Lys Leu Thr Ile Thr Val Gly Ile Val Gly
            260                 265                 270

Leu Pro Asn Val Gly Lys Ser Ser Leu Ile Asn Ser Leu Lys Arg Ser
        275                 280                 285

Arg Val Val Asn Val Gly Ser Thr Pro Gly Ile Thr Arg Ser Met Gln
    290                 295                 300

Glu Val Gln Leu Asp Lys Lys Val Lys Leu Leu Asp Cys Pro Gly Val
305                 310                 315                 320

Val Met Leu Lys Ser Ser Asn Ser Gly Val Ser Val Ala Leu Arg Asn
                325                 330                 335
```

```
Cys Lys Lys Val Glu Lys Ile Glu Asp Pro Val Ala Pro Val Lys Gln
            340                 345                 350

Ile Leu Ser Ile Cys Pro His Glu Lys Leu Leu Ser Leu Tyr Lys Val
            355                 360                 365

Pro Asn Phe Gly Ser Val Asp Asp Phe Leu Gln Lys Val Ala Thr Val
370                 375                 380

Arg Gly Lys Leu Lys Gly Gly Val Val Asp Val Glu Ala Ala Ala
385                 390                 395                 400

Arg Ile Val Leu His Asp Trp Asn Glu Gly Lys Ile Pro Tyr Phe Thr
                405                 410                 415

Leu Pro Pro Lys Arg Asp Ala Gly Glu Asp Ser Asp Ala Val Ile Ile
            420                 425                 430

Ser Glu Asp Gly Lys Glu Phe Asn Ile Asp Glu Ile Tyr Lys Ala Glu
            435                 440                 445

Ser Ser Tyr Ile Gly Gly Leu Lys Ser Ile Glu Glu Phe His His Ile
            450                 455                 460

Glu Ile Pro Pro Asn Ala Pro Leu Ala Ile Asp Glu Glu Met Leu Glu
465                 470                 475                 480

Asp Gly Gly Lys Lys Pro Ser Glu Ala Ile Gln Glu Ser Arg Asp Arg
                485                 490                 495

Glu Glu Gln Met Pro Asp Val Lys Asp Ser Gly Gly Ser Lys Ala Ala
            500                 505                 510

Ser Ala Ser Thr Gln Asn Asp Lys Leu Tyr Thr Ala Glu Gly Val Leu
            515                 520                 525

Asp Pro Arg Lys Ser Lys Ala Glu Lys Lys Arg Arg Lys Ala Ser Arg
            530                 535                 540

Pro Ser Ala Leu Asn Asp Met Asp Ala Asp Tyr Asp Phe Lys Val Asp
545                 550                 555                 560

Tyr Arg Met Glu Asp Gly Gly Ser Glu Gly Ala His Ala Asp Asp Glu
                565                 570                 575

Asp Gly Gly Asp Gly Ser Glu Asp Asn Glu Pro Met Thr Gly Val Asp
            580                 585                 590

Asp Ala

<210> SEQ ID NO 59
<211> LENGTH: 423
<212> TYPE: PRT
<213> ORGANISM: Zea mays

<400> SEQUENCE: 59

Met Ala Gln Ala Val Val Pro Ala Met Gln Cys Arg Val Gly Val Lys
1               5                   10                  15

Ala Ala Ala Gly Arg Val Trp Ser Ala Gly Arg Thr Arg Thr Gly Arg
            20                  25                  30

Gly Gly Ala Ser Pro Gly Phe Lys Val Met Ala Val Ser Thr Gly Ser
        35                  40                  45

Thr Gly Val Val Pro Arg Leu Glu Gln Leu Leu Asn Met Asp Thr Thr
50              55                  60

Pro Tyr Thr Asp Lys Val Ile Ala Glu Tyr Ile Trp Val Gly Gly Ser
65                  70                  75                  80

Gly Ile Asp Ile Arg Ser Lys Ser Arg Thr Ile Ser Lys Pro Val Glu
                85                  90                  95

Asp Pro Ser Glu Leu Pro Lys Trp Asn Tyr Asp Gly Ser Ser Thr Gly
            100                 105                 110
```

-continued

Gln Ala Pro Gly Glu Asp Ser Glu Val Ile Leu Tyr Pro Gln Ala Ile
            115                 120                 125

Phe Lys Asp Pro Phe Arg Gly Gly Asn Asn Val Leu Val Ile Cys Asp
        130                 135                 140

Thr Tyr Thr Pro Gln Gly Glu Pro Leu Pro Thr Asn Lys Arg His Arg
145                 150                 155                 160

Ala Ala Gln Ile Phe Ser Asp Pro Lys Val Ala Glu Gln Val Pro Trp
                165                 170                 175

Phe Gly Ile Glu Gln Glu Tyr Thr Leu Leu Gln Lys Asp Val Asn Trp
            180                 185                 190

Pro Leu Gly Trp Pro Val Gly Gly Phe Pro Gly Pro Gln Gly Pro Tyr
        195                 200                 205

Tyr Cys Ala Val Gly Ala Asp Lys Ser Phe Gly Arg Asp Ile Ser Asp
210                 215                 220

Ala His Tyr Lys Ala Cys Leu Tyr Ala Gly Ile Asn Ile Ser Gly Thr
225                 230                 235                 240

Asn Gly Glu Val Met Pro Gly Gln Trp Glu Tyr Gln Val Gly Pro Ser
                245                 250                 255

Val Gly Ile Glu Ala Gly Asp His Ile Trp Ile Ser Arg Tyr Ile Leu
            260                 265                 270

Glu Arg Ile Thr Glu Gln Ala Gly Val Val Leu Thr Leu Asp Pro Lys
        275                 280                 285

Pro Ile Gln Gly Asp Trp Asn Gly Ala Gly Cys His Thr Asn Tyr Ser
290                 295                 300

Thr Lys Thr Met Arg Glu Asp Gly Gly Phe Glu Ile Lys Arg Ala
305                 310                 315                 320

Ile Leu Asn Leu Ser Leu Arg His Asp Leu His Ile Ser Ala Tyr Gly
                325                 330                 335

Glu Gly Asn Glu Arg Arg Leu Thr Gly Lys His Glu Thr Ala Ser Ile
            340                 345                 350

Gly Thr Phe Ser Trp Gly Val Ala Asn Arg Gly Cys Ser Ile Arg Val
        355                 360                 365

Gly Arg Asp Thr Glu Ala Lys Gly Lys Gly Tyr Leu Glu Asp Arg Arg
370                 375                 380

Pro Ala Ser Asn Met Asp Pro Tyr Ile Val Thr Gly Leu Leu Ala Glu
385                 390                 395                 400

Thr Thr Ile Leu Trp Gln Pro Ser Leu Glu Ala Glu Ala Leu Ala Ala
                405                 410                 415

Lys Lys Leu Ala Leu Lys Val
            420

<210> SEQ ID NO 60
<211> LENGTH: 971
<212> TYPE: PRT
<213> ORGANISM: Zea mays

<400> SEQUENCE: 60

Met Ile Val Gln Pro Ile Glu Leu Arg Ala Trp Thr Ala Phe Pro Gly
1               5                   10                  15

Ser Ala Gln Glu Gly Ile Gly Arg Met Ala Ala Ser Val Ser Arg Ala
            20                  25                  30

Ile Cys Val Gln Lys Pro Gly Ser Lys Cys Thr Arg Asp Arg Glu Ala
        35                  40                  45

Thr Ser Phe Ala Arg Arg Ser Val Ala Ala Pro Arg Pro Pro His Ala

-continued

```
                50                  55                  60
Lys Ala Gly Val Ile Arg Ser Asp Ser Gly Ala Gly Arg Gly Gln
 65                  70                  75                  80

His Cys Ser Pro Leu Arg Ala Val Val Asp Ala Ala Pro Ile Gln Thr
                     85                  90                  95

Thr Lys Lys Arg Val Phe His Phe Gly Lys Gly Lys Ser Glu Gly Asn
                100                 105                 110

Lys Thr Met Lys Glu Leu Leu Gly Gly Lys Gly Ala Asn Leu Ala Glu
            115                 120                 125

Met Ala Ser Ile Gly Leu Ser Val Pro Pro Gly Phe Thr Val Ser Thr
    130                 135                 140

Glu Ala Cys Gln Gln Tyr Gln Asp Ala Gly Cys Ala Leu Pro Ala Gly
145                 150                 155                 160

Leu Trp Ala Glu Ile Val Asp Gly Leu Gln Trp Val Glu Glu Tyr Met
                165                 170                 175

Gly Ala Thr Leu Gly Asp Pro Gln Arg Pro Leu Leu Leu Ser Val Arg
                180                 185                 190

Ser Gly Ala Ala Val Ser Met Pro Gly Met Met Asp Thr Val Leu Asn
            195                 200                 205

Leu Gly Leu Asn Asp Glu Val Ala Ala Gly Leu Ala Ala Lys Ser Gly
    210                 215                 220

Glu Arg Phe Ala Tyr Asp Ser Phe Arg Arg Phe Leu Asp Met Phe Gly
225                 230                 235                 240

Asn Val Val Met Asp Ile Pro Arg Ser Leu Phe Glu Glu Lys Leu Glu
                245                 250                 255

His Met Lys Glu Ser Lys Gly Leu Lys Asn Asp Thr Asp Leu Thr Ala
                260                 265                 270

Ser Asp Leu Lys Glu Leu Val Gly Gln Tyr Lys Glu Val Tyr Leu Ser
            275                 280                 285

Ala Lys Gly Glu Pro Phe Pro Ser Asp Pro Lys Lys Gln Leu Glu Leu
    290                 295                 300

Ala Val Leu Ala Val Phe Asn Ser Trp Glu Ser Pro Arg Ala Lys Lys
305                 310                 315                 320

Tyr Arg Ser Ile Asn Gln Ile Thr Gly Leu Arg Gly Thr Ala Val Ser
                325                 330                 335

Val Gln Cys Met Val Phe Gly Asn Met Gly Asn Thr Ser Asp Thr Gly
                340                 345                 350

Val Leu Phe Thr Arg Asn Pro Asn Thr Gly Glu Lys Lys Leu Tyr Gly
            355                 360                 365

Glu Phe Leu Val Asn Ala Gln Gly Glu Asp Val Val Ala Gly Ile Arg
    370                 375                 380

Thr Pro Glu Asp Leu Asp Ala Met Lys Asn Leu Met Pro Gln Ala Tyr
385                 390                 395                 400

Asp Glu Leu Val Glu Asn Cys Asn Ile Leu Glu Ser His Tyr Lys Glu
                405                 410                 415

Met Gln Asp Ile Glu Phe Thr Val Gln Glu Asn Arg Leu Trp Met Leu
                420                 425                 430

Gln Cys Arg Thr Gly Lys Arg Thr Gly Lys Ser Ala Val Lys Ile Ala
            435                 440                 445

Val Asp Met Val Asn Glu Gly Leu Val Glu Pro Arg Ser Ala Ile Lys
    450                 455                 460

Met Val Glu Pro Gly His Leu Asp Gln Leu Leu His Pro Gln Phe Glu
465                 470                 475                 480
```

```
Asn Pro Ser Thr Tyr Lys Asp Gln Val Ile Ala Thr Gly Leu Pro Ala
            485                 490                 495

Ser Pro Gly Ala Ala Val Gly Gln Val Val Phe Thr Ala Glu Asp Ala
            500                 505                 510

Glu Ala Trp His Pro Gln Gly Lys Ala Ala Ile Leu Val Arg Ala Glu
            515                 520                 525

Thr Ser Pro Glu Asp Val Gly Gly Met His Ala Ala Val Gly Ile Leu
            530                 535                 540

Thr Glu Arg Gly Gly Met Thr Ser His Ala Ala Val Val Ala Arg Gly
545                 550                 555                 560

Trp Gly Lys Cys Cys Val Ser Gly Cys Ser Gly Ile Arg Val Asn Asp
                565                 570                 575

Ala Glu Lys Leu Val Thr Ile Gly Gly His Val Leu Arg Glu Gly Glu
            580                 585                 590

Trp Leu Ser Leu Asn Gly Ser Ala Gly Glu Val Ile Leu Gly Lys Gln
            595                 600                 605

Pro Leu Ser Pro Pro Ala Leu Ser Gly Asp Leu Gly Thr Phe Met Ala
            610                 615                 620

Trp Val Asp Asp Val Arg Lys Leu Lys Val Leu Ala Asn Ala Asp Thr
625                 630                 635                 640

Pro Asp Asp Ala Leu Thr Ala Arg Asn Asn Gly Ala Gln Gly Ile Gly
            645                 650                 655

Leu Cys Arg Thr Glu His Met Phe Phe Ala Ser Asp Glu Arg Ile Lys
            660                 665                 670

Ala Val Arg Gln Met Ile Met Ala Pro Thr Leu Glu Leu Arg Gln Gln
            675                 680                 685

Ala Leu Asp Arg Leu Leu Pro Tyr Gln Arg Ser Asp Phe Glu Gly Ile
            690                 695                 700

Phe Arg Ala Met Asp Gly Leu Pro Val Thr Ile Arg Leu Leu Asp Pro
705                 710                 715                 720

Pro Leu His Glu Phe Leu Pro Glu Gly Asn Ile Glu Asp Ile Val Ser
            725                 730                 735

Glu Leu Cys Ala Glu Thr Gly Ala Asn Gln Glu Asp Ala Leu Ala Arg
            740                 745                 750

Ile Glu Lys Leu Ser Glu Val Asn Pro Met Leu Gly Phe Arg Gly Cys
            755                 760                 765

Arg Leu Gly Ile Ser Tyr Pro Glu Leu Thr Glu Met Gln Ala Arg Ala
            770                 775                 780

Ile Phe Glu Ala Ala Ile Ala Met Thr Asn Gln Gly Val Gln Val Phe
785                 790                 795                 800

Pro Glu Ile Met Val Pro Leu Val Gly Thr Pro Gln Glu Leu Gly His
            805                 810                 815

Gln Val Thr Leu Ile Arg Gln Val Ala Glu Lys Val Phe Ala Asn Val
            820                 825                 830

Gly Lys Thr Ile Gly Tyr Lys Val Gly Thr Met Ile Glu Ile Pro Arg
            835                 840                 845

Ala Ala Leu Val Ala Asp Glu Ile Ala Glu Gln Ala Glu Phe Phe Ser
            850                 855                 860

Phe Gly Thr Asn Asp Leu Thr Gln Met Thr Phe Gly Tyr Ser Arg Asp
865                 870                 875                 880

Asp Val Gly Lys Phe Ile Pro Val Tyr Leu Ala Gln Gly Ile Leu Lys
            885                 890                 895
```

-continued

```
His Asp Pro Phe Glu Val Leu Asp Gln Arg Gly Val Gly Glu Leu Val
            900                 905                 910

Lys Phe Ala Thr Glu Arg Gly Arg Lys Ala Arg Pro Asn Leu Lys Val
        915                 920                 925

Gly Ile Cys Gly Glu His Gly Gly Glu Pro Ser Ser Val Ala Phe Phe
    930                 935                 940

Ala Lys Ala Gly Leu Asp Tyr Val Ser Cys Ser Pro Phe Arg Val Pro
945                 950                 955                 960

Ile Ala Arg Leu Ala Ala Ala Gln Val Leu Val
                965                 970

<210> SEQ ID NO 61
<211> LENGTH: 263
<212> TYPE: PRT
<213> ORGANISM: Sorghum bicolor

<400> SEQUENCE: 61

Met Leu Glu Leu Arg Leu Val Gln Gly Ser Leu Leu Lys Lys Val Leu
1               5                   10                  15

Glu Ala Ile Arg Glu Leu Val Thr Asp Ala Asn Phe Asp Cys Ser Gly
            20                  25                  30

Thr Gly Phe Ser Leu Gln Ala Met Asp Ser Ser His Val Ala Leu Val
        35                  40                  45

Ala Leu Leu Leu Arg Ala Glu Gly Phe Glu His Tyr Arg Cys Asp Arg
    50                  55                  60

Asn Leu Ser Met Gly Met Asn Leu Asn Asn Met Ala Lys Met Leu Arg
65                  70                  75                  80

Cys Ala Gly Asn Asp Asp Ile Ile Thr Ile Lys Ala Asp Asp Gly Ser
                85                  90                  95

Asp Thr Val Thr Phe Met Phe Glu Ser Pro Lys Gln Asp Lys Ile Ala
            100                 105                 110

Asp Phe Glu Met Lys Leu Met Asp Ile Asp Ser Glu His Leu Gly Ile
        115                 120                 125

Pro Asp Ser Glu Tyr Gln Ala Ile Val Arg Met Pro Ser Ala Glu Phe
    130                 135                 140

Met Arg Ile Cys Lys Asp Leu Ser Ser Ile Gly Asp Thr Val Val Ile
145                 150                 155                 160

Ser Val Thr Lys Glu Gly Val Lys Phe Ser Thr Ser Gly Glu Ile Gly
                165                 170                 175

Ser Ala Asn Ile Val Cys Arg Gln Asn Gln Thr Ile Asp Lys Pro Glu
            180                 185                 190

Glu Ala Thr Ile Ile Glu Met Gln Glu Pro Val Ser Leu Thr Phe Ala
        195                 200                 205

Leu Arg Tyr Met Asn Ser Phe Thr Lys Ala Ser Ser Leu Ser Glu Gln
    210                 215                 220

Val Thr Ile Ser Leu Ser Ser Glu Leu Pro Val Val Val Glu Tyr Lys
225                 230                 235                 240

Ile Ala Glu Met Gly Tyr Ile Arg Phe Tyr Leu Ala Pro Lys Ile Glu
                245                 250                 255

Glu Asp Glu Glu Met Lys Ala
            260

<210> SEQ ID NO 62
<211> LENGTH: 447
<212> TYPE: PRT
<213> ORGANISM: Escherichia coli CFT073
```

<400> SEQUENCE: 62

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Val Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Val Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His

-continued

```
                405                 410                 415
Gly Gly Glu Gly Glu Gln Thr Asn Tyr Val Gln Gly Ala Asn Ile Ala
            420                 425                 430
Gly Phe Val Lys Val Ala Asp Ala Met Leu Ser Gln Gly Val Ile
            435                 440                 445

<210> SEQ ID NO 63
<211> LENGTH: 594
<212> TYPE: PRT
<213> ORGANISM: Zea mays

<400> SEQUENCE: 63

Met Val Lys Arg Ser Lys Lys Ser Lys Ser Lys Arg Val Thr Leu Arg
1               5                   10                  15
Gln Lys His Lys Val Gln Arg Lys Val Lys Glu His His Arg Lys Lys
            20                  25                  30
Arg Lys Glu Ala Lys Lys Ala Gly Lys Ala Gly Gln Arg Arg Lys Val
        35                  40                  45
Glu Lys Asp Pro Gly Ile Pro Asn Glu Trp Pro Phe Lys Glu Gln Glu
    50                  55                  60
Leu Lys Ala Leu Glu Ala Arg Arg Ala Gln Ala Leu Gln Glu Leu Glu
65                  70                  75                  80
Leu Lys Lys Gln Ala Arg Lys Glu Arg Ala Gln Lys Arg Lys Ala Gly
                85                  90                  95
Leu Leu Glu Asp Glu Asp Ile Ala Ser Leu Ala Ser Ala Ala Ser Ala
            100                 105                 110
Gln Gly Ser Glu Phe Ala Ala Lys Glu Asn Ala Pro Leu Leu Val Ala
        115                 120                 125
Lys Ile Asn Asp His Ser Glu Arg Ser Phe Tyr Lys Glu Leu Val Lys
    130                 135                 140
Val Ile Glu Ala Ser Asp Val Ile Val Glu Val Leu Asp Ala Arg Asp
145                 150                 155                 160
Pro Leu Gly Thr Arg Cys Ile Asp Met Glu Lys Met Val Arg Lys Ala
                165                 170                 175
Asp Pro Ser Lys Arg Ile Val Leu Leu Leu Asn Lys Ile Asp Leu Val
            180                 185                 190
Pro Lys Glu Ala Ala Glu Lys Trp Leu Thr Tyr Leu Arg Glu Glu Leu
        195                 200                 205
Pro Thr Val Ala Phe Lys Cys Asn Thr Gln Glu Gln Arg Thr Lys Leu
    210                 215                 220
Gly Trp Lys Ser Ser Lys Leu Asp Lys Thr Ser Asn Ile Pro Gln Ser
225                 230                 235                 240
Ser Asp Cys Leu Gly Ala Glu Asn Leu Ile Lys Leu Leu Lys Asn Tyr
                245                 250                 255
Ser Arg Ser His Glu Leu Lys Leu Ala Ile Thr Val Gly Ile Val Gly
            260                 265                 270
Leu Pro Asn Val Gly Lys Ser Ser Leu Ile Asn Ser Leu Lys Arg Ser
        275                 280                 285
Arg Val Val Asn Val Gly Ser Thr Pro Gly Ile Thr Arg Ser Met Gln
    290                 295                 300
Glu Val Gln Leu Asp Lys Lys Val Lys Leu Leu Asp Cys Pro Gly Val
305                 310                 315                 320
Val Met Leu Lys Ser Ser Asn Ser Gly Val Ser Val Ala Leu Arg Asn
                325                 330                 335
```

```
Cys Lys Lys Val Glu Lys Ile Glu Asp Pro Val Ala Pro Val Lys Glu
            340                 345                 350

Ile Leu Ser Ile Cys Pro His Glu Lys Leu Leu Ser Leu Tyr Lys Val
        355                 360                 365

Pro Asn Phe Gly Ser Val Asp Asp Phe Leu Gln Lys Val Ala Thr Val
    370                 375                 380

Arg Gly Lys Leu Lys Lys Gly Val Val Asp Val Glu Ala Ala Ala
385                 390                 395                 400

Arg Ile Val Leu His Asp Trp Asn Glu Gly Lys Ile Pro Tyr Phe Thr
                405                 410                 415

Leu Pro Pro Lys Arg Asp Ala Gly Glu Asp Ser Asp Ala Val Ile Ile
            420                 425                 430

Ser Glu Asp Gly Lys Glu Phe Asn Ile Asp Asp Ile Tyr Lys Ala Glu
        435                 440                 445

Ser Ser Tyr Ile Gly Gly Leu Lys Ser Ile Glu Glu Phe His His Ile
    450                 455                 460

Glu Ile Pro Pro Asn Ala Pro Ala Ile Asp Glu Glu Met Leu Glu
465                 470                 475                 480

Asp Gly Gly Lys Lys Pro Ser Glu Ala Ile Gln Glu Ser Arg Asp Arg
                485                 490                 495

Glu Glu Gln Met Pro Asp Val Lys Asp Ser Gly Gly Ser Lys Ala Ala
            500                 505                 510

Ser Ala Ser Thr Gln Asn Asp Lys Leu Tyr Thr Ala Glu Gly Val Leu
        515                 520                 525

Asp Pro Arg Lys Ser Lys Ala Glu Lys Lys Arg Arg Lys Ala Ser Arg
    530                 535                 540

Pro Ser Ala Leu Asn Asp Met Asp Ala Asp Tyr Asp Phe Lys Val Asp
545                 550                 555                 560

Tyr Arg Met Glu Asp Gly Gly Ser Glu Gly Ala His Ala Asp Asp Glu
                565                 570                 575

Asp Gly Gly Asp Gly Ser Glu Asp Asn Glu Pro Met Thr Gly Val Asp
            580                 585                 590

Asp Ala

<210> SEQ ID NO 64
<211> LENGTH: 178
<212> TYPE: PRT
<213> ORGANISM: Zea mays

<400> SEQUENCE: 64

Met Ala Glu Ala Pro Ala Ser Pro Gly Gly Gly Gly Ser His Glu
1               5                   10                  15

Ser Gly Ser Pro Arg Gly Gly Gly Gly Ser Val Arg Glu Gln
            20                  25                  30

Asp Arg Phe Leu Pro Ile Ala Asn Ile Ser Arg Ile Met Lys Lys Ala
            35                  40                  45

Ile Pro Ala Asn Gly Lys Ile Ala Lys Asp Ala Lys Glu Thr Val Gln
        50                  55                  60

Glu Cys Val Ser Glu Phe Ile Ser Phe Ile Thr Ser Glu Ala Ser Asp
65                  70                  75                  80

Lys Cys Gln Arg Glu Lys Arg Lys Thr Ile Asn Gly Asp Asp Leu Leu
                85                  90                  95

Trp Ala Met Ala Thr Leu Gly Phe Glu Asp Tyr Ile Glu Pro Leu Lys
            100                 105                 110
```

```
Val Tyr Leu Gln Lys Tyr Arg Glu Met Glu Gly Asp Ser Lys Leu Thr
            115                 120                 125

Ala Lys Ser Ser Asp Gly Ser Ile Lys Lys Asp Ala Leu Gly His Val
130                 135                 140

Gly Ala Ser Ser Ala Ala Glu Gly Met Gly Gln Gln Gly Ala Tyr
145                 150                 155                 160

Asn Gln Gly Met Gly Tyr Met Gln Pro Gln Tyr His Asn Gly Asp Ile
                165                 170                 175

Ser Asn

<210> SEQ ID NO 65
<211> LENGTH: 447
<212> TYPE: PRT
<213> ORGANISM: Escherichia coli O157:H7 EDL933

<400> SEQUENCE: 65

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
50                  55                  60

Val Val Trp Val Asp Asp Arg Asn Gln Val Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ser Ser
        275                 280                 285

Arg Asp Gly Arg Val Ala Asp Tyr Ala Lys Glu Phe Gly Leu Val Tyr
    290                 295                 300
```

```
Leu Glu Gly Gln Gln Pro Trp Ser Val Pro Val Asp Ile Ala Leu Pro
305                 310                 315                 320

Cys Ala Thr Gln Asn Glu Leu Asp Val Asp Ala Ala His Gln Leu Ile
            325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
            355                 360                 365

Gly Lys Ala Ala Asn Ala Gly Val Ala Thr Ser Gly Leu Glu Met
    370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
            435                 440                 445

<210> SEQ ID NO 66
<211> LENGTH: 447
<212> TYPE: PRT
<213> ORGANISM: Escherichia coli

<400> SEQUENCE: 66

Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
                20                  25                  30

Thr Thr Leu Trp Pro Phe Leu Glu Gln Asn Pro Lys Tyr Arg Gln Met
            35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
            115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
            195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240
```

-continued

```
Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Pro Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445

<210> SEQ ID NO 67
<211> LENGTH: 947
<212> TYPE: PRT
<213> ORGANISM: Zea mays

<400> SEQUENCE: 67

Met Ala Ala Ser Val Ser Arg Ala Ile Cys Val Gln Lys Pro Gly Ser
1               5                   10                  15

Lys Cys Thr Arg Asp Arg Glu Ala Thr Ser Phe Ala Arg Arg Ser Val
            20                  25                  30

Ala Ala Pro Arg Pro His Ala Lys Ala Ala Gly Val Ile Arg Ser
        35                  40                  45

Asp Ser Gly Ala Gly Arg Gly Gln His Cys Ser Pro Leu Arg Ala Val
    50                  55                  60

Val Asp Ala Ala Pro Ile Gln Thr Thr Lys Lys Arg Val Phe His Phe
65                  70                  75                  80

Gly Lys Gly Lys Ser Glu Gly Asn Lys Thr Met Lys Glu Leu Leu Gly
                85                  90                  95

Gly Lys Gly Ala Asn Leu Ala Glu Met Ala Ser Ile Gly Leu Ser Val
            100                 105                 110

Pro Pro Gly Phe Thr Val Ser Thr Glu Ala Cys Gln Gln Tyr Gln Asp
        115                 120                 125

Ala Gly Cys Ala Leu Pro Ala Gly Leu Trp Ala Glu Ile Val Asp Gly
    130                 135                 140

Leu Gln Trp Val Glu Glu Tyr Met Gly Ala Thr Leu Gly Asp Pro Gln
145                 150                 155                 160

Arg Pro Leu Leu Leu Ser Val Arg Ser Gly Ala Ala Val Ser Met Pro
```

-continued

```
                165                 170                 175
Gly Met Met Asp Thr Val Leu Asn Leu Gly Leu Asn Asp Glu Val Ala
            180                 185                 190
Ala Gly Leu Ala Ala Lys Ser Gly Glu Arg Phe Ala Tyr Asp Ser Phe
        195                 200                 205
Arg Arg Phe Leu Asp Met Phe Gly Asn Val Val Met Asp Ile Pro Arg
    210                 215                 220
Ser Leu Phe Glu Glu Lys Leu Glu His Met Lys Glu Ser Lys Gly Leu
225                 230                 235                 240
Lys Asn Asp Thr Asp Leu Thr Ala Ser Asp Leu Lys Glu Leu Val Gly
                245                 250                 255
Gln Tyr Lys Glu Val Tyr Leu Ser Ala Lys Gly Glu Pro Phe Pro Ser
            260                 265                 270
Asp Pro Lys Lys Gln Leu Glu Leu Ala Val Leu Ala Val Phe Asn Ser
        275                 280                 285
Trp Glu Ser Pro Arg Ala Lys Lys Tyr Arg Ser Ile Asn Gln Ile Thr
    290                 295                 300
Gly Leu Arg Gly Thr Ala Val Asn Val Gln Cys Met Val Phe Gly Asn
305                 310                 315                 320
Met Gly Asn Thr Ser Gly Thr Gly Val Leu Phe Thr Arg Asn Pro Asn
                325                 330                 335
Thr Gly Glu Lys Lys Leu Tyr Gly Glu Phe Leu Val Asn Ala Gln Gly
            340                 345                 350
Glu Asp Val Val Ala Gly Ile Arg Thr Pro Glu Asp Leu Asp Ala Met
        355                 360                 365
Lys Asn Leu Met Pro Gln Ala Tyr Asp Glu Leu Val Glu Asn Cys Asn
    370                 375                 380
Ile Leu Glu Ser His Tyr Lys Glu Met Gln Asp Ile Glu Phe Thr Val
385                 390                 395                 400
Gln Glu Asn Arg Leu Trp Met Leu Gln Cys Arg Thr Gly Lys Arg Thr
                405                 410                 415
Gly Lys Ser Ala Val Lys Ile Ala Val Asp Met Val Asn Glu Gly Leu
            420                 425                 430
Val Glu Pro Arg Ser Ala Ile Lys Met Val Glu Pro Gly His Leu Asp
        435                 440                 445
Gln Leu Leu His Pro Gln Phe Glu Asn Pro Ser Ala Tyr Lys Asp Gln
    450                 455                 460
Val Ile Ala Thr Gly Leu Pro Ala Ser Pro Gly Ala Ala Val Gly Gln
465                 470                 475                 480
Val Val Phe Thr Ala Glu Asp Ala Glu Ala Trp His Ser Gln Gly Lys
                485                 490                 495
Ala Ala Ile Leu Val Arg Ala Glu Thr Ser Pro Glu Asp Val Gly Gly
            500                 505                 510
Met His Ala Ala Val Gly Ile Leu Thr Glu Arg Gly Gly Met Thr Ser
        515                 520                 525
His Ala Ala Val Val Ala Arg Trp Trp Gly Lys Cys Cys Val Ser Gly
    530                 535                 540
Cys Ser Gly Ile Arg Val Asn Asp Ala Glu Lys Leu Val Thr Ile Gly
545                 550                 555                 560
Ser His Val Leu Arg Glu Gly Glu Trp Leu Ser Leu Asn Gly Ser Thr
                565                 570                 575
Gly Glu Val Ile Leu Gly Lys Gln Pro Leu Ser Pro Pro Ala Leu Ser
            580                 585                 590
```

Gly Asp Leu Gly Thr Phe Met Ala Trp Val Asp Val Arg Lys Leu
            595                 600                 605

Lys Val Leu Ala Asn Ala Asp Thr Pro Asp Asp Ala Leu Thr Ala Arg
            610                 615                 620

Asn Asn Gly Ala Gln Gly Ile Gly Leu Cys Arg Thr Glu His Met Phe
625                 630                 635                 640

Phe Ala Ser Asp Glu Arg Ile Lys Ala Val Arg Gln Met Ile Met Ala
                645                 650                 655

Pro Thr Leu Glu Leu Arg Gln Gln Ala Leu Asp Arg Leu Leu Thr Tyr
            660                 665                 670

Gln Arg Ser Asp Phe Glu Gly Ile Phe Arg Ala Met Asp Gly Leu Pro
            675                 680                 685

Val Thr Ile Arg Leu Leu Asp His Pro Ser Tyr Glu Phe Leu Pro Glu
            690                 695                 700

Gly Asn Ile Glu Asp Ile Val Ser Glu Leu Cys Ala Glu Thr Gly Ala
705                 710                 715                 720

Asn Gln Glu Asp Ala Leu Ala Arg Ile Glu Lys Leu Ser Glu Val Asn
                725                 730                 735

Pro Met Leu Gly Phe Arg Gly Cys Arg Leu Gly Ile Ser Tyr Pro Glu
            740                 745                 750

Leu Thr Glu Met Gln Ala Arg Ala Ile Phe Glu Ala Ala Ile Ala Met
            755                 760                 765

Thr Asn Gln Gly Val Gln Val Phe Pro Glu Ile Met Val Pro Leu Val
            770                 775                 780

Gly Thr Pro Gln Glu Leu Gly His Gln Val Thr Leu Ile Arg Gln Val
785                 790                 795                 800

Ala Glu Lys Val Phe Ala Asn Val Gly Lys Thr Ile Gly Tyr Lys Val
                805                 810                 815

Gly Thr Met Ile Glu Ile Pro Arg Ala Ala Leu Val Ala Asp Glu Ile
            820                 825                 830

Ala Glu Gln Ala Glu Phe Phe Ser Phe Gly Thr Asn Asp Leu Thr Gln
            835                 840                 845

Met Thr Phe Gly Tyr Ser Arg Asp Asp Val Gly Lys Phe Ile Pro Val
            850                 855                 860

His Leu Ala Gln Gly Ile Leu Gln His Asp Pro Phe Glu Val Leu Asp
865                 870                 875                 880

Gln Arg Gly Val Gly Glu Leu Val Lys Phe Ala Thr Glu Arg Gly Arg
                885                 890                 895

Lys Ala Arg Pro Asn Leu Lys Val Gly Ile Cys Gly Glu His Gly Gly
            900                 905                 910

Glu Pro Ser Ser Val Ala Phe Phe Ala Lys Ala Gly Leu Asp Phe Val
            915                 920                 925

Ser Cys Ser Pro Phe Arg Val Pro Ile Ala Arg Leu Ala Ala Ala Gln
            930                 935                 940

Val Leu Val
945

<210> SEQ ID NO 68
<211> LENGTH: 179
<212> TYPE: PRT
<213> ORGANISM: Zea mays

<400> SEQUENCE: 68

Met Ala Glu Ala Pro Ala Ser Pro Gly Gly Gly Gly Gly Ser His Glu

```
1               5                  10                 15
Ser Gly Ser Pro Arg Gly Gly Gly Gly Ser Val Arg Glu Gln
                20                 25             30

Asp Arg Phe Leu Pro Ile Ala Asn Ile Ser Arg Ile Met Lys Lys Ala
            35                 40                 45

Ile Pro Ala Asn Gly Lys Ile Ala Lys Asp Ala Lys Glu Thr Val Gln
    50                 55                 60

Glu Cys Val Ser Glu Phe Ile Ser Phe Ile Thr Ser Glu Ala Ser Asp
65                 70                 75                 80

Lys Cys Gln Arg Glu Lys Arg Lys Thr Ile Asn Gly Asp Asp Leu Leu
                85                 90                 95

Trp Ala Met Ala Thr Leu Gly Phe Glu Asp Tyr Ile Glu Pro Leu Lys
            100                105                110

Val Tyr Leu Gln Lys Tyr Arg Glu Met Glu Gly Asp Ser Lys Leu Thr
            115                120                125

Ala Lys Ser Ser Asp Gly Ser Ile Lys Lys Asp Ala Leu Gly His Val
        130                135                140

Gly Ala Ser Ser Ala Ala Glu Gly Met Gly Gln Gln Gly Ala Tyr
145                150                155                160

Asn Gln Gly Met Gly Tyr Met Gln Pro Gln Tyr His Asn Gly Asp Ile
                165                170                175

Ser Asn Val

<210> SEQ ID NO 69
<211> LENGTH: 447
<212> TYPE: PRT
<213> ORGANISM: Escherichia coli 042

<400> SEQUENCE: 69

Met Asp Gln Thr Tyr Ser Leu Glu Ser Phe Leu Asn His Val Gln Lys
1               5                  10                 15

Arg Asp Pro Asn Gln Thr Glu Phe Ala Gln Ala Val Arg Glu Val Met
                20                 25             30

Thr Thr Leu Trp Pro Phe Leu Glu Gln Asn Pro Lys Tyr Arg Gln Met
            35                 40                 45

Ser Leu Leu Glu Arg Leu Val Glu Pro Glu Arg Val Ile Gln Phe Arg
    50                 55                 60

Val Val Trp Val Asp Asp Arg Asn Gln Val Gln Val Asn Arg Ala Trp
65                 70                 75                 80

Arg Val Gln Phe Ser Ser Ala Ile Gly Pro Tyr Lys Gly Gly Met Arg
                85                 90                 95

Phe His Pro Ser Val Asn Leu Ser Ile Leu Lys Phe Leu Gly Phe Glu
            100                105                110

Gln Thr Phe Lys Asn Ala Leu Thr Thr Leu Pro Met Gly Gly Gly Lys
            115                120                125

Gly Gly Ser Asp Phe Asp Pro Lys Gly Lys Ser Glu Gly Glu Val Met
        130                135                140

Arg Phe Cys Gln Ala Leu Met Thr Glu Leu Tyr Arg His Leu Gly Ala
145                150                155                160

Asp Thr Asp Val Pro Ala Gly Asp Ile Gly Val Gly Gly Arg Glu Val
                165                170                175

Gly Phe Met Ala Gly Met Met Lys Lys Leu Ser Asn Asn Thr Ala Cys
            180                185                190

Val Phe Thr Gly Lys Gly Leu Ser Phe Gly Gly Ser Leu Ile Arg Pro
```

195                 200                 205
Glu Ala Thr Gly Tyr Gly Leu Val Tyr Phe Thr Glu Ala Met Leu Lys
    210                 215                 220
Arg His Gly Met Gly Phe Glu Gly Met Arg Val Ser Val Ser Gly Ser
225                 230                 235                 240
Gly Asn Val Ala Gln Tyr Ala Ile Glu Lys Ala Met Glu Phe Gly Ala
                245                 250                 255
Arg Val Ile Thr Ala Ser Asp Ser Ser Gly Thr Val Val Asp Glu Ser
            260                 265                 270
Gly Phe Thr Lys Glu Lys Leu Ala Arg Leu Ile Glu Ile Lys Ala Ser
        275                 280                 285
Arg Asp Gly Arg Val Ala Asp Tyr Ala Lys Glu Phe Gly Leu Val Tyr
    290                 295                 300
Leu Glu Gly Gln Gln Pro Trp Ser Val Pro Val Asp Ile Ala Leu Pro
305                 310                 315                 320
Cys Ala Thr Gln Asn Glu Leu Asp Val Asp Ala Ala His Gln Leu Ile
                325                 330                 335
Ala Thr Gly Val Lys Ala Val Ala Glu Gly Ala Asn Met Pro Thr Thr
            340                 345                 350
Ile Glu Ala Thr Glu Leu Phe Gln Gln Ala Gly Val Leu Phe Ala Pro
        355                 360                 365
Gly Lys Ala Ala Asn Ala Gly Gly Val Ala Thr Ser Gly Leu Glu Met
    370                 375                 380
Ala Gln Asn Ala Ala Arg Leu Gly Trp Lys Ala Glu Lys Val Asp Ala
385                 390                 395                 400
Arg Leu His His Ile Met Leu Asp Ile His His Ala Cys Val Glu His
                405                 410                 415
Gly Gly Glu Gly Glu Gln Thr Asn Tyr Val Gln Gly Ala Asn Ile Ala
            420                 425                 430
Gly Phe Val Lys Val Ala Asp Ala Met Leu Ala Gln Gly Val Ile
        435                 440                 445

<210> SEQ ID NO 70
<211> LENGTH: 345
<212> TYPE: PRT
<213> ORGANISM: Glycine max

<400> SEQUENCE: 70

Met Cys Gly Gly Ala Ile Ile Ser Asp Phe Ile Pro Ala Ala Ile
1               5                   10                  15
Ala Gly Ser Arg Arg Leu Thr Ala Asp Tyr Leu Trp Pro Asp Leu Lys
                20                  25                  30
Lys Arg Lys Ser Asp Leu Asp Val Asp Phe Glu Ala Asp Phe Arg Asp
            35                  40                  45
Phe Lys Asp Asp Ser Asp Ile Asp Asp Asp Asp His Gln Val
        50                  55                  60
Lys Pro Phe Ala Phe Ala Ala Ser Ser Arg Leu Ser Thr Ala Ala Lys
65                  70                  75                  80
Ser Val Ala Phe Gln Gly Arg Ala Glu Ile Ser Ala Asn Arg Lys Arg
                85                  90                  95
Lys Asn Gln Tyr Arg Gly Ile Arg Gln Arg Pro Trp Gly Lys Trp Ala
            100                 105                 110
Ala Glu Ile Arg Asp Pro Arg Lys Gly Val Arg Val Trp Leu Gly Thr
        115                 120                 125

```
Phe Asn Thr Ala Glu Glu Ala Ala Arg Ala Tyr Asp Ala Glu Ala Arg
    130                 135                 140
Arg Ile Arg Gly Lys Lys Ala Lys Val Asn Phe Pro Glu Ala Pro Gly
145                 150                 155                 160
Thr Ser Ser Val Lys Arg Ser Lys Val Asn Pro Gln Glu Asn Leu Lys
                165                 170                 175
Thr Val Gln Pro Asn Leu Gly His Lys Phe Ser Ala Gly Asn Asn His
            180                 185                 190
Met Asp Leu Val Glu Gln Lys Pro Leu Val Ser Gln Tyr Ala Asn Met
        195                 200                 205
Ala Ser Phe Pro Gly Ser Gly Asn Gly Leu Arg Ser Leu Pro Ser Ser
    210                 215                 220
Asp Asp Ala Thr Leu Tyr Phe Ser Ser Asp Gln Gly Ser Asn Ser Phe
225                 230                 235                 240
Asp Tyr Ala Pro Glu Ile Ser Ser Met Leu Ser Ala Pro Leu Asp Cys
                245                 250                 255
Glu Ser His Phe Val Gln Asn Ala Asn Gln Gln Pro Asn Ser Gln
            260                 265                 270
Asn Val Val Ser Ile Glu Asp Ser Ala Lys Thr Leu Ser Glu Glu
        275                 280                 285
Leu Val Asp Ile Glu Ser Glu Leu Lys Phe Phe Gln Met Pro Tyr Leu
    290                 295                 300
Glu Gly Ser Trp Gly Asp Thr Ser Leu Glu Ser Leu Leu Ser Gly Asp
305                 310                 315                 320
Thr Thr Gln Asp Gly Gly Asn Leu Met Asn Leu Trp Cys Leu Asp Asp
                325                 330                 335
Ile Pro Ser Met Ala Gly Gly Val Phe
                340                 345

<210> SEQ ID NO 71
<211> LENGTH: 185
<212> TYPE: PRT
<213> ORGANISM: Zea mays

<400> SEQUENCE: 71

Met Ala Glu Ala Pro Ala Ser Pro Gly Gly Gly Gly Ser His Glu
1               5                   10                  15
Ser Gly Ser Pro Arg Gly Gly Gly Gly Gly Ser Val Arg Glu Gln
                20                  25                  30
Asp Arg Phe Leu Pro Ile Ala Asn Ile Ser Arg Ile Met Lys Lys Ala
            35                  40                  45
Ile Pro Ala Asn Gly Lys Thr Ile Pro Ala Asn Gly Lys Ile Ala Lys
50                  55                  60
Asp Ala Lys Glu Thr Val Gln Glu Cys Val Ser Glu Phe Ile Ser Phe
65                  70                  75                  80
Ile Thr Ser Glu Ala Ser Asp Lys Cys Gln Arg Glu Lys Arg Lys Thr
                85                  90                  95
Ile Asn Gly Asp Asp Leu Leu Trp Ala Met Ala Thr Leu Gly Phe Glu
            100                 105                 110
Asp Tyr Ile Glu Pro Leu Lys Val Tyr Leu Gln Lys Tyr Arg Glu Met
        115                 120                 125
Glu Gly Asp Ser Lys Leu Thr Ala Lys Ser Ser Asp Gly Ser Ile Lys
    130                 135                 140
Lys Asp Ala Leu Gly His Val Gly Ala Ser Ser Ser Ala Ala Gln Gly
145                 150                 155                 160
```

Met Gly Gln Gln Gly Ala Tyr Asn Gln Gly Met Gly Tyr Met Gln Pro
                165                 170                 175

Gln Tyr His Asn Gly Asp Ile Ser Asn
            180                 185

<210> SEQ ID NO 72
<211> LENGTH: 355
<212> TYPE: PRT
<213> ORGANISM: Arabidopsis thaliana

<400> SEQUENCE: 72

Ile Tyr His Arg Lys Val Val Phe Thr Tyr Val Arg Ala Lys Arg Phe
1               5                   10                  15

Tyr His Phe Leu Asn Ile Glu Met Val Thr Asp Phe Lys Ser Leu Leu
            20                  25                  30

Pro Val Ile Asp Ile Ser Pro Leu Ala Lys Cys Asp Asp Phe Asp
        35                  40                  45

Met Ala Glu Asp Ala Gly Val Val Glu Val Val Gly Lys Leu Asp Arg
50                  55                  60

Ala Cys Arg Asp Val Gly Phe Phe Tyr Val Ile Gly His Gly Ile Ser
65                  70                  75                  80

Asp Asp Leu Ile Asn Lys Val Lys Glu Met Thr His Gln Phe Phe Glu
            85                  90                  95

Leu Pro Tyr Glu Glu Lys Leu Lys Ile Lys Ile Thr Pro Thr Ala Gly
        100                 105                 110

Tyr Arg Gly Tyr Gln Arg Ile Gly Val Asn Phe Thr Ser Gly Lys Gln
    115                 120                 125

Asp Met His Glu Ala Ile Asp Cys Tyr Arg Glu Phe Lys Gln Gly Lys
130                 135                 140

His Gly Asp Ile Gly Lys Val Leu Glu Gly Pro Asn Gln Trp Pro Gly
145                 150                 155                 160

Asn Pro Gln Glu Tyr Lys Asp Leu Met Glu Lys Tyr Ile Lys Leu Cys
                165                 170                 175

Thr Asp Leu Ser Arg Asn Ile Leu Arg Gly Ile Ser Leu Ala Leu Gly
            180                 185                 190

Gly Ser Pro Tyr Glu Phe Glu Gly Lys Met Leu Arg Asp Pro Phe Trp
        195                 200                 205

Val Met Arg Ile Ile Gly Tyr Pro Gly Val Asn Gln Glu Asn Val Ile
    210                 215                 220

Gly Cys Gly Ala His Thr Asp Tyr Gly Leu Leu Thr Leu Ile Asn Gln
225                 230                 235                 240

Asp Asp Asp Lys Thr Ala Leu Gln Val Lys Asn Val Asp Gly Asp Trp
                245                 250                 255

Ile Pro Ala Ile Pro Ile Pro Gly Ser Phe Ile Cys Asn Ile Gly Asp
            260                 265                 270

Met Leu Thr Ile Leu Ser Asn Gly Val Tyr Gln Ser Thr Leu His Lys
        275                 280                 285

Val Ile Asn Asn Ser Pro Lys Tyr Arg Val Cys Val Ala Phe Phe Tyr
    290                 295                 300

Glu Thr Asn Phe Glu Ala Glu Val Glu Pro Leu Asp Ile Phe Lys Glu
305                 310                 315                 320

Lys His Pro Arg Lys Glu Thr Ser Gln Val Ala Lys Arg Val Val Tyr
                325                 330                 335

Gly Gln His Leu Ile Asn Lys Val Leu Thr Thr Phe Ala Asn Leu Val

```
                    340                 345                 350

Glu Asn Ser
        355

<210> SEQ ID NO 73
<211> LENGTH: 131
<212> TYPE: PRT
<213> ORGANISM: Arabidopsis thaliana

<400> SEQUENCE: 73

Met Asp Gln Gly Gly Arg Ser Gly Ser Gly Gly Gly Gly Gly Ala Glu
1               5                   10                  15

Gln Gly Lys Tyr Arg Gly Val Arg Arg Pro Trp Gly Lys Tyr Ala
            20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Asn
65                  70                  75                  80

Asn Met Gly Thr Gly Ser Ser Ser Thr Ala Ala Asn Ser Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys
    130

<210> SEQ ID NO 74
<211> LENGTH: 286
<212> TYPE: PRT
<213> ORGANISM: Oryza sativa Japonica Group

<400> SEQUENCE: 74

Met Gly Met Ala Asn Glu Glu Ser Pro Asn Tyr Gln Val Lys Lys Gly
1               5                   10                  15

Gly Arg Ile Pro Pro Arg Ser Ser Leu Ile Tyr Pro Phe Met Ser Met
            20                  25                  30

Gly Pro Ala Ala Gly Glu Gly Cys Gly Leu Cys Gly Ala Asp Gly Gly
        35                  40                  45

Gly Cys Cys Ser Arg His Arg His Asp Asp Gly Phe Pro Phe Val
    50                  55                  60

Phe Pro Pro Ser Ala Cys Gln Gly Ile Gly Ala Pro Ala Pro Val
65                  70                  75                  80

His Glu Phe Gln Phe Phe Gly Asn Asp Gly Gly Asp Gly Glu
                85                  90                  95

Ser Val Ala Trp Leu Phe Asp Asp Tyr Pro Pro Pro Ser Pro Val Ala
            100                 105                 110

Ala Ala Ala Gly Met His His Arg Gln Pro Pro Tyr Asp Gly Val Val
        115                 120                 125

Ala Pro Pro Ser Leu Phe Arg Arg Asn Thr Gly Ala Gly Gly Leu Thr
    130                 135                 140

Phe Asp Val Ser Leu Gly Glu Arg Pro Asp Leu Asp Ala Gly Leu Gly
145                 150                 155                 160

Leu Gly Gly Gly Gly Gly Arg His Ala Glu Ala Ala Ala Ser Ala Thr
```

165                 170                 175
Ile Met Ser Tyr Cys Gly Ser Thr Phe Thr Asp Ala Ser Ser Met
            180                 185                 190

Pro Lys Glu Met Val Ala Ala Met Ala Asp Asp Gly Glu Ser Leu Asn
        195                 200                 205

Pro Asn Thr Val Val Gly Ala Met Val Glu Arg Glu Ala Lys Leu Met
    210                 215                 220

Arg Tyr Lys Glu Lys Arg Lys Arg Cys Tyr Glu Lys Gln Ile Arg
225                 230                 235                 240

Tyr Ala Ser Arg Lys Ala Tyr Ala Glu Met Arg Pro Arg Val Arg Gly
                245                 250                 255

Arg Phe Ala Lys Glu Pro Asp Gln Glu Ala Val Ala Pro Pro Ser Thr
            260                 265                 270

Tyr Val Asp Pro Ser Arg Leu Glu Leu Gly Gln Trp Phe Arg
        275                 280                 285

<210> SEQ ID NO 75
<211> LENGTH: 272
<212> TYPE: PRT
<213> ORGANISM: Zea mays

<400> SEQUENCE: 75

Met Ala Pro Gln Ser Leu Asp Leu Gly Leu Ser Leu Gly Leu Gly Val
1               5                   10                  15

Ala Ala Phe Gln Pro Ser Ser Phe Cys His Pro Gly Asn Ala Val Val
            20                  25                  30

Val Pro Ala Ala Ala Glu Arg Glu Ala Ser Pro Ala Ala Glu Glu
        35                  40                  45

Arg Glu Arg Arg Cys Ser Pro Ala Gly Ser Pro Val Ser Ser Gly Ser
    50                  55                  60

Gly Ser Gly Asn Lys Arg Ala Ala Ala Glu Arg Ser Ala Gly Ala Gly
65              70                  75                  80

Ala Gly Ser Gly Asp Glu Asp Asp Gly Ala Ala Arg Lys Lys Leu
            85                  90                  95

Arg Leu Ser Lys Asp Gln Ala Ala Val Leu Glu Glu Cys Phe Lys Thr
        100                 105                 110

His His Thr Leu Thr Pro Lys Gln Lys Val Ala Leu Ala Ser Ser Leu
    115                 120                 125

Gly Leu Arg Pro Arg Gln Val Glu Val Trp Phe Gln Asn Arg Arg Ala
130                 135                 140

Arg Thr Lys Leu Lys Gln Thr Glu Val Asp Cys Glu Tyr Leu Lys Arg
145                 150                 155                 160

Trp Cys Glu Gln Leu Ala Glu Glu Asn Arg Arg Leu Gly Lys Glu Val
                165                 170                 175

Ala Glu Leu Arg Ala Leu Ser Ala Ala Pro Ala Ala Pro Leu Thr Thr
            180                 185                 190

Leu Thr Met Cys Leu Ser Cys Arg Val Ala Ser Ser Ser Pro Ser
        195                 200                 205

Ser Ser Ser Ser Pro Arg Pro Ser Ile Pro Gly Ala Ala Ala Ser
    210                 215                 220

Gly Gly Ser Met Ala Ser Pro Ala Ala Ala Thr Leu Pro Ala His
225                 230                 235                 240

Arg Gln Phe Phe Cys Gly Phe Arg Asp Ala Gly Ala Ala Ala Ala
                245                 250                 255

```
Tyr Gly Thr Ala Ser Ala Gly Leu Ala Lys Pro Val Arg Ala Arg
            260                 265                 270
```

<210> SEQ ID NO 76
<211> LENGTH: 594
<212> TYPE: PRT
<213> ORGANISM: Zea mays

<400> SEQUENCE: 76

```
Met Val Lys Arg Ser Lys Lys Ser Lys Ser Arg Val Thr Leu Arg
1               5                   10                  15

Gln Lys His Lys Val Gln Arg Lys Val Lys Glu His His Arg Lys Lys
            20                  25                  30

Arg Lys Glu Ala Lys Lys Ala Gly Lys Ala Gly Gln Arg Arg Lys Val
            35                  40                  45

Glu Lys Asp Pro Gly Ile Pro Asn Glu Trp Pro Phe Lys Glu Gln Glu
50                  55                  60

Leu Lys Ala Leu Glu Ala Arg Arg Ala Gln Ala Leu Gln Glu Leu Glu
65                  70                  75                  80

Leu Lys Lys Gln Ala Arg Lys Glu Arg Ala Gln Lys Arg Lys Ala Gly
            85                  90                  95

Leu Leu Glu Asp Glu Asp Ile Ala Ser Leu Ala Ser Ala Ala Ser Ala
            100                 105                 110

Gln Gly Ser Glu Phe Ala Ala Lys Glu Asn Ala Pro Leu Leu Val Ala
            115                 120                 125

Lys Ile Asn Asp His Ser Glu Arg Ser Phe Tyr Lys Glu Leu Val Lys
            130                 135                 140

Val Ile Glu Ala Ser Asp Val Ile Met Glu Val Leu Asp Ala Arg Asp
145                 150                 155                 160

Pro Leu Gly Thr Arg Cys Ile Asp Met Glu Lys Met Val Arg Lys Ala
            165                 170                 175

Asp Pro Ser Lys Arg Ile Val Leu Leu Leu Asn Lys Ile Asp Leu Val
            180                 185                 190

Pro Lys Glu Ala Val Glu Lys Trp Leu Thr Tyr Leu Arg Glu Glu Leu
            195                 200                 205

Pro Thr Val Ala Phe Lys Cys Asn Thr Gln Glu Gln Arg Thr Lys Leu
            210                 215                 220

Gly Trp Lys Ser Ser Lys Leu Asp Lys Thr Ser Asn Ile Pro Gln Ser
225                 230                 235                 240

Ser Asp Cys Leu Gly Ala Glu Asn Leu Ile Lys Leu Leu Lys Asn Tyr
            245                 250                 255

Ser Arg Ser His Glu Leu Lys Leu Ala Ile Thr Val Gly Ile Val Gly
            260                 265                 270

Leu Pro Asn Val Gly Lys Ser Ser Leu Ile Asn Ser Leu Lys Arg Ser
            275                 280                 285

Arg Val Val Asn Val Gly Ser Thr Pro Gly Ile Thr Arg Ser Met Gln
            290                 295                 300

Glu Val Gln Leu Asp Lys Lys Val Lys Leu Leu Asp Cys Pro Gly Val
305                 310                 315                 320

Val Met Leu Lys Ser Ser Asn Ser Gly Val Ser Val Ala Leu Arg Asn
            325                 330                 335

Cys Lys Arg Val Glu Lys Ile Glu Asp Pro Val Ala Pro Val Lys Glu
            340                 345                 350

Ile Leu Ser Ile Cys Pro His Glu Lys Leu Leu Ser Leu Tyr Lys Val
            355                 360                 365
```

Pro Asn Phe Gly Ser Val Asp Asp Phe Leu Gln Lys Val Ala Thr Val
            370                 375                 380

Arg Gly Lys Leu Lys Lys Gly Gly Val Val Asp Val Glu Ala Ala Ala
385                 390                 395                 400

Arg Ile Val Leu His Asp Trp Asn Glu Gly Lys Ile Pro Tyr Phe Thr
                405                 410                 415

Leu Pro Pro Lys Arg Asp Ala Gly Glu Asp Ser Asp Ala Val Ile Ile
            420                 425                 430

Ser Glu Asp Gly Lys Glu Phe Asn Ile Asp Glu Ile Tyr Lys Ala Glu
            435                 440                 445

Ser Ser Tyr Ile Gly Gly Leu Lys Ser Ile Glu Glu Phe His His Ile
            450                 455                 460

Glu Ile Pro Pro Asn Ala Pro Leu Ala Ile Asp Glu Glu Met Leu Glu
465                 470                 475                 480

Asp Gly Gly Lys Lys Pro Ser Glu Ala Ile Gln Glu Ser Arg Asp Arg
            485                 490                 495

Glu Glu Gln Met Pro Asp Val Lys Asp Ser Gly Gly Ser Lys Ala Ala
            500                 505                 510

Ser Ala Ser Thr Gln Asn Asp Lys Leu Tyr Thr Ala Asp Ala Ile Leu
            515                 520                 525

Asp Pro His Lys Arg Lys Ala Glu Lys Lys Arg Arg Lys Ala Ser Arg
            530                 535                 540

Pro Ser Ala Leu Asn Asp Met Asp Ala Asp Tyr Asp Phe Lys Val Asp
545                 550                 555                 560

Tyr Arg Met Glu Asp Gly Gly Ser Glu Gly Ala His Ala Asp Asp Glu
                565                 570                 575

Asp Gly Gly Asp Gly Ser Glu Asp Asn Glu Pro Met Thr Gly Val Asp
            580                 585                 590

Asp Ala

<210> SEQ ID NO 77
<211> LENGTH: 133
<212> TYPE: PRT
<213> ORGANISM: Arabidopsis thaliana

<400> SEQUENCE: 77

Met Asp Gln Gly Gly Arg Ser Ser Gly Ser Gly Gly Gly Gly Ala Glu
1               5                   10                  15

Gln Gly Lys Tyr Arg Gly Val Arg Arg Arg Pro Trp Gly Lys Tyr Ala
            20                  25                  30

Ala Glu Ile Arg Asp Ser Arg Lys His Gly Glu Arg Val Trp Leu Gly
            35                  40                  45

Thr Phe Asp Thr Ala Glu Asp Ala Ala Arg Ala Tyr Asp Arg Ala Ala
            50                  55                  60

Tyr Ser Met Arg Gly Lys Ala Ala Ile Leu Asn Phe Pro His Glu Tyr
65                  70                  75                  80

Asn Met Gly Thr Gly Ser Ser Thr Ala Ala Asn Ser Ser Ser Ser
            85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
            115                 120                 125

Met Gly Lys Arg Gln
    130

<210> SEQ ID NO 78
<211> LENGTH: 497
<212> TYPE: PRT
<213> ORGANISM: Arabidopsis thaliana

<400> SEQUENCE: 78

```
Met Ile Ile Tyr Ile Leu Leu Leu Asn Arg Thr Ser His His Arg
1               5                   10                  15

Asp Ser Ala Ser Asn Ser Asn His Lys Cys Gln Gln Gln Lys Pro
            20                  25                  30

Arg Lys Asp Lys Gln Lys Gln Val Glu Gln Asn Thr Lys Lys Ile Glu
        35                  40                      45

Glu His Gln Ile Lys Ser Glu Ser Thr Leu Leu Ile Ser Asn His Asn
    50                  55                      60

Val Asn Met Ser Ser Gln Ser Asn Asn Ser Glu Ser Thr Ser Thr Asn
65                  70                  75                  80

Asn Ser Ser Lys Pro His Thr Gly Gly Asp Ile Arg Trp Asp Ala Val
                85                  90                  95

Asn Ser Leu Lys Ser Arg Gly Ile Lys Leu Gly Ile Ser Asp Phe Arg
            100                 105                 110

Val Leu Lys Arg Leu Gly Tyr Gly Asp Ile Gly Ser Val Tyr Leu Val
        115                 120                 125

Glu Leu Lys Gly Ala Asn Pro Thr Thr Tyr Phe Ala Met Lys Val Met
    130                 135                 140

Asp Lys Ala Ser Leu Val Ser Arg Asn Lys Leu Leu Arg Ala Gln Thr
145                 150                 155                 160

Glu Arg Glu Ile Leu Ser Gln Leu Asp His Pro Phe Leu Pro Thr Leu
                165                 170                 175

Tyr Ser His Phe Glu Thr Asp Lys Phe Tyr Cys Leu Val Met Glu Phe
            180                 185                 190

Cys Ser Gly Gly Asn Leu Tyr Ser Leu Arg Gln Lys Gln Pro Asn Lys
        195                 200                 205

Cys Phe Thr Glu Asp Ala Ala Arg Phe Phe Ala Ser Glu Val Leu Leu
    210                 215                 220

Ala Leu Glu Tyr Leu His Met Leu Gly Ile Val Tyr Arg Asp Leu Lys
225                 230                 235                 240

Pro Glu Asn Val Leu Val Arg Asp Asp Gly His Ile Met Leu Ser Asp
                245                 250                 255

Phe Asp Leu Ser Leu Arg Cys Ser Val Asn Pro Thr Leu Val Lys Ser
            260                 265                 270

Phe Asn Gly Gly Gly Thr Thr Gly Ile Ile Asp Asp Asn Ala Ala Val
        275                 280                 285

Gln Gly Cys Tyr Gln Pro Ser Ala Phe Phe Pro Arg Met Leu Gln Ser
    290                 295                 300

Ser Lys Lys Asn Arg Lys Ser Lys Ser Asp Phe Asp Gly Ser Leu Pro
305                 310                 315                 320

Glu Leu Met Ala Glu Pro Thr Asn Val Lys Ser Met Ser Phe Val Gly
                325                 330                 335

Thr His Glu Tyr Leu Ala Pro Glu Ile Ile Lys Asn Glu Gly His Gly
            340                 345                 350

Ser Ala Val Asp Trp Trp Thr Phe Gly Ile Phe Ile Tyr Glu Leu Leu
        355                 360                 365

His Gly Ala Thr Pro Phe Lys Gly Gln Gly Asn Lys Ala Thr Leu Tyr
```

```
                370              375              380
Asn Val Ile Gly Gln Pro Leu Arg Phe Pro Glu Tyr Ser Gln Val Ser
385              390              395              400

Ser Thr Ala Lys Asp Leu Ile Lys Gly Leu Leu Val Lys Glu Pro Gln
            405              410              415

Asn Arg Ile Ala Tyr Lys Arg Gly Ala Thr Glu Ile Lys Gln His Pro
            420              425              430

Phe Phe Glu Gly Val Asn Trp Ala Leu Ile Arg Gly Glu Thr Pro Pro
            435              440              445

His Leu Pro Glu Pro Val Asp Phe Ser Cys Tyr Val Lys Lys Glu Lys
            450              455              460

Glu Ser Leu Pro Pro Ala Ala Thr Glu Lys Lys Ser Lys Met Phe Asp
465              470              475              480

Glu Ala Asn Lys Ser Gly Ser Asp Pro Asp Tyr Ile Val Phe Glu Tyr
            485              490              495

Phe

<210> SEQ ID NO 79
<211> LENGTH: 131
<212> TYPE: PRT
<213> ORGANISM: Arabidopsis thaliana

<400> SEQUENCE: 79

Met Asp Gln Gly Gly Arg Ser Ser Gly Ser Gly Gly Gly Gly Ala Glu
1               5                   10                  15

Gln Gly Lys Tyr Arg Gly Val Arg Arg Arg Pro Trp Gly Lys Tyr Ala
            20                  25                  30

Ala Glu Ile Arg Asp Ser Arg Lys His Gly Glu Arg Val Trp Leu Gly
            35                  40                  45

Thr Phe Asp Thr Ala Glu Asp Ala Ala Arg Ala Tyr Asp Arg Ala Ala
        50                  55                  60

Tyr Ser Met Arg Gly Lys Ala Ala Ile Leu Asn Phe Pro His Glu Tyr
65              70                  75                  80

Asn Met Gly Thr Gly Ser Ser Ser Thr Ala Ala Asn Ser Ser Ser Ser
            85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Val Gly Lys
    130

<210> SEQ ID NO 80
<211> LENGTH: 690
<212> TYPE: PRT
<213> ORGANISM: Arabidopsis thaliana

<400> SEQUENCE: 80

Met Asp Ala Thr Glu Gln Ser Leu Arg Gln Ser Leu Ser Glu Lys Ser
1               5                   10                  15

Ser Ser Val Glu Ala Gln Gly Asn Ala Val Arg Ala Leu Lys Ala Ser
            20                  25                  30

Arg Ala Ala Lys Pro Glu Ile Asp Ala Ala Ile Glu Gln Leu Asn Lys
            35                  40                  45

Leu Lys Leu Glu Lys Ser Thr Val Glu Lys Glu Leu Gln Ser Ile Ile
        50                  55                  60
```

```
Ser Ser Ser Gly Asn Gly Ser Leu Asn Arg Glu Ala Phe Arg Lys Ala
 65                  70                  75                  80

Val Val Asn Thr Leu Glu Arg Arg Leu Phe Tyr Ile Pro Ser Phe Lys
                 85                  90                  95

Ile Tyr Ser Gly Val Ala Gly Leu Phe Asp Tyr Gly Pro Pro Gly Cys
                100                 105                 110

Ala Ile Lys Ser Asn Val Leu Ser Phe Trp Arg Gln His Phe Ile Leu
                115                 120                 125

Glu Glu Asn Met Leu Glu Val Asp Cys Pro Cys Val Thr Pro Glu Val
                130                 135                 140

Val Leu Lys Ala Ser Gly His Val Asp Lys Phe Thr Asp Leu Met Val
145                 150                 155                 160

Lys Asp Glu Lys Thr Gly Thr Cys Tyr Arg Ala Asp His Leu Leu Lys
                165                 170                 175

Asp Tyr Cys Thr Glu Lys Leu Glu Lys Asp Leu Thr Ile Ser Ala Glu
                180                 185                 190

Lys Ala Ala Glu Leu Lys Asp Val Leu Ala Val Met Glu Asp Phe Ser
                195                 200                 205

Pro Glu Gln Leu Gly Ala Lys Ile Arg Glu Tyr Gly Ile Thr Ala Pro
210                 215                 220

Asp Thr Lys Asn Pro Leu Ser Asp Pro Tyr Pro Phe Asn Leu Met Phe
225                 230                 235                 240

Gln Thr Ser Ile Gly Pro Ser Gly Leu Ile Pro Gly Tyr Met Arg Pro
                245                 250                 255

Glu Thr Ala Gln Gly Ile Phe Val Asn Phe Lys Asp Leu Tyr Tyr Tyr
                260                 265                 270

Asn Gly Lys Lys Leu Pro Phe Ala Ala Ala Gln Ile Gly Gln Ala Phe
                275                 280                 285

Arg Asn Glu Ile Ser Pro Arg Gln Gly Leu Leu Arg Val Arg Glu Phe
290                 295                 300

Thr Leu Ala Glu Ile Glu His Phe Val Asp Pro Glu Asn Lys Ser His
305                 310                 315                 320

Pro Lys Phe Ser Asp Val Ala Lys Leu Glu Phe Leu Met Phe Pro Arg
                325                 330                 335

Glu Glu Gln Met Ser Gly Gln Ser Ala Lys Lys Leu Cys Leu Gly Glu
                340                 345                 350

Ala Val Ala Lys Gly Thr Val Asn Asn Glu Thr Leu Gly Tyr Phe Ile
                355                 360                 365

Gly Arg Val Tyr Leu Phe Leu Thr Arg Leu Gly Ile Asp Lys Glu Arg
                370                 375                 380

Leu Arg Phe Arg Gln His Leu Ala Asn Glu Met Ala His Tyr Ala Ala
385                 390                 395                 400

Asp Cys Trp Asp Ala Glu Ile Glu Ser Ser Tyr Gly Trp Ile Glu Cys
                405                 410                 415

Val Gly Ile Ala Asp Arg Ser Ala Tyr Asp Leu Arg Ala His Ser Asp
                420                 425                 430

Lys Ser Gly Thr Pro Leu Val Ala Glu Glu Lys Phe Ala Glu Pro Lys
                435                 440                 445

Glu Val Glu Lys Leu Val Ile Thr Pro Val Lys Lys Glu Leu Gly Leu
                450                 455                 460

Ala Phe Lys Gly Asn Gln Lys Asn Val Val Glu Ser Leu Glu Ala Met
465                 470                 475                 480
```

Asn Glu Glu Glu Ala Met Glu Met Lys Ala Thr Leu Glu Ser Lys Gly
                            485                 490                 495

Glu Val Glu Phe Tyr Val Cys Thr Leu Lys Lys Ser Val Asn Ile Lys
            500                 505                 510

Lys Asn Met Val Ser Ile Ser Lys Glu Lys Lys Glu His Gln Arg
            515                 520                 525

Val Phe Thr Pro Ser Val Ile Glu Pro Ser Phe Gly Ile Gly Arg Ile
            530                 535                 540

Ile Tyr Cys Leu Tyr Glu His Cys Phe Ser Thr Arg Pro Ser Lys Ala
545                 550                 555                 560

Gly Asp Glu Gln Leu Asn Leu Phe Arg Phe Pro Pro Leu Val Ala Pro
                    565                 570                 575

Ile Lys Cys Thr Val Phe Pro Leu Val Gln Asn Gln Gln Phe Glu Glu
                580                 585                 590

Ala Ala Lys Val Ile Ser Lys Glu Leu Ala Ser Val Gly Ile Ser His
            595                 600                 605

Lys Ile Asp Ile Thr Gly Thr Ser Ile Gly Lys Arg Tyr Ala Arg Thr
            610                 615                 620

Asp Glu Leu Gly Val Pro Phe Ala Ile Thr Val Asp Ser Asp Thr Ser
625                 630                 635                 640

Val Thr Ile Arg Glu Arg Asp Ser Lys Asp Gln Val Arg Val Thr Leu
                645                 650                 655

Lys Glu Ala Ala Ser Val Val Ser Ser Val Ser Glu Gly Lys Met Thr
                660                 665                 670

Trp Gln Asp Val Trp Ala Thr Phe Pro His His Ser Ser Ala Ala Ala
            675                 680                 685

Asp Glu
    690

<210> SEQ ID NO 81
<211> LENGTH: 460
<212> TYPE: PRT
<213> ORGANISM: Arabidopsis thaliana

<400> SEQUENCE: 81

Met Thr Val Val Gly Asp Val Ala Pro Ile Pro Arg Arg Asn Ser Ser
1               5                   10                  15

Thr Cys Ser Asn Asp Ile Ala Ala Pro Leu Leu Pro Glu Cys His Gly
                20                  25                  30

Asp Glu Val Ala His Asp Glu Phe Asn Gly Ala Ser Phe Ser Gly Ala
            35                  40                  45

Val Phe Asn Leu Ala Thr Thr Ile Gly Ala Gly Ile Met Ala Leu
    50                  55                  60

Pro Ala Thr Met Lys Ile Leu Gly Leu Gly Leu Gly Ile Thr Met Ile
65                  70                  75                  80

Val Val Met Ala Phe Leu Thr Asp Ala Ser Ile Glu Phe Leu Leu Arg
                85                  90                  95

Phe Ser Lys Ala Gly Lys Asn Arg Ser Tyr Gly Gly Leu Met Gly Gly
            100                 105                 110

Ser Phe Gly Asn Pro Gly Arg Ile Leu Leu Gln Val Ala Val Leu Val
            115                 120                 125

Asn Asn Ile Gly Val Leu Ile Val Tyr Met Ile Ile Gly Asp Val
            130                 135                 140

Leu Ala Gly Lys Thr Glu Asp Gly Ile His His Phe Gly Val Leu Glu
145                 150                 155                 160

```
Gly Trp Phe Gly His His Trp Trp Asn Gly Arg Ala Ala Ile Leu Leu
                165                 170                 175

Ile Thr Thr Leu Gly Val Phe Ala Pro Leu Ala Cys Phe Lys Arg Ile
            180                 185                 190

Asp Ser Leu Lys Phe Thr Ser Ala Leu Ser Val Ala Leu Ala Val Val
            195                 200                 205

Phe Leu Ile Ile Thr Ala Gly Ile Ser Ile Met Lys Leu Ile Ser Gly
210                 215                 220

Gly Val Ala Met Pro Arg Leu Leu Pro Asp Val Thr Asp Leu Thr Ser
225                 230                 235                 240

Phe Trp Asn Leu Phe Thr Val Val Pro Val Leu Val Thr Ala Phe Ile
                245                 250                 255

Cys His Tyr Asn Val His Ser Ile Gln Asn Glu Leu Glu Asp Pro Ser
                260                 265                 270

Gln Ile Arg Pro Val Val Arg Ser Ala Leu Met Leu Cys Ser Ser Val
            275                 280                 285

Tyr Ile Met Thr Ser Ile Phe Gly Phe Leu Leu Phe Gly Asp Asp Thr
290                 295                 300

Leu Asp Asp Val Leu Ala Asn Phe Asp Thr Asp Leu Gly Ile Pro Phe
305                 310                 315                 320

Gly Ser Ile Leu Asn Asp Ala Val Arg Val Ser Tyr Ala Leu His Leu
                325                 330                 335

Met Leu Val Phe Pro Ile Val Phe Cys Pro Leu Arg Ile Asn Ile Asp
                340                 345                 350

Gly Leu Leu Phe Pro Ser Ala Arg Ser Leu Ser Thr Ser Asn Val Arg
            355                 360                 365

Phe Gly Cys Leu Thr Ala Gly Leu Ile Ser Val Ile Phe Leu Gly Ala
370                 375                 380

Asn Phe Ile Pro Ser Ile Trp Asp Ala Phe Gln Phe Thr Gly Ala Thr
385                 390                 395                 400

Ala Ala Val Cys Leu Gly Phe Ile Phe Pro Ala Ser Ile Ile Leu Lys
                405                 410                 415

Asp Arg His Asp Lys Ala Thr Asn Arg Asp Thr Thr Leu Ala Ile Phe
                420                 425                 430

Met Ile Val Leu Ala Val Leu Ser Asn Ala Ile Ala Ile Tyr Ser Asp
            435                 440                 445

Ala Tyr Ala Leu Phe Lys Lys Asn Ala Pro Arg Glu
450                 455                 460

<210> SEQ ID NO 82
<211> LENGTH: 180
<212> TYPE: PRT
<213> ORGANISM: Zea mays

<400> SEQUENCE: 82

Met Ala Asp Ala Pro Ala Ser Pro Gly Gly Gly Gly Ser His Glu
1               5                   10                  15

Ser Gly Ser Pro Arg Gly Gly Gly Gly Gly Gly Ser Val Arg
            20                  25                  30

Glu Gln Asp Arg Phe Leu Pro Ile Ala Asn Ile Ser Arg Ile Met Lys
                35                  40                  45

Lys Ala Ile Pro Ala Asn Gly Lys Ile Ala Lys Asp Ala Lys Glu Thr
            50                  55                  60

Val Gln Glu Cys Val Ser Glu Phe Ile Ser Phe Ile Thr Ser Glu Ala
```

-continued

```
                65                  70                  75                  80
Ser Asp Lys Cys Gln Arg Glu Lys Arg Lys Thr Ile Asn Gly Asp Asp
                    85                  90                  95

Leu Leu Trp Ala Met Ala Thr Leu Gly Phe Glu Asp Tyr Ile Glu Pro
                100                 105                 110

Leu Lys Val Tyr Leu Gln Lys Tyr Arg Glu Met Gly Asp Ser Lys
                115                 120                 125

Leu Thr Ser Lys Ser Ser Asp Gly Ser Ile Lys Lys Asp Ala Leu Gly
130                 135                 140

His Val Gly Ala Ser Ser Ala Val Gln Gly Met Gly Gln Gln Gly
145                 150                 155                 160

Thr Tyr Asn Gln Gly Met Gly Tyr Met Gln Pro Gln Tyr His Asn Gly
                165                 170                 175

Asp Ile Ser Asn
            180

<210> SEQ ID NO 83
<211> LENGTH: 971
<212> TYPE: PRT
<213> ORGANISM: Zea mays

<400> SEQUENCE: 83

Met Ile Val Gln Pro Ile Glu Leu Arg Ala Trp Thr Ala Phe Pro Gly
1               5                   10                  15

Ser Ala Gln Glu Gly Ile Gly Arg Met Ala Ala Ser Val Ser Arg Ala
                20                  25                  30

Ile Cys Val Gln Lys Pro Gly Ser Lys Cys Thr Arg Asp Arg Glu Ala
            35                  40                  45

Thr Ser Phe Ala Arg Arg Ser Val Ala Ala Pro Arg Pro His Ala
        50                  55                  60

Lys Ala Ala Gly Val Ile Arg Ser Asp Ser Gly Ala Gly Arg Gly Gln
65                  70                  75                  80

His Cys Ser Pro Leu Arg Ala Val Val Asp Ala Ala Pro Ile Gln Thr
                85                  90                  95

Thr Lys Lys Arg Val Phe His Phe Gly Lys Gly Lys Ser Glu Gly Asn
                100                 105                 110

Lys Thr Met Lys Glu Leu Leu Gly Gly Lys Gly Ala Asn Leu Ala Glu
            115                 120                 125

Met Ala Ser Ile Gly Leu Ser Val Pro Pro Gly Phe Thr Val Ser Thr
130                 135                 140

Glu Ala Cys Gln Gln Tyr Gln Asp Ala Gly Cys Ala Leu Pro Ala Gly
145                 150                 155                 160

Leu Trp Ala Glu Ile Val Asp Gly Leu Gln Trp Val Glu Glu Tyr Met
                165                 170                 175

Gly Ala Thr Leu Gly Asp Pro Gln Arg Pro Leu Leu Leu Ser Val Arg
                180                 185                 190

Ser Gly Ala Ala Val Ser Met Pro Gly Met Met Asp Thr Val Leu Asn
            195                 200                 205

Leu Gly Leu Asn Asp Glu Val Ala Ala Gly Leu Ala Ala Lys Ser Gly
        210                 215                 220

Glu Arg Phe Ala Tyr Asp Ser Phe Arg Arg Phe Leu Asp Met Phe Gly
225                 230                 235                 240

Asn Val Val Met Asp Ile Pro Arg Ser Leu Phe Glu Glu Lys Leu Glu
                245                 250                 255
```

```
His Met Lys Glu Ser Lys Gly Leu Lys Asn Asp Thr Asp Leu Thr Ala
                260                 265                 270

Ser Asp Leu Lys Glu Leu Val Gly Gln Tyr Lys Glu Val Tyr Leu Ser
            275                 280                 285

Ala Lys Gly Glu Pro Phe Pro Ser Asp Pro Lys Lys Gln Leu Glu Leu
        290                 295                 300

Ala Val Leu Ala Val Phe Asn Ser Trp Glu Ser Pro Arg Ala Lys Lys
305                 310                 315                 320

Tyr Arg Ser Ile Asn Gln Ile Thr Gly Leu Arg Gly Thr Ala Val Asn
                325                 330                 335

Val Gln Cys Met Val Phe Gly Asn Met Gly Asn Thr Ser Gly Thr Gly
            340                 345                 350

Val Leu Phe Thr Arg Asn Pro Asn Thr Gly Glu Lys Lys Leu Tyr Gly
        355                 360                 365

Glu Phe Leu Val Asn Ala Gln Gly Glu Asp Val Val Ala Gly Ile Arg
    370                 375                 380

Thr Pro Glu Asp Leu Asp Ala Met Lys Asn Leu Met Pro Gln Ala Tyr
385                 390                 395                 400

Asp Glu Leu Val Glu Asn Cys Asn Ile Leu Glu Ser His Tyr Lys Glu
                405                 410                 415

Met Gln Asp Ile Glu Phe Thr Val Gln Glu Asn Arg Leu Trp Met Leu
            420                 425                 430

Gln Cys Arg Thr Gly Lys Arg Thr Gly Lys Ser Ala Val Lys Ile Ala
        435                 440                 445

Val Asp Met Val Asn Glu Gly Leu Val Glu Pro Arg Ser Ala Ile Lys
450                 455                 460

Met Val Glu Pro Gly His Leu Asp Gln Leu Leu His Pro Gln Phe Glu
465                 470                 475                 480

Asn Pro Ser Ala Tyr Lys Asp Gln Val Ile Ala Thr Gly Leu Pro Ala
                485                 490                 495

Ser Pro Gly Ala Ala Val Gly Gln Val Val Phe Thr Ala Glu Asp Ala
            500                 505                 510

Glu Ala Trp His Ser Gln Gly Lys Ala Ala Ile Leu Val Arg Ala Glu
        515                 520                 525

Thr Ser Pro Glu Asp Val Gly Gly Met His Ala Ala Val Gly Ile Leu
    530                 535                 540

Thr Glu Arg Gly Gly Met Thr Ser His Ala Ala Val Val Ala Arg Gly
545                 550                 555                 560

Trp Gly Lys Cys Cys Val Ser Gly Cys Ser Gly Ile Arg Val Asn Asp
                565                 570                 575

Ala Glu Lys Leu Val Thr Ile Gly Gly His Val Leu Arg Glu Gly Glu
            580                 585                 590

Trp Leu Ser Leu Asn Gly Ser Thr Gly Glu Val Ile Leu Gly Lys Gln
        595                 600                 605

Pro Leu Ser Pro Ala Leu Ser Gly Asp Leu Gly Thr Phe Met Ala
    610                 615                 620

Trp Val Asp Asp Val Arg Lys Leu Lys Val Leu Ala Asn Ala Asp Thr
625                 630                 635                 640

Pro Asp Asp Ala Leu Thr Ala Arg Asn Asn Gly Ala Gln Gly Ile Gly
                645                 650                 655

Leu Cys Arg Thr Glu His Met Phe Phe Ala Ser Asp Glu Arg Ile Lys
            660                 665                 670

Ala Val Arg Gln Met Ile Met Ala Pro Thr Leu Glu Leu Arg Gln Gln
```

```
                675                 680                 685

Ala Leu Asp Arg Leu Leu Pro Tyr Gln Arg Ser Asp Phe Glu Gly Ile
        690                 695                 700

Phe Arg Ala Met Asp Gly Leu Pro Val Thr Ile Arg Leu Leu Asp Pro
705                 710                 715                 720

Pro Leu His Glu Phe Leu Pro Glu Gly Asn Ile Glu Asp Ile Val Ser
                725                 730                 735

Glu Leu Cys Ala Glu Thr Gly Ala Asn Gln Glu Asp Ala Leu Ala Arg
        740                 745                 750

Ile Glu Lys Leu Ser Glu Val Asn Pro Met Leu Gly Phe Arg Gly Cys
        755                 760                 765

Arg Leu Gly Ile Ser Tyr Pro Glu Leu Thr Glu Met Gln Ala Arg Ala
770                 775                 780

Ile Phe Glu Ala Ala Ile Ala Met Thr Asn Gln Gly Val Gln Val Phe
785                 790                 795                 800

Pro Glu Ile Met Val Pro Leu Val Gly Thr Pro Gln Glu Leu Gly His
                805                 810                 815

Gln Val Thr Leu Ile Arg Gln Val Ala Glu Lys Val Phe Ala Asn Val
                820                 825                 830

Gly Lys Thr Ile Gly Tyr Lys Val Gly Thr Met Ile Glu Ile Pro Arg
        835                 840                 845

Ala Ala Leu Val Ala Asp Glu Ile Ala Glu Gln Ala Glu Phe Phe Ser
        850                 855                 860

Phe Gly Thr Asn Asp Leu Thr Gln Met Thr Phe Gly Tyr Ser Arg Asp
865                 870                 875                 880

Asp Val Gly Lys Phe Ile Pro Val Tyr Leu Ala Gln Gly Ile Leu Gln
                885                 890                 895

His Asp Pro Phe Glu Val Leu Asp Gln Arg Gly Val Gly Glu Leu Val
                900                 905                 910

Lys Phe Ala Thr Glu Arg Gly Arg Lys Ala Arg Pro Asn Leu Lys Val
        915                 920                 925

Gly Ile Cys Gly Glu His Gly Gly Glu Pro Ser Ser Val Ala Phe Phe
        930                 935                 940

Ala Lys Ala Gly Leu Asp Tyr Val Ser Cys Ser Pro Phe Arg Val Pro
945                 950                 955                 960

Ile Ala Arg Leu Ala Ala Gln Val Leu Val
                965                 970

<210> SEQ ID NO 84
<211> LENGTH: 523
<212> TYPE: PRT
<213> ORGANISM: Chlorella sorokiniana

<400> SEQUENCE: 84

Cys Arg Pro Pro Ser Ser Pro Ser Leu Ser Trp Pro Pro Gly Leu Arg
1               5                   10                  15

Ser Pro Ala Leu Pro Arg Ala Val Cys Ala Arg Gly Arg Ser Ala
                20                  25                  30

Lys Arg Asp Val Ala Ala Lys Arg Leu Arg Ser Arg Ser Pro Arg Met
        35                  40                  45

Asp Ala Thr Thr Gly Asp Phe Thr Ala Leu Gln Lys Ala Val Lys Gln
        50                  55                  60

Met Ala Thr Lys Ala Gly Thr Glu Gly Leu Val His Gly Ile Lys Asn
65                  70                  75                  80
```

```
Pro Glu Leu Arg Gln Leu Leu Thr Glu Ile Phe Met Lys Asp Pro Glu
             85                  90                  95

Gln Gln Glu Phe Met Gln Ala Val Arg Glu Val Ala Val Ser Leu Gln
            100                 105                 110

Pro Val Phe Glu Lys Arg Pro Glu Leu Leu Pro Ile Phe Lys Gln Ile
        115                 120                 125

Val Glu Pro Glu Arg Val Ile Thr Phe Arg Val Ser Trp Leu Asp Asp
    130                 135                 140

Ala Gly Asn Leu Gln Val Asn Arg Gly Phe Arg Val Gln Tyr Ser Ser
145                 150                 155                 160

Ala Ile Gly Pro Tyr Lys Gly Leu Arg Phe His Pro Ser Val Asn
            165                 170                 175

Leu Ser Ile Met Lys Phe Leu Ala Phe Glu Gln Ile Phe Lys Asn Ser
            180                 185                 190

Leu Thr Thr Leu Pro Met Gly Gly Lys Gly Gly Ser Asp Phe Asp
            195                 200                 205

Pro Lys Gly Lys Ser Asp Ala Glu Val Met Arg Leu Trp Gln Ser Phe
    210                 215                 220

Met Thr Glu Leu Gln Arg His Ile Ser Tyr Val Gln Asp Val Pro Ala
225                 230                 235                 240

Gly Asp Ile Gly Val Gly Ala Arg Glu Ile Gly Tyr Leu Phe Gly Gln
            245                 250                 255

Tyr Lys Arg Ile Thr Lys Asn Tyr Thr Gly Val Leu Thr Gly Lys Gly
            260                 265                 270

Gln Glu Tyr Gly Gly Ser Glu Ile Arg Pro Glu Ala Thr Gly Tyr Gly
    275                 280                 285

Ala Val Leu Phe Val Glu Asn Val Leu Lys Asp Lys Gly Glu Ser Leu
    290                 295                 300

Lys Gly Lys Arg Cys Leu Val Ser Gly Ala Gly Asn Val Ala Gln Tyr
305                 310                 315                 320

Cys Ala Glu Leu Leu Leu Glu Lys Gly Ala Ile Val Leu Ser Leu Ser
            325                 330                 335

Asp Ser Gln Gly Tyr Val Tyr Glu Pro Asn Gly Phe Thr Arg Glu Gln
            340                 345                 350

Leu Gln Ala Val Gln Asp Met Lys Lys Lys Asn Asn Ser Ala Arg Ile
            355                 360                 365

Ser Glu Tyr Lys Ser Asp Thr Ala Val Tyr Val Gly Asp Arg Arg Lys
    370                 375                 380

Pro Trp Glu Leu Asp Cys Gln Val Asp Ile Ala Phe Pro Cys Ala Thr
385                 390                 395                 400

Gln Asn Glu Ile Asp Glu His Asp Ala Glu Leu Leu Ile Lys His Gly
            405                 410                 415

Cys Gln Tyr Val Val Glu Gly Ala Asn Met Pro Ser Thr Asn Glu Ala
            420                 425                 430

Ile His Lys Tyr Asn Lys Ala Gly Ile Ile Tyr Cys Pro Gly Lys Ala
            435                 440                 445

Ala Asn Ala Gly Gly Val Ala Val Ser Gly Leu Glu Met Thr Gln Asn
    450                 455                 460

Arg Met Ser Leu Asn Trp Thr Arg Glu Glu Val Arg Asp Lys Leu Glu
465                 470                 475                 480

Arg Ile Met Lys Asp Ile Tyr Asp Ser Ala Met Gly Pro Ser Arg Glu
            485                 490                 495

Tyr Asn Val Asp Leu Ala Ala Gly Ala Asn Ile Ala Gly Phe Thr Lys
```

```
                    500                 505                 510
Val Ala Asp Ala Val Lys Ala Gln Gly Ala Val
            515                 520

<210> SEQ ID NO 85
<211> LENGTH: 947
<212> TYPE: PRT
<213> ORGANISM: Zea mays

<400> SEQUENCE: 85

Met Thr Ala Ser Val Ser Arg Ala Ile Cys Val Gln Lys Pro Gly Ser
1               5                   10                  15

Lys Cys Thr Arg Asp Arg Glu Ala Thr Ser Phe Ala Arg Arg Ser Val
            20                  25                  30

Ala Ala Pro Arg Pro His Ala Lys Ala Ala Gly Val Ile Arg Ser
            35                  40                  45

Asp Ser Gly Ala Gly Arg Gly Gln His Cys Ser Pro Leu Arg Ala Val
        50                  55                  60

Val Asp Ala Ala Pro Ile Gln Thr Thr Lys Lys Arg Val Phe His Phe
65                  70                  75                  80

Gly Lys Gly Lys Ser Glu Gly Asn Lys Thr Met Lys Glu Leu Leu Gly
                85                  90                  95

Gly Lys Gly Ala Asn Leu Ala Glu Met Ala Ser Ile Gly Leu Ser Val
            100                 105                 110

Pro Pro Gly Phe Thr Val Ser Thr Glu Ala Cys Gln Gln Tyr Gln Asp
        115                 120                 125

Ala Gly Cys Ala Leu Pro Ala Gly Leu Trp Ala Glu Ile Val Asp Gly
    130                 135                 140

Leu Gln Trp Val Glu Glu Tyr Met Gly Ala Thr Leu Gly Asp Pro Gln
145                 150                 155                 160

Arg Pro Leu Leu Leu Ser Val Arg Ser Gly Ala Ala Val Ser Met Pro
                165                 170                 175

Gly Met Met Asp Thr Val Leu Asn Leu Gly Leu Asn Asp Glu Val Ala
            180                 185                 190

Ala Gly Leu Ala Ala Lys Ser Gly Glu Arg Phe Ala Tyr Asp Ser Phe
        195                 200                 205

Arg Arg Phe Leu Asp Met Phe Gly Asn Val Val Met Asp Ile Pro Arg
    210                 215                 220

Ser Leu Phe Glu Glu Lys Leu Glu His Met Lys Glu Ser Lys Gly Leu
225                 230                 235                 240

Lys Asn Asp Thr Asp Leu Thr Ala Ser Asp Leu Lys Glu Leu Val Gly
                245                 250                 255

Gln Tyr Lys Glu Val Tyr Leu Ser Ala Lys Gly Glu Pro Phe Pro Ser
            260                 265                 270

Asp Pro Lys Lys Gln Leu Glu Leu Ala Val Leu Ala Val Phe Asn Ser
        275                 280                 285

Trp Glu Ser Pro Arg Ala Lys Lys Tyr Arg Ser Ile Asn Gln Ile Thr
    290                 295                 300

Gly Leu Arg Gly Thr Ala Val Asn Val Gln Cys Met Val Phe Gly Asn
305                 310                 315                 320

Met Gly Asn Thr Ser Gly Thr Gly Val Leu Phe Thr Arg Asn Pro Asn
                325                 330                 335

Thr Gly Glu Lys Lys Leu Tyr Gly Glu Phe Leu Val Asn Ala Gln Gly
            340                 345                 350
```

```
Glu Asp Val Ala Gly Ile Arg Thr Pro Glu Asp Leu Asp Ala Met
            355                 360                 365
Lys Asn Leu Met Pro Gln Ala Tyr Asp Glu Leu Val Glu Asn Cys Asn
    370                 375                 380
Ile Leu Glu Ser His Tyr Lys Glu Met Gln Asp Ile Glu Phe Thr Val
385                 390                 395                 400
Gln Glu Asn Arg Leu Trp Met Leu Gln Cys Arg Thr Gly Lys Arg Thr
                405                 410                 415
Gly Lys Ser Ala Val Lys Ile Ala Val Asp Met Val Asn Glu Gly Leu
            420                 425                 430
Val Glu Pro Arg Ser Ala Ile Lys Met Val Glu Pro Gly His Leu Asp
        435                 440                 445
Gln Leu Leu His Pro Gln Phe Glu Asn Pro Ser Ala Tyr Lys Asp Gln
    450                 455                 460
Val Ile Ala Thr Gly Leu Pro Ala Ser Pro Gly Ala Ala Val Gly Gln
465                 470                 475                 480
Val Val Phe Thr Ala Glu Asp Ala Glu Ala Trp His Ser Gln Gly Lys
                485                 490                 495
Ala Ala Ile Leu Val Arg Ala Glu Thr Ser Pro Glu Asp Val Gly Gly
            500                 505                 510
Met His Ala Ala Val Gly Ile Leu Thr Glu Arg Gly Gly Met Thr Ser
        515                 520                 525
His Ala Ala Val Val Ala Arg Gly Trp Gly Lys Cys Cys Val Ser Gly
    530                 535                 540
Cys Ser Gly Ile Arg Val Asn Asp Ala Glu Lys Leu Val Thr Ile Gly
545                 550                 555                 560
Gly His Val Leu Arg Glu Gly Glu Trp Leu Ser Leu Asn Gly Ser Thr
                565                 570                 575
Gly Glu Val Ile Leu Gly Lys Gln Pro Leu Ser Pro Pro Ala Leu Ser
            580                 585                 590
Gly Asp Leu Gly Thr Phe Met Ala Trp Val Asp Asp Val Arg Lys Leu
        595                 600                 605
Lys Val Leu Ala Asn Ala Asp Thr Pro Asp Asp Ala Leu Thr Ala Arg
    610                 615                 620
Asn Asn Gly Ala Gln Gly Ile Gly Leu Cys Arg Thr Glu His Met Phe
625                 630                 635                 640
Phe Ala Ser Asp Glu Arg Ile Lys Ala Val Arg Gln Met Ile Met Ala
                645                 650                 655
Pro Thr Leu Glu Leu Arg Gln Gln Ala Leu Asp Arg Leu Leu Pro Tyr
            660                 665                 670
Gln Arg Ser Asp Phe Glu Gly Ile Phe Arg Ala Met Asp Gly Leu Pro
        675                 680                 685
Val Thr Ile Arg Leu Leu Asp Pro Pro Leu His Glu Phe Leu Pro Glu
    690                 695                 700
Gly Asn Ile Glu Asp Ile Val Ser Glu Leu Cys Ala Glu Thr Gly Ala
705                 710                 715                 720
Asn Gln Glu Asp Ala Leu Ala Arg Ile Glu Lys Leu Ser Glu Val Asn
                725                 730                 735
Pro Met Leu Gly Phe Arg Gly Cys Arg Leu Gly Ile Ser Tyr Pro Glu
            740                 745                 750
Leu Thr Glu Met Gln Ala Arg Ala Ile Phe Glu Ala Ala Ile Ala Met
        755                 760                 765
Thr Asn Gln Gly Val Gln Val Phe Pro Glu Ile Met Val Pro Leu Val
```

-continued

```
               770                 775                 780
Gly Thr Pro Gln Glu Leu Gly His Gln Val Thr Leu Ile Arg Gln Val
785                 790                 795                 800

Ala Glu Lys Val Phe Ala Asn Val Gly Lys Thr Ile Gly Tyr Lys Val
                805                 810                 815

Gly Thr Met Ile Glu Ile Pro Arg Ala Ala Leu Val Ala Asp Glu Ile
                820                 825                 830

Ala Glu Gln Ala Glu Phe Phe Ser Phe Gly Thr Asn Asp Leu Thr Gln
                835                 840                 845

Met Thr Phe Gly Tyr Ser Arg Asp Asp Val Gly Lys Phe Ile Pro Val
                850                 855                 860

Tyr Leu Ala Gln Gly Ile Leu Gln His Asp Pro Phe Glu Val Leu Asp
865                 870                 875                 880

Gln Arg Gly Val Gly Glu Leu Val Lys Leu Ala Thr Glu Arg Gly Arg
                885                 890                 895

Lys Ala Arg Pro Asn Leu Lys Val Gly Ile Cys Gly Glu His Gly Gly
                900                 905                 910

Glu Pro Ser Ser Val Ala Phe Phe Ala Lys Ala Gly Leu Asp Tyr Val
                915                 920                 925

Ser Cys Ser Pro Phe Arg Val Pro Ile Ala Arg Leu Ala Ala Ala Gln
                930                 935                 940

Val Leu Val
945

<210> SEQ ID NO 86
<211> LENGTH: 947
<212> TYPE: PRT
<213> ORGANISM: Zea mays

<400> SEQUENCE: 86

Met Ala Ala Ser Val Ser Arg Ala Ile Cys Val Gln Lys Pro Gly Ser
1               5                   10                  15

Lys Cys Thr Arg Asp Arg Glu Ala Thr Ser Phe Ala Arg Arg Ser Val
                20                  25                  30

Ala Ala Pro Arg Pro His Ala Lys Ala Arg Arg His Pro Leu
                35                  40                  45

Arg Leu Arg Arg Gly Thr Gly Pro His Cys Ser Pro Leu Arg Ala Val
        50                  55                  60

Val Asp Ala Ala Pro Ile Gln Thr Thr Lys Lys Arg Val Phe His Phe
65                  70                  75                  80

Gly Lys Gly Lys Ser Glu Gly Asn Lys Thr Met Lys Glu Leu Leu Gly
                85                  90                  95

Gly Lys Gly Ala Asn Leu Ala Glu Met Ala Ser Ile Gly Leu Ser Val
                100                 105                 110

Pro Pro Gly Phe Thr Val Ser Thr Glu Ala Cys Gln Gln Tyr Gln Asp
                115                 120                 125

Ala Gly Cys Ala Leu Pro Ala Gly Leu Trp Ala Glu Ile Val Asp Gly
        130                 135                 140

Leu Gln Trp Val Glu Glu Tyr Met Gly Ala Thr Leu Gly Asp Pro Gln
145                 150                 155                 160

Arg Pro Leu Leu Leu Ser Val Arg Ser Gly Ala Ala Val Ser Met Pro
                165                 170                 175

Gly Met Met Asp Thr Val Leu Asn Leu Gly Leu Asn Asp Glu Val Ala
                180                 185                 190
```

-continued

```
Ala Gly Leu Ala Ala Lys Ser Gly Glu Arg Phe Ala Tyr Asp Ser Phe
            195                 200                 205
Arg Arg Phe Leu Asp Met Phe Gly Asn Val Val Met Asp Ile Pro Arg
210                 215                 220
Ser Leu Phe Glu Glu Lys Leu Glu His Met Lys Glu Ser Lys Gly Leu
225                 230                 235                 240
Lys Asn Asp Thr Asp Leu Thr Ala Ser Asp Leu Lys Glu Leu Val Gly
                245                 250                 255
Gln Tyr Lys Glu Val Tyr Leu Ser Ala Lys Gly Glu Pro Phe Pro Ser
            260                 265                 270
Asp Pro Lys Lys Gln Leu Glu Leu Ala Val Leu Ala Val Phe Asn Ser
        275                 280                 285
Trp Glu Ser Pro Arg Ala Lys Lys Tyr Arg Ser Ile Asn Gln Ile Thr
    290                 295                 300
Gly Leu Arg Gly Thr Ala Val Asn Val Gln Cys Met Val Phe Gly Asn
305                 310                 315                 320
Met Gly Asn Thr Ser Gly Thr Gly Val Leu Phe Thr Arg Asn Pro Asn
                325                 330                 335
Thr Gly Glu Lys Lys Leu Tyr Gly Glu Phe Leu Val Asn Ala Gln Gly
            340                 345                 350
Glu Asp Val Val Ala Gly Ile Arg Thr Pro Glu Asp Leu Asp Ala Met
        355                 360                 365
Lys Asn Leu Met Pro Gln Ala Tyr Asp Glu Leu Val Glu Asn Cys Asn
    370                 375                 380
Ile Leu Glu Ser His Tyr Lys Glu Met Gln Asp Ile Glu Phe Thr Val
385                 390                 395                 400
Gln Glu Asn Arg Leu Trp Met Leu Gln Cys Arg Thr Gly Lys Arg Thr
                405                 410                 415
Gly Lys Ser Ala Val Lys Ile Ala Val Asp Met Val Asn Glu Gly Leu
            420                 425                 430
Val Glu Pro Arg Ser Ala Ile Lys Met Val Glu Pro Gly His Leu Asp
        435                 440                 445
Gln Leu Leu His Pro Gln Phe Glu Asn Pro Ser Ala Tyr Lys Asp Gln
    450                 455                 460
Val Ile Ala Thr Gly Leu Pro Ala Ser Pro Gly Ala Ala Val Gly Gln
465                 470                 475                 480
Val Val Phe Thr Ala Glu Asp Ala Glu Ala Trp His Ser Gln Gly Lys
                485                 490                 495
Ala Ala Ile Leu Val Arg Ala Glu Thr Ser Pro Glu Asp Val Gly Gly
            500                 505                 510
Met His Ala Ala Val Gly Ile Leu Thr Glu Arg Gly Gly Met Thr Ser
        515                 520                 525
His Ala Ala Val Val Ala Arg Trp Trp Gly Lys Cys Cys Val Ser Gly
    530                 535                 540
Cys Ser Gly Ile Arg Val Asn Asp Ala Glu Lys Leu Val Thr Ile Gly
545                 550                 555                 560
Ser His Val Leu Arg Glu Gly Glu Trp Leu Ser Leu Asn Gly Ser Thr
                565                 570                 575
Gly Glu Val Ile Leu Gly Lys Gln Pro Leu Ser Pro Ala Leu Ser
            580                 585                 590
Gly Asp Leu Gly Thr Phe Met Ala Trp Val Asp Val Arg Lys Leu
        595                 600                 605
Lys Val Leu Ala Asn Ala Asp Thr Pro Asp Asp Ala Leu Thr Ala Arg
```

```
                610                 615                 620
Asn Asn Gly Ala Gln Gly Ile Gly Leu Cys Arg Thr Glu His Met Phe
625                 630                 635                 640

Phe Ala Ser Asp Glu Arg Ile Lys Ala Val Arg Gln Met Ile Met Ala
                645                 650                 655

Pro Thr Leu Glu Leu Arg Gln Gln Ala Leu Asp Arg Leu Leu Thr Tyr
                660                 665                 670

Gln Arg Ser Asp Phe Glu Gly Ile Phe Arg Ala Met Asp Gly Leu Pro
                675                 680                 685

Val Thr Ile Arg Leu Leu Asp His Pro Ser Tyr Glu Phe Leu Pro Glu
690                 695                 700

Gly Asn Ile Glu Asp Ile Val Ser Glu Leu Cys Ala Glu Thr Gly Ala
705                 710                 715                 720

Asn Gln Glu Asp Ala Leu Ala Arg Ile Glu Lys Leu Ser Glu Val Asn
                725                 730                 735

Pro Met Leu Gly Phe Arg Gly Cys Arg Leu Gly Ile Ser Tyr Pro Glu
                740                 745                 750

Leu Thr Glu Met Gln Ala Arg Ala Ile Phe Glu Ala Ala Ile Ala Met
                755                 760                 765

Thr Asn Gln Gly Val Gln Val Phe Pro Glu Ile Met Val Pro Leu Val
770                 775                 780

Gly Thr Pro Gln Glu Leu Gly His Gln Val Thr Leu Ile Arg Gln Val
785                 790                 795                 800

Ala Glu Lys Val Phe Ala Asn Val Gly Lys Thr Ile Gly Tyr Lys Val
                805                 810                 815

Gly Thr Met Ile Glu Ile Pro Arg Ala Ala Leu Val Ala Asp Glu Ile
                820                 825                 830

Ala Glu Gln Ala Glu Phe Phe Ser Phe Gly Thr Asn Asp Leu Thr Gln
                835                 840                 845

Met Thr Phe Gly Tyr Ser Arg Asp Asp Val Gly Lys Phe Ile Pro Val
850                 855                 860

His Leu Ala Gln Gly Ile Leu Gln His Asp Pro Phe Glu Val Leu Asp
865                 870                 875                 880

Gln Arg Gly Val Gly Glu Leu Val Lys Phe Ala Thr Glu Arg Gly Arg
                885                 890                 895

Lys Ala Arg Pro Asn Leu Lys Val Gly Ile Cys Gly Glu His Gly Gly
                900                 905                 910

Glu Pro Ser Ser Val Ala Phe Phe Ala Lys Ala Gly Leu Asp Phe Val
                915                 920                 925

Ser Cys Ser Pro Phe Arg Val Pro Ile Ala Arg Leu Ala Ala Ala Gln
                930                 935                 940

Val Leu Val
945

<210> SEQ ID NO 87
<211> LENGTH: 282
<212> TYPE: PRT
<213> ORGANISM: Arabidopsis thaliana

<400> SEQUENCE: 87

Met Gly Thr Arg Ala Leu Gln Ile Pro Leu Leu Glu Gly Glu Thr Asp
1               5                   10                  15

Asn Tyr Asp Gly Val Thr Val Met Val Glu Pro Met Asp Ser Glu
                20                  25                  30
```

Val Phe Thr Glu Ser Leu Arg Ala Ser Leu Ser His Trp Arg Glu Glu
         35                  40                  45

Gly Lys Lys Gly Ile Trp Ile Lys Leu Pro Leu Gly Leu Ala Asn Leu
 50                  55                  60

Val Glu Ala Ala Val Ser Glu Gly Phe Arg Tyr His His Ala Glu Pro
65                  70                  75                  80

Glu Tyr Leu Met Leu Val Ser Trp Ile Ser Glu Thr Pro Asp Thr Ile
                 85                  90                  95

Pro Ala Asn Ala Ser His Val Val Gly Ala Gly Ala Leu Val Ile Asn
             100                 105                 110

Lys Asn Thr Lys Glu Val Leu Val Val Gln Glu Arg Ser Gly Phe Phe
         115                 120                 125

Lys Asp Lys Asn Val Trp Lys Leu Pro Thr Gly Val Ile Asn Glu Gly
130                 135                 140

Glu Asp Ile Trp Thr Gly Val Ala Arg Glu Val Glu Glu Thr Gly
145                 150                 155                 160

Ile Ile Ala Asp Phe Val Glu Val Leu Ala Phe Arg Gln Ser His Lys
                165                 170                 175

Ala Ile Leu Lys Lys Lys Thr Asp Met Phe Phe Leu Cys Val Leu Ser
            180                 185                 190

Pro Arg Ser Tyr Asp Ile Thr Glu Gln Lys Ser Glu Ile Leu Gln Ala
        195                 200                 205

Lys Trp Met Pro Ile Gln Glu Tyr Ile Asp Gln Pro Trp Asn Lys Lys
    210                 215                 220

Asn Glu Met Phe Lys Phe Met Ala Asn Ile Cys Gln Lys Lys Cys Glu
225                 230                 235                 240

Glu Glu Tyr Leu Gly Phe Ala Ile Val Pro Thr Thr Thr Ser Ser Gly
                245                 250                 255

Lys Glu Ser Phe Ile Tyr Cys Asn Ala Asp His Ala Lys Arg Leu Lys
            260                 265                 270

Val Ser Arg Asp Gln Ala Ser Ala Ser Leu
        275                 280

<210> SEQ ID NO 88
<211> LENGTH: 567
<212> TYPE: PRT
<213> ORGANISM: Arabidopsis thaliana

<400> SEQUENCE: 88

Ile Val Leu Val Val Ala Val Leu Thr His Thr Ala Ser Ala Ala Val
1               5                   10                  15

Arg Glu Tyr His Trp Glu Val Glu Tyr Lys Tyr Trp Ser Pro Asp Cys
                20                  25                  30

Lys Glu Gly Ala Val Met Thr Val Asn Gly Phe Pro Gly Pro Thr
            35                  40                  45

Ile Lys Ala Phe Ala Gly Asp Thr Ile Val Val Asn Leu Thr Asn Lys
        50                  55                  60

Leu Thr Thr Glu Gly Leu Val Ile His Trp His Gly Ile Arg Gln Phe
65                  70                  75                  80

Gly Ser Pro Trp Ala Asp Gly Ala Ala Gly Val Thr Gln Cys Ala Ile
                85                  90                  95

Asn Pro Gly Glu Thr Phe Thr Tyr Asn Phe Thr Val Glu Lys Pro Gly
            100                 105                 110

Thr His Phe Tyr His Gly His Tyr Gly Met Gln Arg Ser Ala Gly Leu
        115                 120                 125

Tyr Gly Ser Leu Ile Val Asp Val Ala Lys Gly Lys Ser Glu Arg Leu
    130                 135                 140

Arg Tyr Asp Gly Glu Phe Asn Leu Leu Leu Ser Asp Trp Trp His Glu
145                 150                 155                 160

Ala Ile Pro Ser Gln Glu Leu Gly Leu Ser Ser Lys Pro Met Arg Trp
                165                 170                 175

Ile Gly Glu Ala Gln Ser Ile Leu Ile Asn Gly Arg Gly Gln Phe Asn
                180                 185                 190

Cys Ser Leu Ala Ala Gln Phe Ser Asn Asn Thr Ser Leu Pro Met Cys
            195                 200                 205

Thr Phe Lys Glu Gly Asp Gln Cys Ala Pro Gln Ile Leu His Val Glu
    210                 215                 220

Pro Asn Lys Thr Tyr Arg Ile Arg Leu Ser Ser Thr Thr Ala Leu Ala
225                 230                 235                 240

Ser Leu Asn Leu Ala Val Gln Gly His Lys Leu Val Val Glu Ala
                245                 250                 255

Asp Gly Asn Tyr Ile Thr Pro Phe Thr Thr Asp Ile Asp Ile Tyr
                260                 265                 270

Ser Gly Glu Ser Tyr Ser Val Leu Leu Thr Thr Asp Gln Asp Pro Ser
            275                 280                 285

His Asn Tyr Tyr Ile Ser Val Gly Val Arg Gly Arg Lys Pro Asn Thr
    290                 295                 300

Thr Gln Ala Leu Thr Ile Leu Asn Tyr Val Thr Ala Pro Ala Ser Lys
305                 310                 315                 320

Leu Pro Ser Ser Pro Pro Val Thr Pro Arg Trp Asp Asp Phe Glu
                325                 330                 335

Arg Ser Lys Asn Phe Ser Lys Lys Ile Phe Ser Ala Met Gly Ser Pro
                340                 345                 350

Ser Pro Pro Lys Lys Tyr Arg Lys Arg Leu Ile Leu Leu Asn Thr Gln
            355                 360                 365

Asn Leu Ile Asp Gly Tyr Thr Lys Trp Ala Ile Asn Asn Val Ser Leu
    370                 375                 380

Val Thr Pro Ala Thr Pro Tyr Leu Gly Ser Val Lys Tyr Asn Leu Lys
385                 390                 395                 400

Leu Gly Phe Asn Arg Lys Ser Pro Pro Arg Ser Tyr Arg Met Asp Tyr
                405                 410                 415

Asp Ile Met Asn Pro Pro Phe Pro Asn Thr Thr Gly Asn Gly
                420                 425                 430

Ile Tyr Val Phe Pro Phe Asn Val Thr Val Asp Val Ile Gln Asn
            435                 440                 445

Ala Asn Val Leu Lys Gly Ile Val Ser Glu Ile His Pro Trp His Leu
    450                 455                 460

His Gly His Asp Phe Trp Val Leu Gly Tyr Gly Asp Gly Lys Phe Lys
465                 470                 475                 480

Pro Gly Ile Asp Glu Lys Thr Tyr Asn Leu Lys Asn Pro Pro Leu Arg
                485                 490                 495

Asn Thr Ala Ile Leu Tyr Pro Tyr Gly Trp Thr Ala Ile Arg Phe Val
                500                 505                 510

Thr Asp Asn Pro Gly Val Trp Phe Phe His Cys His Ile Glu Pro His
            515                 520                 525

Leu His Met Gly Met Gly Val Val Phe Ala Glu Gly Leu Asn Arg Ile
    530                 535                 540

```
Gly Lys Val Pro Asp Glu Ala Leu Gly Cys Gly Leu Thr Lys Gln Phe
545                 550                 555                 560

Leu Met Asn Arg Asn Arg Asn
                565
```

<210> SEQ ID NO 89
<211> LENGTH: 523
<212> TYPE: PRT
<213> ORGANISM: Chlorella sorokiniana

<400> SEQUENCE: 89

```
Cys Arg Pro Pro Ser Ser Pro Ser Leu Ser Trp Pro Pro Gly Leu Arg
1               5                   10                  15

Ser Pro Ala Leu Pro Arg Ala Val Ala Cys Ala Arg Gly Arg Ser Ala
                20                  25                  30

Lys Arg Asp Val Ala Ala Lys Arg Leu Arg Ser Arg Ser Pro Arg Met
            35                  40                  45

Asp Ala Thr Thr Gly Asp Phe Thr Ala Leu Gln Lys Ala Val Lys Gln
50                  55                  60

Met Ala Thr Lys Ala Gly Thr Glu Gly Leu Val His Gly Ile Lys Asn
65                  70                  75                  80

Pro Glu Leu Arg Gln Leu Leu Thr Glu Ile Phe Met Lys Asp Pro Glu
                85                  90                  95

Gln Gln Glu Phe Met Gln Ala Val Arg Glu Val Ala Val Ser Leu Gln
            100                 105                 110

Pro Val Phe Glu Lys Arg Pro Glu Leu Leu Pro Ile Phe Lys Gln Ile
        115                 120                 125

Val Glu Pro Glu Arg Val Ile Thr Phe Arg Val Ser Trp Leu Asp Asp
130                 135                 140

Ala Gly Asn Leu Gln Val Asn Arg Gly Phe Arg Val Gln Tyr Ser Ser
145                 150                 155                 160

Ala Ile Gly Pro Tyr Lys Gly Gly Leu Arg Phe His Pro Ser Val Asn
                165                 170                 175

Leu Ser Ile Met Lys Phe Leu Ala Phe Glu Gln Ile Phe Lys Asn Ser
            180                 185                 190

Leu Thr Thr Leu Pro Met Gly Gly Gly Lys Gly Gly Ser Asp Phe Asp
        195                 200                 205

Pro Lys Gly Lys Ser Asp Ala Glu Val Met Arg Phe Cys Gln Ser Phe
210                 215                 220

Met Thr Glu Leu Gln Arg His Ile Ser Tyr Val Gln Asp Val Pro Ala
225                 230                 235                 240

Gly Asp Ile Gly Val Gly Ala Arg Glu Ile Gly Tyr Leu Phe Gly Gln
                245                 250                 255

Tyr Lys Arg Ile Thr Lys Asn Tyr Thr Gly Val Leu Thr Gly Lys Gly
            260                 265                 270

Gln Glu Tyr Gly Gly Ser Glu Ile Arg Pro Glu Ala Thr Gly Tyr Gly
        275                 280                 285

Ala Val Leu Phe Val Glu Asn Val Leu Lys Asp Lys Gly Glu Ser Leu
290                 295                 300

Lys Gly Lys Arg Cys Leu Val Ser Gly Ala Gly Asn Val Ala Gln Tyr
305                 310                 315                 320

Cys Ala Glu Leu Leu Leu Glu Lys Gly Ala Ile Val Leu Ser Leu Ser
                325                 330                 335

Asp Ser Gln Gly Tyr Val Tyr Glu Pro Asn Gly Phe Thr Arg Glu Gln
            340                 345                 350
```

```
Leu Gln Ala Val Gln Asp Met Lys Lys Asn Asn Ser Ala Arg Ile
        355                 360                 365

Ser Glu Tyr Lys Ser Asp Thr Ala Val Tyr Val Gly Asp Arg Arg Lys
    370                 375                 380

Pro Trp Glu Leu Asp Cys Gln Val Asp Ile Ala Phe Pro Cys Ala Thr
385                 390                 395                 400

Gln Asn Glu Ile Asp Glu His Asp Ala Glu Leu Leu Ile Lys His Gly
                405                 410                 415

Cys Gln Tyr Val Val Glu Gly Ala Asn Met Pro Ser Thr Asn Glu Ala
                420                 425                 430

Ile His Lys Tyr Asn Lys Ala Gly Ile Ile Tyr Cys Pro Gly Lys Ala
                435                 440                 445

Ala Asn Ala Gly Gly Val Ala Val Ser Gly Leu Glu Met Thr Gln Asn
            450                 455                 460

Arg Met Ser Leu Asn Trp Thr Arg Glu Glu Val Arg Asp Lys Leu Glu
465                 470                 475                 480

Arg Ile Met Lys Asp Ile Tyr Asp Ser Ala Met Gly Pro Ser Arg Glu
                485                 490                 495

Tyr Asn Val Asp Leu Ala Ala Gly Ala Asn Ile Ala Gly Phe Thr Lys
                500                 505                 510

Val Ala Asp Ala Val Lys Ala Gln Gly Ala Val
            515                 520

<210> SEQ ID NO 90
<211> LENGTH: 131
<212> TYPE: PRT
<213> ORGANISM: Arabidopsis thaliana

<400> SEQUENCE: 90

Met Asp Gln Gly Gly Arg Ser Ser Gly Ser Gly Gly Gly Gly Ala Glu
1               5                   10                  15

Gln Gly Lys Tyr Arg Gly Val Arg Arg Arg Pro Trp Gly Lys Tyr Ala
            20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Tyr
65                  70                  75                  80

Asn Met Gly Thr Gly Ser Ser Ser Thr Ala Ala Asn Ser Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys
    130

<210> SEQ ID NO 91
<211> LENGTH: 423
<212> TYPE: PRT
<213> ORGANISM: Zea mays

<400> SEQUENCE: 91

Met Ala Gln Ala Val Val Pro Ala Met Gln Cys Arg Val Gly Val Lys
1               5                   10                  15
```

-continued

Ala Ala Ala Gly Arg Val Trp Ser Ala Gly Arg Thr Arg Thr Gly Arg
            20                  25                  30
Gly Gly Ala Ser Pro Gly Phe Lys Val Met Ala Val Ser Thr Gly Ser
            35                  40                  45
Thr Gly Val Val Pro Arg Leu Glu Gln Leu Leu Asn Met Asp Thr Thr
 50                  55                  60
Pro Tyr Thr Asp Lys Val Ile Ala Glu Tyr Ile Trp Val Gly Gly Ser
 65                  70                  75                  80
Gly Ile Asp Ile Arg Ser Lys Ser Arg Thr Ile Ser Lys Pro Val Glu
                85                  90                  95
Asp Pro Ser Glu Leu Pro Lys Trp Asn Tyr Asp Gly Ser Ser Thr Gly
            100                 105                 110
Gln Ala Pro Gly Glu Asp Ser Glu Val Ile Leu Tyr Pro Gln Ala Ile
            115                 120                 125
Phe Lys Asp Pro Phe Arg Gly Gly Asn Asn Val Leu Val Ile Cys Asp
130                 135                 140
Thr Tyr Thr Pro Gln Gly Glu Pro Leu Pro Thr Asn Lys Arg His Arg
145                 150                 155                 160
Ala Ala Gln Ile Phe Ser Asp Pro Lys Val Gly Glu Gln Val Pro Trp
                165                 170                 175
Phe Gly Ile Glu Gln Glu Tyr Thr Leu Leu Gln Lys Asp Val Asn Trp
            180                 185                 190
Pro Leu Gly Trp Pro Val Gly Gly Phe Pro Gly Pro Gln Gly Pro Tyr
            195                 200                 205
Tyr Cys Ala Val Gly Ala Asp Lys Ser Phe Gly Arg Asp Ile Ser Asp
210                 215                 220
Ala His Tyr Lys Ala Cys Leu Tyr Ala Gly Ile Asn Ile Ser Gly Thr
225                 230                 235                 240
Asn Gly Glu Val Met Pro Gly Gln Trp Glu Tyr Gln Val Gly Pro Ser
                245                 250                 255
Val Gly Ile Glu Ala Gly Asp His Ile Trp Ile Ser Arg Tyr Ile Leu
            260                 265                 270
Glu Arg Ile Thr Glu Gln Ala Gly Val Val Leu Thr Leu Asp Pro Lys
            275                 280                 285
Pro Ile Gln Gly Asp Trp Asn Gly Ala Gly Cys His Thr Asn Tyr Ser
290                 295                 300
Thr Lys Thr Met Arg Glu Asp Gly Gly Phe Glu Glu Ile Lys Arg Ala
305                 310                 315                 320
Ile Leu Asn Leu Ser Leu Arg His Asp Leu His Ile Ser Ala Tyr Gly
                325                 330                 335
Glu Gly Asn Glu Arg Arg Leu Thr Gly Lys His Glu Thr Ala Ser Ile
            340                 345                 350
Gly Thr Phe Ser Trp Gly Val Ala Asn Arg Gly Cys Ser Ile Arg Val
            355                 360                 365
Gly Arg Asp Thr Glu Ala Lys Gly Lys Gly Tyr Leu Glu Asp Arg Arg
370                 375                 380
Pro Ala Ser Asn Met Asp Pro Tyr Ile Val Thr Gly Leu Leu Ala Glu
385                 390                 395                 400
Thr Thr Ile Leu Trp Gln Pro Ser Leu Glu Ala Glu Ala Leu Ala Ala
                405                 410                 415
Lys Lys Leu Ala Leu Lys Val
            420

<210> SEQ ID NO 92
<211> LENGTH: 263
<212> TYPE: PRT
<213> ORGANISM: Zea mays

<400> SEQUENCE: 92

```
Met Leu Glu Leu Arg Leu Val Gln Gly Ser Leu Leu Lys Lys Val Leu
1               5                   10                  15

Glu Ala Ile Arg Glu Leu Val Asn Asp Ala Asn Phe Asp Cys Ser Gly
            20                  25                  30

Thr Gly Phe Ser Leu Gln Ala Met Asp Ser Ser His Val Ala Leu Val
        35                  40                  45

Ala Leu Leu Leu Arg Ala Glu Gly Phe Glu His Tyr Arg Cys Asp Arg
    50                  55                  60

Asn Leu Ser Met Gly Met Asn Leu Asn Asn Met Ala Lys Met Leu Arg
65                  70                  75                  80

Cys Ala Gly Asn Asp Asp Ile Ile Thr Ile Lys Ala Asp Asp Gly Ser
                85                  90                  95

Asp Thr Val Thr Phe Met Phe Glu Ser Pro Lys Gln Asp Lys Ile Ala
            100                 105                 110

Asp Phe Glu Met Lys Leu Met Asp Ile Asp Ser Glu His Leu Gly Ile
        115                 120                 125

Pro Asp Ser Glu Tyr Gln Ala Ile Val Arg Met Pro Ser Ser Glu Phe
    130                 135                 140

Met Arg Ile Cys Lys Asp Leu Ser Ser Ile Gly Asp Thr Val Val Ile
145                 150                 155                 160

Ser Val Thr Lys Glu Gly Val Lys Phe Ser Thr Ser Gly Glu Ile Gly
                165                 170                 175

Ser Ala Asn Ile Val Cys Arg Gln Asn Gln Thr Ile Asp Lys Pro Glu
            180                 185                 190

Glu Ala Thr Ile Ile Glu Met Gln Pro Val Ser Leu Thr Phe Ala
        195                 200                 205

Leu Arg Tyr Met Asn Ser Phe Thr Lys Ala Ser Ser Leu Ser Glu Gln
    210                 215                 220

Val Thr Ile Ser Leu Ser Ser Glu Leu Pro Val Val Glu Tyr Lys
225                 230                 235                 240

Ile Ala Glu Met Gly Tyr Ile Arg Phe Tyr Leu Ala Pro Lys Ile Glu
                245                 250                 255

Asp Asp Glu Glu Met Lys Pro
            260
```

<210> SEQ ID NO 93
<211> LENGTH: 1388
<212> TYPE: DNA
<213> ORGANISM: Artificial Sequence
<220> FEATURE:
<223> OTHER INFORMATION: seed preferred promoter

<400> SEQUENCE: 93

```
atcaacaaat tactcctcaa tcacactcct atagaaaacg gtttaagcta tcattacatg      60
tctagttggt tttactcagc cctagaagtg ttgtttattg catcactttc cacgaagcac     120
aattttcttt tttacaatc accagacctc acaggctcac acatatgctt tagagcacat      180 tctaaactt gaactataaa agctgttaac actaatacac tatgcgttct tttttgctcc     240
aaacactttt gatccattat taggagacac tccacttaga aagattttct aatcctttgg    300
```

-continued

| | |
|---|---|
| tcaactagga agttcaaggt ttttctaaac agaaattcat ttcacaagta atttaattta | 360 |
| taaggaaatg aatagagaaa tcaaatcatt gaagaactac aaaatataga ttcaaggtca | 420 |
| ggtctaagaa atatttcctg aagctcaaaa aagagttttc ctctcacatt atagaattgg | 480 |
| cctttacttc aacattttcc cacctattcc acatttggtc agaacatttt taattacttg | 540 |
| tggatcaatt tccggttgaa atgggtttgg tgaatatccg gttcagttat atggtggccg | 600 |
| ttggaattgg cttattagtt gtggccgttg ttgaagccgt tggtattggt aagggagaag | 660 |
| cagacttgtg gctatgagtc tatgaccatg actcgtgatt atggagctgt cttatgaccc | 720 |
| tgaccatcac cttgatctgg tggattccaa tgttttcttc ttcttctaat aaaatattat | 780 |
| ggtcaataca ggtgctaatt aagatggtaa taatttctta tgtttctgtg gtaaagtttg | 840 |
| attcaattcc gtagttttag ataatcttat ttccatacat aaattttata gttttatcta | 900 |
| ctttgttctt atgttttatc tctagccaag agttattatt attatcagaa gaagaaaaaa | 960 |
| aaaagaagca tatatacaaa aggtttaata aaatgtatta tacaaggcaa ttatccaaat | 1020 |
| ttttttttgtt ttggtttaca ttgatgctct caggatttca taaggataga gagatctatt | 1080 |
| cgtatacgtg tcacgtcatg agtgggtgtt tcgccaatcc atgaaacgca cctagatatc | 1140 |
| taaaacacat atcaattgcg aatctgcgaa gtgcagccaa ttaaccacgt aagcaaacaa | 1200 |
| acaatctaaa ccccaaaaaa aatctatgac tagccaatag caacctcaga gattgatatt | 1260 |
| tcaagataag acagtattta gatttctgta ttatatatag cgaaaatcgc atcaatacca | 1320 |
| aaccacccat ttcttggctt acaacaacaa atcttaaacg ttttactttg tgctgcacta | 1380 |
| ctcaacct | 1388 |

<210> SEQ ID NO 94
<211> LENGTH: 1785
<212> TYPE: DNA
<213> ORGANISM: Artificial Sequence
<220> FEATURE:
<223> OTHER INFORMATION: root preferred promoter

<400> SEQUENCE: 94

| | |
|---|---|
| taggaaaaaa gtttatattc ctacccaaac tttcggcacc agagacaaat taggtttgtt | 60 |
| cagaaaatca gtcgctcatc gacagactta acaccacaaa atcatcagaa tttctttggg | 120 |
| acaaaatgga aaatgttctt cacggctcca cctaccaaaa tttcgatatc aagctcaaaa | 180 |
| gcatacacaa actataacta attccatagt tacgtaatct taacttcgaa ttcaacaaca | 240 |
| catgcatgca tcgactgaat cttcaacaaa tgcaatcaaa cacacaaaat tgctaccaaa | 300 |
| aaaatatgat ttttttttta tgatttcaat tttcatccgg cacttagtcc aaaactttt | 360 |
| ttgtgtgtca acatttttta aaaaaatctt taaacggata tctgatctaa gagcatgttc | 420 |
| ataggtgata cttacaaaat attttttaaga aattttttag tattatttat aatgtttgtt | 480 |
| taataaatat atataagatt ttttgctttt atcaaatgtg accaatcaga agaaccacg | 540 |
| tcagatgata ctgatatgac aaatatgata ctgatcaaac atattctaat tgctttacta | 600 |
| atataaaaat aattttttgga cttgtgatac tctaaaaata tcacccatat acatggtcta | 660 |
| atatatggat cgtaaaaaac tcatatataa tattaataag tagtagaaga gcgtagacca | 720 |
| tgtcctgggt cgtcgtccaa atgaccacaa gaagatttca aaacagagga aaatatttct | 780 |
| cattaaataa gttttcctga cgcataagat aacattatta caagattcag aaaaagaaag | 840 |
| gtgaaaggat aatgtttctc ctactatata agatgtgtac atctgaaaaa atatgaatat | 900 |
| atttgtaacg tttgactgtt attacatgat taatacgata taaatattaa catttttttt | 960 |

```
caaaataaaa gtaatatagt aaggaaatga aaagaggcat gaagcatgcc tcttttttg    1020 gtcggctgcc gtttacaatt gccaattgcg atagttactc ttcttgcgtg tacgactttt    1080
gttttttttt acatattcgc caataatttg acgttttcta ttagtttgtt tgatactctg    1140
ttgtcttgct aaaactcaat aaaacattaa attactttct tgaatgaagc tggaacaaat    1200
ctaacataaa tagaaaatga tgggcaagtt gatgttattc gtaaatttat ttagattata    1260
ttatataaaa agcaatccaa ttatatatct catatataca atttcttatc ttactttgtc    1320
aatgtcatat acgtaactaa aacttgcgga aatagaaaat gccacgtgta tggtggacat    1380
aatccgaatc tctctctttc ttctataaat agtggccatt cccattggtt gaaatcacaa    1440
aagcatcata agaagaagaa gaaactacaa tagttaatca atcaaagaga agtaagagaa    1500
caggtaaacc cctagattct ctcttcttta catttatatg catatatgta gactatgtag    1560
ttcgagcttc atggtacaaa attcaataaa ctcttcttat gacttcgttt acaattgtgt    1620
ttgtgaatag acacaaaaga ttagttttgt ttactttaga ttcaaaacac ttcgggccta    1680
tcctgtatat atgctgatca gatgcatgtg gttgattaat ctttaatctc atcatattaa    1740
ttactaattt tttgtttgtt tgattaattt gtgtgtggta aaggt                    1785
```

<210> SEQ ID NO 95
<211> LENGTH: 1243
<212> TYPE: DNA
<213> ORGANISM: Artificial Sequence
<220> FEATURE:
<223> OTHER INFORMATION: meristem and endosperm preferred promoter

<400> SEQUENCE: 95

```
aaaaccaccg agggacctga tctgcaccgg ttttgatagt tgagggaccc gttgtgtctg      60
gttttccgat cgagggacga aaatcggatt cggtgtaaag ttaagggacc tcagatgaac     120
ttattccgga gcatgattgg gaagggagga cataaggccc atgtcgcatg tgtttggacg     180
gtccagatct ccagatcact cagcaggatc ggccgcgttc gcgtagcacc cgcggtttga     240
ttcggcttcc cgcaaggcgg cggccggtgg ccgtgccgcc gtagcttccg ccggaagcga     300
gcacgccgcc gccgccgacc cggctctgcg tttgcaccgc cttgcacgcg atacatcggg     360
atagatagct actactctct ccgtttcaca atgtaaatca ttctactatt ttccacattc     420
atattgatgt taatgaatat agacatatat atctatttag attcattaac atcaatatga     480
atgtaggaaa tgctagaatg acttacattg tgaattgtga aatggacgaa gtacctacga     540
tggatggatg caggatcatg aaagaattaa tgcaagatcg tatctgccgc atgcaaaatc     600
ttactaattg cgctgcatat atgcatgaca gcctgcatgc gggcgtgtaa gcgtgttcat     660
ccattaggaa gtaaccttgt cattacttat accagtacta catactatat agtattgatt     720
tcatgagcaa atctacaaaa ctggaaagca ataaggaata cgggactgga aaagactcaa     780
cattaatcac caaatatttc gccttctcca gcagaatata tatctctcca tcttgatcac     840
tgtacacact gacagtgtac gcataaacgc agcagccagc ttaactgtcg tctcaccgtc     900
gcacactggc cttccatctc aggctagctt tctcagccac ccatcgtaca tgtcaactcg     960
gcgcgcgcac aggcacaaat tacgtacaaa acgcatgacc aaatcaaaac caccggagaa    1020
gaatcgctcc cgcgcgcggc ggcggcgcgc acgtacgaat gcacgcacgc acgcccaacc    1080
ccacgacacg atcgcgcgcg acgccggcga caccggccat ccaccgcgc cctcacctcg    1140 ccgactataa atacgtaggc atctgcttga tcttgtcatc catctcacca ccaaaaaaaa    1200
```
aggaaaaaaa aacaaaacac accaagccaa ataaaagcga caa            1243

<210> SEQ ID NO 96
<211> LENGTH: 2439
<212> TYPE: DNA
<213> ORGANISM: Artificial Sequence
<220> FEATURE:
<223> OTHER INFORMATION: root specific promoter

<400> SEQUENCE: 96

```
ggaagctaac tagtcacggc gaatacatga cgacatcggc ctacaacgca caacttcttg    60
gcataaaagc ttcaatttca atgcccctat ctggaagccc taggcgccgc gcaaatgtaa   120
aacattcgct tcgcttggct tgttatccaa aatagagtat ggacctccga cagattggca   180
acccgtgggt aatcgaaaat ggctccatct gcccctttgt cgaaggaatc aggaaacggc   240
cctcacctcc tggcggagtg tagatatgtg aaagaatcta ggcgacactt gcagactgga   300
caacatgtga acaaataaga ccaacgttat ggcaacaagc ctcgacgcta ctcaagtggt   360
gggaggccac cgcatgttcc aacgaagcgc caaagaaagc cttgcagact ctaatgctat   420
tagtcgccta ggatatttgg aatgaaagga accgcagagt ttttcagcac caagagcttc   480
cggtggctag tctgatagcc aaaattaagg aggatgccaa acatgggtc ttggcgggcg    540
cgaaacacct tgataggtgg cttaccttt aacatgttcg ggccaaaggc cttgagacgg    600
taaagttttc tatttgcgct tgcgcatgta caattttatt cctctattca atgaaattgg   660
tggctcactg gttcattaaa aaaaaagaa tctagcctgt tcgggaagaa gaggatttta    720
ttcgtgagag agagagagag agagagagag agagggagag agaaggagga ggaggatttt   780
caggcttcgc attgcccaac ctctgcttct gttggcccaa gaagaatccc aggcgcccat   840
gggctggcag tttaccacgg acctacctag cctaccttag ctatctaagc gggccgacct   900
agtagctacg tgcctagtgt agattaaagt tggcgggcca gcaggaagcc acgctgcaat   960
ggcatcttcc cctgtccttc gcgtacgtga aaacaaaccc aggtaagctt agaatcttct  1020
tgcccgttgg actgggacac ccaccaatcc caccatgccc cgatattcct ccggtctcgg  1080
ttcatgtgat gtcctctctt gtgtgatcac ggagcaagca ttcttaaacg gcaaaagaaa  1140
atcaccaact tgctcacgca gtcacgctgc accgcgcgaa gcgacgcccg ataggccaag  1200
atcgcgagat aaaataacaa ccaatgatca taaggaaaca agcccgcgat gtgtcgtgtg  1260
cagcaatctt ggtcatttgc gggatcgagt gcttcacggc taaccaaata ttcggccgat  1320
gatttaacac attatcagcg tagatgtacg tacgatttgt taattaatct acgagccttg  1380
ctagggcagg tgttctgcca gccaatccag atcgccctcg tatgcacgct cacatgatgg  1440
cagggcaggg ttcacatgag ctctaacggt cgattaatta atcccggggc tcgactataa  1500
atacctccct aatcccatga tcaaaaccat ctcaagcagc ctaatcatct ccagctgatc  1560
aagagctctt aattagctag ctagtgatta gctgcgcttg tgatcgatcg atctcgggta  1620
cgtagcaata gatctaccgt cttcggtacg cgctcactcc gccctctgcc tttgttactg  1680
ccacgttct ctgaatgctc tcttgtgtgg tgattgctga gagtggttta gctggatcta   1740
gaattacact ctgaaatcgt gttctgcctg tgctgattac ttgccgtcct ttgtagcagc  1800
aaaatatagg gacatggtag tacgaaacga agatagaacc tacacagcaa tacgagaaat  1860
gtgtaatttg gtgcttagcg gtatttattt aagcacatgt tggtgttata gggcacttgg  1920
attcagaagt ttgctgttaa tttaggcaca ggcttcatac tacatgggtc aatagtatag  1980
ggattcatat tataggcgat actataataa tttgttcgtc tgcagagctt attatttgcc  2040
```

```
aaaattagat attcctattc tgttttgtt tgtgtgctgt taaattgtta acgcctgaag    2100
gaataaatat aaatgacgaa attttgatgt ttatctctgc tcctttattg tgaccataag    2160
tcaagatcag atgcacttgt tttaaatatt gttgtctgaa gaaataagta ctgacagtat    2220
tttgatgcat tgatctgctt gtttgttgta acaaaattta aaaataaaga gtttcctttt    2280
tgttgctctc cttacctcct gatggtatct agtatctacc aactgacact atattgcttc    2340
tctttacata cgtatcttgc tcgatgcctt ctccctagtg ttgaccagtg ttactcacat    2400
agtctttgct catttcattg taatgcagat accaagcgg                            2439
```

<210> SEQ ID NO 97
<211> LENGTH: 2327
<212> TYPE: DNA
<213> ORGANISM: Artificial Sequence
<220> FEATURE:
<223> OTHER INFORMATION: endosperm specific promoter

<400> SEQUENCE: 97

```
tgtttggact ccagaaaatt tacgggagtt ggtggagcag gtcattaagt actataaaaa      60
atcatgtagc tgaagctgca agtatttaga agacatttag ataagttatt ttatttatca    120
tttagattaa gaaaatttaa aactatttaa attgatatta taaactacag ctccacactg    180
gagctagatc ctggagtcat tacaaacacc cccttaatgg gaaagagaa gataatgtat     240 atctaattat tgtttctgtg tcacctatag ctattagttc aaaacttcat aatcactggt    300
acaaataagc tctagagagg cggttcggaa cccattttta ttgttgtttt tcaaaaccac    360
tagtgttagg gaccgccagt ggaaactgaa acgccattgg aaattgattt tcactgatgg    420
tgagctaaga aaaccgccat tggtaatcct ttgcagaaaa cataaactag gttttaaaaa    480
tagtaaacaa atatttttat taggagaggc cccacatagt cgcaccattt ttcgcgcatt    540
attcacgcgc tacgcaacca atggtaattg aacctcagag acttcactct tgtgtagcct    600
cctttgccac tccactaaac acttacttgt gtcttgattg cattttgttg cccacatatt    660
agaacaaaca gagtgtaaat tgattgtttg aggctaaaa caaattcaaa tgaaaaagta    720
gtcaactact aaattgaata attgtttatg ttctaccact tttatttgg tacttttccc      780 atcggaggcg gtttgtaaaa tttgcatttt aagttttaca aatttcaatg aaattttgag    840
agcccaaatg atttcaaata aaaagttgt caactacaat gttttataac ttttaatttg    900 gtggttttt aaacaagctc atttgaaaaa ctaaaatgat cgattctaca tgattttag       960 gtcgattttt taaggaatcg cctgtacaaa tatttctact gacagttttt aagaaaccac    1020
ctgtggaaat catagatttg tactagcggt ttttctcaag taactgctag tagaaatatg    1080 gtggtttct taagaaaact gtttgtagga atgcacgatt tatataaatg gatttgttaa    1140
gaaaaccgct agtggaatgt tctttcaact aacggttatt gagtcgtgac agccaattta    1200
atttccttga taactaaaag cggctgtaaa aattagacca tgatgtaggc acggagctgt    1260
tttgtactga atgcgcccac tgttttgttg gaaaagtgca tgtacttatt attcattctg    1320
tttatttcta gctggcattc agttcttaca gccacagatt atgcaaaacg cctatttctg    1380
ccagcaaatt tacaggaaaa gtcatggact ttttccgggtt attttcctat aagtacagcc    1440
attcctttca cttacaggcc ccaacattag cacaaagaac acaatagacc actgatttaa    1500
cacctgcagg accaggtggg cccaccgtct tcggtacgcg ctcactccgc cctctgcctt    1560
tgttactgcc acgtttctct gaatgctctc ttgtgtggtg attgctgaga gtggtttagc    1620
```

| | |
|---|---|
| tggatctaga attacactct gaaatcgtgt tctgcctgtg ctgattactt gccgtccttt | 1680 |
| gtagcagcaa atataggga catggtagta cgaaacgaag atagaaccta cacagcaata | 1740 |
| cgagaaatgt gtaatttggt gcttagcggt atttatttaa gcacatgttg gtgttatagg | 1800 |
| gcacttggat tcagaagttt gctgttaatt taggcacagg cttcatacta catgggtcaa | 1860 |
| tagtataggg attcatatta taggcgatac tataataatt tgttcgtctg cagagcttat | 1920 |
| tatttgccaa aattagatat tcctattctg tttttgtttg tgtgctgtta aattgttaac | 1980 |
| gcctgaagga ataaatataa atgacgaaat tttgatgttt atctctgctc ctttattgtg | 2040 |
| accataagtc aagatcagat gcacttgttt taaatattgt tgtctgaaga aataagtact | 2100 |
| gacagtattt tgatgcattg atctgcttgt ttgttgtaac aaaatttaaa aataaagagt | 2160 |
| ttccttttg ttgctctcct tacctcctga tggtatctag tatctaccaa ctgacactat | 2220 |
| attgcttctc tttacatacg tatcttgctc gatgccttct ccctagtgtt gaccagtgtt | 2280 |
| actcacatag tctttgctca tttcattgta atgcagatac caagcgg | 2327 |

<210> SEQ ID NO 98
<211> LENGTH: 1713
<212> TYPE: DNA
<213> ORGANISM: Artificial Sequence
<220> FEATURE:
<223> OTHER INFORMATION: endosperm specific promoter

<400> SEQUENCE: 98

| | |
|---|---|
| atatagattt cttaacgaca atctcgcatt gtttattgcc tcacatggtg acacacagct | 60 |
| cttacatttg tccttatact cacggtgcag tgcactacta ctgtaacccc atggtctgga | 120 |
| aaacagcaac gcaaccttc tgccttggaa cagcaagcta tacagcgcta tataacaaac | 180 |
| ttgcacaata atatgctaca tttctgaaag caaactccgc ttatcttcgc gttaaggaat | 240 |
| ggtattacac ttaaaatgac aaaatatcac actttagaac cccacgcctt tacctaaaaa | 300 |
| aaagttgatt gatacaagaa caaatgttta cagcttgtta cacctcccat caagcaaaga | 360 |
| aatggaatct tatatagatt tcttaacgac aatctcgcat tgtttattgc tcacatggt | 420 |
| gacacacagc tcttacattt gtccttatac tcacggtgca gtgcactact actgtaaccc | 480 |
| catggtctgg aaaacagcaa cgcaaccttt ctgccttgga acagcaagct atacagcgct | 540 |
| atataacaaa cttgcacaat aatatgctac atttctgaaa gcaaactccg cttatcttcg | 600 |
| cgttaaggaa tggtattaca cttaaaatga caaaatatca cactttagaa ccccacgcct | 660 |
| ttacctaaaa aaaagttgat tgatacaaga caaatgttt acagcttgtt cacctcccca | 720 |
| tcaagcaaag aaatggaatc ttttattta tgtacacgtg tacgggtagc tattgtttat | 780 |
| aaattgcaga agacacctca acatgatgga taattgtata cgcaaaacta ctttcctcga | 840 |
| attccccatt ctataaattc cagttaaact taattcgtaa gatcaatcat aattctcgag | 900 |
| ttgcaaacca ccgtcttcgg tacgcgctca ctccgccctc tgcctttgtt actgccacgt | 960 |
| ttctctgaat gctctcttgt gtggtgattg ctgagagtgg tttagctgga tctagaatta | 1020 |
| cactctgaaa tcgtgttctg cctgtgctga ttacttgccg tcctttgtag cagcaaaata | 1080 |
| tagggacatg gtagtacgaa acgaagatag aacctacaca gcaatacgag aaatgtgtaa | 1140 |
| tttggtgctt agcggtattt atttaagcac atgttggtgt tatagggcac ttggattcag | 1200 |
| aagtttgctg ttaatttagg cacaggcttc atactcatg ggtcaatagt atagggattc | 1260 |
| atattatagg cgatactata ataatttgtt cgtctgcaga gcttattatt tgccaaaatt | 1320 |
| agatattcct attctgtttt tgtttgtgtg ctgttaaatt gttaacgcct gaaggaataa | 1380 |

-continued

| | |
|---|---|
| atataaatga cgaaattttg atgtttatct ctgctccttt attgtgacca taagtcaaga | 1440 |
| tcagatgcac ttgttttaaa tattgttgtc tgaagaaata agtactgaca gtattttgat | 1500 |
| gcattgatct gcttgtttgt tgtaacaaaa tttaaaaata aagagtttcc tttttgttgc | 1560 |
| tctccttacc tcctgatggt atctagtatc taccaactga cactatattg cttctcttta | 1620 |
| catacgtatc ttgctcgatg ccttctccct agtgttgacc agtgttactc acatagtctt | 1680 |
| tgctcatttc attgtaatgc agataccaag cgg | 1713 |

<210> SEQ ID NO 99
<211> LENGTH: 2516
<212> TYPE: DNA
<213> ORGANISM: Artificial Sequence
<220> FEATURE:
<223> OTHER INFORMATION: seed specific promoter

<400> SEQUENCE: 99

| | |
|---|---|
| acactttat tatcgcgtca aatcagtacc tcaatcgata ttgtagccta gtgttcttat | 60 |
| taaatgggaa gaattcgagg acacactaat tccttgctaa cacacactta tgctccattt | 120 |
| ggatgtcgat attggagggc atggaactga attggtttca attacaaatc agccatgata | 180 |
| ttgtaatgag atgtaatttc aattctattc tttggatgtc actgaattgg agtttggaat | 240 |
| tgtgtggtcc aattccacct tatatagaag agggatgctc tgtattggga gagtgagttt | 300 |
| ctagttatag tctagcttcg ggaaattgag tctctcgttc caaatctcaa ttccatgtgc | 360 |
| aaccaaacaa tagaattctg gaaagctgat tccaattcct aattccgtgc tccaatatct | 420 |
| acatccaaac gggtgttaca taaatataga aatgacatat caaccatgca aaaccacatt | 480 |
| ggcgatgttg aacaaaggcg aacacccaca tactatgtac cgcacacggc atctcttct | 540 |
| caaaggtcga accacgtgtg ttccatgcat gcgtggaaca tgcaaggttg tcacgtatag | 600 |
| ggaatgatga cacacgagag cgcctacaag gcaacaaaca ccttacgtac cacgtagagt | 660 |
| gcattttgct accacctgcc accggatgac atgtatgcat gcatgcgttg tgtacgcata | 720 |
| cactgctgtc tgctggtgcc caaagaccat ctagaacagc atcttttaat tctccatttc | 780 |
| cctcacgcca ttgctagtgc cttgcacatg ctcgcactcc ctaacacatc ttcctcccctt | 840 |
| tattttttcgt tgccaattgc tagttgttca aatgccacgt tttccttaca cagctgtagg | 900 |
| gcaccgtacc acgtagaatg cattcctcgc caccaacaga caacacggcc gggcatatgt | 960 |
| acgtcttacg ccggaccatc accagtatat atgatgctag ggatcagtgg gcgccccttt | 1020 |
| tgcctcgtcc tcccggggcg gcattcctat gtcctaactg aagcaaccca cgcgccgcca | 1080 |
| tttctgttgc gaatgagtcc atggacatat gtgccaacag aacccctcgg aaggcaccat | 1140 |
| ctatctatct atctctcaag caatattata tttggcaccct acgctcaagt acatagacag | 1200 |
| tgtgcacggc attgtgcagc tggaaagccc gcccgacacg agggctgcca aatcgacagc | 1260 |
| tccgcgccct tggaaatcct agtcacttgt tcacaattga ccaatctacc cttgaagcac | 1320 |
| acggtggatg gtactgccac atttggctta tagggcata gaggacaatg aatgcaactg | 1380 |
| gagcgggaag gagagcttta atttgtaagt actcggtgaa cacggcacct gatgatgatg | 1440 |
| atgatggaca gcgaggaatt gttataaaag gcgcccgtcc ctcccatggc tcaagaacaa | 1500 |
| gggaatcgaa gccattccct cttcaagagg ggatcatcag attgggctta ttattccta | 1560 |
| ttactccagg taattcttag tttgttgccc ttccaaaccct ttacatctca tataagaatg | 1620 |
| attattacat gcaagattat gttgacatgc gtcgtcatgg tatttttttt aggcaaggat | 1680 |

```
cggagttgct ctgaattgac tgaaccagat ctaccgtctt cggtacgcgc tcactccgcc   1740
ctctgccttt gttactgcca cgtttctctg aatgctctct tgtgtggtga ttgctgagag   1800
tggtttagct ggatctagaa ttacactctg aaatcgtgtt ctgcctgtgc tgattacttg   1860
ccgtcctttg tagcagcaaa atatagggac atggtagtac gaaacgaaga tagaacctac   1920
acagcaatac gagaaatgtg taatttggtg cttagcggta tttatttaag cacatgttgg   1980
tgttataggg cacttggatt cagaagtttg ctgttaattt aggcacaggc ttcatactac   2040
atgggtcaat agtataggga ttcatattat aggcgatact ataataattt gttcgtctgc   2100
agagcttatt atttgccaaa attagatatt cctattctgt ttttgtttgt gtgctgttaa   2160
attgttaacg cctgaaggaa taaatataaa tgacgaaatt ttgatgttta tctctgctcc   2220
tttattgtga ccataagtca agatcagatg cacttgtttt aaatattgtt gtctgaagaa   2280
ataagtactg acagtatttt gatgcattga tctgcttgtt tgttgtaaca aaatttaaaa   2340
ataaagagtt tcctttttgt tgctctcctt acctcctgat ggtatctagt atctaccaac   2400
tgacactata ttgcttctct ttacatacgt atcttgctcg atgccttctc cctagtgttg   2460
accagtgtta ctcacatagt ctttgctcat ttcattgtaa tgcagatacc aagcgg       2516

<210> SEQ ID NO 100
<211> LENGTH: 2282
<212> TYPE: DNA
<213> ORGANISM: Artificial Sequence
<220> FEATURE:
<223> OTHER INFORMATION: seed preferred promoter

<400> SEQUENCE: 100
gaggtgcata aggctggcaa gacgacagtt aggaacgcat gcgagcgagg ttgacggacg     60
cgataaggtt agcgcatgcg tcgaacgcgg gctggcgagg gtggaaggca tgataaggct    120
attgggtagc gcaaaatgtg tagacagcgg gcgagtgagg atggcagtgg tggcatgcat    180
ggacgcggtt ggagcatacg cgacaagaat ggagcacgac gtagatttcg ggaggccgtg    240
gttggagcgc ccgcgggcga gatggcggcc atggttagag cgcccgtggt tacgggtggg    300
ttcatggcga gcgagggggt tgcaagattt ccagggcgct cgggtcggtt gcaagctcca    360
cggtggaggc gtgacggaga cgacgtgggg agggaggtcg tggggaaatt cggacgagca    420
gaggcgtggc aggtgtggca tggggaggga ggtcgcgggg agggcgcagg gaggtggcat    480
ggggagggag gctggggacg aagatgatgt gggcccagag ggacgcggga caaagaattg    540
cgtatgataa cgggttgatt cgtagaattt taggcggtat ttataaaaat gacgcaggac    600
agccattggt actgatactt taatatagta gagaagagat ataaattagg acgggtacaa    660
caagaccaca cgtactaaca tttttttttg tcacaggctg ctctaataca tatctctatg    720
ataagcgagc tagggatgct agcgtgtcca tttgattcct atataaatct ccaattatag    780
ctgtagcaat taatttaata aacacccaac aatagatcaa atctcatagc aaatcataat    840
catgaatgct ccaaaatcag ctagctggct ctcccttatc ttcgtttttc cttcttctcc    900
tgcaacgaaa agaaaaaaaa agaaaagaaa agaaaacggc cgcttgtggt actaactccc    960
aactacgcac ctaccgcgcg cataactctt ggccgcctgc cctcatcacc tccgcgtcgc   1020
cgtcgactca tccttatcct ccccatcacg ctcaccccgc gcccgcaccg cgccatccgt   1080
actttcccgg ccgccccacc gctggccgcc ccgacgtgtc gcgccgccac cggaaggtcc   1140
cgggccgtcg ggcgggcaga gcgcctgcag cggtggaccc acgccacgct gacgcgggcg   1200
cgcgtccgtc caagaaacct gacgtaagca gtgacagaat tggcgccgcc tctcggcgtc   1260
```

```
cacgtgtcgt ggtcaacctg tcagagtggg gctccgtgtg tgcgctaccg caggggcccg    1320
gcgcacgggc cacacgtgtc gcggtcgacc gcggctataa atgcccggct ccgcactcgg    1380
aacaagtttc aagctctcct cccctcttcc taccattagc agtagccaca gccagaacac    1440
cagcagacag cagcatcagc agggaggaac agcggcccac cgtcttcggt acgcgctcac    1500
tccgccctct gcctttgtta ctgccacgtt tctctgaatg ctctcttgtg tggtgattgc    1560
tgagagtggt ttagctggat ctagaattac actctgaaat cgtgttctgc ctgtgctgat    1620
tacttgccgt cctttgtagc agcaaaatat agggacatgg tagtacgaaa cgaagataga    1680
acctacacag caatacgaga aatgtgtaat ttggtgctta gcggtattta tttaagcaca    1740
tgttggtgtt atagggcact tggattcaga agtttgctgt taatttaggc acaggcttca    1800
tactacatgg gtcaatagta tagggattca tattataggc gatactataa taatttgttc    1860
gtctgcagag cttattattt gccaaaatta gatattccta ttctgttttt gtttgtgtgc    1920
tgttaaattg ttaacgcctg aaggaataaa tataaatgac gaaattttga tgtttatctc    1980
tgctccttta ttgtgaccat aagtcaagat cagatgcact tgttttaaat attgttgtct    2040
gaagaaataa gtactgacag tattttgatg cattgatctg cttgtttgtt gtaacaaaat    2100
ttaaaaataa agagtttcct ttttgttgct ctccttacct cctgatggta tctagtatct    2160
accaactgac actatattgc ttctctttac atacgtatct tgctcgatgc cttctcccta    2220
gtgttgacca gtgttactca catagtcttt gctcatttca ttgtaatgca gataccaagc    2280
gg                                                                   2282

<210> SEQ ID NO 101
<211> LENGTH: 1546
<212> TYPE: DNA
<213> ORGANISM: Artificial Sequence
<220> FEATURE:
<223> OTHER INFORMATION: meristem and cob enhanced promoter

<400> SEQUENCE: 101
cctagcgtcc cctgcccaaa agtgggctca acaagcctaa atacatataa tttataccac      60
gtgcaacaca tttattcatc catatcacat gtcatgcaag gcataagcat catgttaact     120
tagttatact gacatacatt tatgagttga gatgtccagg atgtgagcgc atgagcccat     180
tgtccattca ggaccaagac aggctactaa gcactttcta cataacttgt atgtgctaac     240
tatagcatgc ttatatggct ctctccaaag ttcaaagcta gctcaaatct tttgatttaa     300
taaaacttaa atttgtttga tttcagataa actgataatt tttataatat ttagagtgag     360
ttgaaaacag aaactggccg caaatccacc tcaagccttt tgatttgacc taaaaaaaag     420
aagcccccac aaacaccact ccacactagt gcactgtctc tctccaaagg cagctgcatt     480
ggcctccagc cttttcccta ctgtgccgcg cgccctccct tctctctaat aatagcatag     540
ggagagaagg catactccga ggcatccttc tcctttccct ctccttcccc aaacccttt      600 cctctttccc tcgccccaag aacttcatct catctccagg cgcccctttt gcgcttgcgc     660
aggaggagct cacggggaca gtgggcggag agctcgatcg ctgcaccact acttcactgg     720
aggtccgccc actcccgggc ccaccgtctt cggtacgcgc tcactccgcc ctctgccttt     780
gttactgcca cgtttctctg aatgctctct tgtgtggtga ttgctgagag tggtttagct     840
ggatctagaa ttcactctg aaatcgtgtt ctgcctgtgc tgattacttg ccgtcctttg     900
tagcagcaaa atatagggac atggtagtac gaaacgaaga tagaacctac acagcaatac     960
```

-continued

```
gagaaatgtg taatttggtg cttagcggta tttatttaag cacatgttgg tgttataggg    1020
cacttggatt cagaagtttg ctgttaattt aggcacaggc ttcatactac atgggtcaat    1080
agtataggga ttcatattat aggcgatact ataataattt gttcgtctgc agagcttatt    1140
atttgccaaa attagatatt cctattctgt ttttgtttgt gtgctgttaa attgttaacg    1200
cctgaaggaa taaatataaa tgacgaaatt ttgatgttta tctctgctcc tttattgtga    1260
ccataagtca agatcagatg cacttgtttt aaatattgtt gtctgaagaa ataagtactg    1320
acagtatttt gatgcattga tctgcttgtt tgttgtaaca aaatttaaaa ataaagagtt    1380
tcctttttgt tgctctcctt acctcctgat ggtatctagt atctaccaac tgacactata    1440
ttgcttctct ttacatacgt atcttgctcg atgccttctc cctagtgttg accagtgtta    1500
ctcacatagt ctttgctcat ttcattgtaa tgcagatacc aagcgg                  1546
```

TRANSGENIC PLANTS WITH ENHANCED TRAITS

REFERENCE TO RELATED APPLICATIONS

This application is a Divisional of U.S. patent application Ser. No. 16/085,527, filed Sep. 14, 2018, which has been abandoned, which is a 371 National Stage application of International Application No. PCT/US2017/022617, filed Mar. 16, 2017, which claims the benefit of U.S. Provisional Application No. 62/310,136, filed Mar. 18, 2016, the entire contents of each are herein incorporated by reference in their entirety.

INCORPORATION OF SEQUENCE LISTING

The sequence listing file named "MONS_448USD1_SequenceListing.txt", which is 323 kilobytes (measured in MS-WINDOWS) and was created on Mar. 18, 2016, is filed herewith and incorporated herein by reference in its entirety.

FIELD OF THE INVENTION

Disclosed herein are recombinant DNA constructs, plants having altered phenotypes, enhanced traits, increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with altered phenotypes, enhanced traits, increased yield, increased nitrogen use efficiency and increased water use efficiency.

SUMMARY

In one aspect, the present disclosure provides recombinant DNA constructs each comprising: a polynucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-29; or a polynucleotide sequence that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 30-92. The recombinant DNA construct may comprise a promoter, such as a heterologous promoter, functional in a plant cell and operably linked to the polynucleotide sequence. Vectors, plasmids, plants, propagules and plant cells are further provided comprising such a recombinant DNA construct.

Plants comprising a recombinant DNA construct may be a field crop plant, such as corn, soybean, cotton, canola, rice, barley, oat, wheat, turf grass, alfalfa, sugar beet, sunflower, quinoa and sugarcane. A plant comprising a recombinant DNA construct may have an altered phenotype or an enhanced trait as compared to a control plant. The enhanced trait may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and increased water use efficiency as compared to a control plant. The altered phenotype may be, for example, plant height, biomass, canopy area, anthocyanin content, chlorophyll content, water applied, water content, and water use efficiency.

According to another aspect, the present disclosure provides methods for altering a phenotype, enhancing a trait, increasing yield, increasing nitrogen use efficiency, or increasing water use efficiency in a plant comprising producing a transgenic plant comprising a recombinant DNA construct, wherein the recombinant DNA construct comprises: a polynucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-29; or a polynucleotide sequence that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 30-92. The step of producing a transgenic plant may further comprise transforming a plant cell or tissue with the recombinant DNA construct, and regenerating or developing the transgenic plant from the plant cell or tissue comprising the recombinant DNA construct. The transgenic plant may then be crossed to (a) itself; (b) a second plant from the same plant line; (c) a wild type plant; or (d) a second plant from a different plant line, to produce one or more progeny plants; and a plant may be selected from the progeny plants having increased yield, increased nitrogen use efficiency, or increased water use efficiency as compared to a control plant. Plants produced by this method are further provided. According to some embodiments, the transgenic plant may be produced by site-directed integration of the recombinant DNA construct into the genome of a plant cell or tissue using a donor template comprising the recombinant DNA construct, and then regenerating or developing the transgenic plant from the transgenic plant cell or tissue.

According to another aspect, the present disclosure provides recombinant DNA molecules for use as a donor template in site-directed integration, wherein a recombinant DNA molecule comprises an insertion sequence comprising: a polynucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-29; or a polynucleotide sequence that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 30-92. The insertion sequence of the recombinant DNA molecule may comprise a promoter, such as a heterologous promoter, functional in a plant cell and operably linked to the polynucleotide sequence. The recombinant DNA molecule may further comprise at least one homology arm flanking the insertion sequence. Plants, propagules and plant cells are further provided comprising the insertion sequence. According to some embodiments, the recombinant DNA molecule may further comprise an expression cassette encoding a site-specific nuclease and/or one or more guide RNAs.

According to another aspect, the present disclosure provides recombinant DNA molecules for use as a donor template in site-directed integration, wherein a recombinant DNA molecule comprises an insertion sequence for modulation of expression of an endogenous gene, wherein the endogenous gene comprises: a polynucleotide sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 1-29, or a portion thereof; or a polynucleotide sequence that encodes a polypeptide having an amino acid sequence with at least 90%, at least 91%, at least 92%, at least 93%, at least 94%, at least 95%, at least 96%, at least 97%, at least 98%, at least 99% identity, or 100% identity to a sequence selected from the group consisting of SEQ ID NOs: 30-92. The insertion sequence may comprise a promoter, an enhancer, an intron, and/or a terminator region, which may correspond to a promoter, an enhancer, an intron, or a terminator region of an endogenous gene. Plants, propagules and plant cells are further provided comprising the insertion sequence. According to some embodiments, the recombinant DNA molecule may further comprise an expression cassette encoding a site-specific nuclease and/or one or more guide RNAs.

According to another aspect, the present disclosure provides methods for altering a phenotype, enhancing a trait, increasing yield, increasing nitrogen use efficiency, or increasing water use efficiency in a plant comprising: (a) modifying the genome of a plant cell by: (i) identifying an endogenous gene of the plant corresponding to a gene selected from the list of genes in Tables 1 and 12 herein, and their homologs, and (ii) modifying a sequence of the endogenous gene in the plant cell via site-directed integration to modify the expression level of the endogenous gene; and (b) regenerating or developing a plant from the plant cell.

DETAILED DESCRIPTION

In the attached sequence listing:

SEQ ID NOs 1 to 29 are nucleotide sequences of the coding strand of the DNA used in the recombinant DNA constructs imparting an enhanced trait in plants, each representing a coding sequence for a protein.

SEQ ID NOs 30 to 58 are amino acid sequences of the cognate proteins of the DNA molecules with nucleotide sequences of SEQ ID NOs 1 to 29 respectively in the same order.

SEQ ID NOs 59 to 92 are amino acid sequences of proteins homologous to the proteins with amino acid sequences of SEQ ID NOs 30 to 58.

SEQ ID NOs 93 to 101 are nucleotide sequences of DNA molecules used in the recombinant DNA constructs imparting an enhanced trait or altered phenotype in plants, each representing a promoter with a specific expression pattern.

Unless otherwise stated, nucleic acid sequences in the text of this specification are given, when read from left to right, in the 5' to 3' direction. One of skill in the art would be aware that a given DNA sequence is understood to define a corresponding RNA sequence which is identical to the DNA sequence except for replacement of the thymine (T) nucleotide of the DNA with uracil (U) nucleotide. Thus, providing a specific DNA sequence is understood to define the exact RNA equivalent. A given first polynucleotide sequence, whether DNA or RNA, further defines the sequence of its exact complement (which can be DNA or RNA), i.e., a second polynucleotide that hybridizes perfectly to the first polynucleotide by forming Watson-Crick base-pairs. By "essentially identical" or "essentially complementary" to a target gene or a fragment of a target gene is meant that a polynucleotide strand (or at least one strand of a double-stranded polynucleotide) is designed to hybridize (generally under physiological conditions such as those found in a living plant or animal cell) to a target gene or to a fragment of a target gene or to the transcript of the target gene or the fragment of a target gene; one of skill in the art would understand that such hybridization does not necessarily require 100% sequence identity or complementarity. A first nucleic acid sequence is "operably" connected or "linked" with a second nucleic acid sequence when the first nucleic acid sequence is placed in a functional relationship with the second nucleic acid sequence. For example, a promoter sequence is "operably linked" to a DNA sequence if the promoter provides for transcription or expression of the DNA sequence. Generally, operably linked DNA sequences are contiguous.

As used herein, the term "expression" refers to the production of a polynucleotide or a protein by a plant, plant cell or plant tissue which can give rise to an altered phenotype or enhanced trait. Expression can also refer to the process by which information from a gene is used in the synthesis of functional gene products, which may include but are not limited to other polynucleotides or proteins which may serve, e.g., an enzymatic, structural or regulatory function. Gene products having a regulatory function include but are not limited to elements that affect the occurrence or level of transcription or translation of a target protein. In some cases, the expression product is a non-coding functional RNA.

"Modulation" of expression refers to the process of effecting either overexpression or suppression of a polynucleotide or a protein.

The term "suppression" as used herein refers to a lower expression level of a target polynucleotide or target protein in a plant, plant cell or plant tissue, as compared to the expression in a wild-type or control plant, cell or tissue, at any developmental or temporal stage for the gene. The term "target protein" as used in the context of suppression refers to a protein which is suppressed; similarly, "target mRNA" refers to a polynucleotide which can be suppressed or, once expressed, degraded so as to result in suppression of the target protein it encodes. The term "target gene" as used in the context of suppression refers to either "target protein" or "target mRNA". In alternate non-limiting embodiments, suppression of the target protein or target polynucleotide can give rise to an enhanced trait or altered phenotype directly or indirectly. In one exemplary embodiment, the target protein is one which can indirectly increase or decrease the expression of one or more other proteins, the increased or decreased expression, respectively, of which is associated with an enhanced trait or an altered phenotype. In another exemplary embodiment, the target protein can bind to one or more other proteins associated with an altered phenotype or enhanced trait to enhance or inhibit their function and thereby affect the altered phenotype or enhanced trait indirectly.

Suppression can be applied using numerous approaches. Non-limiting examples include: suppressing an endogenous gene(s) or a subset of genes in a pathway, suppressing one or more mutation that has resulted in decreased activity of a protein, suppressing the production of an inhibitory agent, to elevate, reduce or eliminate the level of substrate that an enzyme requires for activity, producing a new protein, activating a normally silent gene; or accumulating a product that does not normally increase under natural conditions.

Conversely, the term "overexpression" as used herein refers to a greater expression level of a polynucleotide or a protein in a plant, plant cell or plant tissue, compared to expression in a wild-type plant, cell or tissue, at any developmental or temporal stage for the gene. Overexpression can take place in plant cells normally lacking expression of polypeptides functionally equivalent or identical to the present polypeptides. Overexpression can also occur in plant cells where endogenous expression of the present polypeptides or functionally equivalent molecules normally occurs, but such normal expression is at a lower level. Overexpression thus results in a greater than normal production, or "overproduction" of the polypeptide in the plant, cell or tissue.

The term "target protein" as used herein in the context of overexpression refers to a protein which is overexpressed; "target mRNA" refers to an mRNA which encodes and is translated to produce the target protein, which can also be overexpressed. The term "target gene" as used in the context of overexpression refers to either "target protein" or "target mRNA". In alternative embodiments, the target protein can effect an enhanced trait or altered phenotype directly or indirectly. In the latter case it may do so, for example, by affecting the expression, function or substrate available to one or more other proteins. In an exemplary embodiment, the target protein can bind to one or more other proteins associated with an altered phenotype or enhanced trait to enhance or inhibit their function.

Overexpression can be achieved using numerous approaches. In one embodiment, overexpression can be achieved by placing the DNA sequence encoding one or more polynucleotides or polypeptides under the control of a promoter, examples of which include but are not limited to endogenous promoters, heterologous promoters, inducible promoters, development specific promoters, and tissue specific promoters. In one exemplary embodiment, the promoter is a constitutive promoter, for example, the cauliflower mosaic virus 35S promoter and other constitutive promoters known in the art. Thus, depending on the promoter used, overexpression can occur throughout a plant, in specific tissues of the plant, in specific stages of development of the plant, or in the presence or absence of different inducing or inducible agents, such as hormones or environmental signals.

Gene Suppression Elements: The gene suppression element can be transcribable DNA of any suitable length, and generally includes at least about 19 to about 27 nucleotides (for example 19, 20, 21, 22, 23, or 24 nucleotides) for every target gene that the recombinant DNA construct is intended to suppress. In many embodiments, the gene suppression element includes more than 23 nucleotides (for example, more than about 30, about 50, about 100, about 200, about 300, about 500, about 1000, about 1500, about 2000, about 3000, about 4000, or about 5000 nucleotides) for every target gene that the recombinant DNA construct is intended to suppress.

Suitable gene suppression elements useful in the recombinant DNA constructs of the invention include at least one element (and, in some embodiments, multiple elements) selected from the group consisting of: (a) DNA that includes at least one anti-sense DNA segment that is anti-sense to at least one segment of the at least one first target gene; (b) DNA that includes multiple copies of at least one anti-sense DNA segment that is anti-sense to at least one segment of the at least one first target gene; (c) DNA that includes at least one sense DNA segment that is at least one segment of the at least one first target gene; (d) DNA that includes multiple copies of at least one sense DNA segment that is at least one segment of the at least one first target gene; (e) DNA that transcribes to RNA for suppressing the at least one first target gene by forming double-stranded RNA and includes at least one anti-sense DNA segment that is anti-sense to at least one segment of the at least one target gene and at least one sense DNA segment that is at least one segment of the at least one first target gene; (f) DNA that transcribes to RNA for suppressing the at least one first target gene by forming a single double-stranded RNA and includes multiple serial anti-sense DNA segments that are anti-sense to at least one segment of the at least one first target gene and multiple serial sense DNA segments that are at least one segment of the at least one first target gene; (g) DNA that transcribes to RNA for suppressing the at least one first target gene by forming multiple double strands of RNA and includes multiple anti-sense DNA segments that are anti-sense to at least one segment of the at least one first target gene and multiple sense DNA segments that are at least one segment of the at least one first target gene, and wherein the multiple anti-sense DNA segments and the multiple sense DNA segments are arranged in a series of inverted repeats; (h) DNA that includes nucleotides derived from a miRNA, preferably a plant miRNA; (i) DNA that includes nucleotides of a siRNA; (j) DNA that transcribes to an RNA aptamer capable of binding to a ligand; and (k) DNA that transcribes to an RNA aptamer capable of binding to a ligand, and DNA that transcribes to regulatory RNA capable of regulating expression of the first target gene, wherein the regulation is dependent on the conformation of the regulatory RNA, and the conformation of the regulatory RNA is allosterically affected by the binding state of the RNA aptamer.

Any of these gene suppression elements, whether transcribing to a single double-stranded RNA or to multiple double-stranded RNAs, can be designed to suppress more than one target gene, including, for example, more than one allele of a target gene, multiple target genes (or multiple segments of at least one target gene) from a single species, or target genes from different species.

Anti-Sense DNA Segments: In one embodiment, the at least one anti-sense DNA segment that is anti-sense to at least one segment of the at least one first target gene includes DNA sequence that is anti-sense or complementary to at least a segment of the at least one first target gene, and can include multiple anti-sense DNA segments, that is, multiple copies of at least one anti-sense DNA segment that is anti-sense to at least one segment of the at least one first target gene. Multiple anti-sense DNA segments can include DNA sequence that is anti-sense or complementary to multiple segments of the at least one first target gene, or to multiple copies of a segment of the at least one first target gene, or to segments of multiple first target genes, or to any combination of these. Multiple anti-sense DNA segments can be fused into a chimera, e.g., including DNA sequences that are anti-sense to multiple segments of one or more first target genes and fused together.

The anti-sense DNA sequence that is anti-sense or complementary to (that is, can form Watson-Crick base-pairs with) at least a segment of the at least one first target gene has at least about 80%, or at least about 85%, or at least about 90%, or at least about 95% complementarity to at least a segment of the at least one first target gene. In one embodiment, the DNA sequence that is anti-sense or complementary to at least a segment of the at least one first target gene has between about 95% to about 100% complementarity to at least a segment of the at least one first target gene. Where the at least one anti-sense DNA segment includes multiple anti-sense DNA segments, the degree of complementarity can be, but need not be, identical for all of the multiple anti-sense DNA segments.

Sense DNA Segments: In another embodiment, the at least one sense DNA segment that is at least one segment of the at least one first target gene includes DNA sequence that corresponds to (that is, has a sequence that is identical or substantially identical to) at least a segment of the at least one first target gene, and can include multiple sense DNA segments, that is, multiple copies of at least one sense DNA segment that corresponds to (that is, has the nucleotide sequence of) at least one segment of the at least one first target gene. Multiple sense DNA segments can include DNA sequence that is or that corresponds to multiple segments of the at least one first target gene, or to multiple copies of a segment of the at least one first target gene, or to segments of multiple first target genes, or to any combination of these. Multiple sense DNA segments can be fused into a chimera, that is, can include DNA sequences corresponding to multiple segments of one or more first target genes and fused together.

The sense DNA sequence that corresponds to at least a segment of the target gene has at least about 80%, or at least about 85%, or at least about 90%, or at least about 95% sequence identity to at least a segment of the target gene. In one embodiment, the DNA sequence that corresponds to at least a segment of the target gene has between about 95% to about 100% sequence identity to at least a segment of the target gene. Where the at least one sense DNA segment includes multiple sense DNA segments, the degree of sequence identity can be, but need not be, identical for all of the multiple sense DNA segments.

Multiple Copies: Where the gene suppression element includes multiple copies of anti-sense or multiple copies of sense DNA sequence, these multiple copies can be arranged serially in tandem repeats. In some embodiments, these multiple copies can be arranged serially end-to-end, that is, in directly connected tandem repeats. In some embodiments, these multiple copies can be arranged serially in interrupted tandem repeats, where one or more spacer DNA segment can be located adjacent to one or more of the multiple copies. Tandem repeats, whether directly connected or interrupted or a combination of both, can include multiple copies of a single anti-sense or multiple copies of a single sense DNA sequence in a serial arrangement or can include multiple copies of more than one anti-sense DNA sequence or of more than one sense DNA sequence in a serial arrangement.

Double-stranded RNA: In those embodiments wherein the gene suppression element includes either at least one anti-sense DNA segment that is anti-sense to at least one segment of the at least one target gene or at least one sense DNA segment that is at least one segment of the at least one target gene, RNA transcribed from either the at least one anti-sense or at least one sense DNA may become double-stranded by the action of an RNA-dependent RNA polymerase. See, for example, U.S. Pat. No. 5,283,184, which is incorporated by reference herein.

In yet other embodiments, the gene suppression element can include DNA that transcribes to RNA for suppressing the at least one first target gene by forming double-stranded RNA and includes at least one anti-sense DNA segment that is anti-sense to at least one segment of the at least one target gene (as described above under the heading "Anti-sense DNA Segments") and at least one sense DNA segment that is at least one segment of the at least one first target gene (as described above under the heading "Sense DNA Segments"). Such a gene suppression element can further include spacer DNA segments. Each at least one anti-sense DNA segment is complementary to at least part of a sense DNA segment in order to permit formation of double-stranded RNA by intramolecular hybridization of the at least one anti-sense DNA segment and the at least one sense DNA segment. Such complementarity between an anti-sense DNA segment and a sense DNA segment can be, but need not be, 100% complementary; in some embodiments, this complementarity can be preferably at least about 80%, or at least about 85%, or at least about 90%, or at least about 95% complementary.

The double-stranded RNA can be in the form of a single dsRNA "stem" (region of base-pairing between sense and anti-sense strands), or can have multiple dsRNA "stems." In one embodiment, the gene suppression element can include DNA that transcribes to RNA for suppressing the at least one first target gene by forming essentially a single double-stranded RNA and includes multiple serial anti-sense DNA segments that are anti-sense to at least one segment of the at least one first target gene and multiple serial sense DNA segments that are at least one segment of the at least one first target gene; the multiple serial anti-sense and multiple serial sense segments can form a single double-stranded RNA "stem" or multiple "stems" in a serial arrangement (with or without non-base paired spacer DNA separating the multiple "stems"). In another embodiment, the gene suppression element includes DNA that transcribes to RNA for suppressing the at least one first target gene by forming multiple dsRNA "stems" of RNA and includes multiple anti-sense DNA segments that are anti-sense to at least one segment of the at least one first target gene and multiple sense DNA segments that are at least one segment of the at least one first target gene, and wherein the multiple anti-sense DNA segments and the multiple sense DNA segments are arranged in a series of dsRNA "stems" (such as, but not limited to "inverted repeats"). Such multiple dsRNA "stems" can further be arranged in series or clusters to form tandem inverted repeats, or structures resembling "hammerhead" or "cloverleaf" shapes. Any of these gene suppression elements can further include spacer DNA segments found within a dsRNA "stem" (for example, as a spacer between multiple anti-sense or sense DNA segments or as a spacer between a base-pairing anti-sense DNA segment and a sense DNA segment) or outside of a double-stranded RNA "stem" (for example, as a loop region separating a pair of inverted repeats). In cases where base-pairing anti-sense and sense DNA segments are of unequal length, the longer segment can act as a spacer.

miRNAs: In a further embodiment, the gene suppression element can include DNA that includes nucleotides derived from a miRNA (microRNA), that is, a DNA sequence that corresponds to a miRNA native to a virus or a eukaryote of interest (including plants and animals, especially invertebrates), or a DNA sequence derived from such a native miRNA but modified to include nucleotide sequences that do not correspond to the native miRNA. While miRNAs have not to date been reported in fungi, fungal miRNAs, should they exist, are also suitable for use in the invention. An embodiment includes a gene suppression element containing DNA that includes nucleotides derived from a viral or plant miRNA.

In a non-limiting example, the nucleotides derived from a miRNA can include DNA that includes nucleotides corresponding to the loop region of a native miRNA and nucleotides that are selected from a target gene sequence. In another non-limiting example, the nucleotides derived from a miRNA can include DNA derived from a miRNA precursor sequence, such as a native pri-miRNA or pre-miRNA sequence, or nucleotides corresponding to the regions of a native miRNA and nucleotides that are selected from a target gene sequence number such that the overall structure (e.g., the placement of mismatches in the stem structure of the pre-miRNA) is preserved to permit the pre-miRNA to be processed into a mature miRNA. In yet another embodiment, the gene suppression element can include DNA that includes nucleotides derived from a miRNA and capable of inducing or guiding in-phase cleavage of an endogenous transcript into trans-acting siRNAs, as described by Allen et al. (2005) Cell, 121:207-221. Thus, the DNA that includes nucleotides derived from a miRNA can include sequence naturally occurring in a miRNA or a miRNA precursor molecule, synthetic sequence, or both.

siRNAs: In yet another embodiment, the gene suppression element can include DNA that includes nucleotides of a small interfering RNA (siRNA). The siRNA can be one or more native siRNAs (such as siRNAs isolated from a non-transgenic eukaryote or from a transgenic eukaryote), or can be one or more DNA sequences predicted to have siRNA activity (such as by use of predictive tools known in the art, see, for example, Reynolds et al. (2004) Nature Biotechnol., 22:326-330). Multiple native or predicted siRNA sequences can be joined in a chimeric siRNA sequence for gene suppression. Such a DNA that includes nucleotides of a siRNA includes at least 19 nucleotides, and in some embodiments includes at least 20, at least 21, at least 22, at least 23, or at least 24 nucleotides. In other embodiments, the DNA that includes nucleotides of a siRNA can contain substantially more than 21 nucleotides, for example, more than about 50, about 100, about 300, about 500, about 1000, about 3000, or about 5000 nucleotides or greater.

Engineered miRNAs and trans-acting siRNAs (ta-siRNAs) are useful for gene suppression with increased specificity. The invention provides recombinant DNA constructs, each including a transcribable engineered miRNA precursor designed to suppress a target sequence, wherein the transcribable engineered miRNA precursor is derived from the fold-back structure of a MIR gene, preferably a plant MIR sequence. These miRNA precursors are also useful for directing in-phase production of siRNAs (e.g., heterologous sequence designed to be processed in a trans-acting siRNA suppression mechanism in planta). The invention further provides a method to suppress expression of a target sequence in a plant cell, including transcribing in a plant cell a recombinant DNA including a transcribable engineered miRNA precursor designed to suppress a target sequence, wherein the transcribable engineered miRNA precursor is derived from the fold-back structure of a MIR gene, preferably a plant MIR sequence, whereby expression of the target sequence is suppressed relative to its expression in the absence of transcription of the recombinant DNA construct.

The mature miRNAs produced, or predicted to be produced, from these miRNA precursors may be engineered for use in suppression of a target gene, e.g., in transcriptional suppression by the miRNA, or to direct in-phase production of siRNAs in a trans-acting siRNA suppression mechanism (see Allen et al. (2005) Cell, 121:207-221, Vaucheret (2005) Science STKE, 2005:pe43, and Yoshikawa et al. (2005) Genes Dev., 19:2164-2175). Plant miRNAs generally have near-perfect complementarity to their target sequences (see, for example, Llave et al. (2002) Science, 297:2053-2056, Rhoades et al. (2002) Cell, 110:513-520, Jones-Rhoades and Bartel (2004) Mol. Cell, 14:787-799). Thus, the mature miRNAs can be engineered to serve as sequences useful for gene suppression of a target sequence, by replacing nucleotides of the mature miRNA sequence with nucleotides of the sequence that is targeted for suppression; see, for example, methods disclosed by Parizotto et al. (2004) Genes Dev., 18:2237-2242 and especially U.S. Patent Application Publications US2004/0053411A1, US2004/0268441A1, US2005/0144669, and US2005/0037988, all of which are incorporated by reference herein. When engineering a novel miRNA to target a specific sequence, one strategy is to select within the target sequence a region with sequence that is as similar as possible to the native miRNA sequence. Alternatively, the native miRNA sequence can be replaced with a region of the target sequence, preferably a region that meets structural and thermodynamic criteria believed to be important for miRNA function (see, for example, U.S. Patent Application Publication US2005/0037988). Sequences are preferably engineered such that the number and placement of mismatches in the stem structure of the fold-back region or pre-miRNA is preserved. Thus, an engineered miRNA or engineered miRNA precursor can be derived from any of the mature miRNA sequences, or their corresponding miRNA precursors (including the fold-back portions of the corresponding MIR genes) disclosed herein. The engineered miRNA precursor can be cloned and expressed (transiently or stably) in a plant cell or tissue or intact plant.

The construction and description of recombinant DNA constructs to modulate small non-coding RNA activities are disclosed in U.S. Patent Application Publication US 2009/0070898 A1, US2011/0296555 A1, US2011/0035839 A1, all of which are incorporated herein by reference in their entirety. In particular, with respect to US2011/0035839 A1, see e.g., sections under the headings "Gene Suppression Elements" in paragraphs 122 to 135, and "Engineered Heterologous miRNA for Controlling Gene Expression in paragraphs 188 to 190.

As used herein a "plant" includes a whole plant, a transgenic plant, meristematic tissue, a shoot organ/structure (for example, leaf, stem and tuber), a root, a flower, a floral organ/structure (for example, a bract, a sepal, a petal, a stamen, a carpel, an anther and an ovule), a seed (including an embryo, endosperm, and a seed coat) and a fruit (the mature ovary), plant tissue (for example, vascular tissue, ground tissue, and the like) and a cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular algae.

As used herein a "transgenic plant cell" means a plant cell that is transformed with stably-integrated, recombinant DNA, for example, by *Agrobacterium*-mediated transformation, by bombardment using microparticles coated with recombinant DNA, or by other means, such as site-directed integration. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "control plant" means a plant that does not contain the recombinant DNA of the present disclosure that imparts an enhanced trait or altered phenotype. A control plant is used to identify and select a transgenic plant that has an enhanced trait or altered phenotype. A suitable control plant can be a non-transgenic plant of the parental line used to generate a transgenic plant, for example, a wild type plant devoid of a recombinant DNA. A suitable control plant can also be a transgenic plant that contains recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isogenic line.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency and increased yield as shown in Tables 7-10, and altered phenotypes as shown in Tables 3-5. In another aspect of the disclosure the trait is increased yield under non-stress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait characteristics or phenotype as compared to a control plant. It is known that there can be natural variations in a modified trait. Therefore, the trait modification observed entails a change of the normal distribution and magnitude of the trait characteristics or phenotype in the plants as compared to a control plant.

The present disclosure relates to a plant with improved economically important characteristics, more specifically increased yield. More specifically the present disclosure relates to a plant comprising a polynucleotide of this disclosure, wherein the plant has increased yield as compared to a control plant. Many plants of this disclosure exhibited increased yield as compared to a control plant. In an embodiment, a plant of the present disclosure exhibited an improved trait that is related to yield, including but not limited to increased nitrogen use efficiency, increased nitrogen stress tolerance, increased water use efficiency and increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, etc.), flowering time and duration, grain fill period. Root architecture and development, photosynthetic efficiency, nutrient uptake, stress tolerance, early vigor, delayed senescence and functional stay green phenotypes can be important factors in determining yield. Optimizing the above mentioned factors can therefore contribute to increasing crop yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear and number of kernels per row, kernel number or weight per ear, weight per kernel, ear number, ear weight, fresh or dry ear biomass (weight)

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiment for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiment, "sugarcane yield" can be measured as cane yield (tons per acre; kg/hectare), total recoverable sugar (pounds per ton), and sugar yield (tons/acre).

In yet still further embodiment, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

In another embodiment, the present disclosure provides a method for the production of plants having altered phenotype, enhanced trait, or increased yield; performance of the method gives plants altered phenotype, enhanced trait, or increased yield.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others.

Further, increased yield can also manifest as (iii) increased total seed yield, which may result from one or more of an increase in seed biomass (seed weight) due to an increase in the seed weight on a per plant and/or on an individual seed basis an increased number of panicles per plant; an increased number of pods; an increased number of nodes; an increased number of flowers ("florets") per panicle/plant; increased seed fill rate; an increased number of filled seeds; increased seed size (length, width, area, perimeter), which can also influence the composition of seeds; and/or increased seed volume, which can also influence the composition of seeds.

Increased yield can also (iv) result in modified architecture, or can occur because of modified plant architecture.

Increased yield can also manifest as (v) increased harvest index, which is expressed as a ratio of the yield of harvestable parts, such as seeds, over the total biomass Increased yield can also manifest as (vi) increased kernel weight, which is extrapolated from the number of filled seeds counted and their total weight. An increased kernel weight can result from an increased seed size and/or seed weight, an increase in embryo size, increased endosperm size, aleurone and/or scutellum, or an increase with respect to other parts of the seed that result in increased kernel weight.

Increased yield can also manifest as (vii) increased ear biomass, which is the weight of the ear and can be represented on a per ear, per plant or per plot basis.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of altering phenotype, enhancing trait, or increasing yield in a plant by producing a plant comprising a polynucleotide sequence of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA construct, transgenic plants can be prepared by crossing a first plant having a stably integrated recombinant DNA construct with a second plant lacking the DNA. For example, recombinant DNA can be introduced into a first plant line that is amenable to transformation to produce a transgenic plant which can be crossed with a second plant line to introgress the recombinant DNA into the second plant line.

Selected transgenic plants transformed with a recombinant DNA construct and having the polynucleotide of this disclosure provides the altered phenotype, enhanced trait, or increased yield compared to a control plant. Use of genetic markers associated with the recombinant DNA can facilitate production of transgenic progeny that is homozygous for the desired recombinant DNA. Progeny plants carrying DNA for both parental traits can be back-crossed into a parent line multiple times, for example usually 6 to 8 generations, to produce a progeny plant with substantially the same genotype as the one reoccurring original transgenic parental line but having the recombinant DNA of the other transgenic parental line. The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, a oligonucleotide, or any fragment thereof. In many instances, a polynucleotide encodes a polypeptide (or protein) or a domain or a fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity, such as transformation, or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such enrichment is not the result of a natural response of a wild-type plant. Alternatively, or additionally, the isolated polypeptide is separated from other cellular components, with which it is typically associated, for example, by any of the various protein purification methods.

As used herein, a "functional fragment" refers to a portion of a polypeptide provided herein which retains full or partial molecular, physiological or biochemical function of the full length polypeptide. A functional fragment often contains the domain(s), such as Pfam domains (see below), identified in the polypeptide provided in the sequence listing.

A "recombinant DNA construct" as used in the present disclosure comprises at least one expression cassette having a promoter operable in plant cells and a polynucleotide of the present disclosure. DNA constructs can be used as a means of delivering recombinant DNA constructs to a plant cell in order to effect stable integration of the recombinant molecule into the plant cell genome. In one embodiment, the polynucleotide can encode a protein or variant of a protein or fragment of a protein that is functionally defined to maintain activity in transgenic host cells including plant cells, plant parts, explants and whole plants. In another embodiment, the polynucleotide can encode a non-coding RNA that interferes with the functioning of endogenous classes of small RNAs that regulate expression, including but not limited to taRNAs, siRNAs and miRNAs. Recombinant DNA constructs are assembled using methods known to persons of ordinary skill in the art and typically comprise a promoter operably linked to DNA, the expression of which provides the enhanced agronomic trait.

Other construct components can include additional regulatory elements, such as 5' leaders and introns for enhancing transcription, 3' untranslated regions (such as polyadenylation signals and sites), and DNA for transit or targeting or signal peptides.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "homolog" or "homologues" means a protein in a group of proteins that perform the same biological function, for example, proteins that belong to the same Pfam protein family and that provide a common enhanced trait in transgenic plants of this disclosure. Homologs are expressed by homologous genes. With reference to homologous genes, homologs include orthologs, for example, genes expressed in different species that evolved from common ancestral genes by speciation and encode proteins retain the same function, but do not include paralogs, i.e., genes that are related by duplication but have evolved to encode proteins with different functions. Homologous genes include naturally occurring alleles and artificially-created variants.

Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about 80%, at least about 85%, at least about 90%, at least about 92%, at least about 93%, at least about 94%, at least about 95%, at least about 96%, at least about 97%, at least about 98%, at least about 99%, or even at least about 99.5% identity over the full length of a protein or its corresponding nucleotide sequence identified as being associated with imparting an enhanced trait or altered phenotype when expressed in plant cells. In one aspect of the disclosure homolog proteins have at least about 80%, at least about 85%, at least about 90%, at least about 92%, at least about 93%, at least about 94%, at least about 95%, at least about 96%, at least about 97%, at least about 98%, at least about 99%, or at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions (UTRs) and their complements. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated or engineered DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria. A promoter may also be heterologous. As used herein, a promoter or other regulatory sequence operably linked to a transcribable DNA sequence, such as a coding sequence, is considered "heterologous" if in nature the promoter or regulatory sequence is not operably linked to the transcribable DNA sequence and/or is not present in the plant host cell to be transformed with the promoter or regulatory sequence. Two or more promoter or regulatory sequences may also be heterologous with respect to each other.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock. Many examples of plant expressible promoters are known in the art.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) Transgenic Res. 6(2):157-166, globulin 1 as disclosed by Belanger et al (1991) Genetics 129:863-872, glutelin 1 as disclosed by Russell (1997) supra, and peroxiredoxin antioxidant (Perl) as disclosed by Stacy et al. (1996) Plant Mol Biol. 31(6):1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule. As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, and vacuolar sorting peptides. For description of the use of chloroplast transit peptides see U.S. Pat. Nos. 5,188,642 and 5,728,925. For description of the transit peptide region of an *Arabidopsis* EPSPS gene in the present disclosure, see Klee, H. J. Et al (MGG (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or an herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. Nos. 5,627,061; 5,633,435; 6,040,497; 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e. g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR sequence and termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a miRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tins 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in U.S. Patent Application Publication 2002/0192813 A1; and the pea (*Pisum sativum*) ribulose biphosphate carboxylase gene (rbs 3'), and 3' elements from the genes within the host plant.

As an alternative to traditional transformation methods, a DNA sequence, such as a transgene, expression cassette(s), etc., may be inserted or integrated into a specific site or locus within the genome of a plant or plant cell via site-directed integration. Recombinant DNA construct(s) and molecule(s) of this disclosure may thus include a donor template sequence comprising at least one transgene, expression cassette, or other DNA sequence for insertion into the genome of the plant or plant cell. Such donor template for site-directed integration may further include one or two homology arms flanking an insertion sequence (i.e., the sequence, transgene, cassette, etc., to be inserted into the plant genome). The recombinant DNA construct(s) of this disclosure may further comprise an expression cassette(s) encoding a site-specific nuclease and/or any associated protein(s) to carry out site-directed integration. These nuclease expressing cassette(s) may be present in the same molecule or vector as the donor template (in cis) or on a separate molecule or vector (in trans). Several methods for site-directed integration are known in the art involving different proteins (or complexes of proteins and/or guide RNA) that cut the genomic DNA to produce a double strand break (DSB) or nick at a desired genomic site or locus. Briefly as understood in the art, during the process of repairing the DSB or nick introduced by the nuclease enzyme, the donor template DNA may become integrated into the genome at the site of the DSB or nick. The presence of the homology arm(s) in the donor template may promote the adoption and targeting of the insertion sequence into the plant genome during the repair process through homologous recombination, although an insertion event may occur through non-homologous end joining (NHEJ). Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome.

As used herein, the term "homology arm" refers to a polynucleotide sequence that has at least 80%, at least 85%, at least 90%, at least 91%, at least 92%, at least 93%, at least 94%, at least 95%, at least 96%, at least 97%, at least 98%, at least 99% or 100% sequence identity to a target sequence in a plant or plant cell that is being transformed. A homology arm can comprise at least 15, at least 20, at least 25, at least 30, at least 40, at least 50, at least 100, at least 250, at least 500, or at least 1000 nucleotides.

As used herein "operably linked" means the association of two or more DNA fragments in a recombinant DNA construct so that the function of one, for example, protein-encoding DNA, is controlled by the other, for example, a promoter.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil, norflurazon, 2,4-D (2,4-dichlorophenoxy) acetic acid, aryloxyphenoxy propionates, p-hydroxyphenyl pyruvate dioxygenase inhibitors (HPPD), and protoporphyrinogen oxidase inhibitors (PPO) herbicides. Polynucleotide molecules encoding proteins involved in herbicide tolerance known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent No. Application Publication 2003/0083480 A1 also for imparting glyphosate tolerance; dicamba monooxygenase disclosed in U.S. Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260. Molecules and methods for imparting insect/nematode/virus resistance are disclosed in U.S. Pat. Nos. 5,250,515; 5,880,275; 6,506,599; 5,986,175 and U.S. Patent Application Publication 2003/0150017 A1.

Plant Cell Transformation Methods

Numerous methods for transforming chromosomes and plastids in a plant cell with recombinant DNA are known in the art that may be used in methods of producing a transgenic plant cell and plant. Two effective methods for transformation are *Agrobacterium*-mediated transformation and microprojectile bombardment-mediated transformation. Microprojectile bombardment methods are illustrated, for example, in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described, for example, in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 8,044,260 (cotton); U.S. Pat. No. 6,384,301 (soybean), U.S. Pat. No. 7,026,528 (wheat) and U.S. Pat. No. 6,329,571 (rice), U.S. Patent Application Publication No. 2004/0087030 A1 (cotton), and U.S. Patent Application Publication No. 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

As introduced above, another method for transforming chromosomes in a plant cell is via insertion of a DNA sequence using a recombinant DNA donor template at a pre-determined site of the genome by methods of site-directed integration. Site-directed integration may be accomplished by any method known in the art, for example, by use of zinc-finger nucleases, engineered or native meganucleases, TALE-endonucleases, or an RNA-guided endonuclease (for example Cas9 or Cpf1). The recombinant DNA construct may be inserted at the pre-determined site by homologous recombination (HR) or by non-homologous end joining (NHEJ). In addition to insertion of a recombinant DNA construct into a plant chromosome at a pre-determined site, genome editing can be achieved through oligonucleotide-directed mutagenesis (ODM) (Oh and May, 2001; U.S. Pat. No. 8,268,622) or by introduction of a double-strand break (DSB) or nick with a site specific nuclease, followed by NHEJ or repair. The repair of the DSB or nick may be used to introduce insertions or deletions at the site of the DSB or nick, and these mutations may result in the introduction of frame-shifts, amino acid substitutions, and/or an early termination codon of protein translation or alteration of a regulatory sequence of a gene. Genome editing may be achieved with or without a donor template molecule.

In addition to direct transformation of a plant material with a recombinant DNA construct, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA construct into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708; 6,118,047 and 8,030,544. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to develop or regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants may be regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an altered phenotype or an enhanced agronomic trait.

Transgenic Plants and Seeds

Transgenic plants derived from transgenic plant cells having a transgenic nucleus of this disclosure are grown to generate transgenic plants having an altered phenotype or an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, and increased nitrogen use efficiency.

Table 1 provides a list of sequences of protein-encoding genes as recombinant DNA for production of transgenic plants with enhanced traits. The elements of Table 1 are described by reference to: "NUC SEQ ID NO." which identifies a DNA sequence; "PEP SEQ ID NO." which identifies an amino acid sequence; "Gene ID" which refers to an arbitrary identifier; and "Gene Name and Description" which is a common name and functional description of the gene.

TABLE 1

Sequences for Protein-Coding Genes

| NUC SEQ ID NO. | PEP SEQ ID NO. | Gene ID | Gene Name and Description |
|---|---|---|---|
| 1 | 30 | T5MON01 | Agrobacterium ornithine carbamoyl transferase (argF) |
| 2 | 31 | T5MON02 | Arabidopsis MADS-box protein (AGL20) |
| 3 | 32 | T5MON03 | Arabidopsis containing Pleckstrin homology domain, 6 regulator of chromosome condensation (RCC1) domains, and Zinc finger domain |
| 4 | 33 | T5MON04 | Arabidopsis Glycyl-tRNA synthetase |
| 5 | 34 | T5MON05 | Arabidopsis L-ascorbate oxidase |
| 6 | 35 | T5MON06 | Arabidopsis glutamate decarboxylase 4 (GAD4) |
| 7 | 36 | T5MON07 | Arabidopsis growth factor like protein |
| 8 | 37 | T5MON08 | Arabidopsis Aromatic and neutral amino acid transporter 1-like (ANT1-like) |
| 9 | 38 | T5MON09 | Arabidopsis putative AP2/EREBP transcription factor (with A33V mutation) |
| 10 | 39 | T5MON10 | Arabidopsis dark inducible 11 (DIN11) |
| 11 | 40 | T5MON11 | Arabidopsis strictosidine synthase family protein, mucin-like (AtSSL7) |
| 12 | 41 | T5MON12 | Arabidopsis purple acid phosphatase precursor (AtPAP) |
| 13 | 42 | T5MON13 | Arabidopsis serine/threonine protein kinase, root hair specific 3 (RHS3) |
| 14 | 43 | T5MON14 | Chlamydomonas reinhardtii PHE0023587_Ferredoxin-dependent glutamate synthase (GSF1) |
| 15 | 44 | T5MON15 | Chlorella sorokiniana NADP-specific glutamate dehydrogenase (NADP-GDH), N terminus residues 1 to 74 truncated |
| 16 | 45 | T5MON16 | E coli glutamate dehydrogenase, NADP-specific (gdhA) |

TABLE 1-continued

Sequences for Protein-Coding Genes

| NUC SEQ ID NO. | PEP SEQ ID NO. | Gene ID | Gene Name and Description |
|---|---|---|---|
| 17 | 46 | T5MON17 | Homeobox fusion protein, Arabidopsis HB-17 N terminus residues 1 to 91 fused to soybean HB-17 C terminus residues 20-213 |
| 18 | 47 | T5MON18 | Soybean AP2-EREBP transcription factor (ERF3) |
| 19 | 48 | T5MON19 | rice Ghd7 |
| 20 | 49 | T5MON20 | Corn pyruvate orthophosphate dikinase 1 (PPDK1) |
| 21 | 50 | T5MON21 | Corn proliferating cell nuclear antigen (PCNA2) |
| 22 | 51 | T5MON23 | Corn Roothairless 1 (RTH1) |
| 23 | 52 | T5MON24 | Corn orphans transcription factor (Orphan46) |
| 24 | 53 | T5MON25 | Corn MADS transcription factor (MADS12) |
| 25 | 54 | T5MON26 | Corn remorin like DNA-binding protein 2 |
| 26 | 55 | T5MON27 | Corn CAAT-box DNA binding protein (NFBa) |
| 27 | 56 | T5MON28 | Corn homeobox-leucine zipper protien, HB transcription factor |
| 28 | 57 | T5MON29 | Corn putative glutamine synthetase (with C299A mutation) |
| 29 | 58 | T5MON30 | Corn putative nucleostemin |

Selecting and Testing Transgenic Plants for Enhanced Traits

Within a population of transgenic plants each developed or regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Further evaluation with vigorous testing is essential for understanding the contributing components to a trait, supporting trait advancement decisions and generating mode of action hypotheses. Transgenic plants having enhanced traits are selected and tested from populations of plants developed, regenerated or derived from plant cells transformed as described herein by evaluating the plants in a variety of assays to detect an enhanced trait, for example, increased water use efficiency or drought tolerance, enhanced high temperature or cold tolerance, increased yield or yield components, desirable architecture, optimum life cycle, increased nitrogen use efficiency, enhanced seed composition such as enhanced seed protein and enhanced seed oil.

These assays can take many forms including, but not limited to, direct screening for the trait in a greenhouse or field trial or by screening for a surrogate trait. Such analyses can be directed to detecting changes in the chemical composition, biomass, yield components, physiological property, root architecture, morphology, or life cycle of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in yield components can be measured by total number of kernels per unit area and its individual weight. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in root architecture can be evaluated by root length and branch number. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Changes in morphology can also be measured with morphometric analysis based on shape parameters, using dimensional measurement such as ear diameter, ear length, kernel row number, internode length, plant height, or stem volume. Changes in life cycle can be measured by macro or microscopic morphological changes partitioned into developmental stages, such as days to pollen shed, days to silking, leaf extension rate. Other selection and testing properties include days to pollen shed, days to silking, leaf extension rate, chlorophyll content, leaf temperature, stand, seedling vigor, internode length, plant height, leaf number, leaf area, tillering, brace roots, stay green or delayed senescence, stalk lodging, root lodging, plant health, bareness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control or standard agronomic practices (SAP). Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, quinoa and sugar cane plants.

EXAMPLES

Example 1. Corn Transformation

This example illustrates transformation methods to produce a transgenic corn plant cell, seed, and plant having altered phenotypes as shown in Tables 3-5, and enhanced traits, increased water use efficiency, increased nitrogen use efficiency, and increased yield and altered traits and phenology as shown in Tables 7, 8 and 10.

For *Agrobacterium*-mediated transformation of corn embryo cells, ears from corn plants were harvested and surface-sterilized by spraying or soaking the ears in ethanol, followed by air drying. Embryos were isolated from individual kernels of surface-sterilized ears. After excision, maize embryos were inoculated with *Agrobacterium* cells containing plasmid DNA with the gene of interest cassette and a plant selectable marker cassette, and then co-cultured with *Agrobacterium* for several days. Co-cultured embryos were transferred to various selection and regeneration media, and transformed R0 plants were recovered 6 to 8 weeks after initiation of selection, which were transplanted into potting soil. Regenerated R0 plants were selfed, and R1 and subsequent progeny generations were obtained.

The above process can be repeated to produce multiple events of transgenic corn plants from cells that were transformed with recombinant DNA having the genes identified in Table 1. Progeny transgenic plants and seeds of the transformed plants were screened for the presence and single copy of the inserted gene, and for various altered or enhanced traits and phenotypes, such as increased water use efficiency, increased yield, and increased nitrogen use efficiency as shown in Tables 3-5, 7, 8 and 10. From each group of multiple events of transgenic plants with a specific recombinant DNA from Table 1, the event(s) that showed increased yield, increased water use efficiency, increased nitrogen use efficiency, and altered phenotypes and traits were identified.

Example 2. Soybean Transformation

This example illustrates plant transformation in producing a transgenic soybean plant cell, seed, and plant having an altered phenotype or an enhanced trait, such as increased water use efficiency, drought tolerance and increased yield as shown in Tables 9 and 10.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA having the genes identified in Table 1. Progeny transgenic plants and seed of the transformed plants were screened for the presence and single copy of the inserted gene, and tested for various altered or enhanced phenotypes and traits as shown in Tables 9 and 10.

Example 3. Identification of Altered Phenotypes in Automated Greenhouse

This example illustrates screening and identification of transgenic corn plants for altered phenotypes in an automated greenhouse (AGH). The apparatus and the methods for automated phenotypic screening of plants are disclosed, for example, in U.S. Patent Publication No. 2011/0135161, which is incorporated herein by reference in its entirety.

Corn plants were tested in three screens in the AGH under different conditions including non-stress, nitrogen deficit, and water deficit stress conditions. All screens began with non-stress conditions during days 0-5 germination phase, after which the plants were grown for 22 days under the screen-specific conditions shown in Table 2.

TABLE 2

Description of the three AGH screens for corn plants

| Screen | Description | Germination phase (5 days) | Screen specific phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

Water deficit is defined as a specific Volumetric Water Content (VWC) that is lower than the VWC of a non-stressed plant. For example, a non-stressed plant might be maintained at 55% VWC, and the VWC for a water-deficit assay might be defined around 30% VWC. Data were collected using visible light and hyperspectral imaging as well as direct measurement of pot weight and amount of water and nutrient applied to individual plants on a daily basis.

Nitrogen deficit is defined (in part) as a specific mM concentration of nitrogen that is lower than the nitrogen concentration of a non-stressed plant. For example, a non-stressed plant might be maintained at 8 mM nitrogen, while the nitrogen concentration applied in a nitrogen-deficit assay might be maintained at a concentration of 2 mM.

Up to ten parameters were measured for each screen. The visible light color imaging based measurements are: biomass, canopy area, and plant height. Biomass (Bmass) is defined as the estimated shoot fresh weight (g) of the plant obtained from images acquired from multiple angles of view. Canopy Area (Cnop) is defined as leaf area as seen in a top-down image ($mm^2$). Plant Height (PlntH) refers to the distance from the top of the pot to the highest point of the plant derived from a side image (mm). Anthocyanin score and area, chlorophyll score and concentration, and water content score are hyperspectral imaging-based parameters. Anthocyanin Score (AntS) is an estimate of anthocyanin in the leaf canopy obtained from a top-down hyperspectral image. Anthocyanin Area (AntA) is an estimate of anthocyanin in the stem obtained from a side-view hyperspectral image. Chlorophyll Score (ClrpS) and Chlorophyll Concentration (ClrpC) are both measurements of chlorophyll in the leaf canopy obtained from a top-down hyperspectral image, where Chlorophyll Score measures in relative units, and Chlorophyll Concentration is measured in parts per million (ppm) units. Water Content Score (WtrCt) is a measurement of water in the leaf canopy obtained from a top-down hyperspectral image. Water Use Efficiency (WUE) is derived from the grams of plant biomass per liter of water added. Water Applied (WtrAp) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 3-5 are summaries of transgenic corn plants comprising the disclosed recombinant DNA constructs with altered phenotypes under non stress, nitrogen deficit, and water deficit conditions, respectively.

The test results are represented by three numbers: the first number before letter "p" denotes number of events with an increase in the tested parameter at $p \leq 0.1$; the second number before letter "n" denotes number of events with a decrease in the tested parameter at $p \leq 0.1$; the third number before letter "t" denotes total number of transgenic events tested for a given parameter in a specific screen. The increase or decrease is measured in comparison to non-transgenic control plants. A designation of "–" indicates that it has not been tested. For example, 2p1n5t indicates that 5 transgenic plant events were screened, of which 2 events showed an increase, and 1 showed a decrease of the measured parameter.

TABLE 3

Summary of transgenic corn plants with altered phenotypes in AGH non-stress screens

| GeneID | AntS | Bmass | Cnop | ClrpS | PlntH | WtrAp | WtrCt | WUE | ClrpC | AntA |
|---|---|---|---|---|---|---|---|---|---|---|
| T5MON15 | 0p1n5t | 0p2n5t | 0p1n5t | 0p0n5t | 0p1n5t | 0p1n5t | 0p0n5t | 0p2n5t | — | — |
| T5MON02 | 0p0n5t | 1p0n5t | 0p0n5t | 1p0n5t | 1p0n5t | 0p0n5t | — | 1p0n5t | — | — |
| T5MON23 | 1p0n5t | 0p0n5t | 0p0n5t | 0p2n5t | 0p1n5t | 1p1n5t | — | 0p0n5t | — | — |
| T5MON17 | 0p0n5t | 0p1n5t | 0p4n5t | 1p0n5t | 0p0n5t | 0p0n5t | 1p1n5t | 0p1n5t | — | — |
| T5MON03 | 0p0n5t | 0p0n5t | 1p0n5t | — | 0p1n5t | 1p0n5t | — | 0p0n5t | 0p0n5t | 0p0n5t |
| T5MON05 | 1p1n10t | 0p2n10t | 0p2n10t | — | 1p3n10t | 0p2n10t | — | 0p1n10t | 2p0n10t | 0p1n10t |
| T5MON16 | 0p1n5t | 0p1n5t | 0p1n5t | — | 1p0n5t | 0p1n5t | — | 0p2n5t | 0p0n5t | — |
| T5MON26 | 0p0n5t | 1p2n5t | 0p1n5t | — | 0p1n5t | 0p0n5t | — | 1p1n5t | 0p0n5t | — |
| T5MON27 | 1p1n7t | 0p0n7t | 3p0n7t | 0p1n7t | 0p1n7t | 0p1n7t | 0p0n7t | 0p0n7t | — | — |
| T5MON06 | 0p0n8t | 1p0n8t | 1p0n8t | 0p0n8t | 0p0n8t | 0p0n8t | 0p0n8t | 0p0n8t | — | — |
| T5MON28 | 0p0n5t | 0p1n5t | 0p1n5t | — | 0p2n5t | 1p2n5t | — | 0p2n5t | 0p0n5t | — |
| T5MON19 | 0p1n5t | 0p1n5t | 0p1n5t | — | 0p2n5t | 0p1n5t | — | 0p2n5t | 0p0n5t | 0p1n5t |
| T5MON29 | 2p1n5t | 0p2n5t | 0p1n5t | — | 0p2n5t | 0p0n5t | — | 0p2n5t | 0p0n5t | 0p0n5t |
| T5MON08 | 0p1n5t | 0p1n5t | 0p0n5t | — | 0p1n5t | 0p0n5t | — | 0p1n5t | 0p1n5t | — |
| T5MON14 | 0p0n5t | 1p0n5t | 0p0n5t | — | 2p0n5t | 1p0n5t | — | 1p0n5t | 0p0n5t | — |

TABLE 4

Summary of transgenic corn plants with altered phenotypes in AGH nitrogen-deficit screens

| GeneID | AntS | Bmass | Cnop | ClrpS | PlntH | WtrAp | WtrCt | WUE | ClrpC | AntA |
|---|---|---|---|---|---|---|---|---|---|---|
| T5MON01 | — | 3p0n5t | 3p0n5t | — | 2p0n5t | 3p0n5t | — | 1p0n5t | — | 1p0n5t |
| T5MON02 | 0p0n5t | 0p0n5t | 0p0n5t | 3p0n5t | 1p0n5t | 1p2n5t | 0p0n5t | 1p0n5t | — | — |
| T5MON03 | 0p0n5t | 0p0n5t | 0p0n5t | — | 0p1n5t | 0p0n5t | — | 0p0n5t | 0p1n5t | 0p0n5t |
| T5MON04 | 0p0n10t | 0p0n10t | 0p1n10t | — | 1p1n10t | 0p2n10t | — | 0p0n10t | 0p0n10t | 1p0n10t |
| T5MON05 | 1p0n10t | 0p0n10t | 0p3n10t | — | 0p3n10t | 1p1n10t | — | 1p1n10t | 1p0n10t | 0p2n10t |
| T5MON06 | 0p1n8t | 0p1n8t | 0p1n8t | 0p1n8t | 0p5n8t | 1p1n8t | 0p1n8t | 0p3n8t | — | — |
| T5MON07 | 0p0n5t | 0p0n5t | 0p0n5t | — | 0p0n5t | 1p0n5t | — | 0p0n5t | 0p1n5t | 1p0n5t |
| T5MON08 | 0p2n5t | 4p0n5t | 1p0n5t | — | 0p0n5t | 3p0n5t | — | 4p0n5t | 2p0n5t | — |
| T5MON14 | 2p0n5t | 0p3n5t | 0p3n5t | — | 0p1n5t | 0p3n5t | — | 0p2n5t | 0p1n5t | — |
| T5MON15 | 0p1n5t | 0p0n5t | 0p2n5t | 0p0n5t | 0p4n5t | 0p3n5t | 0p0n5t | 0p0n5t | — | — |
| T5MON16 | 1p0n5t | 0p1n5t | 0p1n5t | — | 0p2n5t | 0p1n5t | — | 0p1n5t | 1p0n5t | — |
| T5MON17 | 0p1n5t | 0p3n5t | 1p1n5t | 2p0n5t | 0p4n5t | 1p1n5t | 0p3n5t | 0p4n5t | — | — |
| T5MON19 | 0p1n5t | 0p0n5t | 0p2n5t | — | 1p0n5t | 0p5n5t | — | 0p0n5t | 0p0n5t | 0p3n5t |
| T5MON23 | 0p0n5t | 4p0n5t | 2p0n5t | 0p1n5t | 2p0n5t | 4p0n5t | 1p0n5t | 3p0n5t | — | — |

TABLE 4-continued

Summary of transgenic corn plants with altered phenotypes in AGH nitrogen-deficit screens

| GeneID | AntS | Bmass | Cnop | ClrpS | PlntH | WtrAp | WtrCt | WUE | ClrpC | AntA |
|---|---|---|---|---|---|---|---|---|---|---|
| T5MON25 | 0p1n8t | 2p0n8t | 0p1n8t | — | 2p1n8t | 0p4n8t | — | 3p0n8t | 3p1n8t | 0p0n8t |
| T5MON26 | 0p0n5t | 0p2n5t | 0p3n5t | — | 0p2n5t | 0p1n5t | — | 0p2n5t | 0p0n5t | — |
| T5MON27 | 1p0n7t | 0p1n7t | 0p0n7t | 0p0n7t | 0p2n7t | 0p0n7t | 0p0n7t | 0p1n7t | — | — |
| T5MON28 | 0p0n5t | 0p2n5t | 0p0n5t | — | 0p3n5t | 0p1n5t | — | 0p1n5t | 1p0n5t | — |
| T5MON29 | 0p0n5t | 0p0n5t | 0p2n5t | — | 0p1n5t | 0p2n5t | — | 1p0n5t | 1p0n5t | 0p0n5t |

TABLE 5

Summary of transgenic corn plants with altered phenotypes in AGH water-deficit screens

| GeneID | AntS | Bmass | Cnop | ClrpS | PlntH | WtrAp | WtrCt | WUE | ClrpC | AntA |
|---|---|---|---|---|---|---|---|---|---|---|
| T5MON01 | 0p0n5t | 0p2n5t | 0p3n5t | — | 1p1n5t | 0p3n5t | — | 0p0n5t | 0p1n5t | 2p0n5t |
| T5MON02 | 0p0n5t | 1p1n5t | 0p1n5t | 0p3n5t | 0p1n5t | 1p2n5t | 0p1n5t | 0p0n5t | — | — |
| T5MON03 | 0p0n5t | 0p1n5t | 0p0n5t | — | 0p0n5t | 0p3n5t | — | 2p0n5t | 0p0n5t | 1p0n5t |
| T5MON04 | 0p1n10t | 3p1n10t | 4p0n10t | — | 1p1n10t | 1p1n10t | — | 3p0n10t | 3p0n10t | 0p0n10t |
| T5MON05 | 0p1n10t | 0p0n10t | 1p0n10t | — | 1p1n10t | 2p2n10t | — | 0p0n10t | 3p0n10t | 0p4n10t |
| T5MON06 | 0p0n8t | 0p1n8t | 0p0n8t | 0p2n8t | 0p1n8t | 0p3n8t | 0p2n8t | 0p1n8t | — | — |
| T5MON07 | 1p0n5t | 0p0n5t | 0p1n5t | — | 0p1n5t | 1p1n5t | — | 0p0n5t | 1p1n5t | 1p0n5t |
| T5MON08 | 1p0n5t | 0p0n5t | 0p0n5t | — | 0p0n5t | 0p0n5t | — | 0p0n5t | 0p0n5t | — |
| T5MON14 | 0p0n5t | 2p1n5t | 3p1n5t | — | 0p1n5t | 0p1n5t | — | 2p0n5t | 0p0n5t | — |
| T5MON15 | 0p3n5t | 2p0n5t | 3p0n5t | 1p0n5t | 2p0n5t | 3p0n5t | 0p0n5t | 2p0n5t | — | — |
| T5MON16 | 0p0n5t | 0p1n5t | 0p1n5t | — | 0p0n5t | 0p2n5t | — | 0p1n5t | 0p1n5t | — |
| T5MON17 | 0p0n5t | 0p0n5t | 0p0n5t | 1p0n5t | 0p0n5t | 1p0n5t | 0p1n5t | 0p0n5t | — | — |
| T5MON19 | 1p0n5t | 1p0n5t | 2p0n5t | — | 1p0n5t | 3p0n5t | — | 0p0n5t | 0p2n5t | 0p1n5t |
| T5MON23 | 0p0n5t | 4p0n5t | 3p0n5t | 1p0n5t | 4p0n5t | 5p0n5t | 0p0n5t | 0p0n5t | — | — |
| T5MON25 | 0p1n8t | 3p0n8t | 1p0n8t | — | 2p0n8t | 0p0n8t | — | 3p0n8t | 2p0n8t | 0p1n8t |
| T5MON26 | 0p1n5t | 0p2n5t | 0p2n5t | — | 0p1n5t | 0p4n5t | — | 0p0n5t | 0p0n5t | — |
| T5MON27 | 0p2n7t | 1p0n7t | 2p0n7t | 0p0n7t | 0p1n7t | 3p0n7t | 1p0n7t | 0p0n7t | — | — |
| T5MON28 | 1p0n5t | 2p1n5t | 2p0n5t | — | 0p1n5t | 3p0n5t | — | 0p1n5t | 1p0n5t | — |
| T5MON29 | 2p0n5t | 3p1n5t | 1p1n5t | — | 1p0n5t | 2p1n5t | — | 2p1n5t | 0p0n5t | 0p0n5t |

Example 4. Evaluation of Transgenic Plants for Trait Characteristics

Trait assays were conducted to evaluate trait characteristics and phenotypic changes in transgenic plants as compared to non-transgenic controls. Corn and soybean plants were grown in field and greenhouse conditions. Up to 18 parameters were measured for corn in phenology, morphometrics, biomass, and yield component studies at certain plant developmental stages. For root assays, soybean plants were grown in the greenhouse in transparent nutrient medium to allow the root system to be imaged and analyzed.

Corn developmental stages are defined by the following development criteria:
Developed leaf: leaf with a visible leaf collar;
V-Stages: Number of developed leaves on a corn plant corresponds to the plant's vegetative growth stage—i.e., a V6 stage corn plant has 6 developed (fully unfolded) leaves;
R1 (Silking): Plants defined as R1 must have one or more silks extending outside the husk leaves. Determining the reproductive stage of the crop plant at R1 or later is based solely on the development of the primary ear;
R3 (Milk): Typically occurs 18-22 days after silking depending on temperature and relative maturity. Kernels are usually yellow in color and the fluid inside each kernel is milky white;
R6 (Physiological maturity): Typically occurs 55-65 days after silking (depending on temperature and relative maturity group of the germplasm being observed). Kernels have reached their maximum dry matter accumulation at this point, and kernel moisture is approximately 35%.

Soybean developmental stages are defined by criteria as following:
Fully developed trifoliate leaf node: A leaf is considered completely developed when the leaf at the node immediately above it has unrolled sufficiently so the two edges of each leaflet are no longer touching. At the terminal node on the main stem, the leaf is considered completely developed when the leaflets are flat and similar in appearance to older leaves on the plant;
VC: Cotyledons and Unifoliolates are fully expanded;
R1: Beginning of flowering—i.e., one open flower at any node on the main stem.

Table 6 describes the trait assays. TraitRefID is the reference ID of each trait assay. Trait Name is the descriptive name of the assay. Trait Description describes what the assay measures, and how the measurement is conducted. Direction For Positive Call indicates whether an increase or decrease in the measurement quantity corresponds to a "positive" call in the assay results.

TABLE 6

Description of Trait Assays.

| TraitRefID | Trait Assay Name | Description | Direction For Positive Call |
|---|---|---|---|
| DOV12 | Days from Planting to V12 | number of days from the date of planting to the date when 50% of the plants in a plot reaches V12 stage. | decrease |
| P50DR1 | Days to 50% Pollen Shedding | number of days from the date of planting to the date when 50% of the plants in a plot reaches Pollen Shed stage. | decrease |
| S50DR1 | Days to 50% Visible Silk | number of days from the date of planting to the date when 50% of the plants in a plot reaches visible Silking (R1) stage. | decrease |
| STDIR3 | Stalk Diameter at R3 | plot average of the stalk diameter of a plant. It measures maximal "long" axis in the middle of the internode above first visible node. Measurement is taken at R3 stage. | increase |
| KRNR6 | Kernel Row Number at R6 | plot average of the number of rows of kernels on an ear, by counting around the circumference of the ear. Measurement is taken at R6 stage. | increase |
| KRLR6 | Kernels per Row Longitudinally at R6 | (also known as rank number) the plot average of the number of kernels per row longitudinally. It is calculated as the ratio of (total kernel count per ear)/(kernel row number). Measurement is taken at R6 stage. | increase |
| LFTNR3 | Leaf Tip Number at R3 | plot average of the number of leaves per plant, by counting the number of leaf tips. Measurement is taken at R3 stage. | increase |
| PLTHGR | Plant Height Growth Rate from V6 to V12 | plot average of growth rate of a plant from V6 to V12 stage. It is calculated as (Plant Height measured at V12-Plant Height measured at V6)/Days between measurements. | increase |
| PHTR3 | Plant Height at R3 | plot average of plant height. It measures from soil line to base of highest collared leaf. Measurement is taken at R3 stage. | decrease |
| EAR6 | Ear Area at R6 | plot average of size of area of a ear from a 2-dimentional view. The measurement is done through imaging of ear, including kernels and void. Typically 10 representative ears are measured per plot. Measurement is taken at R6 stage. | increase |
| EDR6 | Ear Diameter at R6 | plot average of the ear diameter. It measures maximal "wide" axis over the ear on the largest section of the ear. Measurement is taken at R6 stage. | increase |
| EDWR1 | Ear Dry Weight at R6 | plot average of the ear dry weight of a plant. Measurement is taken at R6 stage. | increase |
| ELR6 | Ear Length at R6 | plot average of the length of ear. It measures from tip of ear in a straight line to the base at the ear node. Measurement is taken at R6 stage. | increase |
| ETVR6 | Ear Tip Void Percentage at R6 | plot average of area percentage of void at the top 30% area of a ear, from a 2-dimentional view. The measurement is done through imaging of ear, including kernels and void. Typically 10 representative ears are measured per plot. Measurement is taken at R6 stage. | decrease |
| EVR6 | Ear Void Percentage at R6 | plot average of area percentage of void on a ear, from a 2-dimentional view. The measurement is done through imaging of ear, including kernels and void. Typically 10 representative ears are measured per plot. Measurement is taken at R6 stage. | decrease |
| KPER6 | Kernels per Ear at R6 | plot average of the number of kernels per ear. It is calculated as (total kernel weight/(Single Kernel Weight * total ear count), where total kernel weight and total ear count are measured from ear samples from an area between 0.19 to 10 square meters, and Single Kernel Weight (SKWTR6) is described below. Measurement is taken at R6 stage. | increase |
| SKWTR6 | Single Kernel Weight at R6 | plot average of weight per kernel. It is calculated as the ratio of (sample kernel weight adjusted to 15.5% moisture)/(sample kernel number). The sample kernel number ranges from 350 to 850. Measurement is taken at R6 stage. | increase |
| RBPN | Root Branch Point Number at VC or V2 | number of root branch tip points of a plant. The measurement is done through imaging of the root system of a plant grown in a transparent Gelzan(TM) gum gel nutrient medium to VC stage for soybean, or to V2 stage for corn. The root system image is skeletonized for the root length measurement. Up to 40 images are taken at various | increase |

TABLE 6-continued

Description of Trait Assays.

| TraitRefID | Trait Assay Name | Description | Direction For Positive Call |
|---|---|---|---|
| RTL | Root Total Length at VC or V2 | angles around the root vertical axis and measurement is averaged over the images. Gelzan is a trademark of CP Kelco U.S., Inc. cumulative length of roots of a plant, as if the roots were all lined up in a row. The measurement is done through imaging of the root system of a plant grown in a transparent Gelzan(TM) gum gel nutrient medium to VC stage for soybean, or to V2 stage for corn. The root system image is skeletonized for the root length measurement. Up to 40 images are taken at various angles around the root vertical axis and measurement is averaged over the images. Gelzan is a trademark of CP Kelco U.S., Inc. | increase |

These trait assays were set up so that the tested transgenic lines were compared to a control line. The collected data were analyzed against the control, and positives were assigned if there was a p-value of 0.2 or less. Tables 7, 8 and 9 are summaries of transgenic plants comprising the disclosed recombinant DNA constructs for corn phenology and morphometrics assays, corn yield/trait component assays, and soybean root assays, respectively.

The test results are represented by three numbers: the first number before letter "p" denotes number of tests of events with a "positive" change as defined in Table 6; the second number before letter "n" denotes number of tests of events with a "negative" change which is in the opposite direction of "positive" as defined in Table 6; the third number before letter "t" denotes total number of tests of transgenic events for a specific assay for a given gene. The "positive" or "negative" change is measured in comparison to non-transgenic control plants. A designation "–" indicates that it has not been tested. For example, 2pln5t indicates that 5 transgenic plant events were tested, of which 2 events showed a "positive" change and 1 showed a "negative" change of the measured parameter. The assay is indicated with its TraitRefID as in Table 6. Note that two constructs of gene T5MON21 were tested in some assays, and the results are listed as T5MON21 and T5MON21x.

TABLE 7

Summary of assay results for corn phenology and morphometrics assays

| Gene_ID | P50DR1 | S50DR1 | KRNR6 | KRLR6 | LFTNR3 | DOV12 | PHTR3 | STDIR3 | PLTHGR |
|---|---|---|---|---|---|---|---|---|---|
| T5MON01 | 2p0n4t | 0p0n4t | — | — | — | 2p0n4t | — | — | 5p0n12t |
| T5MON02 | 6p0n11t | 2p0n11t | 0p1n6t | 3p0n6t | 0p0n3t | — | — | — | — |
| T5MON03 | — | — | 1p0n4t | 1p0n4t | — | — | — | — | — |
| T5MON06 | 1p0n6t | 0p0n5t | — | — | — | — | 2p0n5t | 1p0n5t | — |
| T5MON08 | 1p0n4t | 0p0n4t | 2p0n3t | 1p1n3t | — | — | — | — | — |
| T5MON16 | 0p0n8t | 4p2n8t | 0p0n4t | 0p1n4t | 0p0n4t | — | — | — | — |
| T5MON17 | — | — | 0p3n4t | 0p1n4t | — | — | — | — | — |
| T5MON19 | 2p1n4t | 3p0n4t | — | — | 4p0n4t | — | — | — | — |
| T5MON20 | 2p0n4t | 0p0n4t | 0p1n2t | 0p0n2t | 0p1n2t | — | — | — | — |
| T5MON21 | 0p0n4t | 0p0n4t | 0p1n3t | 1p0n3t | — | — | — | — | — |
| T5MON21x | 0p3n5t | 0p4n5t | 0p2n3t | 0p0n3t | — | — | — | — | — |
| T5MON23 | 2p1n7t | 1p0n6t | — | — | 0p0n1t | — | — | — | — |
| T5MON26 | 2p0n11t | 2p0n11t | 2p0n6t | 0p0n6t | 0p0n3t | — | — | — | — |
| T5MON27 | 0p0n4t | 1p0n5t | 0p0n2t | 0p0n2t | 0p0n2t | — | — | — | — |
| T5MON28 | 2p0n11t | 2p3n11t | 0p3n7t | 0p2n4t | 0p2n4t | 0p2n3t | — | — | — |
| T5MON29 | — | — | 0p0n4t | 0p0n4t | — | — | — | — | — |

TABLE 8

Summary of assay results for corn trait component assays

| GeneID | EAR6 | EDR6 | ELR6 | ETVR6 | EVR6 | KPER6 | SKWTR6 | EDWR1 |
|---|---|---|---|---|---|---|---|---|
| T5MON02 | 1p0n3t | 0p0n3t | 2p0n3t | 1p0n3t | 1p0n3t | 2p0n6t | 0p0n6t | 1p0n3t |
| T5MON03 | — | — | — | — | — | 1p0n4t | 0p1n4t | — |
| T5MON08 | 1p0n6t | 1p0n6t | 1p0n6t | 0p1n6t | 0p1n6t | 1p1n6t | 1p2n6t | — |
| T5MON16 | 2p0n3t | 0p0n3t | 2p0n3t | 0p1n3t | 0p1n3t | 0p0n7t | 2p0n7t | 4p0n7t |
| T5MON17 | — | — | — | — | — | 0p1n4t | 0p0n4t | — |
| T5MON19 | — | — | — | — | — | 0p0n4t | 0p0n4t | — |
| T5MON20 | 0p1n2t | 0p2n2t | 0p1n2t | 1p0n2t | 1p0n2t | 0p0n4t | 0p1n4t | 0p0n2t |

TABLE 8-continued

Summary of assay results for corn trait component assays

| GeneID | EAR6 | EDR6 | ELR6 | ETVR6 | EVR6 | KPER6 | SKWTR6 | EDWR1 |
|---|---|---|---|---|---|---|---|---|
| T5MON21 | 1p0n3t | 1p0n3t | 1p0n3t | 0p1n3t | 0p0n3t | 1p1n3t | 1p0n3t | — |
| T5MON21x | 0p0n3t | 1p1n3t | 0p0n3t | 0p3n3t | 0p3n3t | 0p0n3t | 0p0n3t | — |
| T5MON26 | 2p0n3t | 2p0n3t | 2p0n3t | 0p0n3t | 0p0n3t | 1p0n6t | 0p1n6t | 0p0n3t |
| T5MON27 | 0p0n2t | 0p0n2t | 1p0n2t | 0p0n2t | 0p0n2t | 0p1n2t | 0p0n2t | — |
| T5MON28 | 0p2n3t | 0p1n3t | 0p2n3t | 0p0n3t | 0p0n3t | 0p5n4t | 5p0n7t | 0p1n7t |
| T5MON29 | — | — | — | — | — | 0p0n4t | 0p2n4t | — |

TABLE 9

Summary of assay results for soybean root assays

| Gene_ID | RBPN | RTL |
|---|---|---|
| T5MON12 | 0p0n4t | 1p0n4t |
| T5MON13 | 3p0n4t | 3p0n4t |

Example 5. Phenotypic Evaluation of Transgenic Plants in Field Trials for Increased Nitrogen Use Efficiency, Increased Water Use Efficiency, and Increased Yield Corn field trials were conducted to identify genes that can improve nitrogen use efficiency (NUE) under nitrogen limiting conditions leading to increased yield performance as compared to non transgenic controls. For the Nitrogen field trial results shown in Table 10, each field was planted under nitrogen limiting condition (60 lbs/acre), and corn ear weight or yield was compared to non-transgenic control plants.

Corn field trials were conducted to identify genes that can improve water use efficiency (WUE) under water limiting conditions leading to increased yield performance as compared to non transgenic controls. Results of the water use efficiency trials conducted under managed water limiting conditions are shown in Table 10, and the corn ear weight or yield was compared to non-transgenic control plants.

Corn and soybean field trials were conducted to identify genes that can improve broad-acre yield (BAY) under standard agronomic practice. Results of the broad-acre yield trials conducted under standard agronomic practice are shown in Table 10, and the corn or soybean yield was compared to non-transgenic control plants.

Table 10 provides a list of genes that produce transgenic plants having increased nitrogen use efficiency (NUE), increased water use efficiency (WUE), and/or increased broad-acre yield (BAY) as compared to a control plant. Polynucleotide sequences in constructs with at least one event showing significant yield or ear weight increase across multiple locations at p≤0.2 are included. The genes were expressed with constitutive promoters unless noted otherwise under the "Specific Expression Pattern" column. A promoter of a specific expression pattern was chosen over a constitutive promoter, based on the understanding of the gene function, or based on the observed lack of significant yield increase when the gene was expressed with constitutive promoter. The elements of Table 10 are described as follows: "Crop" refers to the crop in trial, which is either corn or soybean; "Condition" refers to the type of field trial, which is BAY for broad acre yield trial under standard agronomic practice (SAP), WUE for water use efficiency trial, and NUE for nitrogen use efficiency trial; "Specific Expression Pattern" refers to the expected expression pattern or promoter type, instead of constitutive; "Gene ID" refers to the gene identifier as defined in Table 1; "Yield results" refers to the recombinant DNA in a construct with at least one event showing significant yield increase at p≤0.2 across locations. The first number refers to the number of tests of events with significant yield or ear weight increase, whereas the second number refers to the total number of tests of events for each recombinant DNA in the construct. Typically 4 to 8 distinct events per construct are tested.

TABLE 10

Recombinant DNA with protein-coding genes for increased nitrogen use efficiency, increased water use efficiency and increased yield

| Crop | Condition | Specific Expression Pattern | Gene ID | Yield results |
|---|---|---|---|---|
| corn | BAY | | T5MON01 | 1/7 |
| corn | BAY | | T5MON04 | 3/8 |
| corn | BAY | root specific | T5MON05 | 4/28 |
| corn | BAY | root specific | T5MON06 | 7/44 |
| corn | WUE | root specific | T5MON06 | 1/6 |
| corn | BAY | seed specific | T5MON08 | 1/18 |
| corn | WUE | seed specific | T5MON08 | 3/5 |
| corn | BAY | | T5MON14 | 1/15 |
| corn | WUE | | T5MON14 | 2/6 |
| corn | BAY | root specific | T5MON15 | 2/8 |
| corn | BAY | | T5MON16 | 2/20 |
| corn | NUE | | T5MON16 | 5/11 |
| corn | BAY | | T5MON17 | 4/16 |
| corn | BAY | | T5MON19 | 8/19 |
| corn | WUE | meristem & cob enhanced | T5MON21 | 1/7 |
| corn | BAY | seed preferred | T5MON23 | 3/27 |
| corn | NUE | seed preferred | T5MON23 | 1/14 |
| corn | BAY | meristem & endosperm preferred | T5MON27 | 2/24 |
| corn | BAY | | T5MON28 | 1/14 |
| soybean | BAY | | T5MON09 | 3/12 |
| soybean | BAY | | T5MON10 | 3/13 |
| soybean | BAY | | T5MON11 | 6/23 |
| soybean | BAY | | T5MON18 | 2/28 |
| soybean | BAY | seed preferred | T5MON24 | 3/14 |

Table 11 provides a list of polynucleotide sequences of promoters with specific expression patterns. To convey the specific expression patterns, choices of promoters are not limited to those listed in Table 11.

TABLE 11

Promoter sequences and expression patterns

| Nucleotide SEQ ID NO. | Promoter Expression Pattern |
|---|---|
| 93 | seed preferred |
| 94 | root preferred |
| 95 | nneristenn & endosperm preferred |

TABLE 11-continued

Promoter sequences and expression patterns

| Nucleotide SEQ ID NO. | Promoter Expression Pattern |
|---|---|
| 96 | root specific |
| 97 | endosperm specific |
| 98 | endosperm specific |
| 99 | seed specific |
| 100 | seed preferred |
| 101 | nneristenn & cob enhanced |

Example 6. Homolog Identification

This example illustrates the identification of homologs of proteins encoded by the DNA sequences identified in Table 1, which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over 95% of the length of the polypeptide sequences provided in Table 1 are reported below in Tables 12 and 13.

Table 12 provides a list of homolog genes, the elements of which are described as follows: "PEP SEQ ID NO." identifies an amino acid sequence. "Homolog ID" refers to an alphanumeric identifier, the numeric part of which is the NCBI Genbank GI number; and "Gene Name and Description" is a common name and functional description of the gene. Table 13 describes the correspondence between the protein-coding genes in Table 1 and their homologs, and the level of protein sequence alignment between the gene and its homolog.

TABLE 12

Homologous gene information

| PEP SEQ ID NO. | Homolog ID | Gene Name and Description |
|---|---|---|
| 59 | gi_194698766 | gi|194698766|gb|ACF83467.1| unknown [Zea mays] |
| 60 | gi_285013667 | gi|285013667|gb|ADC32810.1| pyruvate orthophosphate dikinase [Zea mays] |
| 61 | gi_242063426 | gi|242063426|ref|XP_002453002.1| hypothetical protein SORBIDRAFT_04g036440 [Sorghum bicolor] |
| 62 | gi_26248016 | gi|26248016|ref|NP_754056.1| glutamate dehydrogenase [Escherichia coli CFT073] |
| 63 | gi_223975805 | gi|223975805|gb|ACN32090.1| unknown [Zea mays] |
| 64 | gi_162457981 | gi|162457981|ref|NP_001105435.1| nuclear transcription factor Y subunit B [Zea mays] |
| 65 | gi_15802172 | gi|15802172|ref|NP_288194.1| glutamate dehydrogenase [Escherichia coli O157:H7 EDL9331 |
| 66 | gi_146126 | gi|146126|gb|AAA23868.1| glutamate dehydrogenase [Escherichia coli] |
| 67 | gi_193806357 | gi|193806357|sp|P11155|Pyruvate, phosphate dikinase 1 [Zea mays] |
| 68 | gi_115840 | gi|115840|sp|P25209| Nuclear transcription factor Y subunit B [Zea mays] |
| 69 | gi_284921680 | gi|284921680|emb|CBG34752.1| NADP-specific glutamate dehydrogenase [Escherichia coli 042] |
| 70 | gi_188039906 | gi|188039906|gb|ACD47129.1| EREBP/AP2 transcription factor [Glycine max] |
| 71 | gi_162462936 | gi|162462936|ref|NP_001106052.1| transcription factor subunit NF-YB2 [Zea mays] |
| 72 | gi_19423910 | gi|19423910|gb|AAL87324.1| unknown protein [Arabidopsis thaliana] |
| 73 | gi_165874954 | gi|165874954|gb|ABY68378.1| At1g04370 [Arabidopsis thaliana] |
| 74 | gi_22093879 | gi|22093879|dbj|BAC07164.1| hypothetical protein [Oryza sativa Japonica Group] |
| 75 | gi_226508884 | gi|226508884|ref|NP_001150756.| homeobox-leucine zipper protein ATHB-4 [Zea mays] |

TABLE 12-continued

Homologous gene information

| PEP SEQ ID NO. | Homolog ID | Gene Name and Description |
|---|---|---|
| 76 | gi_226492268 | gi|226492268|ref|NP_001142481.1| hypothetical protein LOC100274701 [Zea mays] |
| 77 | gi_15219717 | gi|15219717|ref|NP_171932.1| ATERF14 (Ethylene-responsive element binding factor 14); DNA binding/transcription factor [Arabidopsis thaliana] |
| 78 | gi_4966365 | gi|4966365|gb|AAD34696.1| Eukaryotic protein kinase domain [Arabidopsis thaliana] |
| 79 | gi_165874952 | gi|165874952|gb|ABY68377.1| At1g04370 [Arabidopsis thalianal |
| 80 | gi_21592545 | gi|21592545|gb|AAM64494.1| glycyl tRNA synthetase, putative [Arabidopsis thaliana] |
| 81 | gi_222424295 | gi|222424295|dbj|BAH20104.1| AT3G30390 [Arabidopsis thaliana] |
| 82 | gi_226503589 | gi|226503589|ref|NP_001141333.1| CAAT box binding protein1 [Zea mays] |
| 83 | gi_219885341 | gi|219885341|gb|ACL53045.1| unknown [Zea mays] |
| 84 | gi_3980050 | gi|3980050|emb|CAA41635.1| glutamate dehydrogenase (NADP+) [Chlorella sorokiniana] |
| 85 | gi_168586 | gi|168586|gb|AAA33498.1| pyruvate,orthophosphate dikinase [Zea mays] |
| 86 | gi_162460730 | gi|162460730|ref|NP_001105738.1| pyruvate, phosphate dikinase 1, chloroplastic precursor [Zea mays] |
| 87 | gi_21553511 | gi|21553511|gb|AAM62604.1| growth factor like protein [Arabidopsis thaliana] |
| 88 | gi_2208903 | gi|2208903|dbj|BAA20519.1| ascorbate oxidase [Arabidopsis thaliana] |
| 89 | gi_118546 | gi|118546|sp|P28998|NADP-specific glutamate dehydrogenase [Chlorella sorokiniana] |
| 90 | gi_165874950 | gi|165874950|gb|ABY68376.1| At1g04370 [Arabidopsis thaliana] |
| 91 | gi_162459403 | gi|162459403|ref|NP_001105725.1| glutamine synthetase, chloroplastic precursor [Zea mays] |
| 92 | gi_162463830 | gi|162463830|ref|NP_001105461.1| proliferating cell nuclear antigen [Zea mays] |

TABLE 13

Correspondence of Genes and Homologs

| Gene ID | Homolog ID | Percent Gene Coverage | Percent Homolog Coverage | Percent Identity |
|---|---|---|---|---|
| T5MON04 | gi_21592545 | 95 | 100 | 99 |
| T5MON05 | gi_2208903 | 96 | 100 | 99 |
| T5MON07 | gi_21553511 | 100 | 100 | 99 |
| T5MON08 | gi_222424295 | 100 | 100 | 99 |
| T5MON09 | gi_15219717 | 100 | 100 | 99 |
| T5MON09 | gi_165874950 | 98 | 100 | 99 |
| T5MON09 | gi_165874952 | 98 | 100 | 98 |
| T5MON09 | gi_165874954 | 98 | 100 | 98 |
| T5MON10 | gi_19423910 | 99 | 100 | 100 |
| T5MON13 | gi_4966365 | 98 | 99 | 99 |
| T5MON15 | gi_118546 | 100 | 86 | 99 |
| T5MON15 | gi_3980050 | 100 | 86 | 99 |
| T5MON16 | gi_146126 | 100 | 100 | 99 |
| T5MON16 | gi_26248016 | 100 | 100 | 99 |
| T5MON16 | gi_15802172 | 100 | 100 | 99 |
| T5MON16 | gi_284921680 | 100 | 100 | 99 |
| T5MON18 | gi_188039906 | 100 | 100 | 99 |
| T5MON19 | gi_22093879 | 100 | 90 | 98 |
| T5MON20 | gi_219885341 | 100 | 100 | 99 |
| T5MON20 | gi_285013667 | 100 | 100 | 99 |
| T5MON20 | gi_168586 | 98 | 100 | 99 |
| T5MON20 | gi_193806357 | 98 | 100 | 99 |
| T5MON20 | gi_162460730 | 98 | 100 | 97 |
| T5MON21 | gi_162463830 | 100 | 100 | 98 |
| T5MON21 | gi_242063426 | 100 | 100 | 98 |
| T5MON22 | gi_162463830 | 100 | 100 | 98 |
| T5MON22 | gi_242063426 | 100 | 100 | 98 |
| T5MON27 | gi_162457981 | 100 | 100 | 99 |
| T5MON27 | gi_115840 | 100 | 99 | 99 |
| T5MON27 | gi_226503589 | 100 | 100 | 96 |
| T5MON27 | gi_162462936 | 100 | 100 | 96 |
| T5MON28 | gi_226508884 | 96 | 75 | 100 |
| T5MON29 | gi_194698766 | 100 | 100 | 99 |
| T5MON29 | gi_162459403 | 100 | 100 | 99 |
| T5MON30 | gi_223975805 | 100 | 100 | 99 |
| T5MON30 | gi_226492268 | 100 | 100 | 98 |

Example 7. Use of Site-Directed Integration to Introduce Transgenes or Modulate Expression of Endogenous Genes in Plants As introduced above, a DNA sequence comprising a transgene(s), expression cassette(s), etc., such as one or more coding sequences of genes identified in Tables 1 and 12, or homologs thereof, may be inserted or integrated into a specific site or locus within the genome of a plant or plant cell via site-directed integration. A DNA sequence comprising one or more coding sequences of genes identified in Tables 1 and 12, or homologs thereof, may be operably linked to a promoter and/or other regulatory elements, such as a 5' and/or 3' untranslated region (UTR), enhancer, intron, and/or terminator region, which may each be native, non-native, synthetic and/or heterologous to the coding sequence or plant host cell. Recombinant DNA constructs and molecules of this disclosure may thus include a donor template having an insertion sequence comprising at least one transgene, expression cassette, or other DNA sequence for insertion into the genome of the plant or plant cell. Such donor template for site-directed integration may further include one or two homology arms flanking the insertion sequence to promote insertion of the insertion sequence at the desired site or locus. Any site or locus within the genome of a plant may be chosen for site-directed integration of the insertion sequence.

Several methods for site-directed integration are known in the art involving different proteins (or complexes of proteins and/or guide RNA) that cut the genomic DNA to produce a double strand break (DSB) or nick at a desired genomic site or locus. Examples of site-specific nucleases that may be used include zinc-finger nucleases, engineered or native meganucleases, TALE-endonucleases, and RNA-guided endonucleases (e.g., Cas9 or Cpf1). For methods using RNA-guided site-specific nucleases (e.g., Cas9 or Cpf1), the recombinant DNA construct(s) will also comprise a sequence encoding one or more guide RNAs to direct the nuclease to the desired site within the plant genome. The recombinant DNA molecules or constructs of this disclosure may further comprise an expression cassette(s) encoding a site-specific nuclease, a guide RNA, and/or any associated protein(s) to carry out the desired site-directed integration event.

The endogenous genomic loci of a plant or plant cell corresponding to the genes identified in Tables 1 and 12, or a homolog thereof, may be selected for site-specific insertion of a recombinant DNA molecule or sequence capable of modulating expression of the corresponding endogenous genes. As described above, the recombinant DNA molecule or sequence serves as a donor template for integration of an insertion sequence into the plant genome. The donor template may also have one or two homology arms flanking the insertion sequence to promote the targeted insertion event. Although a transgene, expression cassette, or other DNA sequence may be inserted into a desired locus or site of the plant genome via site-directed integration, a donor template may instead be used to replace, insert, or modify a 5' untranslated region (UTR), promoter, enhancer, intron, 3' UTR and/or terminator region of an endogenous gene, or any portion thereof, to modulate the expression level of the endogenous gene. Another method for modifying expression of an endogenous gene is by genome editing of an endogenous gene locus. For example, a targeted genome editing event may be made to disrupt or abolish a regulatory binding site for a transcriptional repressor of an endogenous gene to increase or modify expression of the endogenous gene.

For genome editing or site-specific integration of an insertion sequence of a donor template, a double-strand break (DSB) or nick is made in the selected genomic locus. The DSB or nick may be made with a site-specific nuclease, for example a zinc-finger nuclease, an engineered or native meganuclease, a TALE-endonuclease, or an RNA-guided endonuclease (for example Cas9 or Cpf1). In the presence of a donor template, the DSB or nick may be repaired by homologous recombination between the homology arms of the donor template and the plant genome, resulting in site-directed integration of the insertion sequence to make the targeted genomic modification or insertion at the site of the DSB or nick. For genes shown herein to cause or produce a desired phenotype or trait in a plant, an expression construct or transgene comprising the coding sequence of the gene may be inserted at a desired or selected site within the genome of the plant via site-directed integration as discussed above. Alternatively, the sequence of a corresponding endogenous gene may be modified via site-directed integration to augment or alter the expression level of the endogenous gene, such as by adding a promoter or intron sequence, or by modifying or replacing a 5' UTR sequence, promoter, enhancer, intron, 3' UTR sequence, and/or terminator region, or any portion thereof, of the endogenous gene.

Following transformation of a plant cell with the recombinant molecule(s) or construct(s), the resulting events are screened for site-directed insertion of the donor template insertion sequence or genome modification. Plants containing these confirmed events or modifications may then be tested for modulation of an endogenous gene, expression of an integrated transgene, and/or modification of yield traits or other phenotypes.

What is claimed is:

1. A monocot plant comprising and expressing a recombinant DNA construct, wherein the recombinant DNA construct comprises:
   a) a polynucleotide sequence having at least 95% sequence identity to the nucleotide sequence of SEQ ID NO:21; or
   b) a polynucleotide sequence that encodes a polypeptide having an amino acid sequence having at least 95% sequence identity to the amino acid sequence of SEQ ID NO:50;
   wherein the recombinant DNA construct further comprises a heterologous promoter operably linked to the polynucleotide sequence,
wherein the plant has been selected for having an altered phenotype as compared to a control plant, and wherein the altered phenotype is selected from the group consisting of increased kernels per row, increased kernels per ear, increased ear area, increased ear length, increased ear diameter, and increased single kernel weight.

2. A monocot plant produced by a method comprising producing a transgenic plant comprising and expressing a recombinant DNA construct, wherein the recombinant DNA construct comprises:
   a) a polynucleotide sequence having at least 95% sequence identity to the nucleotide sequence of SEQ ID NO:21; or
   b) a polynucleotide sequence that encodes a polypeptide having an amino acid sequence having at least 95% sequence identity to the amino acid sequence of SEQ ID NO:50;
   wherein the recombinant DNA construct further comprises a heterologous promoter operably linked to the polynucleotide sequence, and
selecting the plant for having an altered phenotype as compared to a control plant, and wherein the altered phenotype is selected from the group consisting of increased kernels per row, increased kernels per ear, increased ear area, increased ear length, increased ear diameter, and increased single kernel weight.

3. The monocot plant of claim 1, wherein the monocot plant is a corn plant.

4. A plant part or propagule of the monocot plant of claim 1, wherein the plant part or propagule comprises the recombinant DNA construct.

5. The monocot plant of claim 1, wherein the recombinant DNA construct comprises a polynucleotide sequence that encodes a polypeptide having an amino acid sequence having at least 97% sequence identity to the amino acid sequence of SEQ ID NO:50.

6. The monocot plant of claim 1, wherein the recombinant DNA construct comprises a polynucleotide sequence that encodes a polypeptide having the amino acid sequence of SEQ ID NO:50.

7. The monocot plant of claim 1, wherein the recombinant DNA construct comprises a polynucleotide sequence having at least 97% sequence identity to the nucleotide sequence of SEQ ID NO:21.

8. The monocot plant of claim 1, wherein the recombinant DNA construct comprises a polynucleotide sequence having the nucleotide sequence of SEQ ID NO:21.

9. The monocot plant of claim 2, wherein the monocot plant is a corn plant.

10. A plant part or propagule of the monocot plant of claim 2, wherein the plant part or propagule comprises the recombinant DNA construct.

11. The monocot plant of claim 2, wherein the recombinant DNA construct comprises a polynucleotide sequence that encodes a polypeptide having an amino acid sequence having at least 97% sequence identity to the amino acid sequence of SEQ ID NO:50.

12. The monocot plant of claim 2, wherein the recombinant DNA construct comprises a polynucleotide sequence that encodes a polypeptide having the amino acid sequence of SEQ ID NO:50.

13. The monocot plant of claim 2, wherein the recombinant DNA construct comprises a polynucleotide sequence having at least 97% sequence identity to the nucleotide sequence of SEQ ID NO:21.

14. The monocot plant of claim 2, wherein the recombinant DNA construct comprises a polynucleotide sequence having the nucleotide sequence of SEQ ID NO:21.

* * * * *